US00RE50267E

(19) United States
(12) Reissued Patent
Tran et al.

(10) Patent Number: US RE50,267 E
(45) Date of Reissued Patent: *Jan. 14, 2025

(54) MODULATORS OF THE PROSTACYCLIN (PGI2) RECEPTOR USEFUL FOR THE TREATMENT OF DISORDERS RELATED THERETO

(71) Applicant: Arena Pharmaceuticals, Inc., San Diego, CA (US)

(72) Inventors: Thuy-Anh Tran, San Diego, CA (US); Weichao Chen, San Diego, CA (US); Bryan A. Kramer, San Diego, CA (US); Abu J. M. Sadeque, San Diego, CA (US); Anna Shifrina, San Diego, CA (US); Young-Jun Shin, San Diego, CA (US); Pureza Vallar, Chula Vista, CA (US); Ning Zou, San Diego, CA (US)

(73) Assignee: ARENA PHARMACEUTICALS, INC., San Diego, CA (US)

( * ) Notice: This patent is subject to a terminal disclaimer.

(21) Appl. No.: 17/747,917

(22) Filed: May 18, 2022

Related U.S. Patent Documents

Reissue of:
(64) Patent No.: 10,668,033
Issued: Jun. 2, 2020
Appl. No.: 15/447,573
Filed: Mar. 2, 2017

U.S. Applications:
(60) Continuation of application No. 14/510,669, filed on Oct. 9, 2014, now abandoned, which is a division of
(Continued)

(51) Int. Cl.
*A61K 31/195* (2006.01)
*A61K 31/27* (2006.01)
(Continued)

(52) U.S. Cl.
CPC ..... *A61K 31/195* (2013.01); *A61K 31/27* (2013.01); *A61K 31/325* (2013.01);
(Continued)

(58) Field of Classification Search
CPC .... A61K 31/195; A61K 31/27; A61K 31/325; A61K 31/381; A61K 31/426; A61K 31/44; A61K 31/4402; A61K 31/4406; A61K 31/4965; A61K 31/196; C07C 271/12; C07C 271/28; C07C 275/24; C07C 275/28; C07C 275/30; C07C 275/34; C07C 309/15; C07C 2601/14; C07C 275/18; C07D 213/75; C07D 241/20; C07D 277/48;
(Continued)

(56) References Cited

U.S. PATENT DOCUMENTS 5,849,919 A 12/1998 Hamanaka et al.
6,746,729 B1 6/2004 Cherkaoul et al.
(Continued)

FOREIGN PATENT DOCUMENTS

CA 2125074 12/1994
CA 2125074 A1 12/1994
(Continued)

OTHER PUBLICATIONS

Aguilar et al. Epoprostenol (prostacyclin) therapy in HIV-associated pulmonary hypertension. Am. J. Respir. Crit. Care Med. 162:1846-1850 (2000).
Archer et al., Nitric oxide deficiency in fenfluramine- and dexfenfluramine-induced pulmonary hypertension. Am. J. Respir. Crit. Care Med. 158:1061-1067 (1998).
Arehart et al., Acceleration of cardiovascular disease by a dysfunctional prostacyclin receptor mutation: potential implications for cyclooxygenase-2 inhibition. Circ. Res. 102(8):986-993 (2008).
Arehart et al., Prostacyclin, atherothrombosis, and cardiovascular disease. Curr. Med. Chem. 14:2161-2169 (2007).
Badesch et al., Continuous intravenous epoprostenol for pulmonary hypertension due to the scleroderma spectrum of disease. A randomized, controlled trial. Ann. Intern. Med. 132:425-434 (2000).
(Continued)

*Primary Examiner* — Alan D Diamond
(74) *Attorney, Agent, or Firm* — WILSON SONSINI GOODRICH & ROSATI

(57) ABSTRACT

The present invention relates to amide derivatives of Formula (XIIIa) and pharmaceutical compositions thereof that modulate the activity of the PGI2 receptor. Compounds of the present invention and pharmaceutical compositions thereof are directed to methods useful in the treatment of: Pulmonary arterial hypertension (PAH); idiopathic PAH; familial PAH; PAH associated with a collagen vascular disease, a congenital heart disease, portal hypertension, HIV infection, ingestion of a drug or toxin, hereditary hemorrhagic telangiectasia, splenectomy, pulmonary veno-occlusive disease (PVOD) or pulmonary capillary hemangiomatosis (PCH); PAH with significant venous or capillary involvement; platelet aggregation; coronary artery disease; myocardial infarction; transient ischemic attack, angina; stroke; ischemia-reperfusion injury; restenosis; atrial fibrillation; blood clot formation in an angioplasty or coronary bypass surgery individual or in an individual suffering from atrial fibrillation; atherosclerosis; atherothrombosis; asthma or a symptom thereof; a diabetic-related disorder such as diabetic peripheral neuropathy, diabetic nephropathy or diabetic retinopathy; glaucoma or other disease of the eye with abnormal intraocular pressure; hypertension; inflammation; psoriasis; psoriatic arthritis; rheumatoid arthritis; Crohn's disease; transplant rejection; multiple sclerosis; systemic lupus erythematosus (SLE); ulcerative colitis; ischemia-reperfusion injury; restenosis, atherosclerosis; acne; type 1 diabetes; type 2 diabetes; sepsis; and chronic obstructive pulmonary disorder (COPD).

4 Claims, 27 Drawing Sheets

Related U.S. Application Data application No. 12/933,196, filed as application No. PCT/US2009/001688 on Mar. 17, 2009, now Pat. No. 8,895,776.

(60) Provisional application No. 61/209,453, filed on Mar. 6, 2009, provisional application No. 61/207,220, filed on Feb. 9, 2009, provisional application No. 61/123,621, filed on Apr. 9, 2008, provisional application No. 61/069,857, filed on Mar. 18, 2008.

(51) Int. Cl.

| | |
|---|---|
| ***A61K 31/325*** | (2006.01) |
| ***A61K 31/381*** | (2006.01) |
| ***A61K 31/426*** | (2006.01) |
| ***A61K 31/44*** | (2006.01) |
| ***A61K 31/4402*** | (2006.01) |
| ***A61K 31/4406*** | (2006.01) |
| ***A61K 31/4965*** | (2006.01) |
| ***C07C 271/12*** | (2006.01) |
| ***C07C 271/28*** | (2006.01) |
| ***C07C 275/24*** | (2006.01) |
| ***C07C 275/28*** | (2006.01) |
| ***C07C 275/30*** | (2006.01) |
| ***C07C 275/34*** | (2006.01) |
| ***C07C 309/15*** | (2006.01) |
| ***C07D 213/75*** | (2006.01) |
| ***C07D 241/20*** | (2006.01) |
| ***C07D 277/48*** | (2006.01) |
| ***C07D 333/36*** | (2006.01) |

(52) U.S. Cl.

CPC ..... *A61K 31/381* (2013.01); *A61K 31/426* (2013.01); *A61K 31/44* (2013.01); *A61K 31/4402* (2013.01); *A61K 31/4406* (2013.01); *A61K 31/4965* (2013.01); *C07C 271/12* (2013.01); *C07C 271/28* (2013.01); *C07C 275/24* (2013.01); *C07C 275/28* (2013.01); *C07C 275/30* (2013.01); *C07C 275/34* (2013.01); *C07C 309/15* (2013.01); *C07D 213/75* (2013.01); *C07D 241/20* (2013.01); *C07D 277/48* (2013.01); *C07D 333/36* (2013.01); *C07B 2200/07* (2013.01); *C07B 2200/13* (2013.01); *C07C 2601/14* (2017.05)

(58) Field of Classification Search

CPC ..... C07D 333/36; C07B 2200/07; C07B 2200/13; C07B 53/00; A61P 9/00; A61P 9/10; A61P 9/12; A61P 11/00; A61P 11/06; A61P 11/16

See application file for complete search history.

(56) References Cited

U.S. PATENT DOCUMENTS

| | | | | |
|---|---|---|---|---|
| 7,115,746 | B2 | 10/2006 | Snoonian et al. | |
| 7,202,253 | B2 | 4/2007 | Hou et al. | |
| 7,226,550 | B2 | 6/2007 | Hou et al. | |
| 8,895,776 | B2 * | 11/2014 | Tran | C07C 271/12 562/439 |
| 10,668,033 | B2 | 6/2020 | Tran et al. | |
| 2003/0144350 | A1 | 7/2003 | Stevenson et al. | |
| 2004/0048844 | A1 | 3/2004 | Nugiel et al. | |
| 2006/0063930 | A1 | 3/2006 | Agoston et al. | |
| 2006/0258728 | A1 | 11/2006 | Tani et al. | |
| 2011/0224262 | A1 | 9/2011 | Tran et al. | |
| 2013/0217706 | A1 | 8/2013 | Tran et al. | |
| 2015/0126527 | A1 | 5/2015 | Tran et al. | |
| 2020/0375930 | A1 | 12/2020 | Tran et al. | |

FOREIGN PATENT DOCUMENTS

| | | | |
|---|---|---|---|
| CN | 1418187 | A | 5/2003 |
| CN | 1516690 | A | 7/2004 |
| CN | 1735598 | A | 2/2006 |
| CN | 1829712 | A | 9/2006 |
| CN | 1882532 | A | 12/2006 |
| EP | 0028829 | | 5/1981 |
| EP | 0028829 | A1 | 5/1981 |
| EP | 0442448 | | 8/1991 |
| EP | 0442448 | A2 | 8/1991 |
| EP | 1013639 | A1 | 6/2000 |
| EP | 1046631 | | 10/2000 |
| EP | 1046631 | A1 | 10/2000 |
| EP | 1716087 | A1 | 11/2006 |
| IN | 1995DE00358 | | 3/1995 |
| IN | 2006DN04486 | | 8/2006 |
| JP | 3160438 | | 7/1991 |
| JP | H03160438 | A | 7/1991 |
| JP | 06329598 | | 11/1994 |
| JP | H06329598 | A | 11/1994 |
| JP | 11269138 | | 10/1999 |
| JP | H11269138 | A | 10/1999 |
| JP | 2005104853 | | 4/2005 |
| JP | 2005104853 | A | 4/2005 |
| JP | 2006083085 | | 3/2006 |
| JP | 2006083085 | A | 3/2006 |
| JP | 2006137856 | | 6/2006 |
| JP | 2006137856 | A | 6/2006 |
| JP | 2007161867 | | 6/2007 |
| JP | 2007161867 | A | 6/2007 |
| WO | WO-9524393 | A1 | 9/1995 |
| WO | WO 02/055484 | | 7/2002 |
| WO | WO-02055484 | A1 | 7/2002 |
| WO | WO 07/051255 | | 5/2007 |
| WO | WO-2007051255 | A1 | 5/2007 |
| WO | WO 07/133653 | | 11/2007 |
| WO | WO-2007133653 | A2 | 11/2007 |
| WO | WO2009/117095 | | 9/2009 |
| WO | WO-2009117095 | A1 | 9/2009 |
| WO | WO2010/077275 | | 7/2010 |
| WO | WO-2010077275 | A1 | 7/2010 |
| WO | WO2011/037613 | | 3/2011 |
| WO | WO-2011037613 | A1 | 3/2011 |

OTHER PUBLICATIONS

Badesch et al., Prostanoid therapy for pulmonary arterial hypertension. Journal of the American College of Cardiology 43(12 Suppl. S):56S-61S (2004).

Berge et al.: Pharmaceutical salts. Journal of Pharmaceutical Sciences 66:1-19 (1977).

Bernabei et al., Iloprost and echistatin protect platelets during simulated extracorporeal circulation. Ann. Thorac. Surg. 59:149-153 (1995).

Boehme et al., Decrease in circulating endothelial cell adhesion molecule and thrombomodulin levels during oral iloprost treatment in rheumatoid arthritis patients: preliminary results. Rheumatol. Int. 26:340-347 (2006).

Burnette et al. PGI2 opens potassium channels in retinal pericytes by cyclic AMP—stimulated, cross-activation of PKG. Exp. Eye Res. 83:1359-1365 (2006).

Cameron et al., The effects of 5-hydroxytryptamine 5-HT2 receptor antagonists on nerve conduction velocity and endoneurial perfusion in diabetic rats. Naunyn Schmiedebergs Arch. Pharmacol. 367:607-614 (2003).

Cameron. Vascular factors and metabolic interactions in the pathogenesis of diabetic neuropathy. Diabetologia 44:1973-1988 (2001).

Chan. Vitamin E and atherosclerosis. J. Nutr. 128:1593-1596 (1998).

Cheng et al., Role of prostacyclin in the cardiovascular response to thromboxane A2. Science 296:539-541 (2002).

Collier et al., Radiosynthesis and in vivo evaluation of the pseudopeptide Σ-opioid antagonist [125I]-ITIPP(ψ) J. Labelled Compd. Radiopharm 42:S264-S266 (1999).

(56) References Cited

OTHER PUBLICATIONS

Cote et al., Disruption of the nonneuronal tph1 gene demonstrates the importance of peripheral serotonin in cardiac function. PNAS 100(23):13525-13530 (2003).
Cotter et al., Prevention and reversal of motor and sensory peripheral nerve conduction abnormalities in streptozotocin-diabetic rats by the prostacyclin analogue iloprost. Naunyn Schmiedebergs Arch. Pharmacol. 347:534-540 (1993).
Czeslick et al., Inhibition of intracellular tumour necrosis factor (TNF)-alpha and interleukin (IL)-6 production in human monocytes by iloprost. Eur. J. Clin. Invest. 33:1013-1017 (2003).
Davi et al, Platelet activation and atherothrombosis. N. Eng. J. Med. 357:2482-2494 (2007).
Di Renzo et al., Iloprost treatment reduces TNF-alpha production and TNF-RII expression in critical limb ischemia patients without affecting IL6. Prostaglandin Leukot. Essent. Fatty Acids 73:405-410 (2005).
Dogan et al., Effect of the prostacyclin analogue, iloprost, on infarct size after permanent focal cerebral ischemia. Gen. Pharmacol. 27:1163-1166 (1996).
Egan et al., COX-2-derived prostacyclin confers atheroprotection on female mice. Science 306:1954-1957 (2004).
Fang et al., Induction of prostacyclin/PGI2 synthase expression after cerebral ischemia—reperfusion. J. Cereb. Blood Flow Metab. 26:491-501 (2006).
Fetalvero et al., Cardioprotective prostacyclin signaling in vascular smooth muscle. Prostaglandins Other Lipid Mediat. 82:109-118 (2007).
Fetalvero et al., The prostacyclin receptor induces human vascular smooth muscle cell differentiation via the protein kinase A pathway. Am. J. Physiol. Heart. Circ. Physiol. 290:H1337-H1346 (2006).
Fries et al., The cardiovascular pharmacology of COX-2 inhibition. Hematology Am. Soc. Hematol. Educ.Program, 2005:445-451 (2005).
Fujiwara et al., A stable prostacyclin analogue reduces high serum TNF-alpha levels in diabetic patients. Exp. Clin. Endocrinol. Diabetes 112:390-394 (2004).
Gabriel et al., High throughput screening technologies for direct cyclic AMP measurement. ASSAY and Drug Development Technologies, 1:291-303 (2003).
Gainza et al., Role of prostacyclin (epoprostenol) as anticoagulant in continuous renal replacement therapies: efficacy, security and cost analysis. J. Nephrol. 19:648-655 (2006).
Gao et al., A 7-day oral treatment of patients with active rheumatoid arthritis using the prostacyclin analog iloprost: cytokine modulation, safety, and clinical effects. Rheumatol. Int. 22:45-51 (2002).
GenBank Accession No. NP 000951 Human PGI2 receptor (2019).
Goya et al., Effects of the prostaglandin I2 analogue, beraprost sodium, on vascular cell adhesion molecule-1 expression in human vascular endothelial cells and circulating vascular cell adhesion molecule-1 level in patients with type 2 diabetes mellitus. Metabolism Clinical and Experimental 52:192-198 (2003).
Guillory. Chapter 5: Generation of Polymorphs, Hydrates, Solvates, and Amorphous Solids. Polymorphism in Pharmaceutical Solids pp. 183-226 (Brittain, H.G., ed., 1999).
Guillory. Generation of polymorphs, hydrates, solvates, and amorphous solids, in Polymorphism in Pharmaceutical Solids, ed. Harry G. Brittan, vol. 95, Marcel Dekker, Inc., New York 1999, pp. 183-226.
Harada et al., Role of neutrophil elastase in development of pulmonary vascular injury and septic shock in rats. Shock 30(4):379-387 (2008).
Hoeper et al., Bosentan therapy for portopulmonary hypertension. Eur. Respir. J. 25:502-508 (2005).
Hoeper et al., Pulmonary hypertension after splenectomy? Ann. Intern. Med. 130(6):506-509 (1999).
Hotta et al., Effects of beraprost sodium and insulin on the electroretinogram, nerve conduction, and nerve blood flow in rats with streptozotocin-induced diabetes. Diabetes 45:361-366 (1996).
Hotta et al. Prevention of abnormalities in motor nerve conduction and nerve blood-flow by a prostacyclin analog, beraprost sodium, in streptozotocin-induced diabetic rats. Prostaglandins 49:339-349 (1995).
Hoyng et al., Iloprost, a stable prostacyclin analog, reduces intraocular pressure. Invest. Ophthalmol Vis. Sci. 28:470-476 (1987).
Humbert et al., Cellular and molecular pathobiology of pulmonary arterial hypertension. J. Am. Coll. Cardiol. 43:13S-24S (2004).
Humbert et al, Short-term and long-term epoprostenol (prostacyclin) therapy in pulmonary hypertension secondary to connective tissue diseases: results of a pilot study Eur. Respir. J. 13:1351-1356 (1999).
Idzko et al, Inhaled iloprost suppresses the cardinal features of asthma via inhibition of airway dendritic cell function. J. Clin. Invest. 117:464-472 (2007).
Indian Patent Application No. IN1995DE00358 358/DEL/1995.
Jaffar et al., Prostaglandin I2-IP signaling blocks allergic pulmonary inflammation by preventing recruitment of CD4+ Th2 cells into the airways in a mouse model of asthma. J. Immunol 179:6193-6203 (2007).
Jozefowski et al., Exogenous but not endogenous prostanoids regulate cytokine secretion from murine bone marrow dendritic cells: EP2, DP, and IP but not EP1, EP3, and FP prostanoid receptors are involved. Int. Immunopharmcol. 3:865-878 (2003).
Klapars et al., A general and efficient copper catalyst for the amidation of aryl halides. J. Am. Chem. Soc. 124: 7421-7428 (2002).
Kobayashi et al., Roles of thromboxane A(2) and prostacyclin in the development of atherosclerosis in apoE-deficient mice. J. Clin. Invest. 114:784-794 (2004).
Koike et al., Enhanced angiogenesis and improvement of neuropathy by cotransfection of human hepatocyte growth factor and prostacyclin synthase gene. FASEB J. 17:779-781 (2003).
Le Bas et al., Radioiodinated analogs of EP 00652218 for the exploration of the tachykinin NK1 receptor by spect. J Labelled Compd. Radiopharm 44:S280-S282 (2001).
Liu et al., Treatments for pulmonary arterial hypertension. Respiratory Medicine, Baillier Tindall, London, GB 100(5):765-774 (2006).
Lundblad et al., Increased cortical cell loss and prolonged hemodynamic depression after traumatic brain injury in mice lacking the IP receptor for prostacyclin. Journal of Cerebral Blood Flow & Metabolism 28:367-376 (2008).
Mardla et al., Potentiation of antiaggregating effect of prostaglandins by alpha-tocopherol and quercetin. Platelets 15:319-324 (2004).
McCormick et al., Prostacyclin analogues: the next drug-eluting stent? Biochem. Soc. Trans. 35:910-911 (2007).
McGoon et al., Screening, early detection, and diagnosis of pulmonary arterial hypertension: ACCP evidence-based clinical practice guidelines. Chest 126:14S-34S (2004).
McLaughlin et al., Pulmonary arterial hypertension. Pulmonary arterial hypertension. Circulation 114(13):1417-1431 (2006).
Miwa et al., Combination therapy with oral sildenafil and beraprost for pulmonary arterial hypertension associated with Crest syndrome. Int. Heart J. 48:417-422 (2007).
Moncada et al., Human arterial and venous tissues generate prostacyclin (prostaglandin x), a potent inhibitor of platelet aggregation. Lancet 1:18-20 (1977).
Morecroft et al., Effect of tryptophan hydroxylase 1 deficiency on the development of hypoxia-induced pulmonary hypertension. Hypertension 49:232-236 (2007).
Moss. Basic terminology of stereochemistry (IUPAC Recommendations 1996). Pure & Appl. Chem. 68(12):2193-2222 (1996).
Murata et al., Altered pain perception and inflammatory response in mice lacking prostacyclin receptor. Nature 388:678-682 (1997).
Naeije et al., Expert opinion on available options treating pulmonary arterial hypertension. Expert Opin.Pharmacother. 8:2247-2265 (2007).
Nagao et al., Role of prostaglandin I2 in airway remodeling induced by repeated allergen challenge in mice. Am. J. Respir. Cell Mol. Biol. 29:314-320 (2003).
Okuda et al., Acute effect of beraprost sodium on lower limb circulation in patients with non-insulin-dependent diabetes mellitus-

(56) References Cited

OTHER PUBLICATIONS evaluation by color Doppler ultrasonography and laser cutaneous blood flowmetry. Prostaglandins 52:375-384 (1996).
Osol (Editor), Remington's Pharmaceutical Sciences, 1980, Philadelphia College of Pharmaceutical Science, Chapter 27: Structure-Activity Relationship and Drug Design, pp. 420-435.
Owada et al., Effect of long-term administration of prostaglandin I(2) in incipient diabetic nephropathy. Nephron 92:788-796 (2002).
PCT/US2009/001688 International Search Report and Written Opinion dated Jul. 22, 2009.
Rabinovitch. Pathobiology of pulmonary hypertension. Annu. Rev. Pathol. Mech. Dis. 2:369-399 (2007).
Raychaudhuri et al., The prostacyclin analogue treprostinil blocks NFkappaB nuclear translocation in human alveolar macrophages. J. Biol. Chem. 277:33344-33348 (2002).
Robbins et al., Epoprostenol for treatment of pulmonary hypertension in patients with systemic lupus erythematosus. Chest 117:14-18 (2000).
Rosenkranz. Pulmonary hypertension: Current diagnosis and treatment. Clin. Res. Cardiol. 96(8):527-541 (2007).
Rosenzweig. Emerging treatments for pulmonary arterial hypertension. Expert Opin. Emerging Drugs 11(4):609-619 (2006).
Rosenzweig et al., Long-term prostacyclin for pulmonary hypertension with associated congenital heart defects. Circulation 99:1858-1865 (1999).
Sato et al., Effect of OP-2507, a novel prostacyclin analogue on ischemia and reperfusion induced arrhythmias in isolated perfused rat heart. Journal of Molecular and Cellular Cardiology, Academic Press, GB, 22:S74 (1990).
Schermuly et al., Antiremodeling effects of iloprost and the dual-selective phosphodiesterase ¾ inhibitor tolafentrine in chronic experimental pulmonary hypertension. Circ. Res. 94:1101-1108 (2004).
Seiler et al., 2-[3-[2-(4,5-Diphenyl-2-oxazolyl) ethyl] phenoxy] acetic acid (BMY 42393): a new, structurally-novel prostacyclin partial agonist: 1). Inhibition of platelet aggregation and mechanism of action. Thrombosis Research 74(2):115-123 (1994).
Shindo et al., Clinical efficacy of a stable prostacyclin analog, iloprost, in diabetic neuropathy. Prostaglandins 41:85-96 (1991).
Shinomiya et al., Regulation of TNFalpha and interleukin-10 production by prostaglandins I(2) and E(2): studies with prostaglandin receptor-deficient mice and prostaglandin E-receptor subtype-selective synthetic agonists. Biochem. Pharmacol. 61:1153-1160 (2001).
Simonneau et al., Clinical classification of pulmonary hypertension. J. Am. Coll. Cardiol. 43:5S-12S (2004).
Stitham et al., Human prostacyclin receptor structure and function from naturally-occurring and synthetic mutations. Prostaglandins Other Lipid Mediat. 82:95-108 (2007).
Strauss et al., Prostanoid therapy for pulmonary arterial hypertension. Clin. Chest. Med. 28:127-142 (2007).
Streiter et al., The role of chelating diamine ligands in the goldberg reaction: a kinetic study on the copper-catalyzed amidation of aryl iodides. JACS Communications, J. Am. Chem. Soc. 127:4120-4121 (2005).
Szekeres et al., Delayed antiischemic effect of PgI2 and of a new stable PgI2 analogue 7-oxo-prostacyclin-Na in experimental model angina in dogs. Journal of Molecular and Cellular Cardiology, Academic Press, GB 15:132 (1983).
Taichman et al., Epidemiology of pulmonary arterial hypertension. Clin. Chest. Med., 28:1-22 (2007).
Takahashi et al., Augmentation of allergic inflammation in prostanoid IP receptor deficient mice. Br. J. Pharmacol, 137:315-322 (2002).
Tawara et al., Effects of combined therapy with a Rho-kinase inhibitor and prostacyclin on monocrotaline-induced pulmonary hypertension in rats. Journal of Cardiovascular Pharmacology 50(2):195-200 (2007).
Tuder et al., Prostacyclin synthase expression is decreased in lungs from patients with severe pulmonary hypertension. Am. J. Respir. Crit. Care Med. 159:1925-1932 (1999).
Ueno et al., Effects of beraprost sodium, a prostacyclin analogue, on diabetic neuropathy in streptozotocin-induced diabetic rats. Jpn. J. Pharmacol, 70:177-182 (1996).
Ueno et al., Effects of beraprost sodium, a prostacyclin analogue, on tail flick response in two models of diabetic-neuropathy in rats and its mechanism. Life Sci. 59:PL105-PL110 (1996).
Van Rijt et al., In vivo depletion of lung CD11c+ dendritic cells during allergen challenge abrogates the characteristic features of asthma. J. Exp. Med., 201:981-991 (2005).
Walther et al., Synthesis of serotonin by a second tryptophan hydroxylase isoform. Science 299:76 (2003).
Wang et al. Deletion of microsomal prostaglandin E synthase-1 augments prostacyclin and retards atherogenesis. Proc. Natl. Acad. Sci. USA 103:14507-14512 (2006).
Xiao et al., Roles of prostaglandin I(2) and thromboxane A(2) in cardiac ischemia-reperfusion injury: a study using mice lacking their respective receptors. Circulation 104:2210-2215 (2001).
Yamada et al., Hypotensive activity of novokinin, a potent analogue of ovokinin(2-7), is mediated by angiotensin AT(2) receptor and prostaglandin IP receptor. Peptides, 29:412-418 (2008).
Yamagishi et al., Beraprost sodium, a prostaglandin I2 analogue, protects against advanced gycation end products-induced injury in cultured retinal pericytes. Mol. Med. 8:546-550 (2002).
Yamashita et al., Beraprost sodium, prostacyclin analogue, attenuates glomerular hyperfiltration and glomerular macrophage infiltration by modulating ecNOS expression in diabetic rats. Diabetes Res. Clin. Pract. 57:149-161 (2002).
Zhang et al., Characterization of the molecular mechanisms of the coupling between intracellular loops of prostacyclin receptor with the C-terminal domain of the Galphas protein in human coronary artery smooth muscle cells. Arch. Biochem. Biophys. 454:80-88 (2006).
Zhou et al., Prostaglandin I2 analogs inhibit proinflammatory cytokine production and T cell stimulatory function of dendritic cells. J. Immunol. 178:702-710 (2007).
Zhu et al., Synthesis and mode of action of (125)I- and (3)H-labeled thieno[2,3-c]pyridine antagonists of cell adhesion molecule expression. J. Org. Chem. 67:943-948 (2002).
Asada et al., "Discovery of a series of acrylic acids and their derivatives as chemical leads for selective EP3 receptor antagonists", Bioorganic & Medicinal Chemistry, Pergamon, GB, vol. 17, No. 18, Sep. 15, 2009, pp. 6567-6582.
Driscoll et al., "Medical therapy for pulmonary arterial hypertension", Expert Opin. Pharmacother., 2008, vol. 9, pp. 65-81.
Higuchi and Stella, Pro-drugs as Novel Delivery Systems, vol. 14 of the A.C.S. Symposium Series; and in Bioreversible Carriers in Drug Design, ed. Edward B. Roche, American Pharmaceutical Association and Pergamon Press 1987.
International Search Report and Written Opinion dated Jul. 22, 2009 in connection with WO 20091117095.
Caojin, et al, "Comparison of Acute Hemodynamic Effects of Aerosolized Iloprost and Inhaled and Inhaled Nitric Oxide in Adult Congenital Heart Disease with Severe Pulmonary Arterial Hypertension," Department of Cardiology, Guangdong General Hospital & Guangdong Cardiovascular Institute, China, Intern Med, vol. 51, Jul. 12, 2012, pp. 2857-2862.
Muller, et al, "Iloprost has potent anti-inflammatory properties on human monocyte-derived dendritic cells," Clinical & Experimental Allergy, Department of Pneumology, University of Freiburg, Germany, 2010, (40), pp. 1214-1221.
Tennis, et al, "The Role of Prostacyclin in Lung Cancer," Translation Research, Division of Pulmonary Sciences and Critical Care Medicine, Department of Medicine, University of Colorado Denver Health Sciences, Denver, Colorado, vol. 155, No. 2, Feb. 2010, pp. 57-61.
Baradia, et al, "Inhalation Therapy to Treat Pulmonary Arterial Hypertension," Pharm. Pat. Analyst, 2012, 1(5), pp. 577-588.
Hattori et al. Discovery of diphenylcarbamate derivatives as highly potent and selective IP receptor agonists: orally active prostacyclin mimetics. Part 3. Bioorg Med Chem Lett 15:3091-3095 (2005).

(56) References Cited

OTHER PUBLICATIONS

Takamura et al. Metabolism investigation leading to novel drug design 2: orally active prostacyclin mimetics. Part 5. Bioorg Med Chem Lett 16:4475-4478 (2006).

* cited by examiner

**Potassium 2-((1*r*,4*r*)-4-(((3-Fluorophenyl)(phenyl)carbamoyloxy)methyl)cyclohexyl)methoxy)acetate Solvate**
Thermogravimetric Analysis (TGA)

MS and MS/MS Spectra of Compound 22 Taurine Conjugate

MODULATORS OF THE PROSTACYCLIN (PGI2) RECEPTOR USEFUL FOR THE TREATMENT OF DISORDERS RELATED THERETO

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

This application is a continuation of U.S. Ser. No. 14/510,669, filed Oct. 9, 2014, which is a divisional of U.S. National Phase application Ser. No. 12/933,196, filed Oct. 14, 2010, which is a § 371 National Phase Application of International Application PCT/US2009/001688, filed Mar. 17, 2019, which claims the benefit of priority of U.S. Provisional Appl. No. 61/069,857, filed Mar. 18, 2008, U.S. Provisional Appl. No. 61/123,621, filed Apr. 9, 2008, U.S. Provisional Appl. No. 61/207,220, filed Feb. 9, 2009, and U.S. Provisional Appl. No. 61/209,453, filed Mar. 6, 2009, each of which is incorporated herein by reference in its entirety.

FIELD OF THE INVENTION

The present invention relates to certain compounds of Formula (Ia) and pharmaceutical compositions thereof that modulate the activity of the PGI2 receptor Compounds of the present invention and pharmaceutical compositions thereof are directed to methods useful in the treatment of: pulmonary arterial hypertension (PAH); idiopathic PAH; familial PAH; PAH associated with a collagen vascular disease, a congenital heart disease, portal hypertension, HIV infection, ingestion of a drug or toxin, hereditary hemorrhagic telangiectasia, splenectomy, pulmonary veno-occlusive disease (PVOD) or pulmonary capillary hemangiomatosis (PCH); PAH with significant venous or capillary involvement; platelet aggregation; coronary artery disease; myocardial infarction; transient ischemic attack; angina; stroke; ischemia-reperfusion injury; restenosis; atrial fibrillation; blood clots formation in an angioplasty of coronary bypass surgery individual or in an individual suffering from atrial fibrillation; atherothrombosis; asthma or a symptom thereof; a diabetic-related disorder such as diabetic peripheral neuropathy, diabetic nephropathy or diabetic retinopathy; glaucoma of other disease of the eye with abnormal intraocular pressure; hypertension; inflammation; psoriasis; psoriatic arthritis; rheumatoid arthritis; Crohn's disease; transplant rejection; multiple sclerosis; systemic lupus erythematosus (SLE); ulcerative colitis; atherosclerosis: acne; type 1 diabetes, type 2 diabetes; sepsis; and chronic obstructive pulmonary disorder (COPD).

BACKGROUND OF THE INVENTION

Prostacyclin (PGI2) is a lipid molecule derived from arachidonic acid through the cyclooxygenase pathway. It is a potent vasodilator, antiproliferative, anti-thrombotic and antiplatelet agent that mediates its effects as an agonist of a G protein-coupled receptor (PGI2 receptor; e.g., human PGI2 receptor, GenBank® Accession No. NP_000951 and alleles thereof). It is known that the binding of PGI2 or other such agonist) to the PGI2 receptor leads to coupling with the Gs protein and increases intracellular cAMP levels. (See, e.g., Zhang et al., Arch. Biochem. Biophys., 2006, 454:80-88.)

Pulmonary arterial hypertension (PAH) is a life-threatening disease characterized by a progressive pulmonary vasculopathy leading to right ventricular hypertrophy. Right heart failure occurs if left untreated. Prostacyclin, which has vasodilatory and antiproliferative effects on the pulmonary vasculature has been found to be low in patients with PAH compared with normal controls. Exogenous administration of prostacyclin or an analog of prostacyclin (i.e., an agonist of the PGI2 receptor) has become an important strategy in the treatment of PAH. (See, e.g., Tuder et al., Am. J. Respir. Crit. Care. Med., 1999, 159:1925-1932; Humbert et al., J. Am. Coll. Cardiol., 2004, 43:13S-24S; Rosenzweig. Expert Opin. Emerging Drugs, 2006, 11:609-619; McLaughlin et al., Circulation, 2006, 114:1417-1431; Rosenkranz, Clin. Res. Cardiol., 2007, 96:527-541; Driscoll et al., Expert Opin. Pharmacother., 2008, 9:65-81.)

Trepostinil and iloprost are FDA-approved analogs of prostacyclin which, like prostacyclin, are not orally-active. Beraprost is an orally-active analog of prostacyclin approved for the treatment of PAH in Japan, but it has failed registration for the treatment of PAH in Europe and in the US. Of the three FDA-approved drugs, prostacyclin is the best studied in PAH patients. The approximate annual cost of treating PAH with these drugs is $25,000 to $200,000 depending on the dose. At present, many experts consider intravenous prostacyclin to be the most reliable agent for managing she sickest PAH patients. Due to the short half-life of prostacyclin, intravenous treatment is complicated by the need for a continuous infusion. Patients are at risk for potentially fatal rebound pulmonary hypertension if the infusion is abruptly disrupted, as well as significant risk of catheter-related complications including sepsis. (See, e.g., Rosenzweig, Expert Opin. Emerging Drugs, 2006, 11:609-619, Naeije et al., Expert Opin. Pharmacother., 2007, 8:2247-2265; Strauss et al., Clin. Chest. Med., 2007, 28:127-142; Driscoll et al., Expert Opin. Pharmacother., 2008, 9:55-81.)

There is considerable interest in developing prostacyclin analogs (i.e., agonists of the PGI2 receptor) for use in the treatment of other diseases, such as atherothrombosis. Developing stable, orally-active analogs of prostacyclin (i.e., stable, orally-active agonists of the PGI2 receptor) is a rate-limiting step in achieving this goal (see, e.g. al., Curr. Med. Chem., 2007, 14:2161-2169; Arehart et al., Circ. Res., 2008, Mar. 6 Epub ahead of print), as well as in the improved management of PAH.

SUMMARY OF THE INVENTION

One aspect of the present invention encompasses certain cyclohexane derivatives selected from compounds of Formula (Ia) and pharmaceutically acceptable salts, solvates and hydrates thereof:

(Ia)

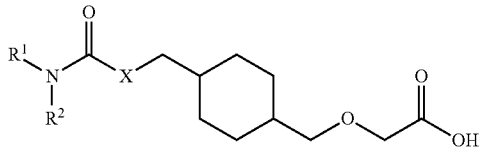

wherein:

$R^1$ and $R^2$ are each independently selected from: H, $C_1$-$C_6$ alkyl, aryl and heteroaryl; wherein $C_1$-$C_6$ alkyl, aryl and heteroaryl are each optionally substituted with one of two substituents selected from: $C_1$-$C_6$ alkoxy, $C_1$-$C_6$ alkyl, aryl, $C_1$-$C_6$ haloalkoxy, $C_1$-$C_6$ halogen and halogen;

X is O or $NR^3$; and $R^3$ is selected from H and $C_1$-$C_6$ alkyl.

One aspect of the present invention encompasses certain cyclohexane derivatives selected from compounds of Formula (XIIIa) and pharmaceutically acceptable salts, solvates and hydrates thereof:

(XIIIa)

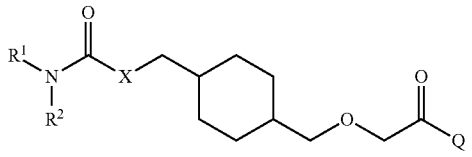

wherein:

$R^1$ and $R^2$ are each independently selected from: H, $C_1$-$C_6$ alkyl, aryl and heteroaryl; wherein $C_1$-$C_6$ alkyl, aryl and heteroaryl are each optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen;

X is O or $NR^3$;

$R^3$ is selected from H and $C_1$-$C_6$ alkyl; and

Q is selected from: OH, —$NHCH_2CH_2SO_3H$, 1-carboxyethylamino, 1-carboxy-4-guanidinobutylamino, 3-amino-1-carboxy-3-oxopropylamino, 1,2-dicarboxyethylamino, 1-carboxy-2-mercaptoethylamino, 4-amino-1-carboxy-4-oxobutylamino, 3-carboxy-1-carboxylatopropylamino, carboxymethylamino, 1-carboxy-2-(1H-imidazol-4-yl)ethylamino, 1-carboxy-2-methylbutylamino, 1-carboxy-3-methylbutylamino, 5-amino-1-carboxypentylamino, 1-carboxy-3-(methylthio)propylamino, 1-carboxy-2-phenylethyl, 2-carboxypyrrolidin-1-yl, 1-carboxy-2-hydroxyethylamino, 1-carboxy-2-hydroxypropylamino, 1-carboxy-2-(1H-indol-3yl)ethylamino, 1-carboxy-2-(4-hydroxyphenyl) ethylamino and 1-carboxy-2-methylpropylamino.

One aspect of the present invention pertains to methods of modulating the activity of a PGI2 receptor by contacting the receptor with a compound of the present invention or a pharmaceutical composition thereof.

One aspect of the present invention pertains to methods of agonizing a PGI2 receptor by contacting the receptor with a compound of the present invention or a pharmaceutical composition thereof.

One aspect of the present invention pertains to methods for the treatment of PAH in an individual, comprising administering to said individual in need thereof, a therapeutically effective amount of a compound of the present invention or a pharmaceutical composition thereof.

One aspect of the present invention pertains to methods for the treatment of idiopathic PAH in an individual, comprising administering to said individual in need thereof, a therapeutically effective amount of a compound of the present invention or a pharmaceutical composition thereof.

One aspect of the present invention pertains to methods for the treatment of familial PAH in an individual, comprising administering to said individual in need thereof, a therapeutically effective amount of a compound of the present invention or a pharmaceutical composition thereof.

One aspect of the present invention pertains to methods for the treatment of PAH associated with a collagen vascular disease in an individual, comprising administering to said individual in need thereof, a therapeutically effective amount of a compound of the present invention or a pharmaceutical composition thereof.

One aspect of the present invention pertains to methods for the treatment of PAH associated with a collagen vascular disease selected from: scleroderma, CREST syndrome, systemic lupus erythematosus (SLE), rheumatoid arthritis, Takayasu's arteritis, polymyositis, and dermatomyositis in an individual, comprising administering to said individual in need thereof, a therapeutically effective amount of a compound of the present invention or a pharmaceutical composition thereof.

One aspect of the present invention pertains to methods for the treatment of PAH associated with a congenital heart disease in an individual, comprising administering to said individual in need thereof, a therapeutically effective amount of a compound of the present invention or a pharmaceutical composition thereof.

One aspect of the present invention pertains to methods for the treatment of PAH associated with a congenital heart disease selected from: atrial septic defect (ASD), ventricular septic defect (VSD) and patent ductus arteriosus in an individual comprising administering to said individual in need thereof, a therapeutically effective amount of a compound of the present invention or a pharmaceutically composition thereof.

One aspect of the present invention pertains to methods for the treatment of PAH associated with portal hypertension in an individual, comprising administering to said individual in need thereof, a therapeutically effective amount of a compound of the present invention or a pharmaceutical composition thereof.

One aspect of the present invention pertains to methods for the treatment of PAH associated with HIV infection in an individual, comprising administering to said individual in need thereof, a therapeutically effective amount of a compound of the present invention or a pharmaceutical composition thereof.

One aspect of the present invention pertains to methods for the treatment of PAH associated with ingestion of a drug or toxin in an individual, comprising administering to said individual in need thereof, a therapeutically effective amount of a compound of the present invention or a pharmaceutical composition thereof.

One aspect of the present invention pertains to methods for the treatment of PAH associated with hereditary hemorrhagic telangiectasia in an individual, comprising administering to said individual in need thereof, a therapeutically effective amount of a compound of the present invention or a pharmaceutical composition thereof.

One aspect of the present invention pertains to methods for the treatment of PAH associated with splenectomy in an individual, comprising administering to said individual in need thereof, a therapeutically effective amount of a compound of the present invention or a pharmaceutical composition thereof.

One aspect of the present invention pertains to methods for the treatment of PAH associated with significant venous or capillary involvement in an individual, comprising administering to said individual in need thereof, a therapeutically effective amount of a compound of the present invention or a pharmaceutical composition thereof.

One aspect of the present invention pertains to methods for the treatment of PAH associated with pulmonary venoocclusive disease (PVOD) in an individual, comprising administering to said individual in need thereof, a therapeutically effective amount of a compound of the present invention or a pharmaceutical composition thereof.

One aspect of the present invention pertains to methods for the treatment of PAH associated with pulmonary capillary hemangiomatosis (PCH) in an individual, comprising administering to said individual in need thereof, a therapeutically effective amount of a compound of the present invention or a pharmaceutical composition thereof.

One aspect of the present invention pertains to methods for the treatment of platelet aggregation in an individual, comprising administering to said individual in need thereof, a therapeutically effective amount of a compound of the present invention of a pharmaceutical composition thereof.

One aspect of the present invention pertains to methods for the treatment of: coronary artery disease, myocardial infarction, transient ischemic attack, angina, stroke, ischemia-reperfusion injury, restenosis or arterial fibrillation in an individual, comprising administering to said individual in need thereof, a therapeutically effective amount of a compound of the present invention or a pharmaceutical composition thereof.

One aspect of the present invention pertains to methods for reducing the risk of blood clot formation in an angioplasty of coronary bypass surgery individual comprising administering to said individual in need thereof, a therapeutically effective amount of a compound of the present invention or a pharmaceutical composition thereof.

One aspect of the present invention pertains to methods for reducing the risk of blood clot formation in an individual suffering from atrial fibrillation comprising administering to said individual in need thereof, a therapeutically effective amount of a compound of the present invention or a pharmaceutical composition thereof.

One apsect of the present invention pertains to methods for the treatment of atherosclerosis in an individual, comprising administering to said individual in need thereof, a therapeutically effective amount of a compound of the present invention or a pharmaceutical composition thereof.

One aspect of the present invention pertains to methods for the treatment of atherothrombosis in an individual, comprising administering to said individual in need thereof, a therapeutically effective amount of a compound of the present invention or a pharmaceutical composition thereof.

One aspect of the present invention pertains to methods for the treatment of asthma in an individual, comprising administering to said individual in need thereof, a therapeutically effective amount of a compound of the present invention or a pharmaceutical composition thereof.

One aspect of the present invention pertains to methods for the treatment of a symptom of asthma in an individual, comprising administering to said individual in need thereof, a therapeutically effective amount of a compound of the present invention or a pharmaceutical composition thereof.

One aspect of the present invention pertains to methods for the treatment of a diabetic-related disorder in an individual, comprising administering to said individual in need thereof, a therapeutically effective amount of a compound of the present invention or a pharmaceutical composition thereof.

One aspect of the present invention pertains to methods for the treatment of diabetic peripheral neuropathy in an individual, comprising administering to said individual in need thereof, a therapeutically effective amount of a compound of the present invention or a pharmaceutical composition thereof.

One aspect of the present invention pertains to methods for the treatment of diabetic nephropathy in an individual, comprising administering to said individual in need thereof, a therapeutically effective amount of a compound of the present invention or a pharmaceutical composition thereof.

One aspect of the present invention pertains to methods for the treatment of diabetic retinopathy in an individual, comprising administering to said individual in need thereof, a therapeutically effective amount of a compound of the present invention or a pharmaceutical composition thereof.

One aspect of the present invention pertains to methods for the treatment of glaucoma or other disease of the eye with abnormal intraocular pressure in an individual, comprising administering to said individual in need thereof, a therapeutically effective amount of a compound of the present invention or a pharmaceutical composition thereof.

One aspect of the present invention pertains to methods for the treatment of hypertension in an individual, comprising administering to said individual in need thereof, a therapeutically effective amount of a compound of the present invention or a pharmaceutical composition thereof.

One aspect of the present invention pertains to methods for the treatment of hypertension intended to confer protection against cerebral ischemia in an individual, comprising administering to said individual in need thereof, a therapeutically effective amount of a compound of the present invention or a pharmaceutical composition thereof.

One aspect of the present invention pertains to methods for the treatment of inflammation in an individual, comprising administering to said individual in need thereof, a therapeutically effective amount of a compound of the present invention or a pharmaceutical composition thereof.

One aspect of the present invention pertains to methods for the treatment of an inflammatory disease in an individual, comprising administering to said individual in need thereof, a therapeutically effective amount of a compound of the present invention or a pharmaceutical composition thereof.

One aspect of the present invention pertains to methods for the treatment of an inflammatory disease selected from: psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis, chronic obstructive pulmonary disorder (COPD) and asthma in an individual, comprising administering to said individual in need thereof, a therapeutically effective amount of a compound of the present invention or a pharmaceutical composition thereof.

One aspect of the present invention pertains to the use of a compound of the present invention in the manufacture of a medicament for the treatment of a PGI2 receptor mediated disorder.

One aspect of the present invention pertains to the use of a compound of the present invention in the manufacture of a medicament for the treatment of PAH.

One aspect of the present invention pertains to the use of a compound of the present invention in the manufacture of a medicament for the treatment of idiopathic PAH.

One aspect of the present invention pertains to the use of a compound of the present invention in the manufacture of a medicament for the treatment of familial PAH.

One aspect of the present invention pertains to the use of a compound of the present invention in the manufacture of a medicament for the treatment of PAH associated with vascular collagen disease.

One aspect of the present invention pertains to the use of a compound of the present invention in the manufacture of a medicament for the treatment of PAH associated with a collagen vascular disease selected from: scleroderma, CREST syndrome, systemic lupus erythematosus (SLE), rheumatoid arthritis, Takayasu's arteritis, polymyositis, and dermatomyositis.

One aspect of the present invention pertains to the use of a compound of the present invention in the manufacture of a medicament for the treatment of PAH associated with a congenital heart disease.

One aspect of the present invention pertains to the use of a compound of the present invention in the manufacture of a medicament for the treatment of PAH associated with a congenital heart disease selected from: atrial septic defect (ASD), ventricular septic defect (VSD) and patent ductus arteriosus.

One aspect of the present invention pertains to the use of a compound of the present invention in the manufacture of a medicament for the treatment of PAH associated with portal hypertension.

One aspect of the present invention pertains to the use of a compound of the present invention in the manufacture of a medicament for the treatment of PAH associated with HIV infection.

One aspect of the present invention pertains to the use of a compound of the present invention in the manufacture of a medicament for the treatment of PAH associated with ingestion of a drug or toxin.

One aspect of the present invention pertains to the use of a compound of the present invention in the manufacture of a medicament for the treatment of PAH associated with hereditary hemorrhagic telangiectasia.

One aspect of the present invention pertains to the use of a compound of the present invention in the manufacture of a medicament for the treatment of PAH associated with splenectomy.

One aspect of the present invention pertains to the use of a compound of the present invention in the manufacture of a medicament for the treatment of PAH associated with significant venous or capillary involvement.

One aspect of the present invention pertains to the use of a compound of the present invention in the manufacture of a medicament for the treatment of PAH associated with pulmonary veno-occlusive disease (PVOD).

One aspect of the present invention pertains to the use of a compound of the present invention in the manufacture of a medicament for the treatment of PAH associated with pulmonary capillary hemangiomatosis (PCH).

One aspect of the present invention pertains to the use of a compound of the present invention in the manufacture of a medicament for the treatment of platelet aggregation.

One aspect of the present invention pertains to the use of a compound of the present invention in the manufacture of a medicament for the treatment of a PGI2 receptor medicated disorder selected from: coronary artery disease, myocardial infraction, transient ischemic attack, angina, stroke, ischemia-reperfusion injury, restenosis and atrial fibrillation.

One aspect of the present invention pertains to the use of a compound of the present invention in the manufacture of a medicament for the treatment of blood clot formation in an angioplasty or coronary bypass surgery individual.

One aspect of the present invention pertains to the use of a compound of the present invention in the manufacture of a medicament for the treatment of blood clot formation in an angioplasty or coronary bypass surgery individual.

One aspect of the present invention pertains to the use of a compound of the present invention in the manufacture of a medicament for the treatment of blood clot formation in an individual suffering from atrial fibrillation.

One aspect of the present invention pertains to the use of a compound of the present invention in the manufacture of a medicament for the treatment of atherosclerosis.

One aspect of the present invention pertains to the use of a compound of the present invention in the manufacture of a medicament for the treatment of atherothrombosis.

One aspect of the present invention pertains to the use of a compound of the present invention in the manufacture of a medicament for the treatment of asthma.

One aspect of the present invention pertains to the use of a compound of the present invention in the manufacture of a medicament for the treatment of a symptom of asthma.

One aspect of the present invention pertains to the use of a compound of the present invention in the manufacture of a medicament for the treatment of a diabetic-related disorder.

One aspect of the present invention pertains to the use of a compound of the present invention in the manufacture of a medicament for the treatment of diabetic peripheral neuropathy.

One aspect of the present invention pertains to the use of a compound of the present invention in the manufacture of a medicament for the treatment of diabetic nephropathy.

One aspect of the present invention pertains to the use of a compound of the present invention in the manufacture of a medicament for the treatment of diabetic retinopathy.

One aspect of the present invention pertains to the use of a compound of the present invention in the manufacture of a medicament for the treatment glaucoma or other disease of the eye with abnormal intraocular pressure.

One aspect of the present invention pertains to the use of a compound of the present invention in the manufacture of a medicament for the treatment of hypertension.

One aspect of the present invention pertains to the use of a compound of the present invention in the manufacture of a medicament for the treatment of hypertension intended to confer protection against cerebral ischemia.

One aspect of the present invention pertains to the use of a compound of the present invention in the manufacture of a medicament for the treatment of inflammation.

One aspect of the present invention pertains to the use of a compound of the present invention in the manufacture of a medicament for the treatment of an inflammatory disease.

One aspect of the present invention pertains to the use of a compound of the present invention in the manufacture of a medicament for the treatment of an inflammatory disease selected from: psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis, chronic obstructive pulmonary disorder (COPD) and asthma.

One aspect of the present invention pertains to the use of a compound of the present invention in the manufacture of a medicament for modulating the activity of a PGI2 receptor.

One aspect of the present invention pertains to the use of a compound of the present invention in the manufacture of a medicament for agonizing a PGI2 receptor.

One aspect of the present invention pertains to compounds of the present invention for use in a method of treatment of the human or animal body by therapy.

One aspect of the present invention pertains to compounds of the present invention for use in a method of treatment of a PGI2 receptor mediated disorder.

One aspect of the present invention pertains to compounds of the present invention for use in a method of treatment of PAH.

One aspect of the present invention pertains to compounds of the present invention for use in a method of treatment of idiopathic PAH.

One aspect of the present invention pertains to compounds of the present invention for use in a method of treatment of familial PAH.

One aspect of the present invention pertains to compounds of the present invention for use in a method of treatment of PAH associated with a collagen vascular disease.

One aspect of the present invention pertains to compounds of the present invention for use in a method of treatment of PAH associated with a collagen vascular disease selected from: scleroderma, CREST syndrome, systemic lupus erythematosus (SLE), rheumatoid arthritis, Takayasu's arteritis, polymyositis, and dermatomyositis.

One aspect of the present invention pertains to compounds of the present invention for use in a method of treatment of PAH associated with a congenital heart disease.

One aspect of the present invention pertains to compounds of the present invention for use in a method of treatment of PAH associated with a congenital heart disease selected from: atrial septic defect (ASD), ventricular septic defect (VSD) and patent ductus arteriosus.

One aspect of the present invention pertains to compounds of the present invention for use in a method of treatment of PAH associated with portal hypertension.

One aspect of the present invention pertains to compounds of the present invention for use in a method of treatment of PAH associated with HIV infection.

One aspect of the present invention pertains to compounds of the present invention for use in a method of treatment of PAH associated with ingestion of a drug or toxin.

One aspect of the present invention pertains to compounds of the present invention for use in a method of treatment of PAH associated with hereditary hemorrhagic telangiectasia.

One aspect of the present invention pertains to compounds of the present invention for use in a method of treatment of PAH associated with splenectomy.

One aspect of the present invention pertains to compounds of the present invention for use in a method of treatment of PAH associated with significant venous or capillary involvement.

One aspect of the present invention pertains to compounds of the present invention for use in a method of treatment of PAH associated with pulmonary veno-occlusive disease (PVOD).

One aspect of the present invention pertains to compounds of the present invention for use in a method of treatment of PAH associated with pulmonary capillary hemangiomatosis (PCH).

One aspect of the present invention pertains to compounds of the present invention for use in a method of treatment of platelet aggregation.

One aspect of the present invention pertains to compounds of the present invention for use in a method of treatment of: coronary artery disease, myocardial infarction, transient ischemic attack, angina, stroke, ischemia-reperfusion injury, restenosis or atrial fibrillation.

One aspect of the present invention pertains to compounds of the present invention for use in a method for the treatment of blood clot formation in an angioplasty or coronary bypass surgery individual.

One aspect of the present invention pertains to compounds of the present invention for use in a method for the treatment of blood clot formation in an individual suffering from atrial fibrillation.

One aspect of the present invention pertains to compounds of the present invention for use in a method of treatment of atherosclerosis.

One aspect of the present invention pertains to compounds of the present invention for use in a method of treatment of atherothrombosis.

One aspect of the present invention pertains to compounds of the present invention for use in a method of treatment of asthma.

One aspect of the present invention pertains to compounds of the present invention for use in a method of treatment of a symptom of asthma.

One aspect of the present invention pertains to compounds of the present invention for use in a method of treatment of a diabetic-related complication.

One aspect of the present invention pertains to compounds of the present invention for use in a method of treatment of a diabetic-related disorder.

One aspect of the present invention pertains to compounds of the present invention for use in a method of treatment of diabetic nephropathy.

One aspect of the present invention pertains to compounds of the present invention for use in a method of treatment of diabetic retinopathy.

One aspect of the present invention pertains to compounds of the present invention for use in a method of treatment of glaucoma or other disease of the eye with abnormal intraocular pressure.

One aspect of the present invention pertains to compounds of the present invention for use in a method of treatment of glaucoma or other disease of the eye with abnormal intraocular pressure.

One aspect of the present invention pertains to compounds of the present invention for use in a method of treatment of hypertension.

One aspect of the present invention pertains to compounds of the present invention for use in a method of treatment of hypertension intended to confer protection against cerebral ischemia.

One aspect of the present invention pertains to compounds of the present invention for use in a method of treatment of inflammation.

One apsect of the present invention pertains to compounds of the present invention for use in a method of treatment of an inflammatory disease.

One aspect of the present invention pertains to compounds of the present invention for use in a method of treatment of an inflammatory disease selected from: psoriasis, psoriatic arthritis, rheumatoid arthritis, Chron's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis, chronic obstructive pulmonary disorder (COPD) and asthma.

One aspect of the present invention pertains to compounds of the present invention for use in a method of modulating the activity of a PGI2 acceptor.

One aspect of the present invention pertains to compounds of the present invention for use in a method of agonizing a PG12 receptor.

One aspect of the present invention pertains to processes for preparing a composition comprising admixing a compound of the present invention and a pharmaceutically acceptable carrier.

One aspect of the present invention pertains to pharmaceutical compositions comprising a compound, salt, hydrate, solvate or crystalline form of the present invention and a pharmaceutically acceptable carrier.

One aspect of the present invention pertains to methods of modulating the activity of a PGI2 receptor by contacting the receptor with a compound, salt, hydrate, solvate or crystalline form of the present invention or a pharmaceutical composition thereof.

One aspect of the present invention pertains to methods of agonizing a PGI2 receptor by contacting the receptor with a compound salt, hydrate, solvate of crystalline form of the present invention or a pharmaceutical composition thereof.

One aspect of the present invention pertains to methods for the treatment of PAH in an individual, comprising administering to said individual in need thereof, a therapeutically effective amount of a compound, salt, hydrate, solvate or crystalline form of the present invention or a pharmaceutical composition thereof.

One aspect of the present invention pertains to methods for the treatment of PAH is an individual, comprising administering to said individual in need thereof, a therapeutically effective amount of a compound, salt, hydrate, solvate or crystalline form of the present invention or a pharmaceutical composition thereof.

One aspect of the present invention pertains to methods for the treatment of familial PAH in an individual, comprising administering to said individual in need thereof, a therapeutically effective amount of a compound, salt, hydrate, solvate or crystalline form of the present invention of a pharmaceutical composition thereof.

One aspect of the present invention pertains to methods for the treatment of PAH associated with a collagen vascular disease in an individual, comprising administering to said individual in need thereof, a therapeutically effective amount of a compound, salt, hydrate, solvate or crystalline form of the present invention or a pharmaceutically composition thereof.

One aspect of the present invention pertains to methods for the treatment of PAH associated with a collagen vascular disease selected from: scleroderma, CREST syndrome, systemic lupus erythematosus (SLE), rheumatoid arthritis, Takayasu's arteritis, polymyositis, and dermatomyositis in an individual, comprising administering to said individual in need thereof, a therapeutically effective amount of a compound, salt, hydrate, solvate or crystalline form of the present invention or a pharmaceutical composition thereof.

one aspect of the present invention pertains to methods for the treatment of PAH associated with a congenital heart disease in an individual, comprising administering to said individual in need thereof, a therapeutically effective amount of a compound, salt, hydrate, solvate or crystalline form of the present invention or a pharmaceutical composition thereof.

One aspect of the present invention pertains to methods for the treatment of PAH associated with a congenital heart disease selected from: atrial septic defect (ASD), ventricular septic defect (VSD) and patient ductus arteriosus in an individual, comprising administering to said individual in need thereof, a therapeutically effective amount of a compound, salt, hydrate, solvate or crystalline form of the present invention or a pharmaceutical composition thereof.

One aspect of the present invention pertains to methods for the treatment of PAH associated with portal hypertension in an individual, comprising administering to said individual in need thereof, a therapeutically effective amount of a compound, salt, hydrate, solvate or crystalline form of the present invention or a pharmaceutical composition thereof.

One aspect of the present invention pertains to methods for the treatment of PAH associated with HIV infection in an individual, comprising administering to said individual in need thereof, a therapeutically effective amount of a compound, salt, hydrate, solvate or crystalline form of the present invention or a pharmaceutical composition thereof.

One aspect of the present invention pertains to methods for the treatment of PAH associated with ingestion of a drug or toxin in an individual, comprising administering to said individual in need thereof, a therapeutically effective amount of a compound, salt, hydrate, solvate or crystalline form of the present invention or a pharmaceutical composition thereof.

One aspect of the present invention pertains to methods for the treatment of PAH associated with hereditary hemorrhagic telangiectasia in an individual, comprising administering to said individual in need thereof, a therapeutically effective amount of a compound, salt, hydrate, solvate or crystalline form of the present invention or a pharmaceutical composition thereof.

One aspect of the present invention pertains to methods for the treatment of PAH associated with splenectomy in an individual, comprising administering to said individual in need thereof, a therapeutically effective amount of a compound, salt, hydrate, solvate or crystalline form of the present invention or a pharmaceutical composition thereof.

One aspect of the present invention pertains to methods for the treatment of PAH associated with significant venous of capillary involvement in an individual, comprising administering to said individual in need thereof, a therapeutically effective amount of a compound, salt, hydrate, solvate or crystalline form of the present invention or a pharmaceutical composition thereof.

One aspect of the present invention pertains to methods for the treatment of PAH associated with pulmonary veno-occlusive disease (PVOD) in an individual, comprising administering to said individual in need thereof, a therapeutically effective amount of a compound, salt, hydrate, solvate or crystalline form of the present invention or a pharmaceutical composition thereof.

One aspect of the present invention pertains to methods for the treatment of PAH associated with pulmonary capillary hemangiomatosis (PCH) in an individual, comprising administering to said individual in need thereof, a therapeutically effective amount of a compound, salt, hydrate, solvate or crystalline form of the present invention or a pharmaceutical composition thereof.

One aspect of the present invention pertains to methods for the treatment of platelet aggregation in an individual, comprising administering to said individual in need thereof, a therapeutically effective amount of a compound, salt, hydrate, solvate or crystalline form of the present invention of a pharmaceutical composition thereof.

One apsect of the present invention pertains to methods for the treatment of: coronary artery disease, myocardial infarction, transient ischemic attack, angina, stroke, ischemia-reperfusion injury, restenosis or atrial fibrillation in an individual, comprising administering to said individual in need thereof, a therapeutically effective amount of a compound, salt, hydrate, solvate or crystalline form of the present invention or a pharmaceutical composition thereof.

One aspect of the present invention pertains to methods for reducing the risk of blood clot formation in an angioplasty or coronary bypass surgery individual comprising administering to said individual in need thereof, a therapeutically effective amount of a compound, salt, hydrate, solvate or crystalline form of the present invention or a pharmaceutical composition thereof.

One aspect of the present invention pertains to methods for reducing the risk of blood clot formation in an individual suffering from atrial fibrillation comprising administering to said individual in need thereof, a therapeutically effective amount of a compound, salt, hydrate, solvate or crystalline form of the present invention or a pharmaceutical composition thereof.

One aspect of the present invention pertains to methods for the treatment of atherosclerosis in an individual, comprising administering to said individual in need thereof, a therapeutically effective amount of a compound, salt, hydrate, solvate or crystalline form of the present invention or a pharmaceutical composition thereof.

One aspect of the present invention pertains to methods for the treatment of atherothrombosis in an individual, comprising administering to said individual in need thereof, a therapeutically effective amount of a compound, salt, hydrate, solvate or crystalline form of the present invention or a pharmaceutical composition thereof.

One aspect of the present invention pertains to methods for the treatment of asthma in an individual, comprising administering to said individual in need thereof, therapeutically effective amount of a compound, salt, hydrate, solvate or crystalline form of the present invention or a pharmaceutical composition thereof.

One aspect of the present invention pertains to methods for the treatment of a symptom of asthma in an individual, comprising administering to said individual in need thereof, a therapeutically effective amount of a compound, salt, hydrate, solvate or crystalline form of the present invention or a pharmaceutical composition thereof.

One aspect of the present invention pertains to methods for the treatment of a diabetic-related disorder in an individual, comprising administering to said individual in need thereof, a therapeutically effective amount of a compound, salt, hydrate, solvate or crystalline form of the present invention or a pharmaceutical composition thereof.

One aspect of the present invention pertains to methods for the treatment of diabetic peripheral neuropathy in an individual, comprising administering to said individual in need thereof, a therapeutically effective amount of a compound, salt, hydrate, solvate or crystalline form of the present invention or a pharmaceutical composition thereof.

One aspect of the present invention pertains to methods for the treatment of diabetic nephropathy in an individual, comprising administering to said individual in need thereof, a therapeutically effective amount of a compound, salt, hydrate, solvate or crystalline form of the present invention or a pharmaceutical composition thereof.

One aspect of the present invention pertains to methods for the treatment of diabetic retinopathy in an individual, comprising administering to said individual in need thereof, a therapeutically effective amount of a compound, salt, hydrate, solvate or crystalline form of the present invention or a pharmaceutical composition thereof.

One aspect of the present invention pertains to methods for the treatment of glaucoma or other disease of the eye with abnormal intraocular pressure in an individual, comprising administering to said individual in need thereof, a therapeutically effective amount of a compound, salt, hydrate, solvate or crystalline form of the present invention or a pharmaceutical composition thereof.

One aspect of the present invention pertains to methods for the treatment of hypertension in an individual, comprising administering to said individual in need thereof, a therapeutically effective amount of a compound, salt, hydrate, solvate or crystalline form of the present invention or a pharmaceutical composition thereof.

One aspect of the present invention pertains to methods for the treatment of hypertension intended to confer protection against cerebral ischemia in an individual, comprising administering to said individual in need thereof, a therapeutically effective amount of a compound, salt, hydrate, solvate or crystalline form of the present invention or a pharmaceutical composition thereof.

One aspect of the present invention pertains to methods for the treatment of inflammation in an individual, comprising administering to said individual in need thereof, a therapeutically effective amount of a compound, salt, hydrate, solvate or crystalline form of the present invention or a pharmaceutical composition thereof.

One aspect of the prevent invention pertains to methods for the treatment of an inflammatory disease in an individual, comprising administering to said individual in need thereof, a therapeutically effective amount of a compound, salt, hydrate, solvate or crystalline form of the present invention or a pharmaceutical composition thereof.

One aspect of the present invention pertains to methods for the treatment of an inflammatory disease selected from: psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis, chronic obstructive pulmonary disorder (COPD) and asthma in an individual, comprising administering to said individual in need thereof, a therapeutically effective amount of a compound, salt, hydrate, solvate or crystalline form of the present invention or a pharmaceutical composition thereof.

One aspect of the present invention pertains to methods for the treatment of a PGI2 receptor mediated disorder in an individual, comprising administering to said individual in need thereof, a therapeutically effective amount of a compound, salt, hydrate, solvate or crystalline form of the present invention or a pharmaceutical composition thereof.

One aspect of the prevent invention pertains to methods for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in an individual; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH) in an individual, comprising administering to said individual in need thereof, a therapeutically effective amount of a compound, salt, hydrate, solvate or crystalline form of the present invention or a pharmaceutical composition thereof.

One aspect of the present invention pertains to methods for the treatment of a disorder selected from: platelet aggregation, coronary artery disease, myocardial infarction, transient ischemic attack, angina, stroke, ischemia-reperfusion injury, restenosis, atrial fibrillation, blood clot formation, atherosclerosis, atherothrombosis, asthma, a symptom of asthma, a diabetic-related disorder, diabetic peripheral neuropathy, diabetic nephropathy, diabetic retinopathy, glaucoma or other disease of the eye with abnormal intraocular pressure, hypertension, inflammation, psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis and chronic obstructive pulmonary disorder (COPD) in an individual, comprising administering to said individual in need thereof, a therapeutically effective amount of a compound, salt, hydrate, solvate of crystalline form of the present invention or a pharmaceutical composition thereof.

One aspect of the present invention pertains to the use of a compound, salt, hydrate, solvate or crystalline form of the present invention, in the manufacture of a medicament for the treatment of a PGI2 receptor mediated disorder.

One aspect of the present invention pertains to the use of a compound, salt, hydrate, solvate or crystalline form of the present invention, in the manufacture of a medicament for the treatment of PAH.

One aspect of the present invention pertains to the use of a compound, salt, hydrate, solvate or crystalline form of the present invention, in the manufacture of a medicament for the treatment of idiopathic PAH.

One aspect of the present invention pertains to the use of a compound, salt, hydrate, solvate or crystalline form of the present invention, in the manufacture of a medicament for the treatment of familial PAH.

One aspect of the present invention pertains to the use of a compound, salt, hydrate, solvate or crystalline form of the present invention, in the manufacture of a medicament for the treatment of PAH associated with vascular collagen disease.

One aspect of the present invention pertains to the use of a compound, salt, hydrate, solvate or crystalline form of the present invention, in the manufacture of a medicament for the treatment of PAH associated with a collagen vascular disease selected from: scleroderma, CREST syndrome, systemic lupus erythemastosus (SLE), rheumatoid arthritis, Takayasu's arteritis, polymyositis, and dermatomyositis.

One aspect of the present invention pertains to the use of a compound, salt, hydrate, solvate or crystalline form of the present invention, in the manufacture of a medicament for the treatment of PMI associated with a congenital heart disease.

One aspect of the present invention pertains to the use of a compound, salt, hydrate, solvate or crystalline form of the present invention, in the manufacture of a medicament for the treatment of PAH associated with congenital heart disease selected from: atrial septic defect (ASD), ventricular septic defect (VSD) and patent ductus arteriosus.

One aspect of the present invention pertains to the use of a compound, salt, hydrate, solvate or crystalline form of the present invention, in the manufacture of a medicament for the treatment of PAH associated with portal hypertension.

One aspect of the present invention pertains to the use of a compound, salt, hydrate, solvate or crystalline form of the present invention, in the manufacture of a medicament for the treatment of PAH associated with HIV infection.

One aspect of the present invention pertains to the use of a compound, salt, hydrate, solvate or crystalline form of the present invention, in the manufacture of a medicament for the treatment of PAH associated with ingestion of a drug or toxin.

One aspect of the present invention pertains to the use of a compound, salt, hydrate, solvate or crystalline form of the present invention, in the manufacture of a medicament for the treatment of PAH associated with hereditary hemorrhagic telangiectasia.

One aspect of the present invention pertains to the use of a compound, salt, hydrate, solvate or crystalline form of the present invention, in the manufacture of a medicament for the treatment of PAH associated with splenectomy.

One aspect of the present invention pertains to the use of a compound, salt, hydrate, solvate or crystalline form of the present invention, in the manufacture of a medicament for the treatment of PAH associated with significant venous or capillary involvement.

One aspect of the present invention pertains to the use of a compound, salt, hydrate, solvate or crystalline form of the present invention, in the manufacture of a medicament for the treatment of PAH associated with pulmonary veno-occlusive disease (PVOD).

One aspect of the present invention pertains to the use of a compound, salt, hydrate, solvate or crystalline form of the present invention, in the manufacture of a medicament for the treatment of PAH associated with pulmonary capillary hemangiomatosis (PCH).

One aspect of the present invention pertains to the use of a compound, salt, hydrate, solvate or crystalline form of the present invention, in the manufacture of a medicament for the treatment of platelet aggregation.

One aspect of the present invention pertains to the use of a compound, salt, hydrate, solvate or crystalline form of the present invention, in the manufacture of a medicament for the treatment of a PGI2 receptor mediated disorder selected from: coronary artery disease, myocardial infarction, transient ischemic attack, angina, stroke, ischemia-reperfusion injury, restenosis and atrial fibrillation.

One aspect of the present invention pertains to the use of a compound, salt, hydrate, solvate or crystalline form of the present invention, in the manufacture of a medicament for the treatment of blood clot formation in an angioplasty or coronary bypass surgery individual.

One aspect of the present invention pertains to the use of a compound, salt, hydrate, solvate or crystalline form of the present invention, in the manufacture of a medicament for the treatment of blood clot formation in an individual suffering from atrial fibrillation.

One aspect of the present invention pertains to the use of a compound, salt, hydrate, solvate or crystalline form of the present invention, in the manufacture of a medicament for the treatment of atherosclerosis.

One aspect of the present invention pertains to the use of a compound, salt, hydrate, solvate or crystalline form of the present invention, in the manufacture of a medicament for the treatment of atherothrombosis.

One aspect of the present invention pertains to the use of a compound, salt, hydrate, solvate or crystalline form of the present invention, in the manufacture of a medicament for the treatment of asthma.

One aspect of the present invention pertains to the use of a compound, salt, hydrate, solvate or crystalline form of the present invention, in the manufacture of a medicament for the treatment of a symptom of asthma.

One aspect of the present invention pertains to the use of a compound, salt, hydrate, solvate or crystalline form of the present invention, in the manufacture of a medicament for the treatment of a diabetic-related disorder.

One aspect of the present invention pertains to the use of a compound, salt, hydrate, solvate or crystalline form of the present invention, in the manufacture of a medicament for the treatment of diabetic peripheral neuropathy.

One aspect of the present invention pertains to the use of a compound, salt, hydrate, solvate or crystalline form of the present invention, in the manufacture of a medicament for the treatment of diabetic nephropathy.

One aspect of the present invention pertains to the use of a compound, salt, hydrate, solvate or crystalline form of the present invention, in the manufacture of a medicament for the treatment of diabetic retinopathy.

One aspect of the presets invention pertains to the use of a compound, salt, hydrate, solvate of crystalline form of the present invention, in the manufacture of a medicament for the treatment of glaucoma or other disease of the eye with abnormal intraocular pressure.

One aspect of the present invention pertains to the use of a compound, salt, hydrate, solvate or crystalline form of the present invention, at the manufacture of a medicament for the treatment of hypertension.

One aspect of the present invention pertains to the use of a compound, salt, hydrate, solvate or crystalline form of the present invention, in the manufacture of a medicament for the treatment of hypertension intended to confer protection against cerebral ischemia.

One aspect of the present invention pertains to the use of a compound, salt, hydrate, solvate or crystalline form of the present invention, in the manufacture of a medicament for the treatment of inflammation.

One aspect of the present invention pertains to the use of a compound, salt, hydrate, solvate or crystalline form of the present invention, in the manufacture of a medicament for the treatment of an inflammatory disease.

One aspect of the present invention pertains to the use of a compound, salt, hydrate, solvate or crystalline form of the present invention, in the manufacture of a medicament for the treatment of an inflammatory disease selected from: psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis, chronic obstructive pulmonary disorder (COPD) and asthma.

One aspect of the present invention pertains to the use of a compound, salt, hydrate, solvate or crystalline form of the present invention, in the manufacture of a medicament for modulating the activity of a PGI2 receptor.

One aspect of the present invention pertains to the use of a compound, salt, hydrate, solvate or crystalline form of the present invention, in the manufacture of a medicament for agonizing a PGI2 receptor.

One aspect of the present invention pertains to the use of a compound, salt, hydrate, solvate or crystalline form of the present invention, in the manufacture of a medicament for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in an individual; PAH associated with portal hypertension; PAH associated with HIV infection; PAH associated with ingestion of ad rug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH).

One aspect of the present invention pertains to the use of a compound, salt, hydrate, solvate or crystalline form of the present invention, in the manufacture of a medicament for the treatment of a disorder selected from: platelet aggregation, coronary artery disease, myocardial infarction, transient ischemic attack, angina, stroke, ischemia-reperfusion injury, restenosis, atrial fibrillation, blood clot formation, atherosclerosis, atherothrombosis, asthma, a symptom of asthma, a diabetic-related disorder, diabetic peripheral neuropathy, diabetic nephropathy, diabetic retinopathy; glaucoma of other disease of the eye with abnormal intraocular pressure, hypertension, inflammation, psoriasis, psoriatic arthritis, rheumatoid arthritis, Chron's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis and chronic obstructive pulmonary disorder (COPD).

One aspect of the present invention pertains to a compound, salt, hydrate, solvate or crystalline form of the present invention for use in a method of treatment of the human or animal body by therapy.

One aspect of the present invention pertains to a compound, salt, hydrate, solvate or crystalline form of the present invention for use in a method of treatment of a PGI2 receptor mediated disorder.

One aspect of the present invention pertains to a compound salt, hydrate, solvate or crystalline form of the present invention for use in a method of treatment of PAH.

One aspect of the present invention pertains to a compound, salt, hydrate, solvate or crystalline form of the present invention for use in a method of treatment of idiopathic PAH.

One aspect of the present invention pertains to a compound, salt, hydrate, solvate or crystalline form of the present invention for use in a method of treatment of familial PAH.

One apsect of the present invention pertains to a compound, salt, hydrate, solvate or crystalline form of the present invention for use in a method of treatment of PAH associated with a collagen vascular disease.

One aspect of the present invention pertains to a compound, salt, hydrate, solvate or crystalline form of the present invention for use in a method of treatment of PAH associated with a collagen vascular disease selected from: scleroderma, CREST syndrome, systemic lupus erythematosus (SLE), rheumatoid arthritis, Takayasu's arteritis, polymyositis, and dermatomyositis.

One aspect of the present invention pertains to a compound, salt, hydrate, solvate or crystalline form of the present invention for use in a method of treatment of PAH associated with a congenital heart disease.

One aspect of the present invention pertains to a compound, salt, hydrate, solvate or crystalline form of the present invention for use in a method of treatment of PAH associated with a congenital heart disease selected from: atrial septic defect (ASD), ventricular septic defect (VSD) and patent ductus arteriosus.

One aspect of the present invention pertains to a compound, salt, hydrate, solvate or crystalline form of the present invention for use in a method of treatment of PAH associated with portal hypertension.

One aspect of the present invention pertains to a compound, salt, hydrate, solvate or crystalline form of the present invention for use in a method of treatment of PAH associated with HIV infection.

One aspect of the present invention pertains to a compound, salt, hydrate, solvate or crystalline form of the present invention for use in a method of treatment of PAH associated with ingestion of a drug or toxin.

One aspect of the present invention pertains to a compound, salt, hydrate, solvate or crystalline form of the present invention for use in a method of treatment of PAH associated with hereditary hemorrhagic telangiectasia.

One aspect of the present invention pertains to a compound, salt, hydrate, solvate or crystalline form of the present invention for use in a method of treatment of PAH associated with splenectomy.

One aspect of the present invention pertains to a compound, salt, hydrate, solvate or crystalline form of the present invention for use in a method of treatment of PAH associated with significant venous or capillary involvement.

One aspect of the present invention pertains to a compound, salt, hydrate, solvate or crystalline form of the present invention for use in a method of treatment of PAH associated with pulmonary veno-occlusive disease (PVOD).

One aspect of the present invention pertains to a compound, salt, hydrate, solvate or crystalline form of the present invention for use in a method of treatment of PAH associated with pulmonary capillary hemangiomatosis (PCH).

One aspect of the present invention pertains to a compound, salt, hydrate, solvate of crystalline form of the present invention for use in a method of treatment of platelet aggregation.

One aspect of the present invention pertains to a compound, salt, hydrate, solvate or crystalline form of the present invention for use in a method of treatment of: coronary artery disease, myocardial infarction, transient ischemic attack, angina, stroke, ischemia-reperfusion injury, restenosis or atrial fibrillation.

One aspect of the present invention pertains to a compound, salt, hydrate, solvate or crystalline form of the present invention for use in a method for the treatment of blood clot formation in an angioplasty or coronary bypass surgery individual.

One aspect of the present invention pertains to a compound, salt, hydrate, solvate or crystalline form of the present invention for use in a method for the treatment of blood clot formation in an individual suffering from atrial fibrillation.

One aspect of the present invention pertains to a compound, salt, hydrate, solvate or crystalline form of the present invention for use in a method of treatment of atherosclerosis.

One aspect of the present invention pertains to a compound, salt, hydrate, solvate or crystalline form of the present invention for use in a method of treatment of atherothrombosis.

One aspect of the present invention pertains to a compound, salt, hydrate, solvate or crystalline form of the present invention for use in a method of treatment of asthma.

One aspect of the present invention pertains to a compound, salt, hydrate, solvate or crystalline form of the present invention for use in a method of treatment of a symptom of asthma.

One aspect of the present invention pertains to a compound, salt, hydrate, solvate of crystalline form of the present invention for use in a method of treatment of a diabetic-related complication.

One aspect of the present invention pertains to a compound, salt, hydrate, solvate or crystalline form of the present invention for use in a method for the treatment of a diabetic-related disorder.

One aspect of the present invention pertains to a compound, salt, hydrate, solvate or crystalline form of the present invention for use in a method of treatment of diabetic peripheral neuropathy.

One aspect of the present invention pertains to a compound, salt, hydrate, solvate or crystalline form of the present invention for use in a method of treatment of diabetic nephropathy.

One aspect of the present invention pertains to a compound, salt, hydrate, solvate or crystalline form of the present invention for use in a method of treatment of glaucoma or other disease of the eye with abnormal intraocular pressure.

One aspect of the present invention pertains to a compound, salt, hydrate, solvate or crystalline form of the present invention for use in a method of treatment of hypertension.

One aspect of the present invention pertains to a compound, salt, hydrate, solvate or crystalline form of the present invention for use in a method of treatment of hypertension intended to confer protection against cerebral ischemia.

One aspect of the present invention pertains to a compound, salt, hydrate, solvate or crystalline form of the present invention for use in a method of treatment of inflammation.

One aspect of the present invention pertains to a compound, salt, hydrate, solvate or crystalline form of the present invention for use in a method of treatment of an inflammatory disease.

One aspect of the present invention pertains to a compound, salt, hydrate, solvate or crystalline form of the present invention for use in a method of treatment of an inflammatory disease selected from: psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis, chronic obstructive pulmonary disorder (COPD) and asthma.

One aspect of the present invention pertains to a compound, salt, hydrate, solvate or crystalline form of the present invention for use in a method of modulating the activity of a PGI2 receptor.

One aspect of the present invention pertains to a compound, salt, hydrate, solvate or crystalline form of the present invention for use in a method of agonizing a PGI2 receptor.

One aspect of the present invention pertains to a compound, salt, hydrate, solvate, crystalline form or pharmaceutical composition of the present invention for use in a method of treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in an individual; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH).

One aspect of the present invention pertains to a compound, salt, hydrate, solvate, crystalline form or pharmaceutical composition of the present invention for use in a method of treatment of a disorder selected from: platelet aggregation, coronary artery disease, myocardial infarction, transient ischemic attack, angina, stroke, ischemia-reperfusion injury, restenosis, atrial fibrillation, blood clot formation, atherosclerosis, atherothrombosis, asthma, a symptom of asthma, a diabetic-related disorder, diabetic peripheral neuropathy, diabetic nephropathy, diabetic retinopathy, glaucoma or other disease of the eye with abnormal intraocular pressure, hypertension, inflammation, psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis and chronic obstructive pulmonary disorder (COPD).

One aspect of the present invention pertains to processes for preparing a composition comprising admixing a compound, salt, hydrate, solvate or crystalline form of the present invention, and a pharmaceutically acceptable carrier.

The present invention further provides, inter alfa, processes for preparing compounds of Formula (II):

(II)

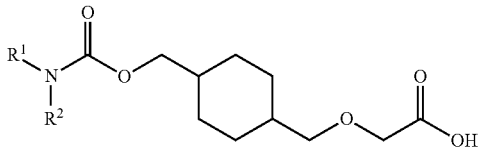

or a salt, solvate or hydrate thereof;

wherein:

$R^1$ is selected from $C_1$-$C_6$ alkyl, aryl and heteroaryl; each optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen; and $R^2$ is selected from: H, $C_1$-$C_6$ alkyl and aryl; wherein said aryl is optionally substituted with one or two substituents selected from: $C_1$-$C_6$ alkyl and halogen;

comprising reacting a compound of Formula (III)

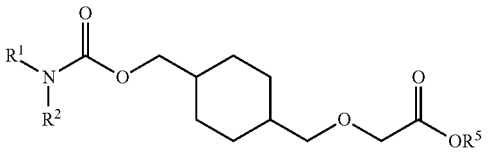

or a salt form thereof;

wherein:

$R^5$ is $C_1$-$C_6$ alkyl;

with a hydrolyzing agent to form a compound of Formula (II) or a salt, solvate or hydrate thereof.

The present invention further provides processes for preparing compounds of Formula (III):

(III)

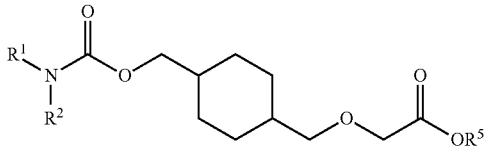

or a salt form thereof;

wherein:

$R^1$ is selected from $C_1$-$C_6$ alkyl, aryl, and heteroaryl; each optionally substituted with one or two substituents selected from: $C_1$-$C_6$ alkoxy; $C_1$-$C_6$ alkyl, aryl, $C_1$-$C_6$ haloalkoxy, $C_1$-$C_6$ haloalkyl and halogen; and $R^2$ is selected from H, $C_1$-$C_6$ alkyl and aryl; wherein said aryl is optionally substituted with one or two substituents selected from: $C_1$-$C_6$ alkyl and halogen; and $R^5$ is $C_1$-$C_6$ alkyl;

comprising reacting a compound of Formula (IV):

(IV)

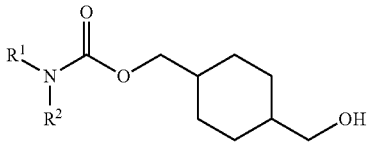

or a salt form thereof;

with a compound of Formula (V):

(V)

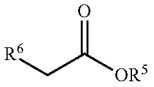

wherein:

$R^6$ is selected from: $C_1$-$C_6$ alkylarylsulfonate, $C_1$-$C_6$ alkylsulfonate, arylsulfonate, $C_1$-$C_6$ haloalkylsulfonate and halogen;

in the presence of a base to form a compound of Formula (III) or a salt form thereof.

The present invention further provides processes for preparing compounds of Formula (IV):

(IV)

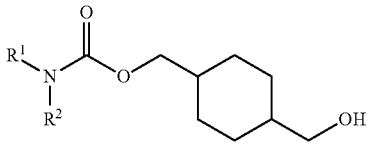

or a salt form thereof;

wherein:

$R^1$ is selected from $C_1$-$C_6$ alkyl, aryl and heteroaryl; each optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen; and $R^2$ is selected from: H, $C_1$-$C_6$ alkyl and aryl; wherein said aryl is optionally substituted with one or two substituents selected from: $C_1$-$C_6$ alkyl and halogen;

comprising reacting a compound of Formula (VI):

(VI)

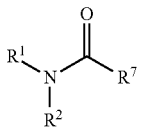

or a salt form thereof;

wherein:

$R^7$ is a first leaving group;

with a compound of formula (VII):

(VII)

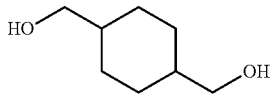

to form a compound of Formula (IV) or a salt form thereof.

The present invention further provides processes for preparing compounds of Formula (VI):

(VI)

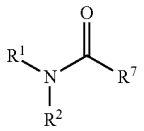

or a salt form thereof;

wherein:

$R^1$ is selected from $C_1$-$C_6$ alkyl, aryl and heteroaryl; each optionally substituted with one or two substituents selected from: $C_1$-$C_6$ alkoxy; $C_1$-$C_6$ alkyl, aryl, $C_1$-$C_6$ haloalkoxy; $C_1$-$C_6$ haloalkyl and halogen; and $R^2$ is selected from: H, $C_1$-$C_6$ alkyl and aryl; wherein said aryl is optionally substituted with one or two substituents selected from: $C_1$-$C_6$ alkyl and halogen; and $R^7$ is a first leaving group;

comprising reacting a compound of Formula (VIII):

(VIII)

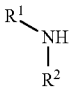

or a salt form thereof;

with a compound of formula (IX):

(IX)

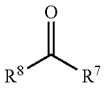

wherein:

$R^8$ is a second leaving group;

to form a compound of Formula (VI) or a salt form thereof.

The present invention further provides processes for preparing salts of compounds of Formula (II):

(II)

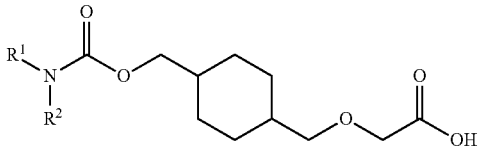

comprising reacting a compound of Formula (II) with a salt-forming reagent to form a salt of a compound of formula (II).

The present invention further provides salts of compounds of Formula (II) prepared by the processes described herein.

The present invention further provides pharmaceutical compositions of compounds of Formula (II) prepared by the processes described herein.

The present invention further provides compounds of Formula (III) and Formula (IV) prepared by the processes described herein.

These and other aspects of the invention disclosed herein will be set forth in greater detail as the patent disclosure proceeds.

methoxy)acetate in the presence of a base and the product is hydrolyzed. In another method a chlorocarbonylamine is reacted with 2-((4-(aminomethyl)cyclohexyl)methoxy)acetic acid in the presence of a base. In another method a secondary amine is reacted with 2-((4-(aminomethyl)cyclohexyl)methoxy)acetate in the presence of triphosgene.

Figure 1:
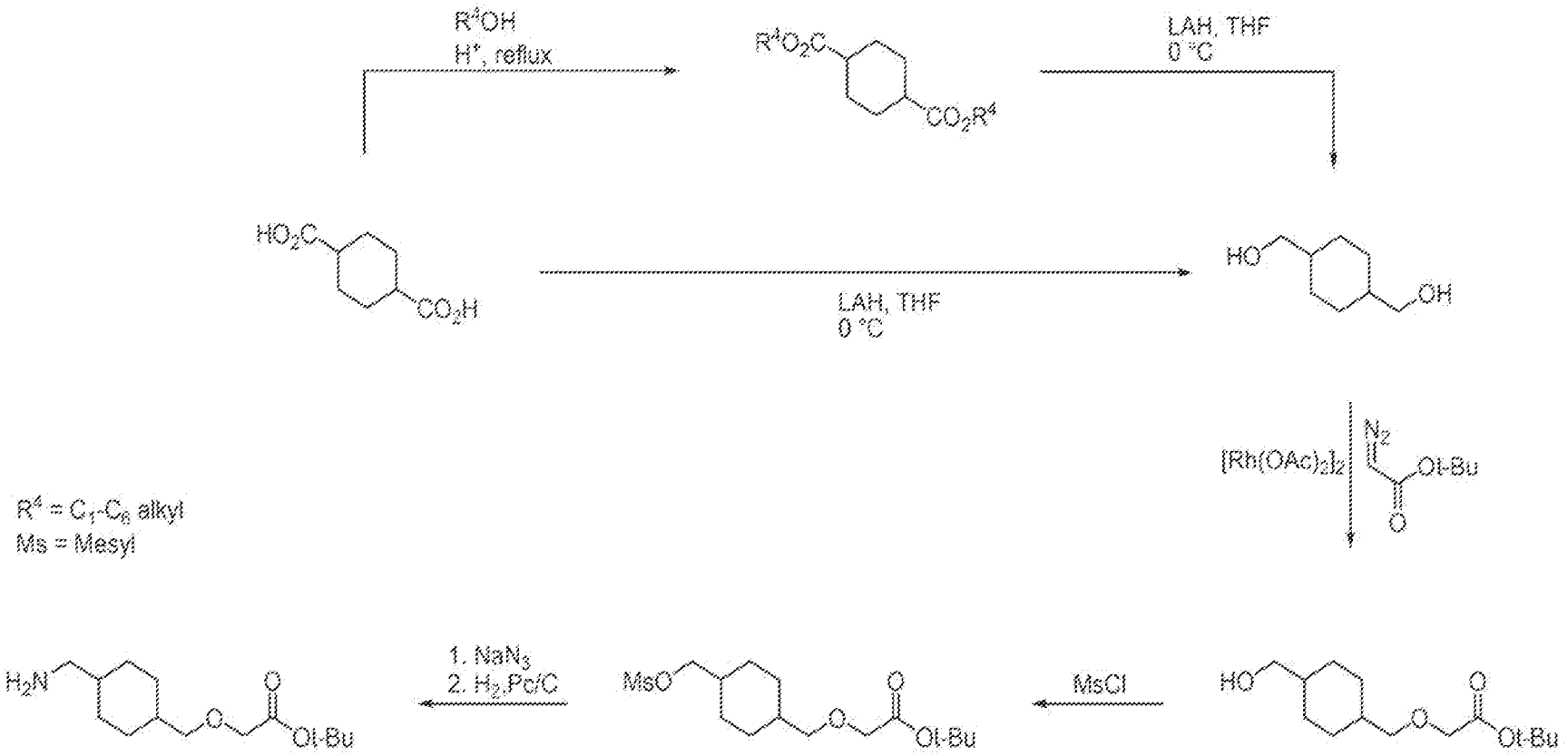
FIG. 1 shows two general methods for preparing an intermediate useful in the synthesis of compounds of the present invention. Cyclohexane-1,4-dicarboxylic acid may be converted to the corresponding diol either directly, or via an ester, by reduction with lithium aluminium hydride. Reaction of the diol, with tert-butyldiazoacetate in the presence of a rhodium catalyst affords a 2-tert-butoxy-2-oxoethoxy derivative which may be converted to an amine via the azide.
Figure 2:
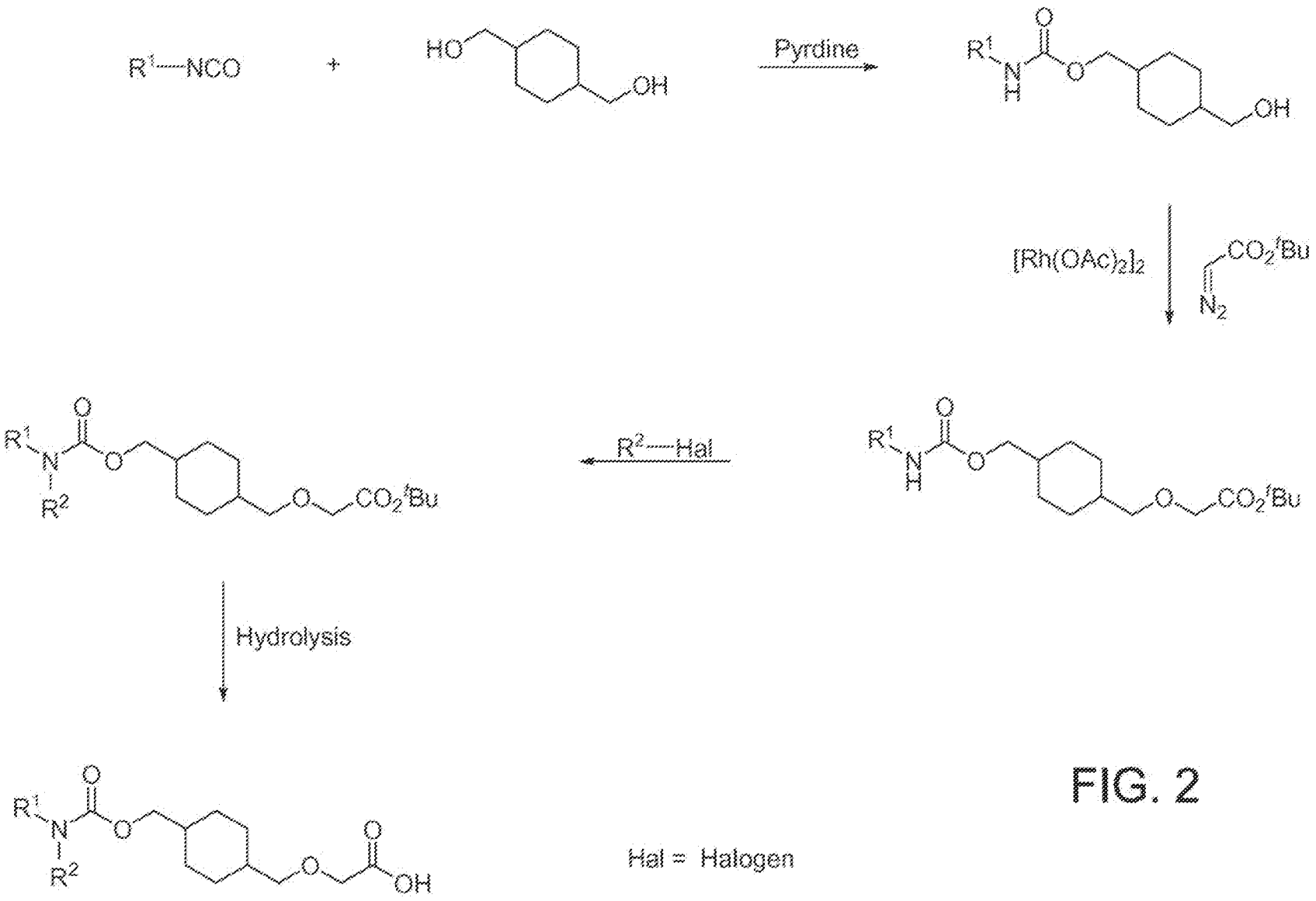
FIG. 2 shows a general method of preparing compounds of the present invention. An isocyanate is coupled to cyclohexane-1,4-diyldimethanol in the presence of pyridine to form a carbamate. This is converted to a 2-tert-butoxy-2-oxoethoxy derivative with tert-butyldiazoacetate in the presence of a rhodium catalyst and the carbamate is alkylated with a halide derivative. Finally the ester is hydrolyzed to leave a compound of Formula (Ia).
Figure 3:
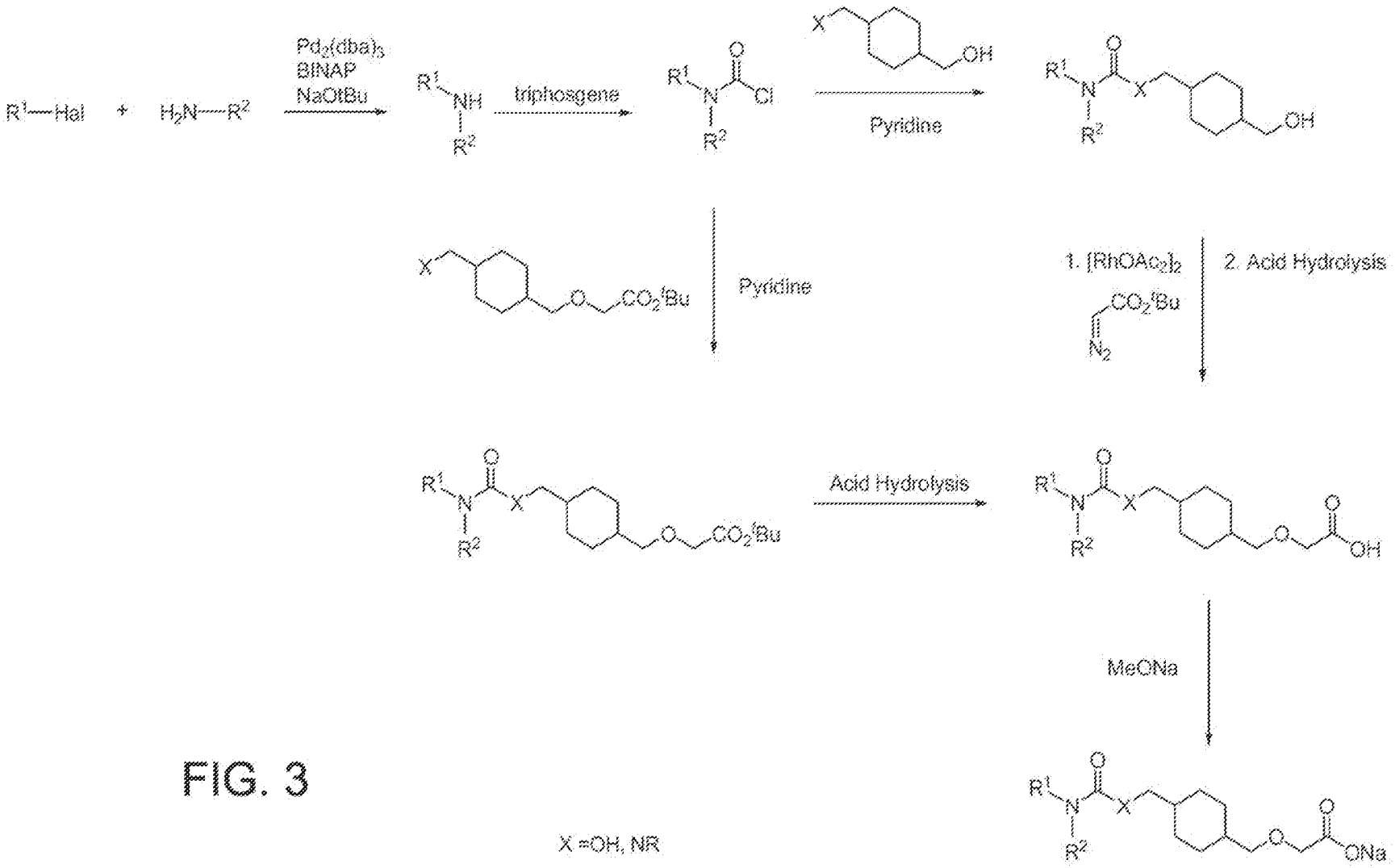
FIG. 3 shows general methods of preparing compounds of the present invention. First, a halide derivative is reacted with an amine in the presence of a palladium catalyst to form a secondary amine. This is reacted with triphosgene to form a chlorocarbonylamine which is reacted with a cyclohexane derivative to form an alcohol. Next, the alcohol is converted in one pot via the 2-tert-butoxy-2-oxoethoxy derivative to a compound of Formula (Ia) by reaction with tert-butyldiazoacetate in the presence of a rhodium catalyst, followed by acidic hydrolysis. Alternatively, a compound of Formula (Ia) may be prepared by reaction of the chlorocarbonylamine with a 2-tert-butoxy-2-oxoethoxycyclohexane derivative in pyridine followed by acidic hydrolysis. A compound of Formula (Ia) may be converted to the corresponding sodium salt by treatment with sodium methoxide.
Figure 4:
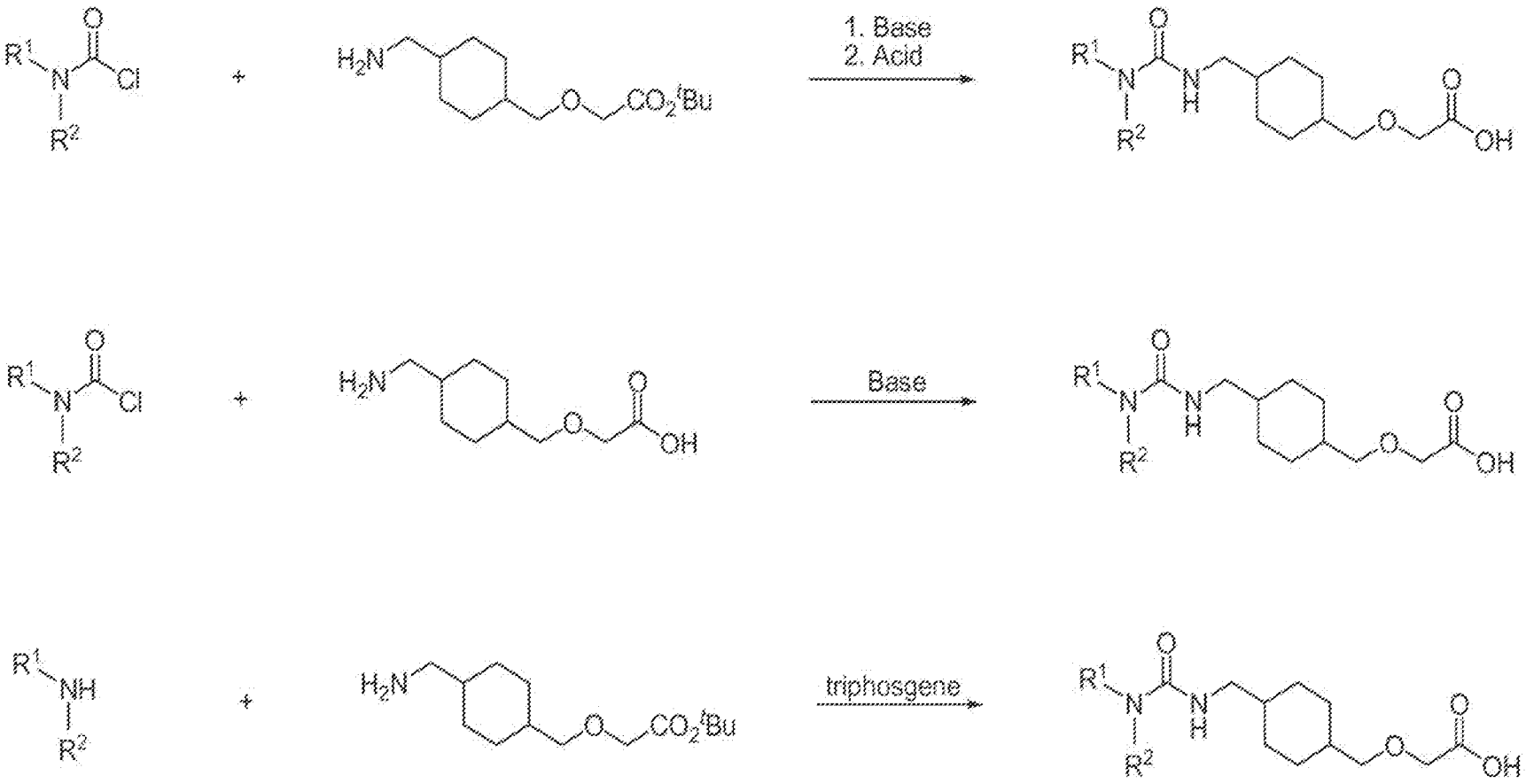
FIG. 4 shows general methods for preparing compounds of Formula (Ia). In one method a chlorocarbonylamine is reacted with tert-butyl 2-((4-aminomethyl)cyclohexyl)
Figure 5:
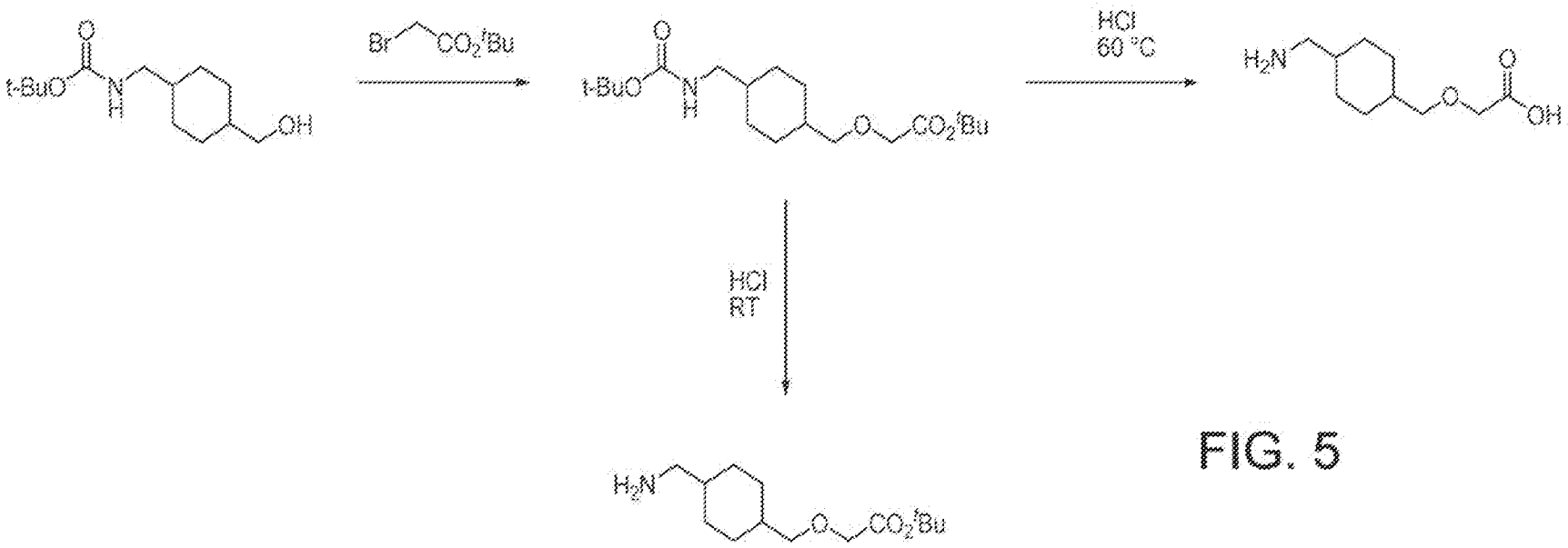

FIG. 5 shows method for preparing intermediates useful in the synthesis of compounds of the present invention. tert-Butyl (4-(hydroxymethyl)cyclohexyl)methylcarbamate can be reacted with bromoacetic acid to form tert-butyl 2-((4-((tert-butoxycarbonylamino)methyl)cyclohexyl) methoxy)acetate. The resulting intermediate may be hydrolyzed with HCl at room temperature to give tert-butyl 2-((4-aminomethyl)cyclohexyl)methoxy)acetate, or hydrolyzed with HCl at 60° C. to give 2-((4-(aminomethyl) cyclohexyl)methoxy)acetic acid.

Figure 6:
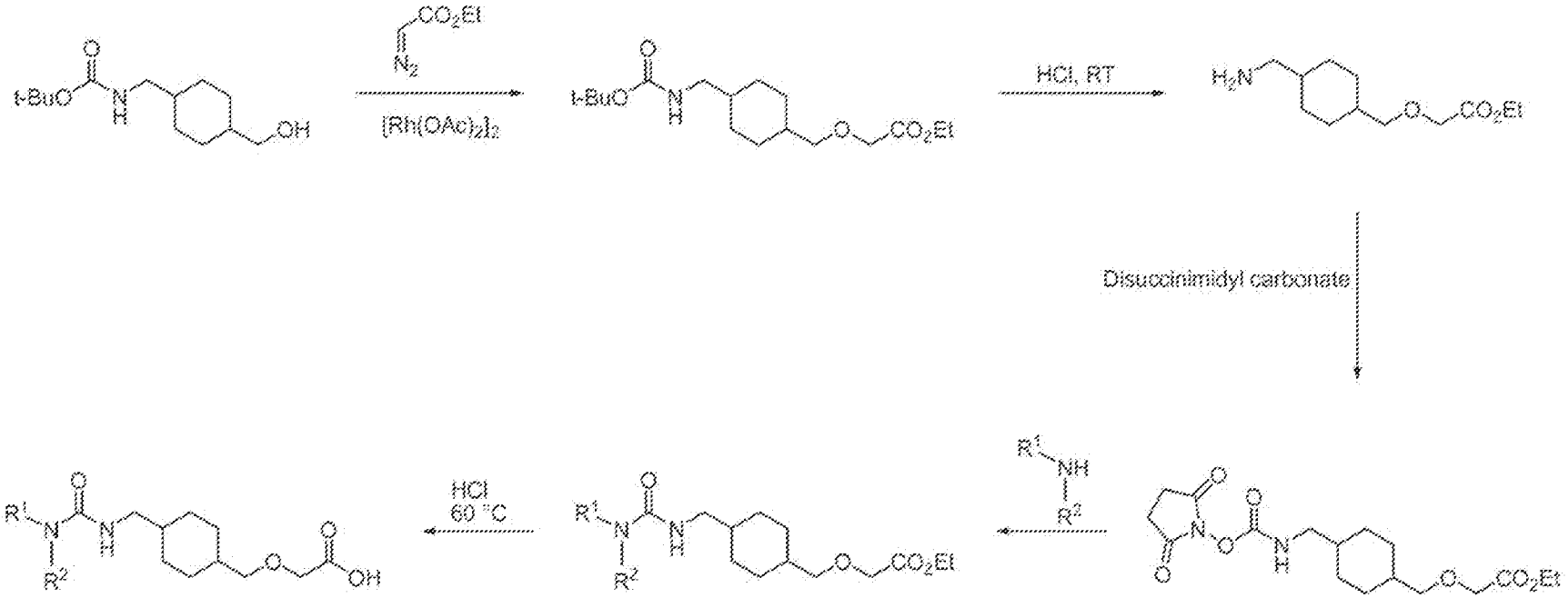

FIG. 6 shows a general method of preparing compounds of the present invention. tert-Butyl (4-(hydroxymethyl)cyclohexyl)methylcarbamate is alkylated with ethyl 2-diazoacetate in the presence of a rhodium catalyst to give ethyl 2-((4-tert-butoxycarbonylamino)methyl)cyclohexyl) methoxy)acetate which may be hydrolyzed to the free amine by treatment with HCl at room temperature. This is reduced with disuccinimidyl carbonate and then a secondary amine to give a urea. Finally the ester is hydrolyzed with HCl at 60° C. to afford a compound of Formula (Ia).

Figure 7:
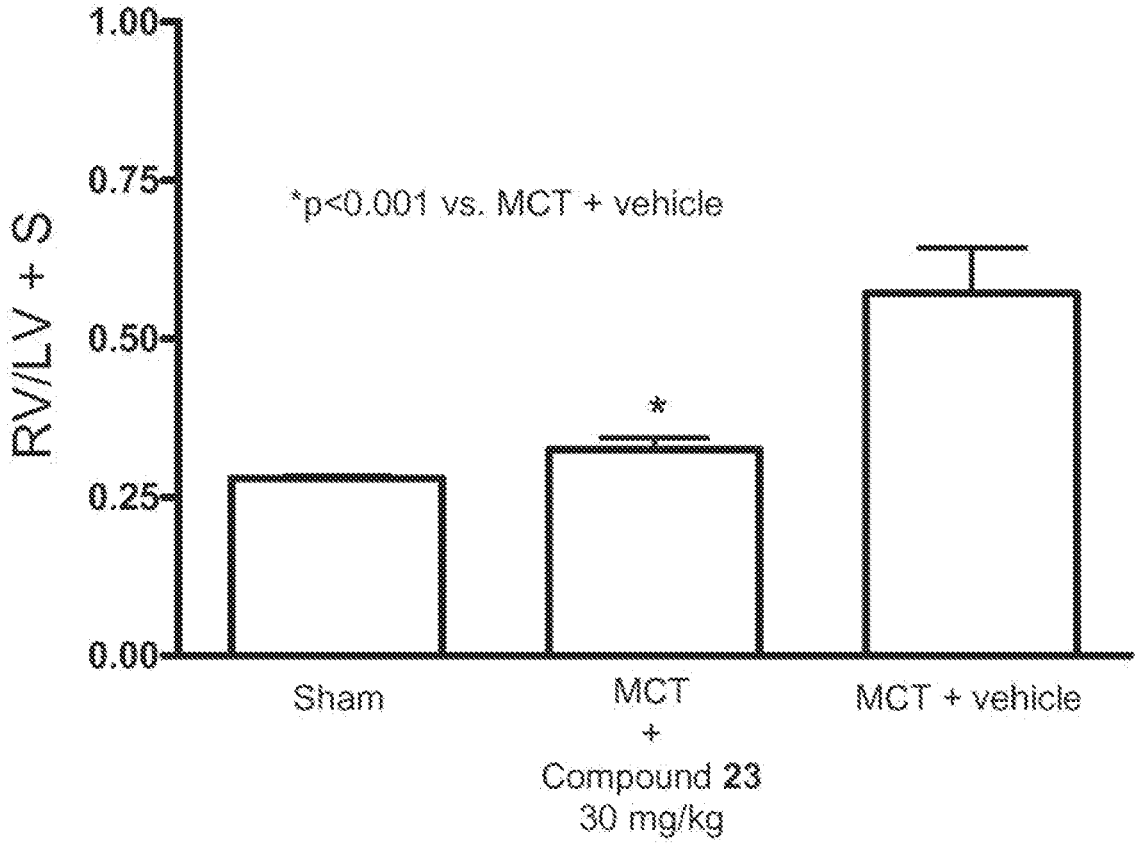

FIG. 7 shows the results of an experiment which measured the ability of Compound 23 to inhibit the right ventricle hypertrophic response to MCT-induced pulmonary arterial hypertension in rat.

Figure 8:
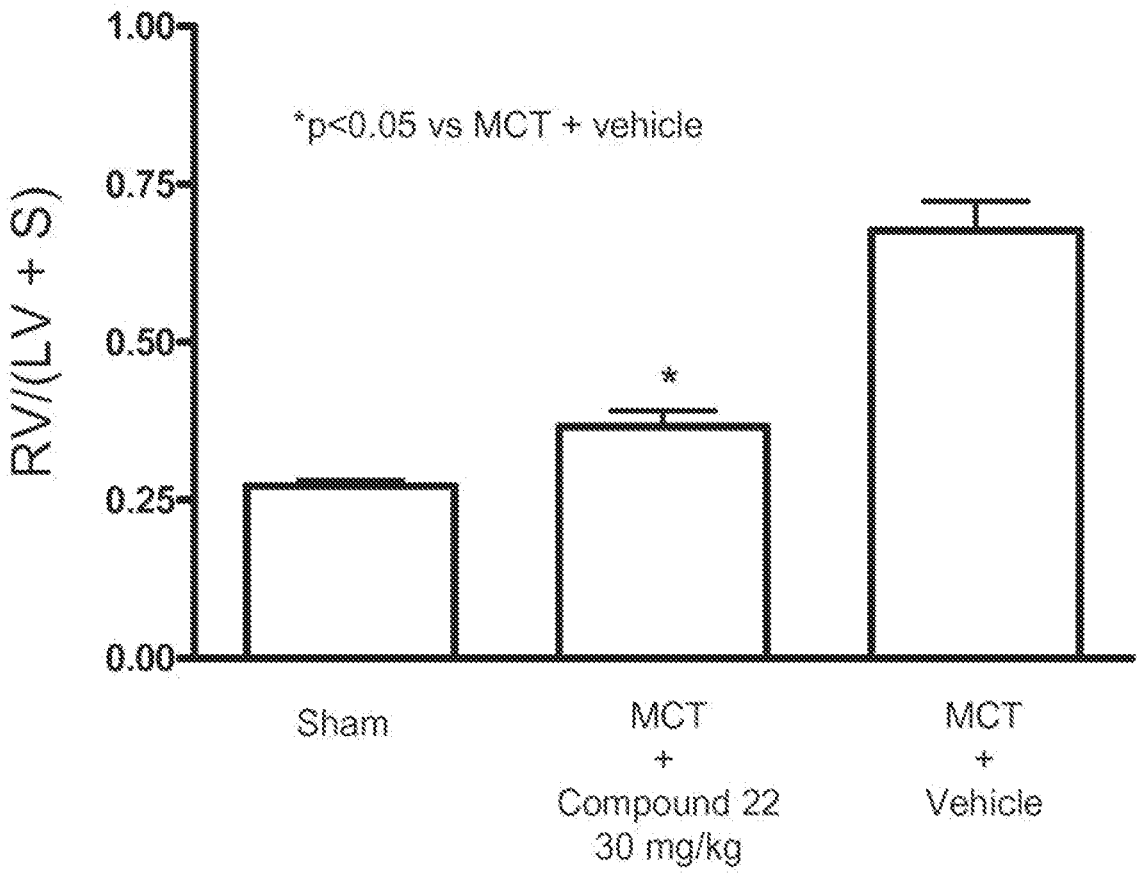

FIG. 8 shows the results of an experiment which measured the ability of Compound 22 to inhibit the right ventricle hypertrophic response to MCT-induced pulmonary arterial hypertension in rat.

Figure 9:
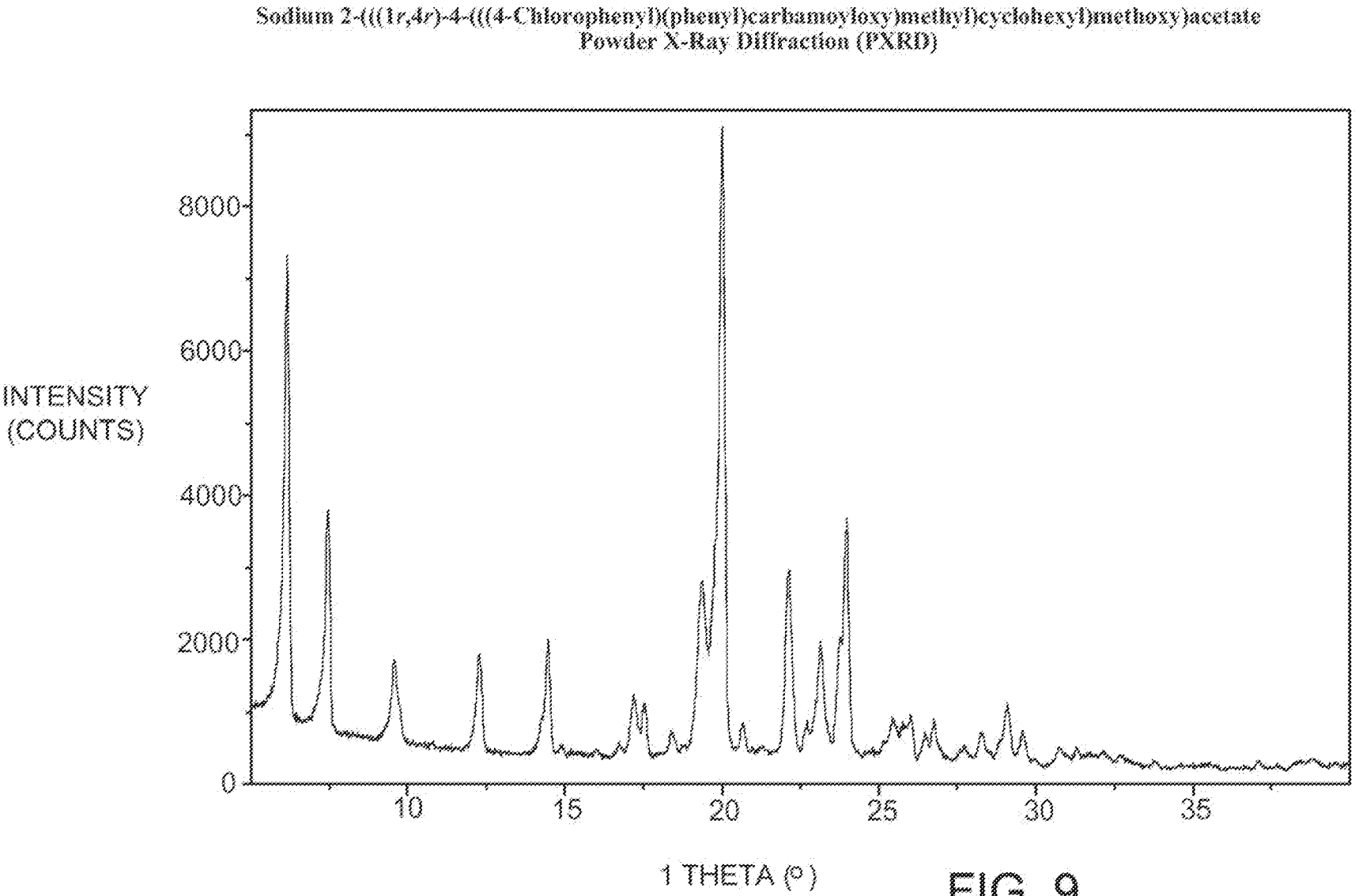

FIG. 9 depicts a powder X-ray diffraction pattern (PXRD) for a sample containing a crystalline form (Form 1) of sodium 2-(((1r,4r)-4-(((4-chlorophenyl)(phenyl)carbamoyloxy)methyl)cyclohexyl)methoxy)acetate (the sodium salt of Compound 22) (PANalytical X'Pert Plus Powder X-Ray Diffractometer: 5.0 to 40.0°20).

Figure 10:
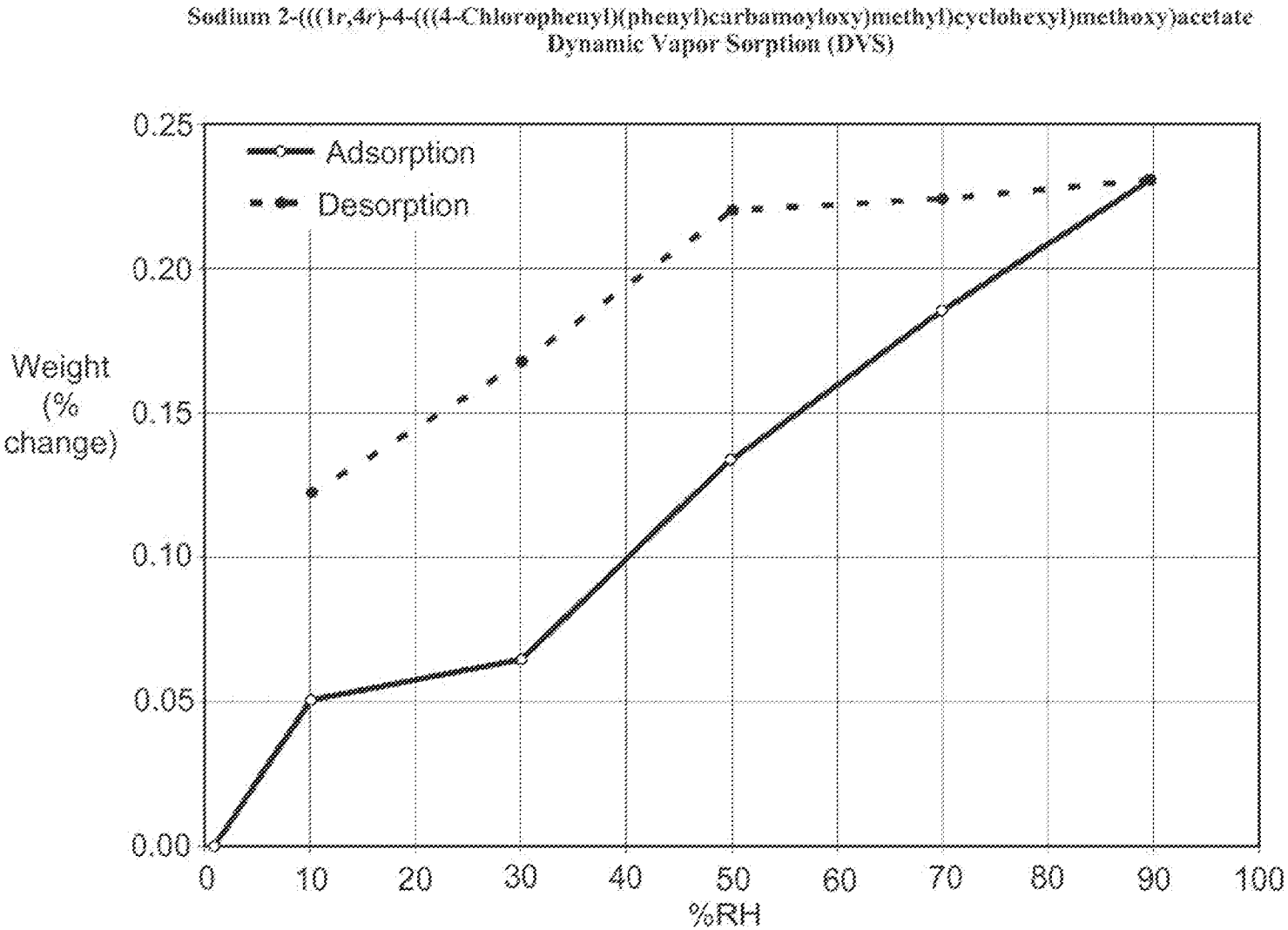

FIG. 10 depicts a dynamic vapor sorption (DVS) profile for Form 1 of the sodium salt of Compound 22 (VTI dynamic vapor sorption analyzer).

Figure 11:
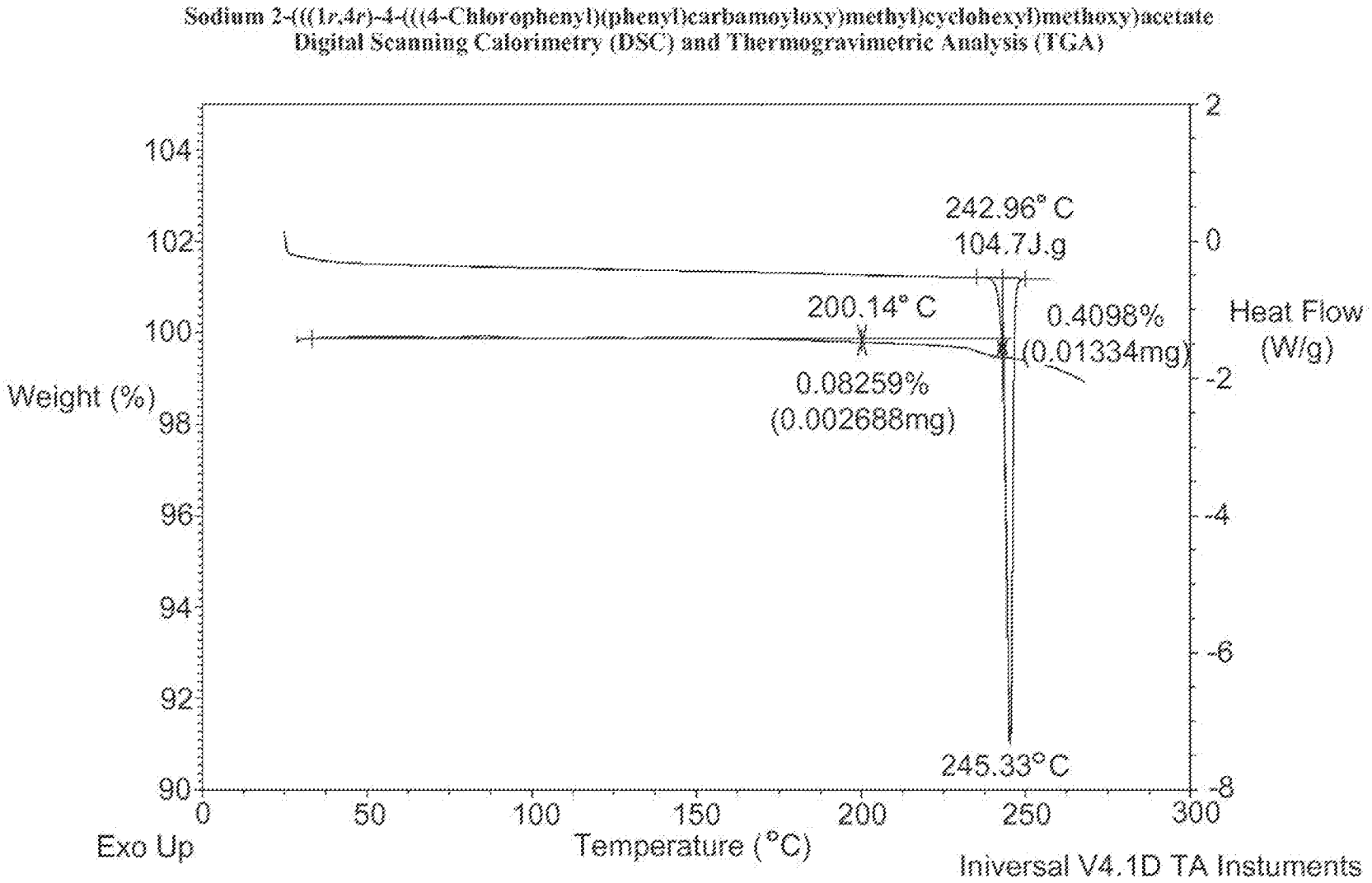

FIG. 11 depicts a differential scanning calorimetry (DSC) thermogram for Form 1 of the sodium salt of Compound 22 (TA Instrument: DSC Q1000; 10° C./min). FIG. 11 also depicts a thermogravimetric analysis (TGA) thermogram for Form 1 of the sodium salt of Compound 22 (TA Instruments TGA Q500 in open cell; 10° C./min).

Figure 12:
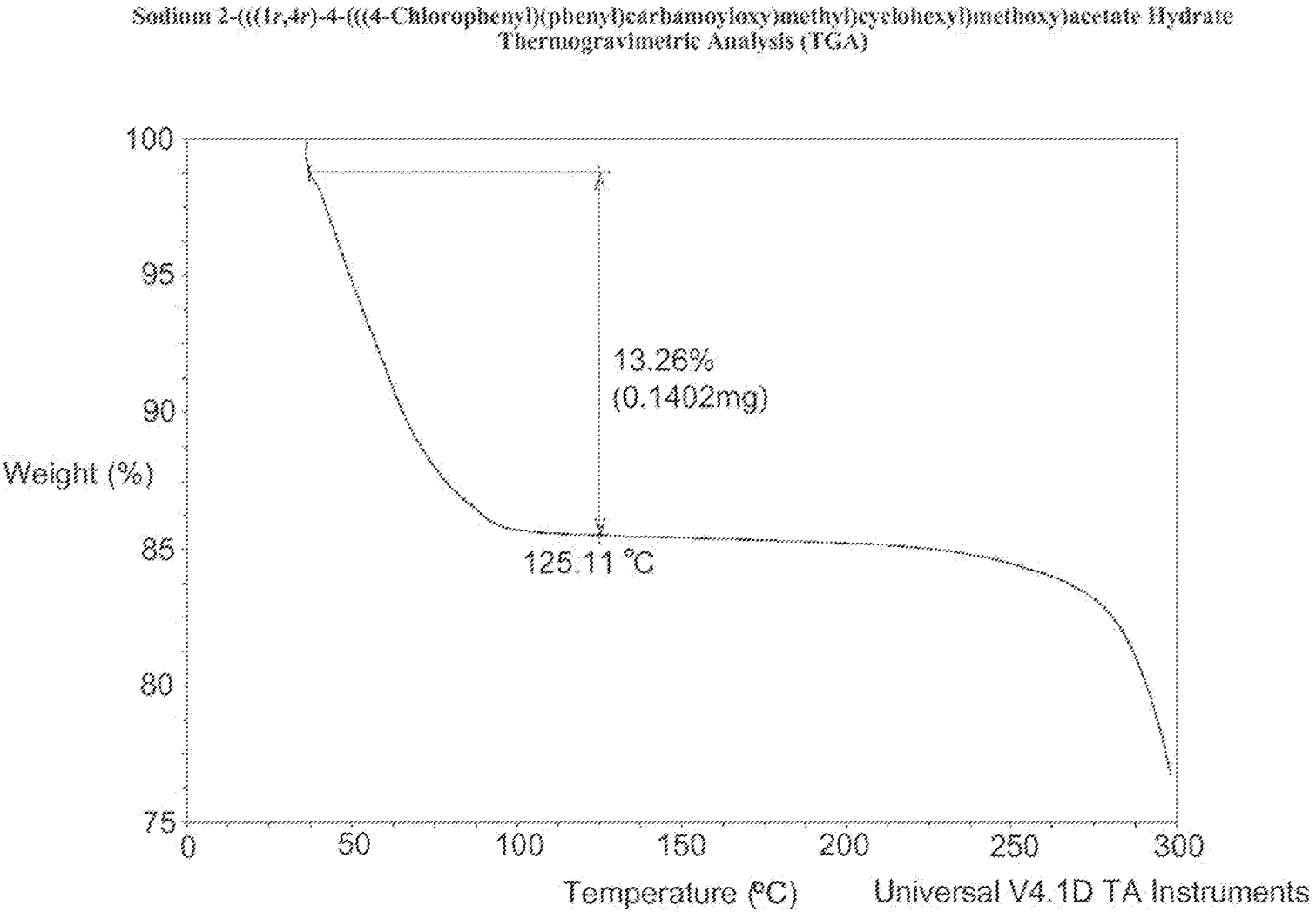

FIG. 12 depicts a thermogravimetric analysis (TGA) thermogram for a hydrate of the sodium salt of Compound 22.

Figure 13:
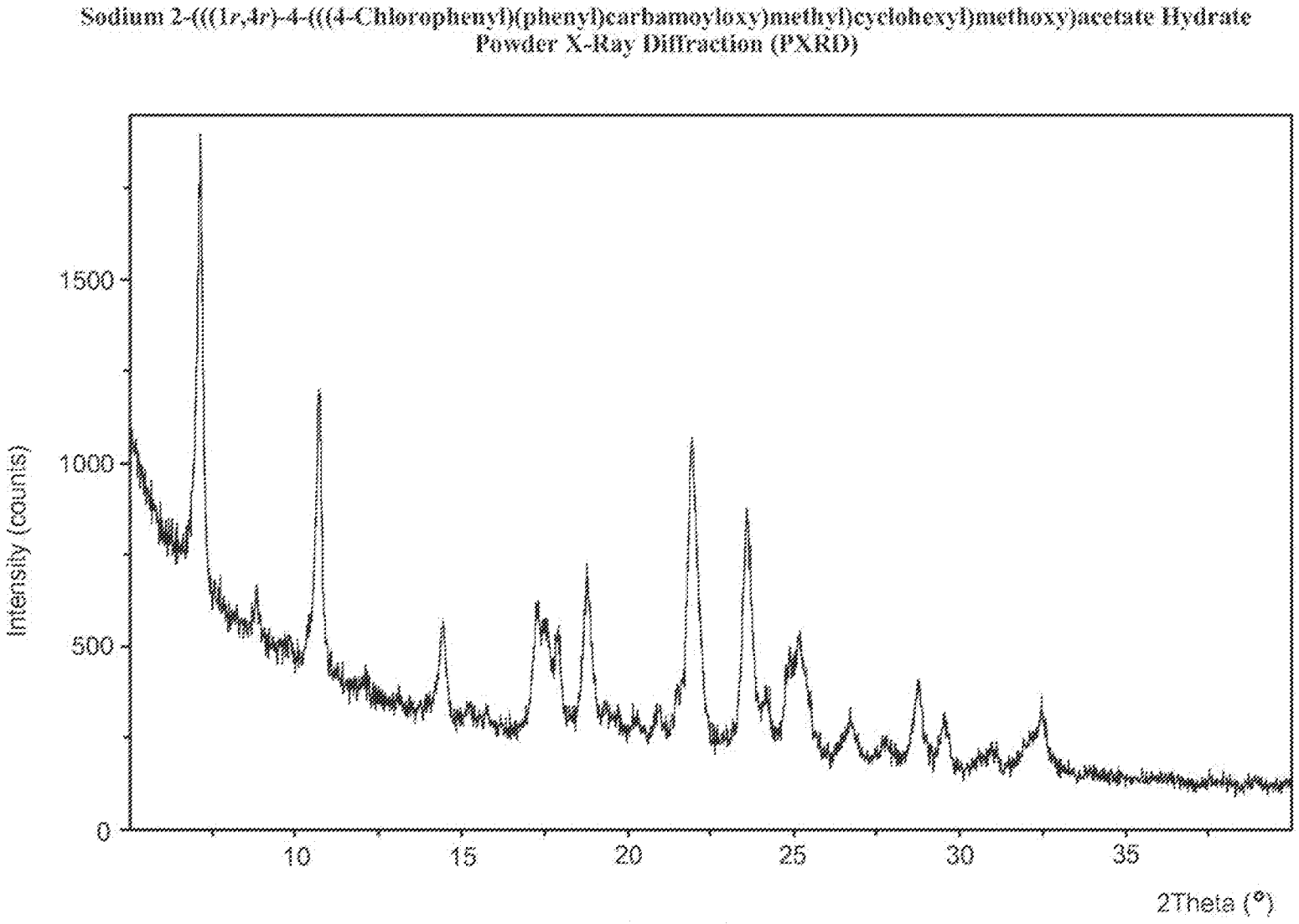

FIG. 13 depicts a powder X-ray diffraction pattern (PXRD) for a sample containing a hydrate of the sodium salt of Compound 22.

Figure 14:
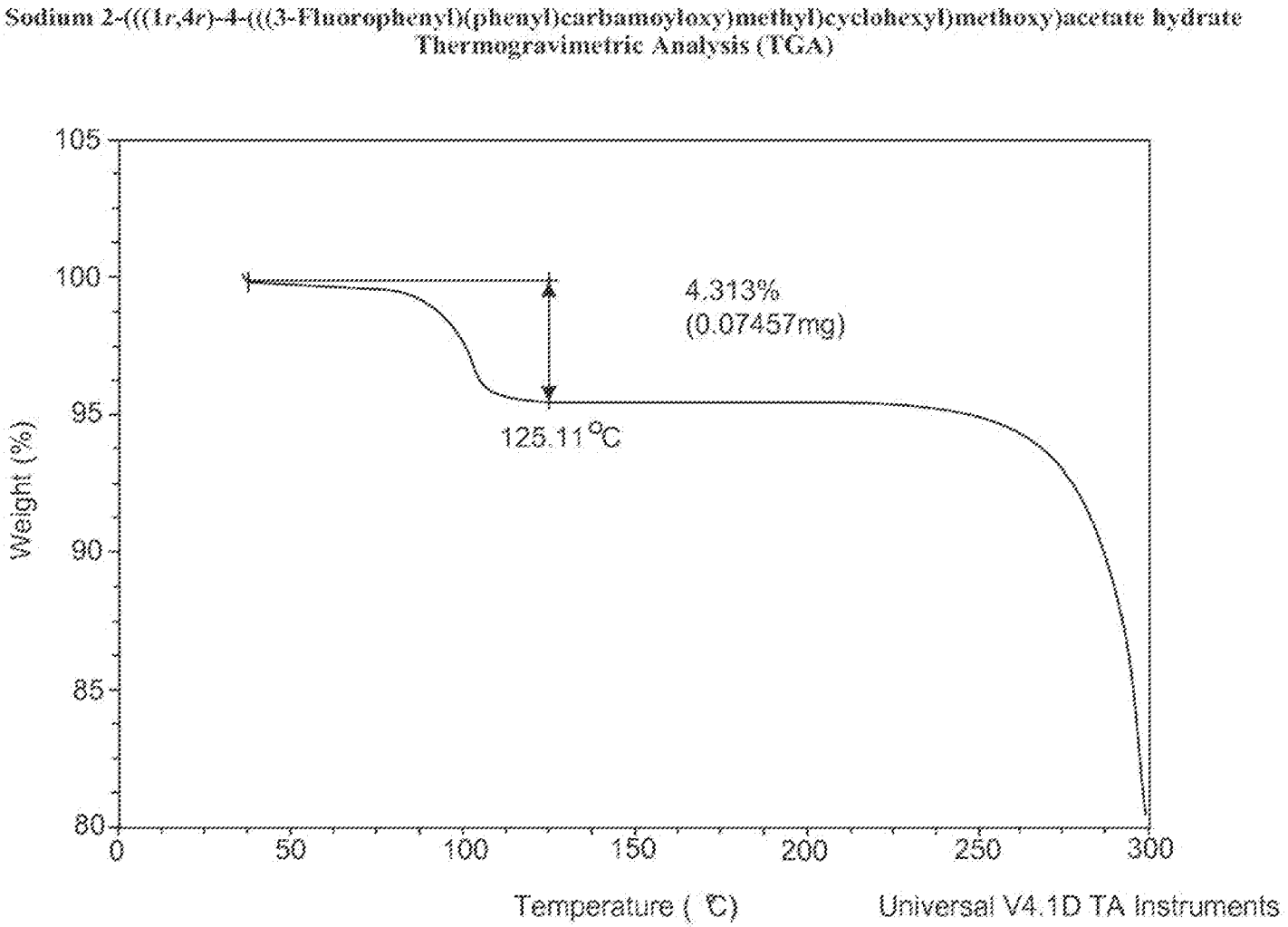

FIG. 14 depicts a thermogravimetric analysis (TGA) thermogram for a hydrate of the sodium salt of Compound 23.

Figure 15:
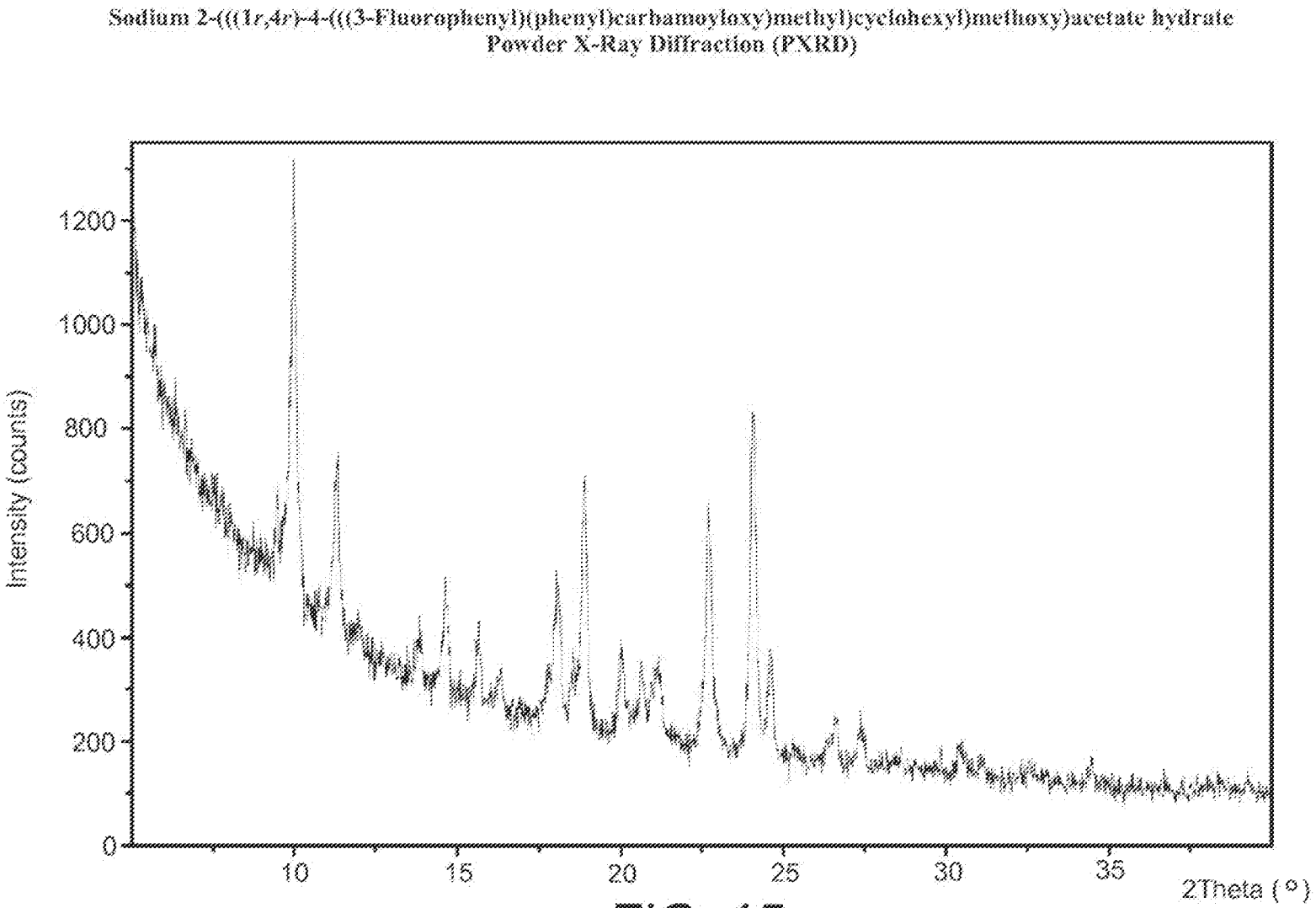

FIG. 15 depicts a powder X-cay diffraction pattern (PXRD) for a sample containing a hydrate of the sodium salt of Compound 23.

Figure 16:
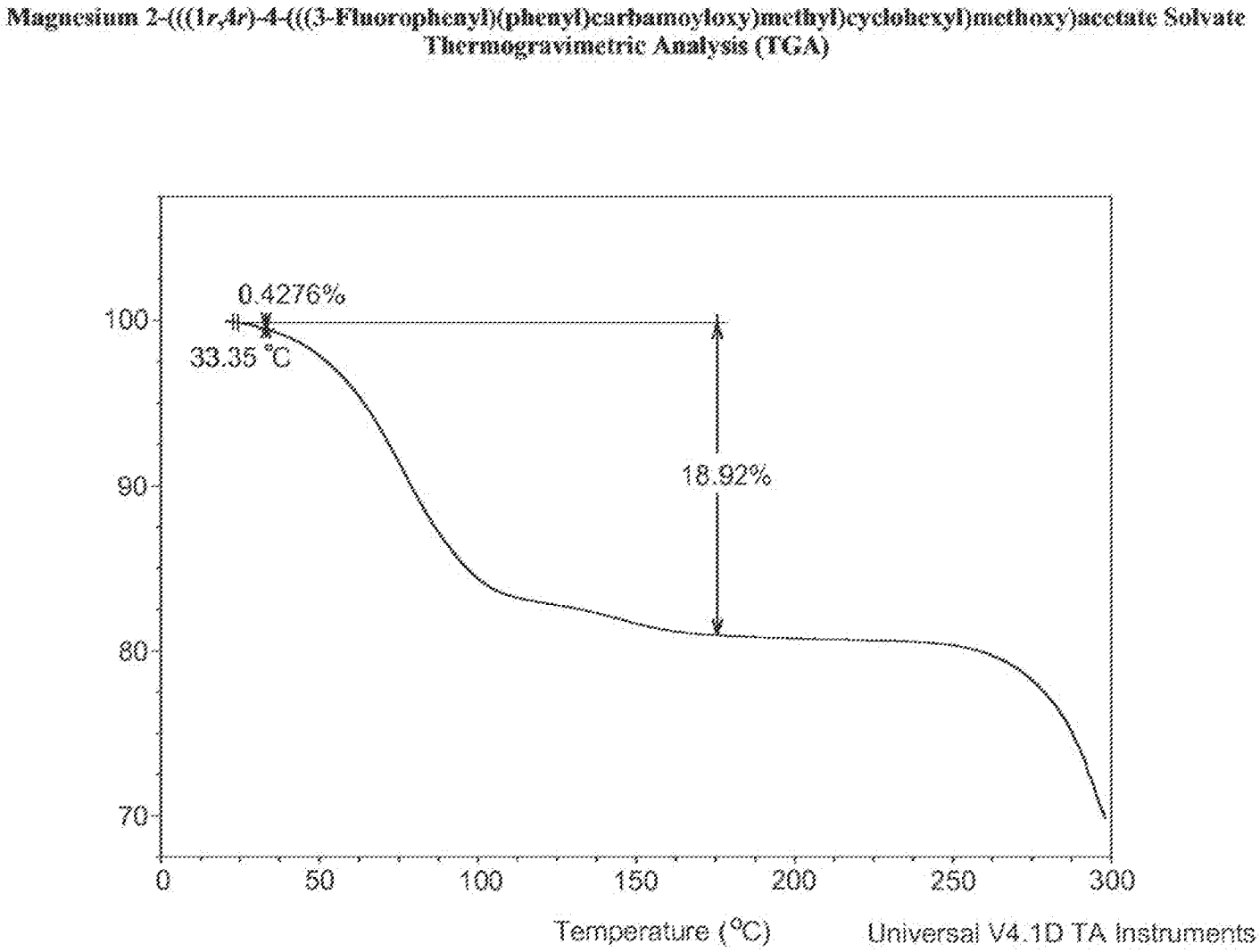

FIG. 16 depicts a thermogravimetric analysis (TGA) thermogram for a solvate of the magnesium salt of Compound 23.

Figure 17:
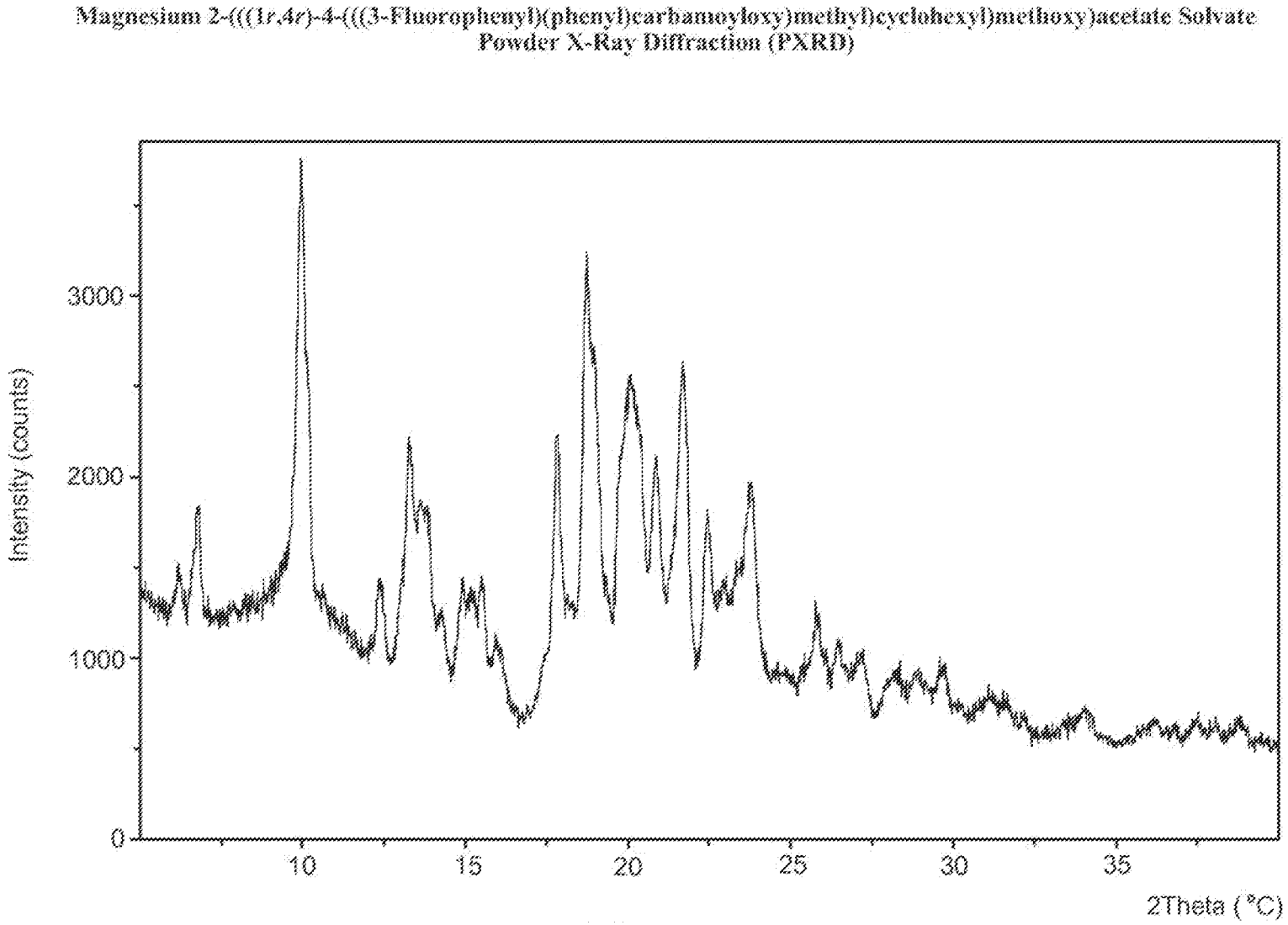

FIG. 17 depicts a powder X-ray diffraction pattern (PXRD) for a sample containing a solvate of the magnesium salt of Compound 23.

Figure 18:
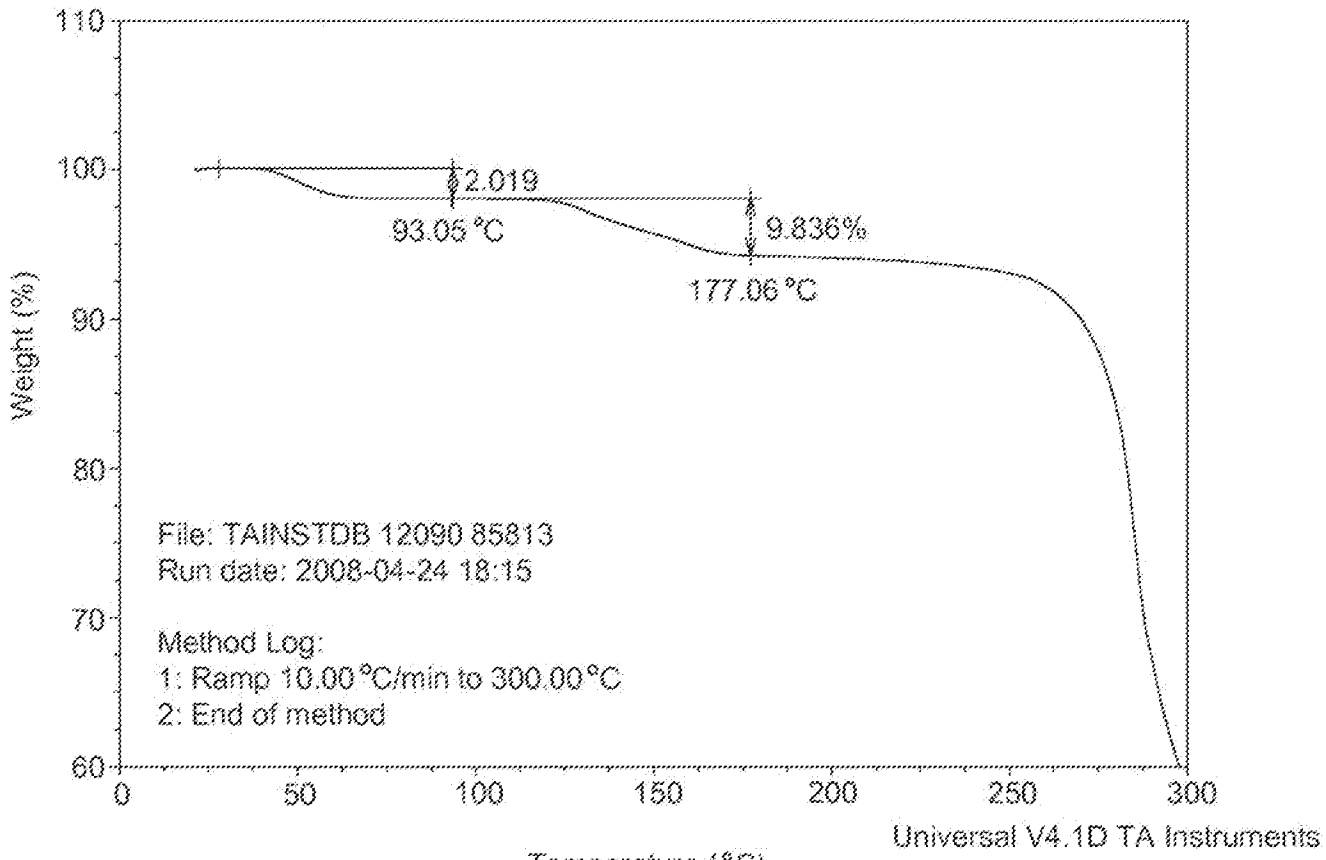

FIG. 18 depicts a thermogravimetric analysis (TGA) thermogram for a solvate of the potassium salt of Compound 23.

Figure 19:
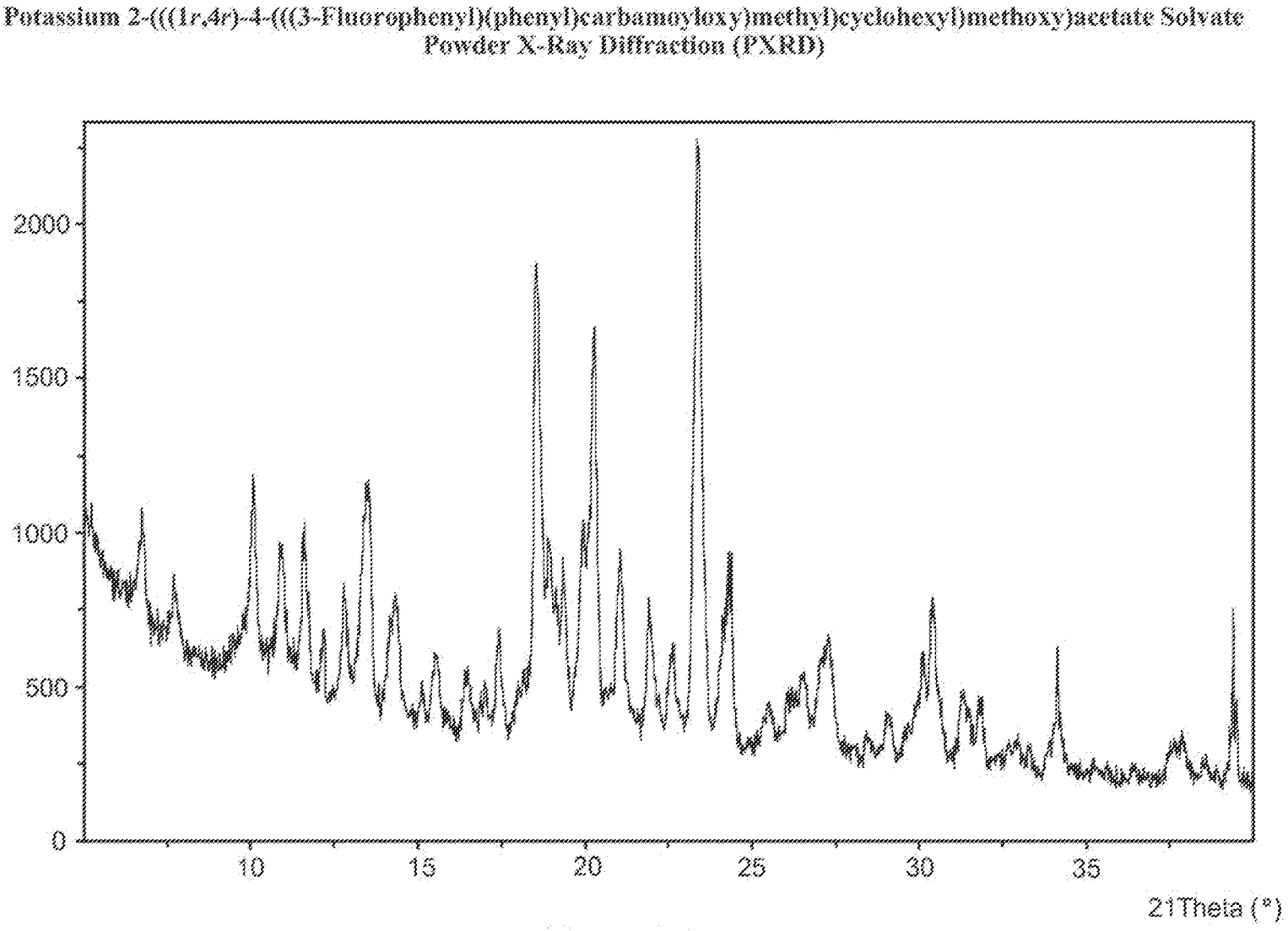

FIG. 19 depicts a powder X-ray diffraction pattern (PXRD) for a sample containing a solvate of the potassium salt of Compound 23.

Figure 20:
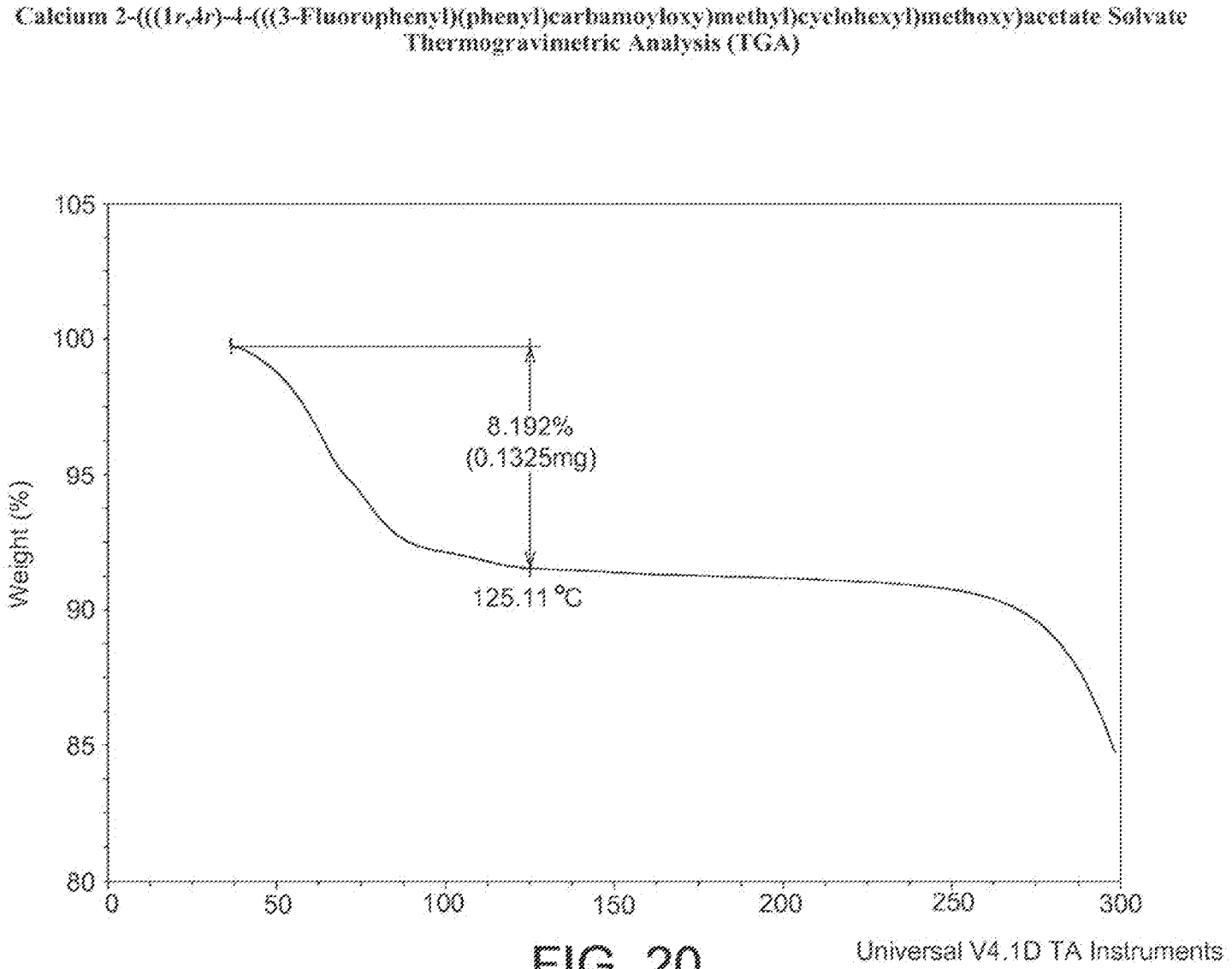

FIG. 20 depicts a thermogravimetric analysis (TGA) thermogram for a solvate of the calcium salt of Compound 23.

Figure 21:
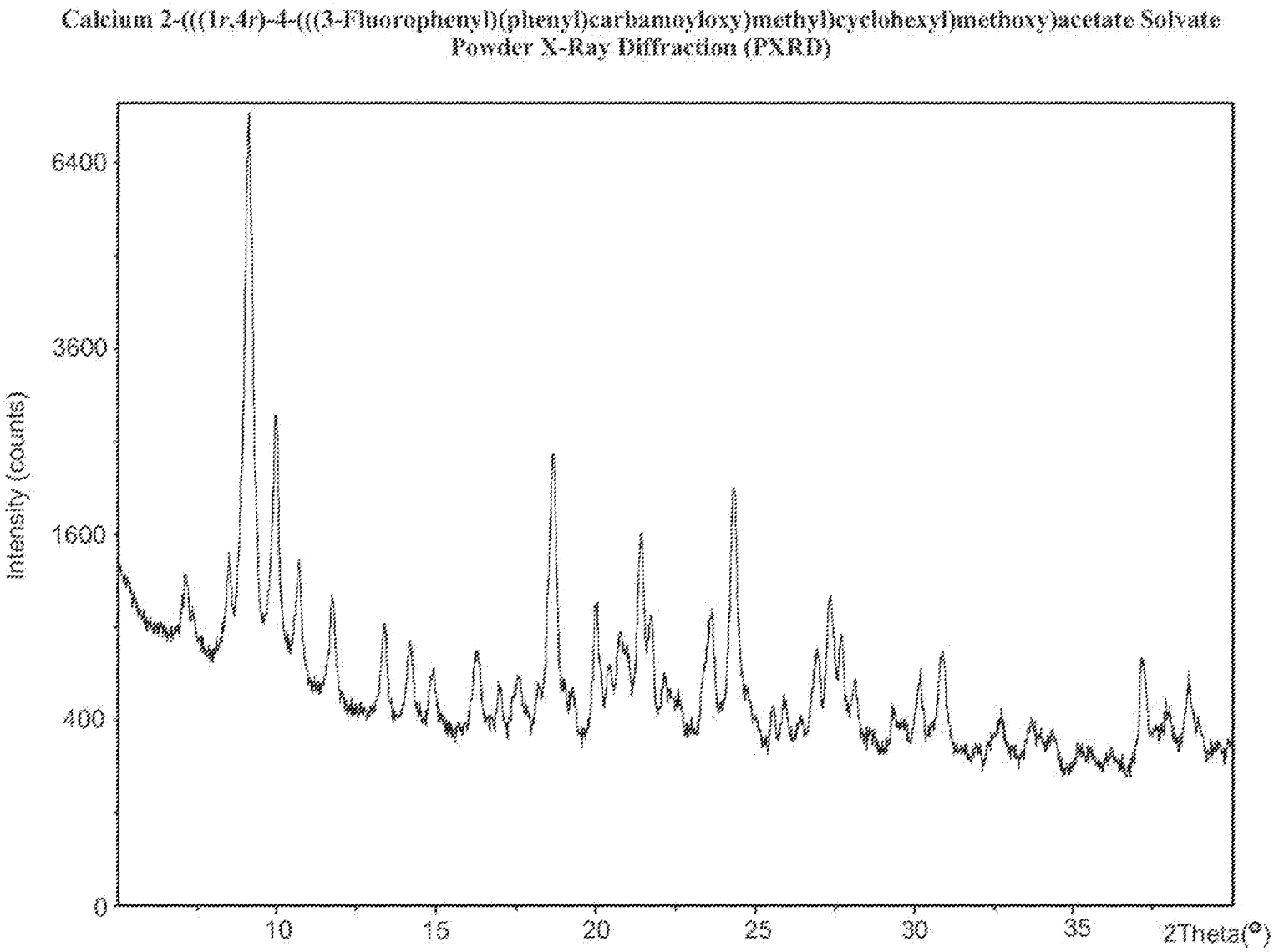

FIG. 21 depicts a powder X-ray diffraction pattern (PXRD) for a sample containing a solvate of the calcium salt of Compound 23.

Figure 22:
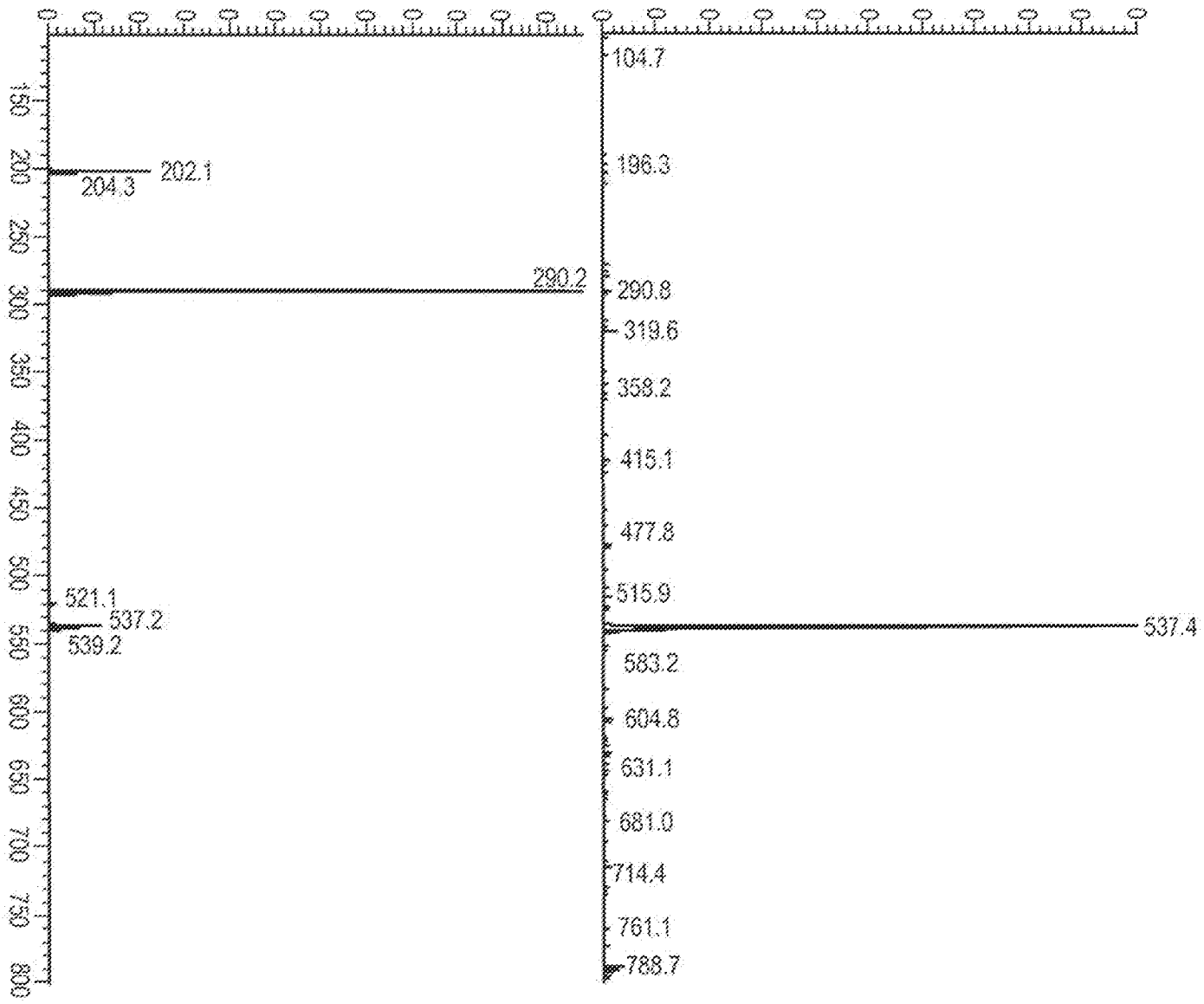

FIG. 22 depicts the MS (top) and MS/MS (bottom) spectra of the taurine conjugate of Compound 22 (Compound 99).

Figure 23:
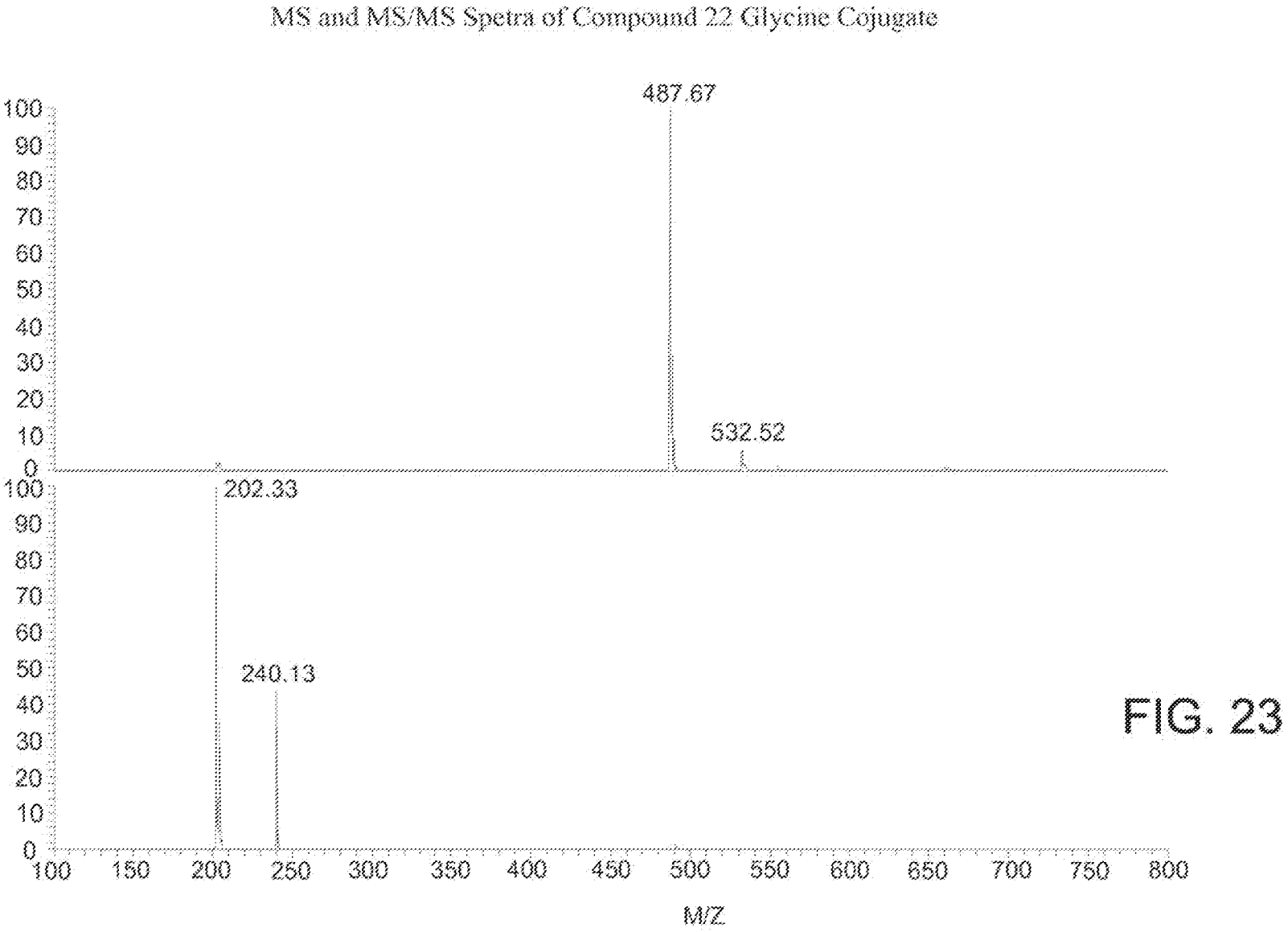

FIG. 23 depicts the MS (top) and MS/MS (bottom) spectra of the glycine conjugate of Compound 22 (Compound 100).

Figure 24:
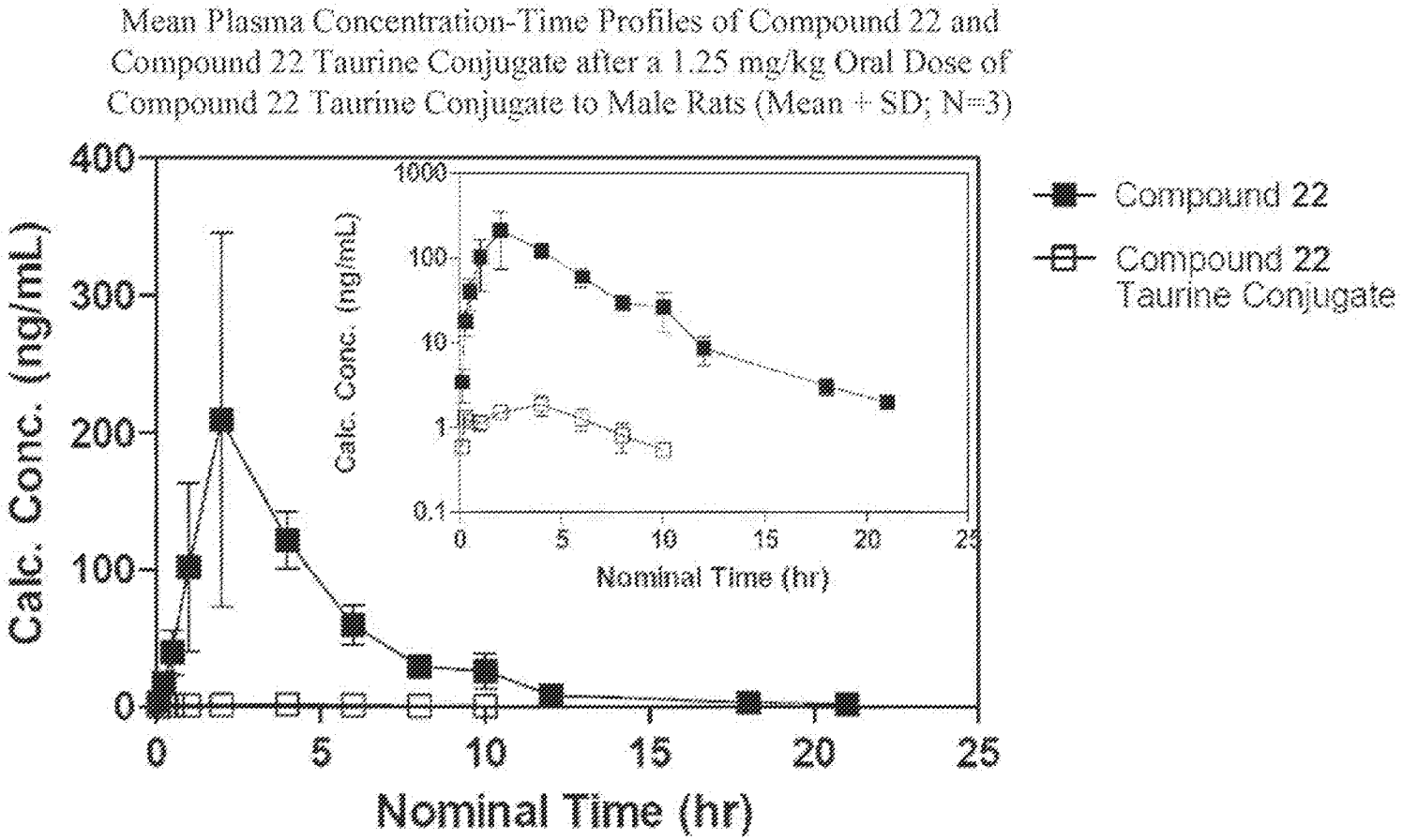

FIG. 24 shows the mean plasma concentration-time profiles of Compound 22 and Compound 22 taurine conjugate (Compound 99) after a 1.25 mg/kg oral dose of Compound 22 taurine conjugate to male rats.

Figure 25:
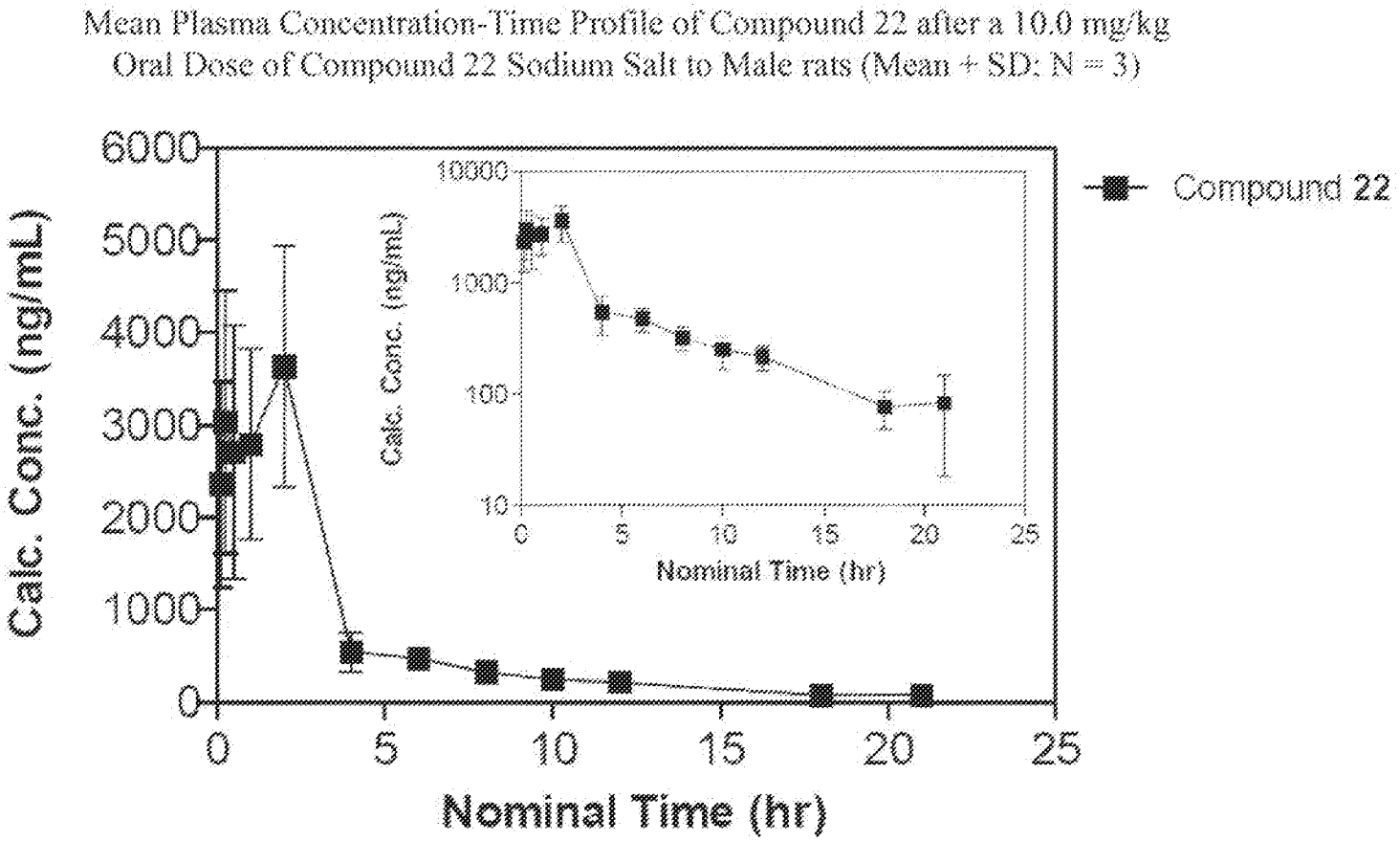

FIG. 25 shows the mean plasma concentration-time profile of Compound 22 after a 10 mg/kg oral dose of Compound 22 sodium salt to male rats.

Figure 26:
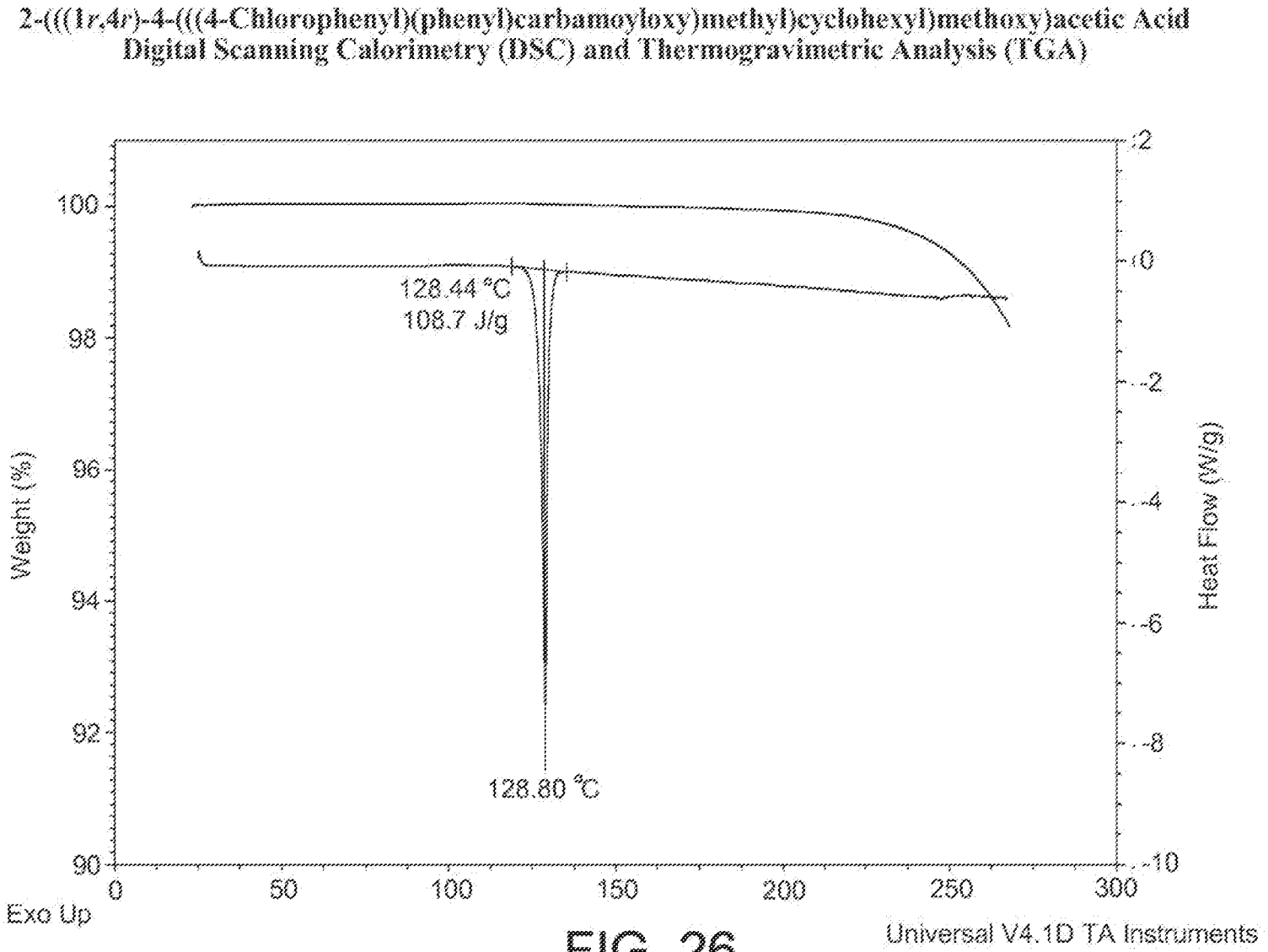

FIG. 26 depicts a differential scanning calorimetry (DSC) thermogram for the crystalline form of Compound 22 of the present invention (TA Instruments DSC Q1000; 10° C./min). FIG. 26 also depicts a thermogravimetric analysis (TGA) thermogram for the crystalline form of Compound 22 of the present invention (TA Instruments TGA Q500 in open cell; 10° C./min).

Figure 27:
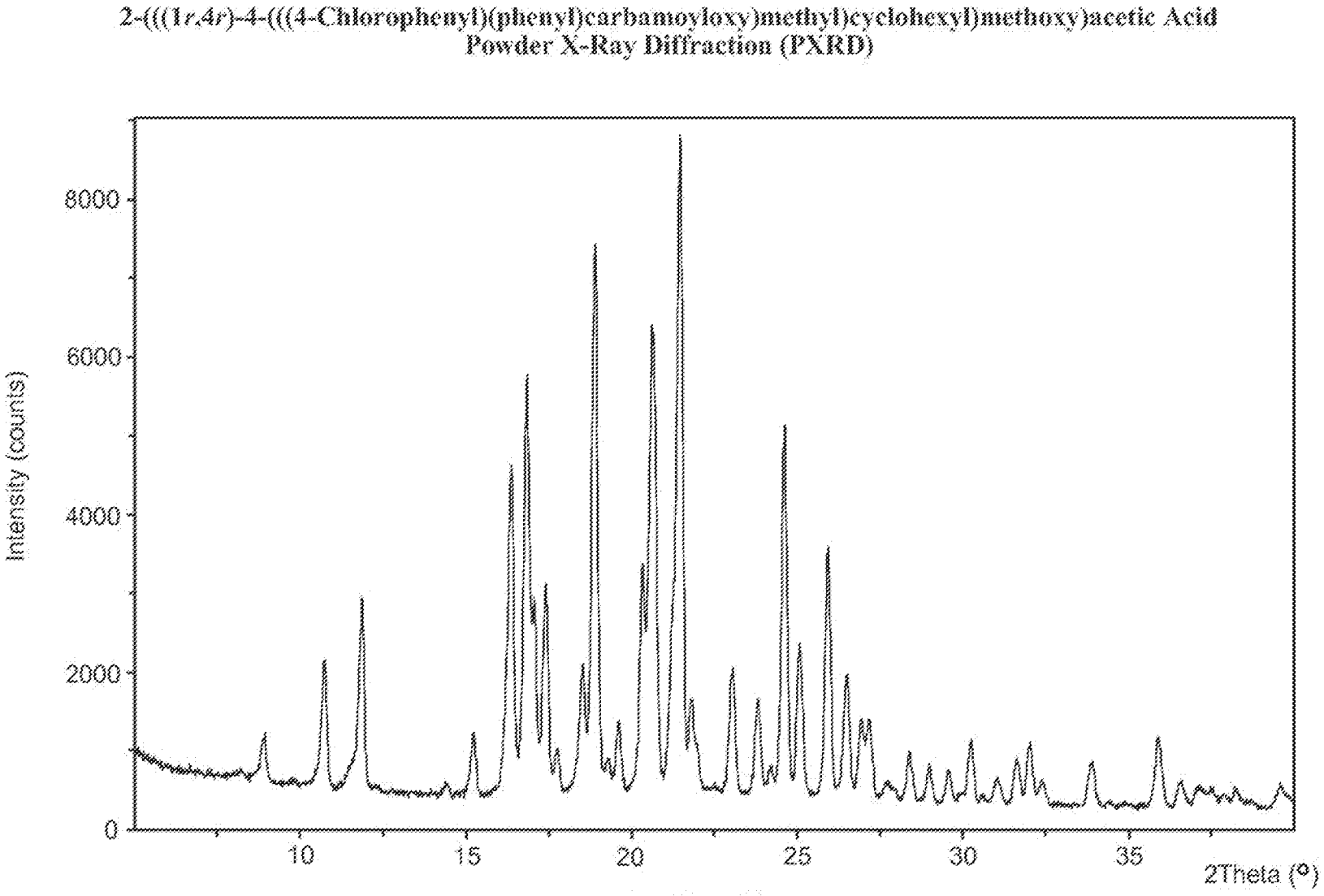

FIG. 27 depicts a powder X-my diffraction pattern (PXRD) for a sample containing the crystalline form of Compound 22 of the present invention (PANalytical X'Pert Plus Powder X-Ray Diffractometer; 5.0 to 40.0° 20).

DETAILED DESCRIPTION OF THE INVENTION

Definitions

For clarity and consistency, the following definitions will be used throughout this patent document.

The term "agonists" is intended to mean moieties that interact and activate the receptor, such as, the PGI2 receptor and initiate a physiological or pharmacological response characteristic of that receptor. For example, when moieties activate the intracellular response upon binding to the receptor, or enhance GTP binding to membranes.

The term "contact or contacting" is intended to mean bringing the indicated moieties together, whether in an in vitro system or an in vivo system. Thus, "contacting" a PGI2 receptor with a compound of the invention includes the administration of a compound of the present invention to an individual, preferably a human, having a PGI2 receptor, as well as, for example, introducing a compound of the invention into a sample containing a cellular or more purified preparation containing a PGI2 receptor.

The term "hydrate" as used herein means a compound of the invention or a salt thereof, that further includes a stoichiometric or non-stoichiometric amount of water bound by non-covalent intermolecular forces.

The term "in need of treatment" and the term "in need thereof," when referring to treatment are used interchangeably to mean a judgment made by a caregiver (e.g. physician, nurse, nurse practitioner, etc. in the case of humans;

veterinarian in the case of animals, including non-human mammals) that an individual or animal requires of will benefit from treatment. This judgment is made based on a variety of factors that are in the realm of a caregiver's expertise, but that includes the knowledge that the individual or animal is ill, or will become ill, as the result of a disease, condition or disorder that is treatable by the compounds of the invention. Accordingly, the compounds of the invention can be used in a protective of preventive manner, or compounds of the invention can be used to alleviate, inhibit or ameliorate the disease, condition or disorder.

The term "individual" is intended to mean any animal, including mammals, preferably mice, rats, other rodents, rabbits, dogs, cats, swine, cattle, sheep, horses, or primates and most preferably humans.

The term "modulate or modulating" is intended to mean an increase or decrease in the amount, quality, response or effect of a particular activity, function or molecule.

The term "pharmaceutical composition" is intended to mean a composition comprising at least one active ingredient; including but not limited to, salts, solvates and hydrates of compounds of the present invention; whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The term "solvate" as used herein means a compound of the invention or a salt, thereof, that further includes a stoichiometric or non-stoichiometric amount of a solvent bound by non-covalent intermolecular forces. Preferred solvents are volatile, non-toxic, and/or acceptable for administration to humans in trace amounts.

The term "therapeutically effective amount" is intended to mean the amount of active compound or pharmaceutical agent that elicits the biological or medicinal response in a tissue, system, animal, individual or human that is being sought by a researcher, veterinarian, medical doctor or other clinician or caregiver, or in an individual, which includes one or more of the following;

(1) Preventing the disease; for example, preventing a disease, condition or disorder in an individual that may be predisposed to the disease, condition or disorder but does not yet experience or display the pathology or symptomatology of the disease.

(2) Inhibiting the disease; for example, inhibiting a disease, condition or disorder in an individual that is experiencing or displaying the pathology or symptomatology of the disease, condition or disorder (i.e., arresting further development of the pathology and/or symptomatology) and (3) Ameliorating the disease; for example, ameliorating a disease, condition or disorder in an individual that is experiencing or displaying the pathology or symptomatology of the disease, condition or disorder (i.e., reversing the pathology and/or symptomatology).

The term "reacting" is used herein as known in the art and generally refers to the bringing together of chemical reagents in such a manner so as to allow their interaction at the molecular level to achieve a chemical or physical transformation of at least one chemical reagent.

Chemical Group, Moiety or Radical

The term "$C_1$-$C_6$ acyl" is intended to mean a $C_1$-$C_6$ alkyl radical attached to the carbon of a carbonyl group wherein the definition of alkyl has the same definition as described herein: some examples include, but are not limited to, acetyl, propionyl, n-butanoyl, sec-butanoyl, pivaloyl, pentanoyl and the like.

The term "$C_1$-$C_6$ alkoxy" is intended to mean a $C_1$-$C_6$ alkyl radical, as defined herein, attached directly to an oxygen atom. The embodiments are 1 to 5 carbons; some embodiments are 1 to 4 carbons; some embodiments are 1 to 3 carbons; and some embodiments are 1 or 2 carbons. Examples include methoxy, ethoxy, n-propoxy, isopropoxy, n-butoxy, t-butoxy, isobutoxy, sec-butoxy and the like.

The term "$C_1$-$C_6$ alkyl"is intended to mean a straight or branched carbon radical containing 1 to 6 carbons. The embodiments are 1 to 5 carbons. The embodiments are 1 to 4 carbons. The embodiments are 1 to 3 carbons. The embodiments are 1 or 2 cartons. The embodiments are 1 carbon. Examples of an alkyl include, but are not limited to, methyl, ethyl, n-propyl, isopropyl, n-butyl, sec-butyl, isobutyl, t-butyl, pentyl, isopentyl, t-pentyl, neo-pentyl, 1-methylbutyl [i.e., —$CH(CH_3)CH_2CH_2CH_3$], 2-methylbutyl [i.e., —$CH_2CH(CH_3)CH_2CH_3$], n-hexyl and the like.

The term "$C_1$-$C_6$ alkylamino" is intended to mean one alkyl radical attached to a NH radical wherein the alkyl radical has the same meaning as described herein. The examples include, but not limited to, methylamino, ethylamino, n-propylamino, isopropylamino, n-butylamino, sec-butylamino, isobutylamino, t-butylamino, and the like. The embodiments are "$C_1$-$C_2$ alkylamino."

The term "$C_1$-$C_6$ alkylcarboxamido" or "$C_1$-$C_6$ alkylcarboxamide" is intended to mean one $C_1$-$C_6$ alkyl group attached to either the carbon or the nitrogen of an amide group, wherein alkyl has the same definition as found herein. The $C_1$-$C_6$ alkylcarboxamido may be represented by the following:

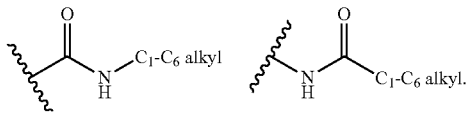

Examples include, but are not limited to, N-methylcarboxamide, N-ethylcarboxamide, N-n-propylcarboxamide, N-isopropylcarboxamide, N-n-butylcarboxamide, N-sec-butylcarboxamide, N-isobutylcarboxamide, N-t-butylcarboxamide and the like.

The term "$C_1$-$C_6$ alkylsulfanyl" is intended to mean a $C_1$-$C_6$ alkyl radical attached to a sulfur atom (i.e., S) wherein the alkyl radical has the same definition as described herein. Examples include, but are not limited to, methylsulfanyl (i.e., $CH_3S$—), ethylsulfanyl, n-propylsulfanyl, isopropylsulfanyl, n-butylsulfanyl, sec-butylsulfanyl, isobutylsulfanyl, t-butylsulfanyl, and the like.

The term "$C_1$-$C_6$ alkylsulfinyl" is intended to mean a $C_1$-$C_6$ alkyl radical attached to the sulfur of a sulfoxide radical having the formula: —S(O)— wherein the alkyl radical has the same definition as described herein. Examples include, but are not limited to, methylsulfinyl, ethylsulfinyl, n-propylsulfinyl, isopropylsulfinyl, n-butylsulfinyl, sec-butylsulfinyl, isobutylsulfinyl, t-butylsulfinyl, and the like.

The term "$C_1$-$C_6$ alkylsulfonamide" is intended to mean the groups shown below:

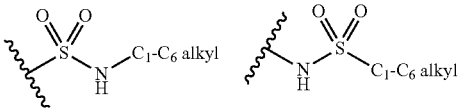

wherein $C_1$-$C_6$ alkyl has the same definition as described herein.

The term "$C_1$-$C_6$ alkylsulfonyl" is intended to mean a $C_1$-$C_6$ alkyl radical attached to the sulfur of a sulfone radical having the formula: —$S(O)_2$ wherein the alkyl radical has the same definition as described herein. Examples include, but are not limited to, methylsulfonyl, ethylsulfonyl, n-propylsulfonyl, iosopropylsulfonyl, n-butylsulfonyl, sec-butylsulfonyl, isobutylsulfonyl, t-butylsulfonyl, and the like.

The term "amino" is intended to mean the group —$NH_2$.

The term "aryl" is intended to mean an aromatic ring radical containing 6 to 10 ring carbons. Examples include phenyl and naphthyl.

The term "carbo-$C_1$-$C_6$-alkoxy" is intended to mean a $C_1$-$C_6$ alkyl ester of a carboxylic acid, wherein the alkyl group is as defined herein. Examples include, but are not limited to, carbomethoxy [—$C(O)OCH_3$], carbo-ethoxy, carbo-propoxy, carbo-isopropoxy, carbo-butoxy, carbo-sec-butoxy, carbo-isobutoxy, carbo-t-butoxy, carbo-n-pentoxy, carbo-isopentoxy, carbo-t-pentoxy, carbo-neo-pentoxy, carbo-n-hexyloxy, and the like.

The term "carboxamide" is intended to mean the group —$CONH_2$.

The term "carboxy" or "carboxyl" is intended to mean the group —$CO_2H$, also referred to as a carboxylic acid group.

The term "cyano" is intended to mean the group —CN.

The term "$C_2$-$C_8$ dialkylamino" is intended to mean an amino substituted with two of the same or different $C_1$-$C_4$ alkyl radicals wherein alkyl radical has the same definition as described herein. The examples include, but are not limited to, dimethylamino, methylethylamino diethylamino, methylpropylamino, methylisopropylamino, ethylpropylamino, ethylisopropylamino, dipropylamino, propylisopropylamino and the like. The embodiments are "$C_2$-$C_4$ dialkylamino."

The term "$C_2$-$C_8$ dialkylcarboxamido" or "$C_2$-$C_8$ dialkylcarboxamide" is intended to mean two alkyl radicals, that are the same or different, attached to an amide group, wherein alkyl has the same definition as described herein. A $C_2$-$C_8$ dialkylcarboxamido may be represented by the following groups:

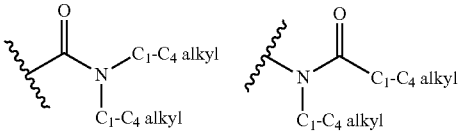

wherein $C_1$-$C_4$ has the same definition as described herein. Examples of a dialkylcarboxamide, include, but are not limited to, N,N-dimethylcarboxamide, N-methyl-N-ethylcarboxamide, N,N-diethylcarboxamide, N-methyl-N-isopropylcarboxamide, and the like.

The term "$C_2$-$C_8$ dialkylsulfonamide" is intended to mean one of the following groups shown below:

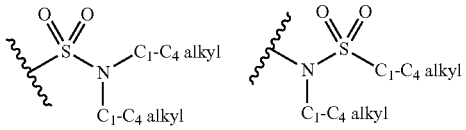

wherein $C_1$-$C_4$ has the same definition as described herein, for example but not limited to, methyl, ethyl, n-propyl, isopropyl, and the like.

The term "guanidino" is intended to mean —NHC(—NH) $NH_2$.

The term "halogen" or "halo" is intended to mean to a fluoro, chloro, bromo or iodo group.

The term "$C_1$-$C_6$ haloalkoxy" is intended to mean a $C_1$-$C_6$ haloalkyl, as defined herein, which is directly attached to an oxygen atom. Examples include, but are not limited to, difluoromethoxy, trifluoromethoxy, 2,2,2-trifluoroethoxy; pentafluoroethoxy and the like.

The term "$C_1$-$C_6$ haloalkyl" is intended to mean a $C_1$-$C_6$ alkyl group, defined herein, wherein the alkyl is substituted with one halogen up to fully substituted and a fully substituted $C_1$-$C_6$ halogen can be represented by the formula $C_nL_{2n+1}$ wherein L is a halogen and "n" is 1, 2, 3, 4, 5 or 6; when more than one halogen is present then they may be the same or different and selected from the group consisting of F, Cl, Br and I, preferably F, some embodiments are 1 to 5 carbons, some embodiments are 1 to 4 carbons, some embodiments are 1 to 3 carbons, and some embodiments are 1 or 2 carbons. Examples of haloalkyl groups includes, but are not limited to, fluoromethyl, difluoromethyl, trifluoromethyl, chlorodifluoromethyl, 2,2,2-trifluoroethyl, pentafluoroethyl and the like.

The term "heteroaryl" is intended to mean an aromatic ring system containing 5 to 14 aromatic ring atoms that may be a single ring, two fused rings or three fused rings wherein at least one aromatic ring atom is a heteroatom selected from, but not limited to, the group consisting of O, S and N wherein the N can be optionally substituted with H, $C_1$-$C_4$ acyl or $C_1$-$C_4$ alkyl. The embodiments contain 5 to 6 ring atoms for example furanyl, thienyl, pyrrolyl, imidazolyl, oxazolyl, thiazolyl, isoxazolyl, pyrazolyl, isothiazolyl, oxadiazolyl, triazolyl, thiadiazolyl, pyridinyl, pyrazinyl, pyrimidinyl, pyridazinyl, triazinyl and the like. The embodiments contain 8 to 14 ring atoms for example carbazolyl, quinolizinyl, quinolinyl, isoquinolinyl, cinnolinyl, phthalazinyl, quinazolinyl, quinoxalinyl, triazinyl, indolyl, isoindolyl, indazolyl, indolizinyl, purinyl, naphthyridinyl, pteridinyl, carbazolyl, acridinyl, phenazinyl, phenothiazinyl, phenoxazinyl, benzoxazolyl, benzothiazolyl, 1H-benzimidazolyl, imidazopyridinyl, benzothienyl, benzofuranyl, isobenzofuran and the like.

The term "heterocyclic" or "heterocyclyl" is intended to mean a ring system containing 3 to 15 ring atoms that may be a single ring, two fused rings of three fused rings, wherein at least one ring atom is a heteroatom of substituted heteroatom selected from, but not limited to, the group consisting of O, S, S(—O), $S(—O)_2$ and NH, wherein the N is optionally substituted with $C_1$-$C_4$ acyl or $C_1$-$C_4$ alkyl. In some embodiments, the ring carbon atoms are optionally substituted with oxo thus forming a carbonyl group. In some embodiments the heterocyclic group is a 3-, 4-, 5-, 6- or 7-membered ring. In some embodiments the heterocyclic group is a bicyclic group in which any of the above-defined heterocyclic rings is fused to a benzene ring. In some embodiments the heterocyclic group is a tricyclic group in which any of the above-defined heterocyclic rings is fused to two benzene rings. Examples of a heterocyclic group include, but are not limited to, [1,3]-dioxolanyl, [1,4]-dioxanyl, [1,4]-oxazepanyl, 10,11-dihydro-5H-dibenzo [b,f] azepinyl, azepanyl, azetidinyl, aziridinyl, chromanyl, dithianyl, imidazolidinyl, imidazolinyl, indolinyl, morpholinyl, piperidinyl, piperazinyl, pyranyl, pyrazolidinyl, pyrazolinyl, pyrrolidinyl, pyrrolinyl, succinimidyl, tetrahydrofuranyl, tetrahydropyranyl, thiochromanyl, thiomorpholinyl, trithianyl, xanthenyl and the like. It is understood that a heterocyclic group can be bonded only at any available ring carbon or ring nitrogen as allowed by the respective formulae unless otherwise specified.

The term "hydroxyl" is intended to mean the group —OH.

The term "nitro"' is intended to mean the group —$NO_2$.

The term "sulfo" is intended to mean the group —$SO_3H$.

The term "thiol" is intended to mean the group —SH.

Compounds of the Invention

One aspect of the present invention pertains to certain compounds as shown in Formula (XIIIa):

(XIIIa)

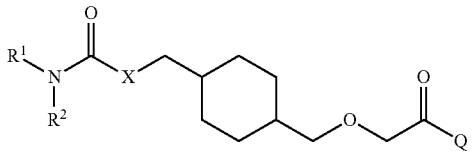

and pharmaceutically acceptable salts, solvates and hydrates thereof;

wherein:

$R^1$, $R^2$, X and Q have the same definitions as described herein, supra and infra.

One aspect of the present invention pertains to certain compounds as shown in Formula (Ia):

(Ia)

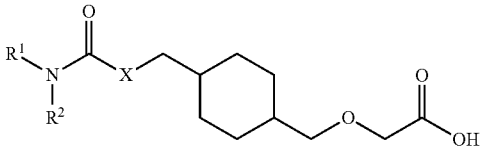

and pharmaceutically acceptable salts, solvates and hydrates thereof;

wherein:

$R^1$, $R^2$ and X have the same definitions as described herein, supra and infra.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables (e.g., $R^1$, $R^2$, $R^3$, $R^4$, $R^5$, $R^6$, $R^7$, $R^8$, $R^9$, $R^{10}$, $R^{11}$, X and Q) contained within the generic chemical formulae described herein, for example, (Ia) (Ic), (Ie), (Ig), (Ii), (Ik), (Im), (II), (XIIIa), (XIIIc), (XIIIe), (XIIIg), (XIIIi), (XIIIk), (XIIIIm) are specifically embraced by the present invention just as if each and every combination was individually explicitly recited, to the extent that such combinations embrace compounds that result in stable compounds (i.e., compounds that can be isolated, characterized and tested for biological activity). In addition, all subcombinations of the chemical groups listed in the embodiments describing such variables, as well as all subcombinations of uses and medical indications described herein, are also specifically embraced by the present invention just as if each and every subcombination of chemical groups and subcombination of uses and medical indications was individually and explicitly recited herein. In addition, all subcombinations of the salts, solvates, hydrates and crystalline forms specifically exemplified herein, as well as all subcombinations of uses thereof and medical indications related thereto described herein, are also specifically embraced by the present invention just as if each and every subcombination of salts, solvates, hydrates and crystalline forms specifically exemplified herein and subcombination of uses thereof and medical indications related thereto was individually and explicitly recited herein.

As used herein, "substituted" indicates that at least one hydrogen atom of the chemical group is replaced by a non-hydrogen substituent or group, the non-hydrogen substituent or group can be monovalent or divalent. When the substituent or group is divalent, then it is understood that this group is further substituted with another substituent or group. When a chemical group herein is "substituted" it may have up to the full valance of substitution; for example, a methyl group can be substituted by 1, 2, or 3 substituents, a methylene group can be substituted by 1 or 2 substituents, a phenyl group can be substituted by 1, 2, 3, 4, or 5 substituents, a naphthyl group can be substituted by 1, 2, 3, 4, 5, 6,or 7 substituents and the like. Likewise, "substituted with one or more substituents" refers to the substitution of a group with one substituent up to the total number of substituents physically allowed by the group. Further, when a group is substituted with more than one group they can be identical or they can be different.

Compounds of the invention can also include tautomeric forms, such as keto-enol tautomers and the like. Tautomeric forms can be in equilibrium or sterically locked into one form by appropriate substitution. It is understood that the various tautomeric forms are within the scope of the compounds of the present invention.

Compounds of the invention can also include all isotopes of atoms occurring in the intermediates and/or final compounds. Isotopes include those atoms having the same atomic number but different mass numbers. For example, isotopes of hydrogen include deuterium and tritium.

It is understood and appreciated that compounds of Formula (Ia) and formulae related thereto may have one or more chiral centers and therefore can exist as enantiomers and/or diastereoisomers. The invention is understood to extend to and embrace all such enantiomers, diastereoisomers and mixtures thereof, including but not limited to racemates. It is understood that compounds of Formula (Ia) and formulae used throughout this disclosure are intended to represent all individual enantiomers and mixtures thereof, unless stated or shown otherwise.

It is understood and appreciated that compounds of Formula (Ia) and formulae related thereto exist as meso isomers. Such meso isomers may be referred to as cis and trans. The cis meso isomers of compounds of Formula (Ia) are named herein using the prefix (1s,4s) and the trans meso isomers of compounds of Forumla (Ia) are named herein using the prefix (1r,4r) as shown below:

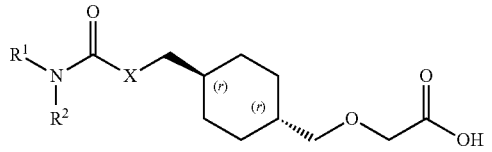

(1r,4r)- or trans- mesoisomer

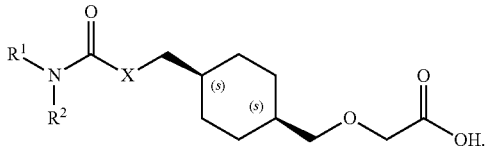

(1s,4s)- or cis- mesoisomer

One aspect of the present invention encompasses certain cyclohexane derivatives selected from compounds of Formula (XIIIa) and pharmaceutically acceptable salts, solvates and hydrates thereof:

(XIIIa)

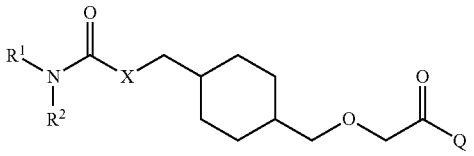

wherein:

$R^1$ and $R^2$ are each independently selected from: H, $C_1$-$C_6$ alkyl, aryl and heteroaryl; wherein $C_1$-$C_6$ alkyl, aryl and heteroaryl are each optionally substituted with one or two substituents selected from: $C_1$-$C_5$ alkoxy, $C_1$-$C_6$ alkyl, aryl, $C_1$-$C_6$ haloalkoxy, $C_1$-$C_6$ haloalkyl and halogen;

X ix O or $NR^3$;

$R^3$ is selected from H and $C_1$-$C_6$ alkyl; and

Q is selected from: OH, —$NHCH_2CH_2SO_3H$, 1-carboxyethylamino, 1-carboxy-4-guanidinobutylamino, 3-amino-1-carboxy-3-oxopropylamino, 1,2--dicarboxyethylamino, 1-carboxy-2-mercaptoethylamino, 4-amino-1-carboxy-4-oxobutylamino, 3-carboxy-1-carboxylatopropylamino, carboxymethylamino, 1-carboxy-2-(1H-imidazol-4-yl)ethylamino, 1-carboxy-2-methylbutylamino, 1-carboxy-3-methylbutylamino, 5-amino-1-carboxypentylamino, 1-carboxy-3-(methylthio)propylamino, 1-carboxy-2-phenylethylamino, 2-carboxypyrrolidin-1-yl, 1-carboxy-2-hydroxyethylamino, 1-carboxy-2-hydroxypropylamino, 1-carboxy-2-(1H-indol-3-yl)ethylamino, 1-carboxy-2-(4-hydroxyphenyl)ethylamino and 1-carboxy-2-methylpropylamino.

One aspect of the present invention encompasses certain cyclohexane derivatives selected from compounds of Formula (Ia) and pharmaceutically acceptable salts, solvates and hydrates thereof:

(Ia)

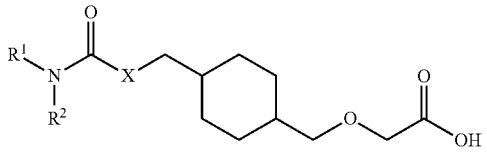

wherein:

$R^1$ and $R^2$ are each independently selected from: H, $C_1$-$C_6$ alkyl, aryl and heteroaryl; wherein $C_1$-$C_6$ alkyl, aryl and heteroaryl are each optionally substituted with one or two substituents selected from: $C_1$-$C_6$ alkoxy; $C_1$-$C_6$ alkyl, aryl, $C_1$-$C_6$ haloalkoxy, $C_1$-$C_6$ haloalkyl, hydroxyl and halogen.

X ix O or $NR^3$; and $R^3$ is selected from H and $C_1$-$C_6$ alkyl.

One aspect of the present invention encompasses certain cyclohexane derivatives selected from compounds of Formula (Ia) and pharmaceutically acceptable salts, solvates and hydrates thereof:

(Ia)

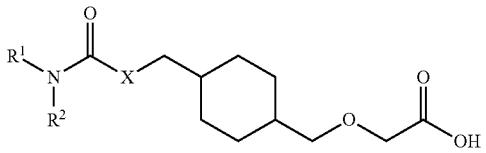

wherein:

$R^1$ and $R^2$ are each independently selected from H, $C_1$-$C_6$ alkyl, aryl and heteroaryl; wherein $C_1$-$C_6$ alkyl, aryl and heteroaryl are each optionally substituted with one or two substituents selected from: $C_1$-$C_6$ alkoxy, $C_1$-$C_6$ alkyl, aryl, $C_1$-$C_6$ haloalkoxy; $C_1$-$C_6$ haloalkyl and halogen;

X is O or $NR^3$; and $R^3$ is selected from H and $C_1$-$C_6$ alkyl.

The Group $R^1$:

In some embodiments, $R^1$ is selected from: H, $C_1$-$C_6$ alkyl, aryl and heteroaryl; wherein $C_1$-$C_6$ alkyl, aryl and heteroaryl are each optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen.

In some embodiments, $R^1$ is selected from: $C_1$-$C_6$ alkyl, aryl and heteroaryl; wherein $C_1$-$C_6$ alkyl, aryl and heteroaryl are each optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen.

In some embodiments, $R^1$ is selected from: $C_1$-$C_6$ alkyl, aryl and heteroaryl; each optionally substituted with one or two substituents selected from: methoxy, ethoxy, methyl, phenyl, trifluoromethyl, trifluoromethoxy, fluoro and chloro.

In some embodiments, $R^1$ is selected form: diphenylmethyl, 2,3-difluorophenyl, 2-fluoro-3-methoxyphenyl, 2-fluorophenyl, 2-fluoropyridin-4-yl, 2-methoxyphenyl, 3-(trifluoromethoxy)phenyl, 3,4-difluorophenyl, 3,5-difluorophenyl, 3,5-dimethylphenyl, 3-chloro-2-fluorophenyl, 3-chloro-4-fluorophenyl, 3-chloro-5-fluorophenyl, 3-chlorophenyl, 3-fluoro-4-methylphenyl, 3-fluorophenyl, 3-methoxyphenyl, 3-tolyl, 3-(trifluoromethyl)phenyl, 4-(trifluoromethoxy)phenyl, 4-chloro-3-fluorophenyl, 4-chlorophenyl, 4-ethoxyphenyl, 4-fluorophenyl, 4-methoxy-2-methylphenyl, 4-methoxyphenyl, 4-tolyl, 5-(trifluoromethyl)pyridin-2-yl, 5-chloropyridin-2-yl, 5-fluoropyridin-2-yl, 5-fluoropyridin-3-yl, 5-methoxypyridin-3-yl, 5-methylpyridin-3-yl, 5-methylthiazol-2-yl, 5-methylthiophen-2-yl, 6-fluoropyridin-3-yl, phenyl, pyrazin-2-yl, pyridin-2-yl and pyridin-3-yl.

In some embodiments, $R^1$ is selected from: $C_1$-$C_6$ alkyl, aryl and heteroaryl; wherein $C_1$-$C_6$ alkyl, aryl and heteroaryl are each optionally substituted with one, two or three substituents selected from: $C_1$-$C_6$ acyl, $C_1$-$C_6$ alkoxy, $C_1$-$C_6$ alkyl, $C_1$-$C_6$ alkylamino, $C_1$-$C_6$ alkylcarboxamide, $C_1$-$C_6$ alkylsulfanyl, $C_1$-$C_6$ alkylsulfinyl, $C_1$-$C_6$ alkylsulfonamide, $C_1$-$C_6$ alkylsulfonyl, amino, aryl, carbo-$C_1$-$C_6$-alkoxy, carboxamide, carboxy, cyano, $C_2$-$C_8$ dialkylamino, $C_2$-$C_8$ dialkylcarboxamide, $C_2$-$C_8$ dialkylsulfonamide, $C_1$-$C_6$ haloalkoxy; $C_1$-$C_6$ haloalkyl, halogen, hydroxyl and nitro.

In some embodiments, $R^1$ is diphenylmethyl.

In some embodiments, $R^1$ is 2,3-difluorophenyl.

In some embodiments, $R^1$ is 2-fluoro-3-methoxyphenyl.

In some embodiments, $R^1$ is 2-fluorophenyl.

In some embodiments, $R^1$ is 2-fluoropyridin-4-yl.

In some embodiments, $R^1$ is 2-methoxyphenyl.

In some embodiments, $R^1$ is 3-(trifluoromethoxy)phenyl.

In some embodiments, $R^1$ is 3,4-difluorophenyl.

In some embodiments, $R^1$ is 3,5-difluorophenyl.

In some embodiments, $R^1$ is 3,5-dimethylphenyl.

In some embodiments, $R^1$ is 3-chloro-2-fluorophenyl.

In some embodiments, $R^1$ is 3-chloro-4-fluorophenyl.

In some embodiments, $R^1$ is 3-chloro-5-fluorophenyl.

In some embodiments, $R^1$ is 3-chlorophenyl.

In some embodiments, $R^1$ is 3-fluoro-4-methylphenyl.

In some embodiments, $R^1$ is 3-fluorophenyl.

In some embodiments, $R^1$ is 3-methoxyphenyl.

In some embodiments, $R^1$ is 3-tolyl.

In some embodiments, $R^1$ is 3-(trifluoromethyl)phenyl.

In some embodiments, $R^1$ is 4-(trifluoromethoxy)phenyl.

In some embodiments, $R^1$ is 4-chloro-3-fluorophenyl.

In some embodiments, $R^1$ is 4-chlorophenyl.

In some embodiments, $R^1$ is 4-ethoxyphenyl.

In some embodiments, $R^1$ is 4-fluorophenyl.

In some embodiments, $R^1$ is 4-methoxy-2methylphenyl.

In some embodiments, $R^1$ is 4-methoxyphenyl.

In some embodiments, $R^1$ is 4-tolyl.

In some embodiments, $R^1$ is 5-(trifluoromethyl)pyridin-2-yl.

In some embodiments, $R^1$ is 5-chloropyridin-2-yl.

In some embodiments, $R^1$ is 5-fluoropyridin-2-yl.

In some embodiments, $R^1$ is 5-fluoropyridin-3-yl.

In some embodiments, $R^1$ is 5-methoxypyridin-3-yl.

In some embodiments, $R^1$ is 5-methylpyridin-3-yl.

In some embodiments, $R^1$ is 5-methylthiazol-2-yl.

In some embodiments, $R^1$ is 5-methylthiophen-2-yl.

In some embodiments, $R^1$ is 6-fluoropyridin-3-yl.

In some embodiments, $R^1$ is phenyl.

In some embodiments, $R^1$ is pyrazin-2-yl.

In some embodiments, $R^1$ is pyridin-2-yl.

In some embodiments, $R^1$ is pyridin-3-yl.

The Group $R^2$:

In some embodiments, $R^2$ is selected from: H, $C_1$-$C_6$ alkyl, aryl and heteroacyl; wherein $C_1$-$C_6$ alkyl, aryl and heteroaryl are each optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen.

In some embodiments, $R^2$ is selected from: H, $C_1$-$C_6$ alkyl and aryl; wherein said aryl is optionally substituted with one or two substituents selected from: $C_1$-$C_6$ alkyl and halogen.

In some embodiments, $R^2$ is selected from: H, $C_1$-$C_6$ alkyl and aryl; wherein said aryl is optionally substituted with one or two substituents selected from: methyl and fluoro.

In some embodiments, $R^2$ is selected from: H, methyl, n-propyl, phenyl, 3-tolyl, 4-tolyl, 3-fluorophenyl and 4-fluorophenyl.

In some embodiments, $R^2$ is selected from: H, $C_1$-$C_6$ alkyl, aryl and heteroaryl; wherein $C_1$-$C_6$ alkyl, aryl and heteroaryl are each optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl, halogen and hydroxy.

In some embodiments, $R^2$ is selected from: H, $C_1$-$C_6$ alkyl and aryl; wherein said aryl is optionally substituted with one or two substituents selected from: $C_1$-$C_6$ alkyl, halogen and hydroxy.

In some embodiments, $R^2$ is selected from: H, $C_1$-$C_6$ alkyl and aryl; wherein said aryl is optionally substituted with one or two substituents selected from: methyl, fluoro and hydroxy.

In some embodiments, $R^2$ is selected from: H, methyl, n-propyl, phenyl, 3-tolyl, 4-tolyl, 3-fluorophenyl, 4-fluorophenyl and 4-hydroxyphenyl.

In some embodiments, $R^2$ is H.

In some embodiments, $R^2$ is methyl.

In some embodiments, $R^2$ is phenyl.

In some embodiments, $R^2$ is 3-tolyl.

In some embodiments, $R^2$ is 4-tolyl.

In some embodiments, $R^2$ is 3--fluorophenyl.

In some embodiments, $R^2$ is 4-fluorophenyl.

In some embodiments, $R^2$ is 4-hydroxyphenyl.

The Group $R^3$:

In some embodiments, $R^3$ is H.

In some embodiments, $R^3$ is $C_1$-$C_6$ alkyl.

In some embodiments, $R^3$ is methyl.

The Group X:

In some embodiments, X is O.

In some embodiments, X is $NR^3$.

The Group Q:

In some embodiments, Q is OH.

In some embodiments, Q is —$NHCH_2CH_2SO_3H$.

In some embodiments, Q is selected from: 1-carboxyethylamio, 1-carboxy-4-guanidinobutylamino, 3-amino-1-carboxy-3-oxopropylamino, 1,2-dicarboxyethylamino, 1-carboxy-2-mercaptoethylamino, 4-amino-1-carboxy-4-oxobutylamino, 3-carboxy-1-carboxylatopropylamino, carboxymethylamino, 1-carboxy-2-(1H-imidazol-4-yl)ethylamino, 1-carboxy-2-methylbutylamino, 1-carboxy-3-methylbutylamino, 5-amino-1-carboxypentyl amino, 1-carboxy-3-(methylthio)propylamino, 1-carboxy-2-phenylethylamino, 2-carboxypyrrolidin-1-yl, 1-carboxy-2-hydroxyethylamino, 1-carboxy-2-hydroxypropylamino 1-carboxy-2-(1H-indol-3-yl)ethylamino, 1-carboxy-2-(4-hydroxyphenyl)ethylamino and 1-carboxy-2-methylpropylamino.

In some embodiments, Q is selected from: (S)-1-carboxyethylamino, (S)-1-carboxy-4-guanidinobutylamino, (S)-3-amino-1-carboxy-3-oxopropylamino, (S)-1,2-dicarboxyethylamino, (S)-1-carboxy-2-mercaptoethylamino, (S)-4-amino-1-carboxy-4-oxobutylamino, (S)-3-carboxy-1-carboxylatopropylamino, carboxymethylamino, (S)-1-carboxy-2-(1H-imidazol-4-yl)ethylamino, (1S,2S)-1-carboxy-2-methylbutylamino, (S)-1-carboxy-3-methylbutylamino, (S)-5-amino-1-carboxypentylamino, (S)-1-carboxy-3-(methylthio)propylamino, (S)-1-carboxy-2-phenylethylamino, (S)-2-carboxypyrrolidin-1-yl, (S)-1-carboxy-2-hydroxyethylamino, (1S,2R)-1-carboxy-2-hydroxypropylamino, (S)-1-carboxy-2-(1H-indol-3-yl) ethylamino, (S)-1-carboxy-2-(4-hydroxyphenyl)ethylamino and (S)-1-carboxy-2-methylpropylamino.

In some embodiments, Q is 1-carboxyethylamino.

In some embodiments, Q is 1-carboxy-4-guanidinobutylamino.

In some embodiments, Q is 3-amino-1-carboxy-3-oxopropylamino.

In some embodiments, Q is 1,2-dicarboxyethylamino.

In some embodiments, Q is 1-carboxy-2-mercaptoethylamino.

In some embodiments, Q is 4-amino-1-carboxy-4-oxobutylamino.

In some embodiments, Q is 3-carboxy-1-carboxylatopropylamino.

In some embodiments, Q is carboxymethylamino.

In some embodiments, Q is 1-carboxy-2-(1H-imidazol-4-yl)ethylamino.

In some embodiments, Q is 1-carboxy-2-methylbutylamino.

In some embodiments, Q is 1-carboxy-3-methylbutylamino.

In some embodiments, Q is 5-amino-1-carboxypentylamino.

In some embodiments, Q is 1-carboxy-3-(methylthio) propylamino.

In some embodiments, Q is 1-carboxy-2-phenylethylamino.

In some embodiments, Q is 2-carboxypyrrolidin-1-yl.

In some embodiments, Q is 1-carboxy-2-hydroxyethylamino.

In some embodiments, Q is 1-carboxy-2-hydroxypropylamino.

In some embodiments, Q is 1-carboxy-2-(1H-indol-3-yl) ethylamino.

In some embodiments, Q is 1-carboxy-2-(4-hydroxyphenyl)ethylamino.

In some embodiments, Q is 1-carboxy-2-methylpropylamino.

In some embodiments, Q is (S)-1-carboxyethylamino.

In some embodiments, Q is (S)-1-carboxy-4-guanidinobutylamino.

In some embodiments, Q is (S)-3-amino-1-carboxy-3-oxopropylamino.

In some embodiments, Q is (S)-1,2-dicarboxyethylamino.

In some embodiments, Q is (S)-1-carboxy-2-mercaptoethylamino.

In some embodiments, Q is (S)-4-amino-1-carboxy-4-oxobutylamino.

In some embodiments, Q is (S)-3-carboxy-1-carboxylatopropylamino.

In some embodiments, Q is carboxymethylamino.

In some embodiments, Q is (S)-1-carboxy-2-(1H-imidazol-4-yl)ethylamino.

In some embodiments, Q is (1S,2S)-1-carboxy-2-methylbutylamino.

In some embodiments, Q is (S)-1-carboxy-3-methylbutylamino.

In some embodiments, Q is (S)-5-amino-1-carboxypentylamino.

In some embodiments, Q is (S)-1-carboxy-3-(methylthio) propylamino.

In some embodiments, Q is (S)-1-carboxy-2-phenylethylamino.

In some embodiments, Q is (S)-2-carboxypyrrolidin-1-yl.

In some embodiments, Q is (S)-1-carboxy-2-hydroxyethylamino.

In some embodiments, Q is (1S,2R)-1-carboxy-2-hydroxypropylamino.

In some embodiments, Q is (S)-1-carboxy-2-(1H-indol-3yl)ethylamino.

In some embodiments, Q is (S)-1-carboxy-2-(4-hydroxyphenyl)ethylamino.

In some embodiments, Q is (S)-1-carboxy-2-methylpropylamino.

Certain Combinations of the Present Invention:

One aspect of the present invention encompasses certain amide derivatives selected from compounds of Formula (XIIIc) and pharmaceutically acceptable salts, solvates and hydrates thereof:

(XIIIc)

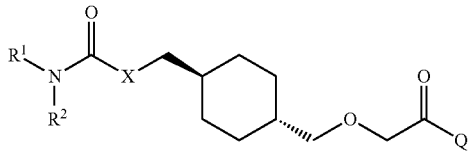

wherein:

$R^1$ and $R^2$ are each independently selected from: H, $C_1$-$C_6$ alkyl, aryl and heteroaryl; wherein $C_1$-$C_6$ alkyl, aryl and heteroaryl are each optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen;

X is O or $NR^3$;

$R^3$ is selected from H and $C_1$-$C_6$ alkyl; and

Q is selected from: OH, —$NHCH_2CH_2SO_3H$, 1-carboxyethylamino, 1-carboxy-4-guanidinobutylamino, 3-amino-1-carboxy-3-oxopropylamino, 1,2-dicarboxyethylamino, 1-carboxy-2-mercaptoethylamino, 4-amino-1-carboxy-4-oxobutylamino, 3-carboxy-1-carboxylatopropylamino, carboxymethylamino, 1-carboxy-2-(1H-imidazol-4-yl)ethylamino, 1-carboxy-2-methylbutylamino, 1-carboxy-3-methylbutylamino, 5-amino-1-carboxypentylamino, 1-carboxy-3-(methylthio)propylamino, 1-carboxy-2-phenylethylamino, 2-carboxypyrrolidin-1-yl, 1-carboxy-2-hydroxyethylamino, 1-carboxy-2-hydroxypropylamino, 1-carboxy-2-(1H-indol-3-yl)ethylamino, 1-carboxy-2-(4-hydroxyphenyl)ethylamino and 1-carboxy-2-methylpropylamino.

One aspect of the present invention encompasses certain amide derivatives selected from compounds of Formula (XIIIc) and pharmaceutically acceptable salts, solvates and hydrates thereof:

(XIIIc)

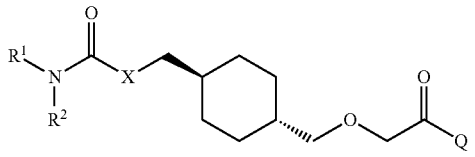

wherein:

$R^1$ is selected from: diphenylmethyl, 2,3-difluorophenyl, 2-fluoro-3-methoxyphenyl, 2-fluorophenyl, 2-fluoropyridin-4-yl, 2-methoxyphenyl, 3-(trifluoromethoxy)phenyl, 3,4-difluorophenyl, 3,5-difluorophenyl, 3,5-dimethylphenyl, 3-chloro-2-fluorophenyl, 3-chloro-4-fluorophenyl, 3-chloro-5-fluorophenyl, 3-chlorophenyl, 3-fluoro-4-methylphenyl, 3-fluorophenyl, 3-methoxyphenyl, 3-tolyl, 3-(trifluoromethyl)phenyl, 4-(trifluoromethoxy)phenyl, 4-chloro-3-fluorophenyl, 4-chlorophenyl, 4-ethoxyphenyl, 4-fluorophenyl, 4-methoxy-2-methylphenyl, 4-methoxyphenyl, 4-tolyl, 5-(trifluoromethyl)pyridin-2-yl, 5-chloropyridin-2-yl, 5-fluoropyridin-2-yl, 5-fluoropyridin-3-yl, 5-methoxypyridin-3-yl, 5-methylpyridin-3-yl, 5-methylthiazol-2-yl, 5-methylthiophen-2-yl, 6-fluoropyridin-3-yl, phenyl, pyrazin-2-yl, pyridin-2-yl and pyridin-3-yl;

$R^2$ is selected from: H, methyl, n-propyl, phenyl, 3-tolyl, 4-tolyl, 3-fluorophenyl and 4-fluorophenyl;

X is O or $NR^3$;

$R^3$ is selected from H and methyl; and

Q is selected from: OH, —$NHCH_2CH_2SO_3H$ and carboxymethylamino.

One aspect of the present invention encompasses certain amide derivatives selected from compounds of Formula (Mile) and pharmaceutically acceptable salts, solvates and hydrates thereof:

(XIIIe)

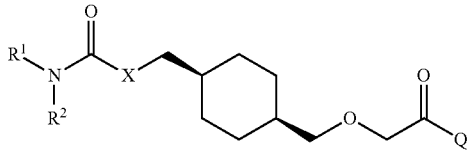

wherein:

$R^1$ and $R^2$ are each independently selected from: H. $C_1$-$C_6$ alkyl, aryl and heteroaryl; wherein $C_1$-$C_6$ alkyl, aryl and heteroaryl are each optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen;

X is O or $NR^3$;

$R^3$ is selected from H and $C_1$-$C_6$ alkyl; and

Q is selected from: OH, —$NHCH_2CH_2SO_3H$, 1-carboxyethylamino, 1-carboxy-4-guanidinobutylamino, 3-amino-1-carboxy-3-oxopropylamino, 1,2-dicarboxyethylamino, 1-carboxy-2-mercaptoethylamino, 4-amino-1-carboxy-4-oxobutylamino, 3-carboxy-1-carboxylatopropylamino, carboxymethylamino, 1-carboxy-2-(1H-imidazol-4-yl)ethylamino, 1-carboxy-2-methylbutylamino, 1-carboxy-3-methylbutylamino, 5-amino-1-carboxypentylamino, 1-carboxy-3-(methylthio)propylamino, 1-carboxy-2-phenylethylamino, 2-carboxypyrrolidin-1-yl, 1-carboxy-2-hydroxyethylamino, 1-carboxy-2-hydroxypropylamino, 1-carboxy-2-(1H-indol-3-yl)ethylamino, 1-carboxy-2-(4-hydroxy)phenyl)ethylamino and 1-carboxy-2-methylpropylamino.

One aspect of the present invention encompasses certain amide derivatives selected from compounds of Formula (XIIIe) and pharmaceutically acceptable salts, solvates and hydrates thereof:

(XIIIe)

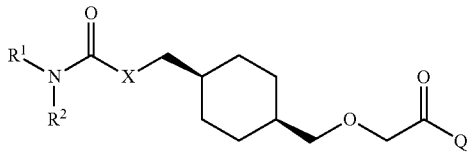

wherein:

$R^1$ is selected from: diphenylmethyl, 2,3-difluorophenyl, 2-fluoro-3-methoxyphenyl, 2-fluorophenyl, 2-fluoropyridin-4-yl, 2-methoxyphenyl, 3-(trifluoromethoxy)phenyl, 3,4-difluorophenyl, 3,5-difluorophenyl, 3,5-dimethylphenyl, 3-chloro-2-fluorophenyl, 3-chloro-4-fluorophenyl, 3-chloro-5-fluorophenyl, 3-chlorophenyl, 3-fluoro-4-methylphenyl, 3-fluorophenyl, 3-methoxyphenyl, 3-tolyl, 3-(trifluoromethyl)phenyl, 4-(trifluoromethoxy)phenyl, 4-chloro-3-fluorophenyl, 4-chlorophenyl, 4-ethoxyphenyl, 4-fluorophenyl, 4-methoxy-2-methylphenyl, 4-methoxyphenyl, 4-tolyl, 5-(trifluoromethyl)pyridin-2-yl, 5-chloropyridin-2-yl, 5-fluoropyridin-2-yl, 5-fluoropyridin-3-yl, 5-methoxypyridin-3-yl, 5-methylpyridin-3-yl, 5methylthiazol-2-yl, 5-methylthiophen-2-yl, 6-fluoropyridin-3-yl, phenyl, pyrazin-2-yl, pyridin-2-yl and pyridin-3-yl;

$R^2$ is selected from: H, methyl, n-propyl, phenyl, 3-tolyl, 4-tolyl, 3-fluorophenyl and 4-fluorophenyl;

X is O or $NR^3$;

$R^3$ is selected from H and methyl; and

Q is selected from: OH, —$NHCH_2CH_2SO_3H$ and carboxymethylamino.

One aspect of the present invention encompasses certain amide derivatives selected from compounds of Formula (XIIIg) and pharmaceutically acceptable salts, solvates and hydrates thereof:

(XIIIg)

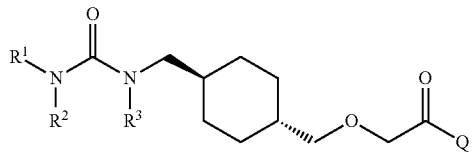

wherein:

$R^1$ and $R^2$ are each independently selected from: H, $C_1$-$C_6$ alkyl, aryl and heteroaryl; wherein $C_1$-$C_6$ alkyl, aryl and heteroaryl are each optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen; and $R^3$ is selected from H and $C_1$-$C_6$ alkyl; and Q is selected from: OH, —$NHCH_2CH_2SO_3H$, 1-carboxyethylamino, 1-carboxy-4-guanidinobutylamino, 3-amino-1-carboxy-3-oxopropylamino, 1,2-dicarboxyethylamino, 1-carboxy-2-mercaptoethylamino, 4-amino-1-carboxy-4-oxobutylamino, 3-carboxy-1-carboxylatopropylamino, carboxymethylamino, 1-carboxy-2-(1H-imidazol-4-yl)ethylamino, 1-carboxy-2-methylbutylamino, 1-carboxy-3-methylbutylamino, 5-amino-1-carboxypentylamino, 1-carboxy-3-(methylthio)propylamino, 1-carboxy-2-phenylethylamino, 2-carboxypyrrolidin-1-yl, 1-carboxy-2-hydroxyethylamino, 1-carboxy-2-hydroxypropylamino, 1-carboxy-2-(1H-indol-3-yl)ethylamino, 1-carboxy-2-(4-hydroxyphenyl)ethylamino and 1-carboxy-2-methylpropylamino.

One aspect of the present invention encompasses certain amide derivatives selected from compounds of Formula (XIIIg) and pharmaceutically acceptable salts, solvates and hydrates thereof:

(XIIIg)

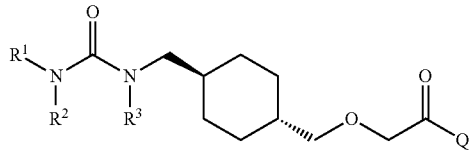

wherein:

$R^1$ is selected from: diphenylmethyl, 2,3-difluorophenyl, 2-fluoro-3-methoxyphenyl, 2-fluorophenyl, 2-fluoropyridin-4-yl, 2-methoxyphenyl, 3-(trifluoromethoxy)phenyl, 3,4-difluorophenyl, 3,5-difluorophenyl, 3,5-dimethylphenyl, 3-chloro-2-fluorophenyl, 3-chloro-4-fluorophenyl, 3-chloro-5-fluorophenyl, 3-chlorophenyl, 3-fluoro-4-methylphenyl, 3-fluorophenyl, 3-methoxyphenyl, 3-tolyl, 3-(trifluoromethyl)phenyl, 4-(trifluoromethoxy)phenyl, 4-chloro-3-fluorophenyl, 4-chlorophenyl, 4-ethoxyphenyl, 4-fluorophenyl, 4-methoxy-2-methylphenyl, 4-methoxyphenyl, 4-tolyl, 5-(trifluoromethyl)pyridin-2-yl, 5-chloropyridin-2-yl, 5-fluoropyridin-2-yl, 5-fluoropyridin-3-yl, 5-methoxypyridin-3-yl, 5-methylpyridin-3-yl, 5-methylthiazol-2-yl, 5-methylthiophen-2-yl, 6-fluoropyridin-3-yl, phenyl, pyrazin-2-yl, pyridin-2-yl and pyridin-3-yl;

$R^2$ is selected from: H, methyl, n-propyl, phenyl, 3-tolyl, 4-tolyl, 3-fluorophenyl and 4-fluorophenyl;

$R^3$ is selected from H and methyl; and

Q is selected from: OH, —$NHCH_2CH_2SO_3H$ and carboxymethylamino.

One aspect of the present invention encompasses certain amide derivatives selected from compounds of Formula (XIIIi) and pharmaceutically acceptable salts, solvates and hydrates thereof:

(XIIIi)

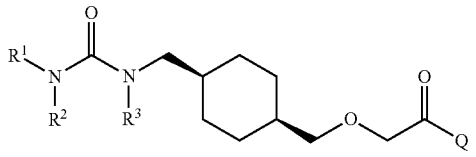

wherein:

$R^1$ and $R^2$ are each independently selected from: H, $C_1$-$C_6$ alkyl, aryl and heteroaryl; wherein $C_1$-$C_6$ alkyl, aryl and heteroaryl are each optionally substituted with one or two substituents selected from: $C_1$-$C_6$ alkoxy, $C_1$-$C_6$ alkyl, aryl, $C_1$-$C_6$ haloalkoxy; $C_1$-$C_6$ haloalkyl and halogen;

$R^3$ is selected from H and $C_1$-$C_6$ alkyl; and

Q is selected from: OH, —$NHCH_2CH_2SO_3H$, 1-carboxyethylamino, 1-carboxy-4-guanidinobutylamino, 3-amino-1-carboxy-3-oxopropylamino, 1,2-dicarboxyethylamino, 1-carboxy-2-mercaptoethylamino, 4-amino-1-carboxy-4-oxobutylamino, 3-carboxy-1-carboxylatopropylamino, carboxymethylamino, 1-carboxy-2-(1H-imidazol-4-yl)ethylamino, 1-carboxy-2-methylbutylamino, 1-carboxy-3-methylbutylamino, 5-amino-1-carboxypentylamino, 1-carboxy-3-(methylthio)propylamino, 1-carboxy-2-phenylethylamino, 2-carboxypyrrolidin-1-yl, 1-carboxy-2-hydroxyethylamino, 1-carboxy-2-hydroxypropylamino, 1-carboxy-2-(1H-indol-3-yl)ethylamino, 1-carboxy-2-(4-hydroxyphenyl)ethylamino and 1-carboxy-2-methylpropylamino.

One aspect of the present invention encompasses certain amide derivatives selected from compounds of Formula (XIIIi) and pharmaceutically acceptable salts, solvates and hydrates thereof:

(XIIIi)

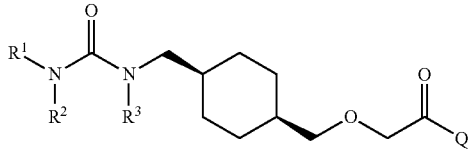

wherein:

$R^1$ is selected from: diphenylmethyl, 2,3-difluorophenyl, 2-fluoro-3-methoxyphenyl, 2-fluorophenyl, 2-fluoropyridin-4-yl, 2-methoxyphenyl, 3-(trifluoromethoxy)phenyl, 3,4-difluorophenyl, 3,5-difluorophenyl, 3,5-dimethylphenyl, 3-chloro-2-fluorophenyl, 3-chloro-4-fluorophenyl, 3-chloro-5-fluorophenyl, 3-chlorophenyl, 3-fluoro-4-methylphenyl, 3-fluorophenyl, 3-methoxyphenyl, 3-tolyl, 3-(trifluoromethyl)phenyl, 4-(trifluoromethoxy)phenyl, 4-chloro-3-fluorophenyl, 4-chlorophenyl, 4-ethoxyphenyl, 4-fluorophenyl, 4-methoxy-2-methylphenyl, 4-methoxyphenyl, 4-tolyl, 5-(trifluoromethyl)pyridin-2-yl, 5-chloropyridin-2-yl, 5-fluoropyridin-2-yl, 5-fluoropyridin-3-yl, 5-methoxypyridin-3-yl, 5-methylpyridin-3-yl, 5-methylthiazol-2-yl, 5-methylthiophen-2-yl, 6-fluoropyridin-3-yl, phenyl, pyrazin-2-yl, pyridin-2-yl and pyridin-3-yl;

$R^2$ is selected from: H, methyl, n-propyl, phenyl, 3-tolyl, 4-tolyl, 3-fluorophenyl and 4-fluorophenyl;

$R^3$ is selected from H and methyl; and

Q is selected from: OH, —$NHCH_2CH_2SO_3H$ and carboxymethylamino.

One aspect of the present invention encompasses certain amide derivatives selected from compounds of Formula (XIIIk) and pharmaceutically acceptable salts, solvates and hydrates thereof:

(XIIIk)

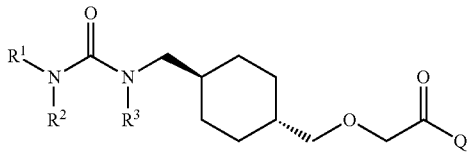

wherein:

$R^1$ and $R^2$ are each independently selected from: H, $C_1$-$C_6$ alkyl, aryl and heteroaryl; wherein $C_1$-$C_6$ alkyl, aryl and heteroaryl are each optionally substituted with one or two substituents selected from: $C_1$-$C_6$ alkoxy, $C_1$-$C_6$ alkyl, aryl, $C_1$-$C_6$ haloalkoxy; $C_1$-$C_6$ haloalkyl and halogen; and Q is selected from: OH, —$NHCH_2CH_2SO_3H$, 1-carboxyethylamino, 1-carboxy-4-guanidinobutylamino, 3-amino-1-carboxy-3-oxopropylamino, 1,2-dicarboxyethylamino, 1-carboxy-2-mercaptoethylamino, 4-amino-1-carboxy-4-oxobutylamino, 3-carboxy-1-carboxylatopropylamino, carboxymethylamino, 1-carboxy-2-(1H-imidazol-4-yl)ethylamino, 1-carboxy-2-methylbutylamino, 1-carboxy-3-methylbutylamino, 5-amino-1-carboxypentylamino, 1-carboxy-3-(methylthio)propylamino, 1-carboxy-2-phenylethylamino, 2-carboxypyrrolidin-1-yl, 1-carboxy-2-hydroxyethylamino, 1-carboxy-2-hydroxypropylamino, 1-carboxy-2-(1H-indol-3-yl)ethylamino, 1-carboxy-2-(4-hydroxyphenyl)ethylamio and 1-carboxy-2-methylpropylamino.

One aspect of the present invention encompasses certain amide derivatives selected from compounds of Formula (XIIIk) and pharmaceutically acceptable salts, solvates and hydrates thereof:

(XIIIk)

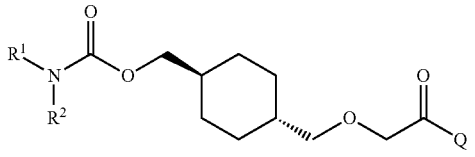

wherein:

$R^1$ is selected from: diphenylmethyl, 2,3-difluorophenyl, 2-fluoro-3-methoxyphenyl, 2-fluorophenyl, 2-fluoropyridin-4-yl, 2-methoxyphenyl, 3-(trifluoromethoxy)phenyl, 3,4-difluorophenyl, 3,5-difluorophenyl, 3,5-dimethylphenyl, 3-chloro-2-fluorophenyl, 3-chloro-4-fluorophenyl, 3-chloro-5-fluorophenyl, 3-chlorophenyl, 3-fluoro-4-methylphenyl, 3-fluorophenyl, 3-methoxyphenyl, 3-tolyl, 3-(trifluoromethyl)phenyl, 4-(trifluoromethoxy)phenyl, 4-chloro-3-fluorophenyl, 4-chlorophenyl, 4-ethoxyphenyl, 4-fluorophenyl, 4-methoxy-2-methylphenyl, 4-methoxyphenyl, 4-tolyl, 5-(trifluoromethyl)pyridin-2-yl, 5-chloropyridin-2-yl, 5-fluoropyridin-2-yl, 5-fluoropyridin-3-yl, 5-methoxypyridin-3-yl, 5-methylpyridin-3-yl, 5-methylthiazol-2-yl, 5-methylthiophen-2-yl, 6-fluoropyridin-3-yl, phenyl, pyrazin-2-yl, pyridin-2-yl and pyridin-3-yl;

$R^2$ is selected from: H, methyl, n-propyl, phenyl, 3-tolyl, 4-tolyl, 3-fluorophenyl and 4-fluorophenyl; and Q is selected from: OH, —$NHCH_2CH_2SO_3H$ and carboxymethylamino.

One aspect of the present invention encompasses certain amide derivatives selected from compounds of Formula (XIIIm) and pharmaceutically acceptable salts, solvates and hydrates thereof:

(XIIIm)

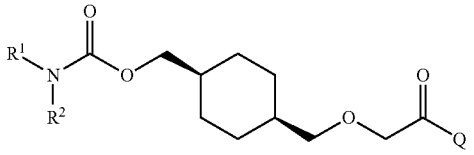

wherein:

$R^1$ and $R^2$ are each independently selected from: H, $C_1$-$C_6$ alkyl, aryl and heteroaryl; wherein $C_1$-$C_6$ alkyl, aryl and heteroaryl are each optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen; and Q is selected from: OH, —$NHCH_2CH_2SO_3H$, 1-carboxyethylamino, 1-carboxy-4-guanidinobutylamino, 3-amino-1-carboxy-3-oxopropylamino, 1,2-dicarboxyethylamino, 1-carboxy-2-mercaptoethylamino, 4-amino-1-carboxy-4-oxobutylamino, 3-carboxy-1-carboxylatopropylamino, carboxymethylamino, 1-carboxy-2-(1H-imidazol-4-yl)ethylamino, 1-carboxy-2-methylbutylamino, 1-carboxy-3-methylbutylamino, 5-amino-1-carboxypentylamino, 1-carboxy-3-(methylthio)propylamino, 1-carboxy-2-phenylethylamino, 2-carboxypyrrolidin-1-yl, 1-carboxy-2-hydroxyethylamino, 1-carboxy-2-hydroxypropylamino, 1-carboxy-2-(1H-indol-3-yl)ethylamino, 1-carboxy-2-(4-hydroxyphenyl)ethylamino and 1-carboxy-2-methylpropylamino.

The compound according to claim 1, selected from compounds of Formula (XIIIm) and pharmaceutically acceptable salts, solvates and hydrates thereof:

(XIIIm)

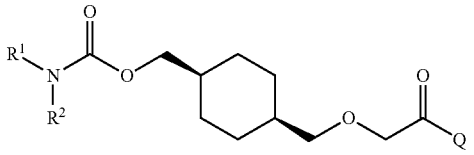

wherein:

$R^1$ is selected from: diphenylmethyl, 2,3-difluorophenyl, 2-fluoro-3-methoxyphenyl, 2-fluorophenyl, 2-fluoropyridin-4-yl, 2-methoxyphenyl, 3-(trifluoromethoxy)phenyl, 3,4-difluorophenyl, 3,5-difluorophenyl, 3,5-dimethylphenyl, 3-chloro-2-fluorophenyl, 3-chloro-4-fluorophenyl, 3-chloro-5-fluorophenyl, 3-chlorophenyl, 3-fluoro-4-methylphenyl, 3-fluorophenyl, 3-methoxyphenyl, 3-tolyl, 3-(trifluoromethyl)phenyl, 4-(trifluoromethoxy)phenyl, 4-chloro-3-fluorophenyl, 4-chlorophenyl, 4-ethoxyphenyl, 4-fluorophenyl, 4-methoxy-2-methylphenyl, 4-methoxyphenyl, 4-tolyl, 5-(trifluoromethyl)pyridin-2-yl, 5-chloropyridin-2-yl, 5-fluoropyridin-2-yl, 5-fluoropyridin-3-yl, 5-methoxypyridin-3-yl, 5-methylpyridin-3-yl, 5-methylthiazol-2-yl, 5-methylthiophen-2-yl, 6-fluoropyridin-3-yl, phenyl, pyrazin-2-yl, pyridin-2-yl and pyridin-3-yl;

$R^2$ is selected from: H, methyl, n-propyl, phenyl, 3-tolyl, 4-tolyl, 3-fluorophenyl and 4-fluorophenyl; and Q is selected from: OH, —$NHCH_2CH_2SO_3H$ and carboxymethylamino.

One aspect of the present invention encompasses certain amide derivatives selected from compounds of Formula (Ia) and pharmaceutically acceptable salts, solvates and hydrates thereof:

(Ia)

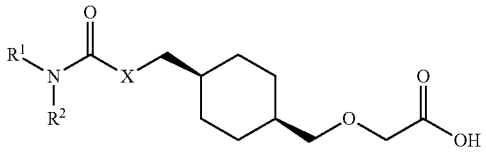

wherein:

$R^1$ and $R^2$ are each independently selected from: H, $C_1$-$C_6$ alkyl, aryl and heteroaryl; wherein $C_1$-$C_6$ alkyl, aryl and heteroaryl are each optionally substituted with one, two or three substituents selected from: $C_1$-$C_6$ acyl, $C_1$-$C_6$ alkoxy, $C_1$-$C_6$ alkyl, $C_1$-$C_6$ alkylamino, $C_1$-$C_6$ alkylcarboxamide, $C_1$-$C_6$ alkylsulfanyl, $C_1$-$C_6$ alkylsulfinyl, $C_1$-$C_6$ alkylsulfonamide, $C_1$-$C_6$ alkylsulfonyl, amino, aryl, carbo-$C_1$-$C_6$-alkoxy, carboxamide, carboxy, cyano, $C_2$-$C_8$ dialkylamino, $C_2$-$C_8$ dialkylcarboxamide, $C_2$-$C_8$ dialkylsulfonamide, $C_1$-$C_6$ haloalkoxy, $C_1$-$C_6$ haloalkyl, halogen, hydroxyl and nitro;

X is O or $NR^3$; and $R^3$ is selected from H and $C_1$-$C_6$ alkyl.

In some embodiments, $R^1$ and $R^2$ are each independently selected from: H, $C_1$-$C_6$ alkyl, aryl and heteroaryl; wherein $C_1$-$C_6$ alkyl, aryl and heteroaryl are each optionally substituted with one, two or three substituents selected from: $C_1$-$C_6$ acyl, $C_1$-$C_6$ alkoxy, $C_1$-$C_6$ alkyl, $C_1$-$C_6$ alkylamino, $C_1$-$C_6$ alkylcarboxamide, $C_1$-$C_6$ alkylsulfanyl, $C_1$-$C_6$ alkylsulfinyl, $C_1$-$C_6$ alkylsulfonamide, $C_1$-$C_6$ alkylsulfonyl, amino, aryl, carbo-$C_1$-$C_6$-alkoxy, carboxamide, carboxy, cyano, $C_2$-$C_8$ dialkylamino, $C_2$-$C_8$ dialkylcarboxamide, $C_2$-$C_8$ dialkylsulfonamide, $C_1$-$C_6$ haloalkoxy, $C_1$-$C_6$ haloalkyl, halogen, hydroxyl and nitro.

In some embodiments, $R^1$ is selected from: $C_1$-$C_6$ alkyl, aryl and heteroaryl; wherein $C_1$-$C_6$ alkyl, aryl and heteroaryl are each optionally substituted with one, two or three substituents selected from: $C_1$-$C_6$ acyl, $C_1$-$C_6$ alkoxy, $C_1$-$C_6$ alkyl, $C_1$-$C_6$ alkylamino, $C_1$-$C_6$ alkylcarboxamide, $C_1$-$C_6$ alkylsulfanyl, $C_1$-$C_6$ alkylsulfinyl, $C_1$-$C_6$ alkylsulfonamide, $C_1$-$C_6$ alkylsulfonyl, amino, aryl, carbo-$C_1$-$C_6$-alkoxy, carboxamide, carboxy, cyano, $C_2$-$C_8$ dialkylamino, $C_2$-$C_8$ dialkylcarboxamide, $C_2$-$C_8$ dialkylsulfonamide, $C_1$-$C_6$ haloalkoxy; $C_1$-$C_6$ haloalkyl, hydrogen, hydroxyl and nitro; and $R^2$ is selected from: H, $C_1$-$C_6$ alkyl and aryl; wherein said aryl is optionally substituted with one of two substituents selected from: $C_1$-$C_6$ alkyl and halogen.

In some embodiments $R^1$ is selected from: $C_1$-$C_6$ alkyl, aryl and heteroaryl; wherein $C_1$-$C_6$ alkyl, aryl and heteroaryl are each optionally substituted with one, two or three substituents selected from: $C_1$-$C_6$ acyl, $C_1$-$C_6$ alkoxy, $C_1$-$C_6$ alkyl, $C_1$-$C_6$ alkylamino, $C_1$-$C_6$ alkylcarboxamide, $C_1$-$C_6$ alkylsulfanyl, $C_1$-$C_6$ alkylsulfinyl, $C_1$-$C_6$ alkylsulfonamide, $C_1$-$C_6$ alkylsulfonyl, amino, aryl, carbo-$C_1$-$C_6$-alkoxy, carboxamide, carboxy, cyano, $C_2$-$C_8$ dialkylamino, $C_2$-$C_8$ dialkylcarboxamide, $C_2$-$C_8$ dialkylsulfonamide, $C_1$-$C_6$ haloalkoxy, $C_1$-$C_6$ haloalkyl, halogen, hydroxyl and nitro; and $R^2$ is selected from: H, methyl, n-propyl, phenyl, 3-tolyl, 4-tolyl, 3-fluorophenyl and 4-fluorophenyl.

In some embodiments, $R^1$ and $R^2$ are each independently selected from: H, $C_1$-$C_6$ alkyl, aryl and heteroaryl; wherein $C_1$-$C_6$ alkyl, aryl and heteroaryl are each optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen.

In some embodiments, $R^1$ and $R^2$ are each independently selected from: H, $C_1$-$C_6$ alkyl, aryl and heteroaryl; wherein $C_1$-$C_6$ alkyl, aryl and heteroaryl are each optionally substituted with one or two substituents selected from: methoxy, ethoxy, methyl, phenyl, trifluoromethyl, trifluoromethoxy, fluoro and chloro.

In some embodiments, $R^1$ and $R^2$ are each independently selected from: H, diphenylmethyl, 2,3-difluorophenyl, 2-fluoro-3-methoxyphenyl, 2-fluorophenyl, 2-fluoropyridin-4-yl, 2-methoxyphenyl, 3-(trifluoromethoxy)phenyl, 3,4-difluorophenyl, 3,5-difluorophenyl, 3,5-dimethylphenyl, 3-chloro-2-fluorophenyl, 3-chloro-4-fluorophenyl, 3-chloro-5-fluorophenyl, 3-chlorophenyl, 3-fluoro-4-methylphenyl, 3-fluorophenyl, 3-methoxyphenyl, 3-tolyl, 3-(trifluoromethyl)phenyl, 4-(trifluoromethoxy)phenyl, 4-chloro-3-fluorophenyl, 4-chlorophenyl, 4-ethoxyphenyl, 4-fluorophenyl, 4-methoxy-2-methylphenyl, 4-methoxyphenyl, 4-tolyl, 5-(trifluoromethyl)pyridin-2-yl, 5-chloropyridin-2-yl, 5-fluoropyridin-2-yl, 5-fluoropyridin-3-yl, 5-methoxypyridin-3-yl, 5-methylpyridin-3-yl, 5-methylthiazol-2-yl, 5-methylthiophen-2-yl, 6-fluoropyridin-3-yl, methyl, phenyl, n-propyl, pyrazin-2-yl, pyridin-2-yl and pyridin-3-yl.

In some embodiments, $R^1$ is selected from: $C_1$-$C_6$ alkyl, aryl and heteroaryl; each optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen; $R^2$ is selected from: H, $C_1$-$C_6$ alkyl and aryl; wherein said aryl is optionally substituted with one or two substituents selected from: $C_1$-$C_6$ alkyl and halogen.

In some embodiments, $R^1$ is selected from: $C_1$-$C_6$ alkyl, aryl and heteroaryl; each optionally substituted with one or two substituents selected from: methoxy, ethoxy, methyl, phenyl, trifluoromethyl, trifluoromethoxy, fluoro and chloro; and $R^2$ is selected from: H, $C_1$-$C_6$ alkyl and aryl; wherein said aryl is optionally substituted with one or two substituents selected from: methyl and fluoro.

In some embodiments, $R^1$ is selected from: diphenylmethyl, 2,3-difluorophenyl, 2-fluoro-3-methoxyphenyl, 2-fluorophenyl, 2-fluoropyridin-4-yl, 2-methoxyphenyl, 3-(trifluoromethoxy)phenyl, 3,4-difluorophenyl, 3,5-difluorophenyl, 3,5-dimethylphenyl, 3-chloro-2-fluorophenyl, 3-chloro-4-fluorophenyl, 3-chloro-5-fluorophenyl, 3-chlorophenyl, 3-fluoro-4-methylphenyl, 3-fluorophenyl, 3-methoxyphenyl, 3-tolyl, 3-(trifluoromethyl)phenyl, 4-(trifluoromethoxy)phenyl, 4-chloro-3-fluorophenyl, 4-chlorophenyl, 4-ethoxyphenyl, 4-fluorophenyl, 4-methoxy-2-methylphenyl, 4-methoxyphenyl, 4-tolyl, 5-(trifluoromethyl)pyridin-2-yl, 5-chloropyridin-2-yl, 5-fluoropyridin-2-yl, 5-fluoropyridin-3-yl, 5-methoxypyridine-3-yl, 5-methylpyridin-3-yl, 5-methylthiazol-2-yl, 5-methylthiophen-2-yl, 6-fluoropyridin-3-yl, phenyl, pyrazin-2-yl, pyridin-2-yl and pyridin-3-yl; and $R^2$ is selected from: H, methyl, n-propyl, phenyl, 3-tolyl, 4-tolyl, 3-fluorophenyl and 4-fluorophenyl.

The embodiments of the present invention pertain to compounds of Formula (Ic) and pharmaceutically acceptable salts, solvates and hydrates thereof:

(Ic)

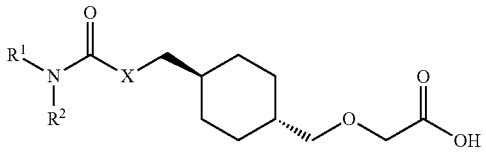

wherein:

$R^1$ and $R^2$ are each independently selected from: H, $C_1$-$C_6$ alkyl, aryl and heteroaryl; wherein $C_1$-$C_6$ alkyl, aryl and heteroaryl are each optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen;

X is O or $NR^3$; and $R^3$ is selected from H and $C_1$-$C_6$ alkyl.

The some embodiments of the present invention pertain to compounds of Formula (Ic) and pharmaceutically acceptable salts, solvates and hydrates thereof:

(Ic)

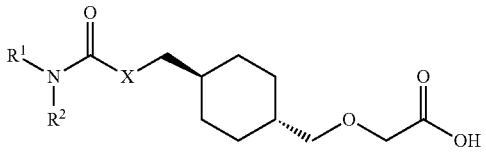

wherein:

$R^1$ is selected from: diphenylmethyl, 2,3-difluorophenyl, 2-fluoro-3-methoxyphenyl, 2-fluorophenyl, 2-fluoropyridin-4-yl, 2-methoxyphenyl, 3-(trifluoromethoxy)phenyl, 3,4-difluorophenyl, 3,5-difluorophenyl, 3,5-dimethylphenyl, 3-chloro-2-fluorophenyl, 3-chloro-4-fluorophenyl, 3-chloro-5-fluorophenyl, 3-chlorophenyl, 3-fluoro-4-methylphenyl, 3-fluorophenyl, 3-methoxyphenyl, 3-tolyl, 3-(trifluoromethyl)phenyl, 4-(trifluoromethoxy)phenyl, 4-chloro-3-fluorophenyl, 4-chlorophenyl, 4-ethoxyphenyl, 4-fluorophenyl, 4-methoxy-2-methylphenyl, 4-methoxyphenyl, 4-tolyl, 5-(trifluoromethyl)pyridin-2-yl, 5-chloropyridin-2-yl, 5-fluoropyridin-2-yl, 5-fluoropyridin-3-yl, 5-methoxypyridin-3-yl, 5-methylpyridin-3-yl, 5-methylthiazol-2-yl, 5-methylthiophen-2-yl, 6-fluoropyridin-3-yl, phenyl, pyrazin-2-yl, pyridin-2-yl and pyridin-3-yl;

$R^2$ is selected from: H, methyl, n-propyl, phenyl, 3-tolyl, 4-tolyl, 3-fluorophenyl and 4-fluorophenyl;

X is O or $NR^3$; and $R^3$ is selected from H and methyl.

The embodiments of the present invention pertain to compounds of Formula (Ie) and pharmaceutically acceptable salts, solvates and hydrates thereof:

(Ie)

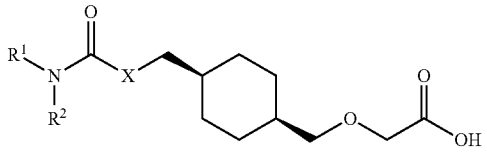

wherein:

$R^1$ and $R^2$ are each independently selected from: H, $C_1$-$C_6$ alkyl, aryl and heteroaryl; wherein $C_1$-$C_6$ alkyl, aryl and heteroaryl are each optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen;

X is O or $NR^3$; and $R^3$ is selected from H and $C_1$-$C_6$ alkyl.

The embodiments of the present invention pertain to compounds of Formula (Ic) and pharmaceutically acceptable salts, solvates and hydrates thereof:

(Ie)

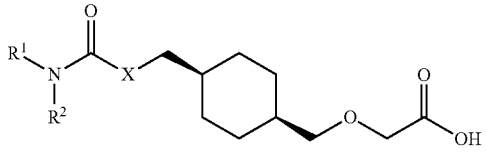

wherein:

$R^1$ is selected from: diphenylmethyl, 2,3-difluorophenyl, 2-fluoro-3-methoxyphenyl, 2-fluorophenyl, 2-fluoropyridin-4-yl, 2-methoxyphenyl, 3-(trifluoromethoxy)phenyl, 3,4-difluorophenyl, 3,5-difluorophenyl, 3,5-dimethylphenyl, 3-chloro-2-fluorophenyl, 3-chloro-4-fluorophenyl, 3-chloro-5-fluorophenyl, 3-chlorophenyl, 3-fluoro-4-methylphenyl, 3-fluorophenyl, 3-methoxyphenyl, 3-tolyl, 3-(trifluoromethyl)phenyl, 4-(trifluoromethoxy)phenyl, 4-chloro-3-fluorophenyl, 4-chlorophenyl, 4-ethoxyphenyl, 4-fluorophenyl, 4-methoxy-2-methylphenyl, 4-methoxyphenyl, 4-tolyl, 5-(trifluoromethyl)pyridin-2-yl, 5-chloropyridin-2-yl, 5-fluoropyridin-2-yl, 5-fluoropyridin-3-yl, 5-methoxypyridin-3-yl, 5-methylpyridin-3-yl, 5-methylthiazol-2-yl, 5-methylthiophen-2-yl, 6-fluoropyridin-3-yl, phenyl, pyrazin-2-yl, pyridin-2-yl and pyridin-3-yl;

$R^2$ is selected from: H, methyl, n-propyl, phenyl, 3-tolyl, 4-tolyl, 3-fluorophenyl and 4-fluorophenyl;

X is O or $NR^3$; and $R^3$ is selected from H and methyl.

The embodiments of the present invention pertain to compounds of Formula (Ig) and pharmaceutically acceptable salts, solvates and hydrates thereof:

(Ig)

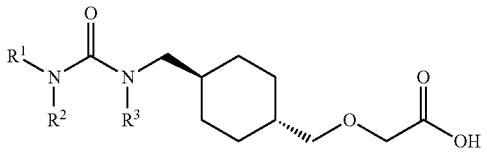

wherein:

$R^1$ and $R^2$ are each independently selected from: H, $C_1$-$C_6$ alkyl, aryl and heteroaryl; wherein $C_1$-$C_6$ alkyl, aryl and heteroaryl are each optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen; and $R^3$ is selected from H and $C_1$-$C_6$ alkyl.

The embodiments of the present invention pertain to compounds of Formula (Ig) and pharmaceutically acceptable salts, solvates and hydrates thereof:

(Ig)

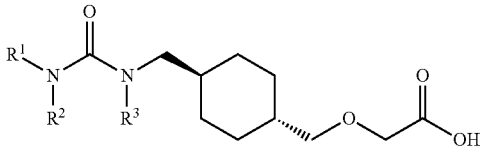

wherein:

$R^1$ is selected from: diphenylmethyl, 2,3-difluorophenyl, 2-fluoro-3-methoxyphenyl, 2-fluorophenyl, 2-fluoropyridin-4-yl, 2-methoxyphenyl, 3-(trifluoromethoxy)phenyl, 3,4-difluorophenyl, 3,5-difluorophenyl, 3,5-dimethylphenyl, 3-chloro-2-fluorophenyl, 3-chloro-4-fluorophenyl, 3-chloro-5-fluorophenyl, 3-chlorophenyl, 3-fluoro-4-methylphenyl, 3-fluorophenyl, 3-methoxyphenyl, 3-tolyl, 3-(trifluoromethyl)phenyl, 4-(trifluoromethoxy)phenyl, 4-chloro-3-fluorophenyl, 4-chlorophenyl, 4-ethoxyphenyl, 4-fluorophenyl, 4-methoxy-2-methylphenyl, 4-methoxyphenyl, 4-tolyl, 5-(trifluoromethyl)pyridin-2-yl, 5-chloropyridin-2-yl, 5-fluoropyridin-2-yl, 5-fluoropyridin-3-yl, 5-methoxypyridin-3-yl, 5-methylpyridin-3-yl, 5-methylthiazol-2-yl, 5-methylthiophen-2-yl, 6-fluoropyridin-3-yl, phenyl, pyrazin-2-yl, pyridin-2-yl and pyridin-3-yl;

$R^2$ is selected from: H, methyl, n-propyl, phenyl, 3-tolyl, 4-tolyl, 3-fluorophenyl and 4-fluorophenyl; and $R^3$ is selected from H and methyl.

The embodiments of the present invention pertain to compounds of Formula (Ii) and pharmaceutically acceptable salts, solvates and hydrates thereof:

(Ii)

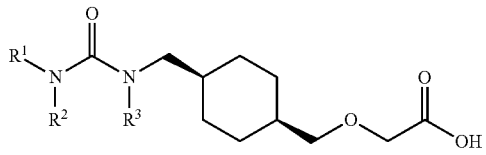

wherein:

$R^1$ and $R^2$ are each independently selected from: H, $C_1$-$C_6$ alkyl, aryl and heteroaryl; wherein $C_1$-$C_6$ alkyl, aryl and heteroaryl are each optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen; and $R^3$ is selected from H and $C_1$-$C_6$ alkyl.

The embodiments of the present invention pertain to compounds of Formula (Ii) and pharmaceutically acceptable salts, solvates and hydrates thereof:

(Ii)

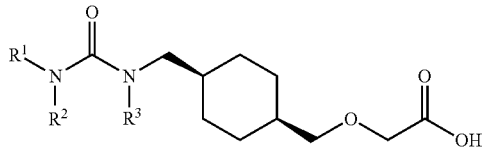

wherein:

$R^1$ is selected from: diphenylmethyl, 2,3-difluorophenyl, 2-fluoro-3-methoxyphenyl, 2-fluorophenyl, 2-fluoropyridin-4-yl, 2-methoxyphenyl, 3-(trifluoromethoxy)phenyl, 3,4-difluorophenyl, 3,5-difluorophenyl, 3,5-dimethylphenyl, 3-chloro-2-fluorophenyl, 3-chloro-4-fluorophenyl, 3-chloro-5-fluorophenyl, 3-chlorophenyl, 3-fluoro-4-methylphenyl, 3-fluorophenyl, 3-methoxyphenyl, 3-tolyl, 3-(trifluoromethyl)phenyl, 4-(trifluoromethoxy)phenyl, 4-chloro-3-fluorophenyl, 4-chlorophenyl, 4-ethoxyphenyl, 4-fluorophenyl, 4-methoxy-2-methylphenyl, 4-methoxyphenyl, 4-tolyl, 5-(trifluoromethyl)pyridin-2-yl, 5-chloropyridin-2-yl, 5-fluoropyridin-2-yl, 5-fluoropyridin-3-yl, 5-methoxypyridin-3-yl, 5-methylpyridin-3-yl, 5-methylthiazol-2-yl, 5-methylthiophen-2-yl, 6-fluoropyridin-3-yl, phenyl, pyrazin-2-yl, pyridin-2-yl and pyridin-3-yl;

$R^2$ is selected from: H, methyl, n-propyl, phenyl, 3-tolyl, 4-tolyl, 3-fluorophenyl and 4-fluorophenyl; and $R^3$ is selected from H and methyl.

The embodiments of the present invention pertain to compounds of Formula (Ik) and pharmaceutically acceptable salts, solvates and hydrates thereof:

(Ik)

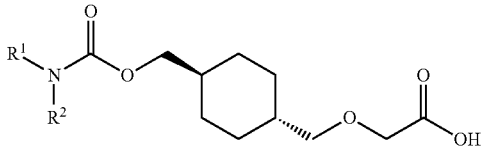

wherein:

$R^1$ and $R^2$ are each independently selected from: H, $C_1$-$C_6$ alkyl, aryl and heteroaryl; wherein $C_1$-$C_6$ alkyl, aryl and heteroaryl are each optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen.

The embodiments of the present invention pertain to compounds of Formula (Ik) and pharmaceutically acceptable salts, solvates and hydrates thereof:

(Ik)

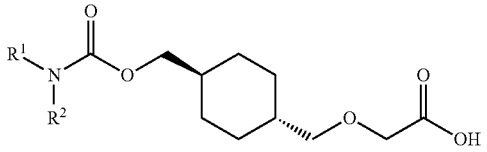

wherein:

$R^1$ is selected from: diphenylmethyl, 2,3-difluorophenyl, 2-fluoro-3-methoxyphenyl, 2-fluorophenyl, 2-fluoropyridin-4-yl, 2-methoxyphenyl, 3-(trifluoromethoxy)phenyl, 3,4-difluorophenyl, 3,5-difluorophenyl, 3,5-dimethylphenyl, 3-chloro-2-fluorophenyl, 3-chloro-4-fluorophenyl, 3-chloro-5-fluorophenyl, 3-chlorophenyl, 3-fluoro-4-methylphenyl, 3-fluorophenyl, 3-methoxyphenyl, 3-tolyl, 3-(trifluoromethyl)phenyl, 4-(trifluoromethoxy)phenyl, 4-chloro-3-fluorophenyl, 4-chlorophenyl, 4-ethoxyphenyl, 4-fluorophenyl, 4-methoxy-2-methylphenyl, 4-methoxyphenyl, 4-tolyl, 5-(trifluoromethyl)pyridin-2-yl, 5-chloropyridin-2-yl, 5-fluoropyridin-2-yl, 5-fluoropyridin-3-yl, 5-methoxypyridin-3-yl, 5-methylpyridin-3-yl, 5-methylthiazol-2-yl, 5-methylthiophen-2-yl, 6-fluoropyridin-3-yl, phenyl, pyrazin-2-yl, pyridin-2-yl and pyridin-3-yl; and $R^2$ is selected from: H, methyl, n-propyl, phenyl, 3-tolyl, 4-tolyl, 3-fluorophenyl and 4-fluorophenyl.

The embodiments of the present invention pertain to compounds of Formula (Im) and pharmaceutically acceptable salts, solvates and hydrates thereof:

(Im)

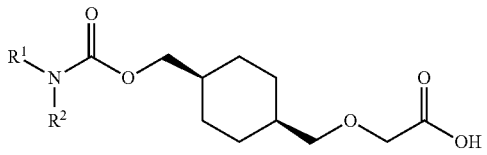

wherein:

$R^1$ and $R^2$ are each independently selected from: H, $C_1$-$C_6$ alkyl, aryl and heteroaryl; wherein $C_1$-$C_6$ alkyl, aryl and heteroaryl are each optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen.

The embodiments of the present invention pertain to compounds of Formula (Im) and pharmaceutically acceptable salts, solvates and hydrates thereof:

(Im)

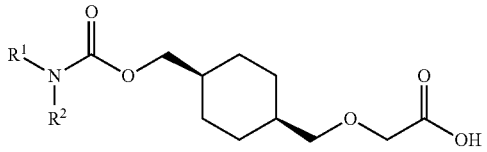

wherein:

$R^1$ is selected from: diphenylmethyl, 2,3-difluorophenyl, 2-fluoro-3-methoxyphenyl, 2-fluorophenyl, 2-fluoropyridin-4-yl, 2-methoxyphenyl, 3-(trifluoromethoxy)phenyl, 3,4-difluorophenyl, 3,5-difluorophenyl, 3,5-dimethylphenyl, 3-chloro-2-fluorophenyl, 3-chloro-4-fluorophenyl, 3-chloro-5-fluorophenyl, 3-chlorophenyl, 3-fluoro-4-methylphenyl, 3-fluorophenyl, 3-methoxyphenyl, 3-tolyl, 3-(trifluoromethyl)phenyl, 4-(trifluoromethoxy)phenyl, 4-chloro-3-fluorophenyl, 4-chlorophenyl, 4-ethoxyphenyl, 4-fluorophenyl, 4-methoxy-2-methylphenyl, 4-methoxyphenyl, 4-tolyl, 5-(trifluoromethyl)pyridin-2-yl, 5-chloropyridin-2-yl, 5-fluoropyridin-2-yl, 5-fluoropyridin-3-yl, 5-methoxypyridin-3-yl, 5-methylpyridin-3-yl, 5-methylthiazol-2-yl, 5-methylthiophen-2-yl, 6-fluoropyridin-3-yl, phenyl, pyrazin-2-yl, pyridin-2-yl and pyridin-3-yl; and $R^2$ is selected from: H, methyl, n-propyl, phenyl, 3-tolyl, 4-tolyl, 3-fluorophenyl and 4-fluorophenyl.

The embodiments of the present invention include every combination of one or more compounds selected from the following group:

2-((4-((3-benzhydrylureido)methyl)cyclohexyl)methoxy) acetic acid;

2-((4-((3,3-diphenylureido)methyl)cyclohexyl)methoxy) acetic acid;

2-((4-((3-(3-fluorophenyl-3-phenylureido)methyl)cyclohexyl)methoxy)acetic acid;

2-((4-((1-methyl-3,3-diphenylureido)methyl)cyclohexyl) methoxy)acetic acid;

2-((4-((diphenylcarbamoyloxy)methyl)cyclohexyl) methoxy)acetic acid;

2-((4-((3-(3-chlorophenyl)-3-phenylureido)methyl)cyclohexyl)methoxy)acetic acid;
2-((-4-((3-(4-fluorophenyl)-3-phenylureido)methyl)cyclohexyl)methoxy)acetic acid;
2-((-4-((3-(2-fluorophenyl)-3-phenylureido)methyl)cyclohexyl)methoxy)acetic acid;
2-((-4-((3-(4-chlorophenyl)-3-phenylureido)methyl)cyclohexyl)methoxy)acetic acid;
2-((-4-((3-phenyl-3-m-tolylureido)methyl)cyclohexyl)methoxy)acetic acid;
2-((-4-((3-phenyl-3-p-tolylureido)methyl)cyclohexyl)methoxy)acetic acid;
2-((-4-((3-methoxyphenyl)(phenyl)carbamoyloxy)methyl)cyclohexyl)methoxy)acetic acid;
2-((-4-((3,3-di p-tolylureido)methyl)cyclohexyl)methoxy)acetic acid;
2-((-4-((3,3-di m-tolylureido)methyl)cyclohexyl)methoxy)acetic acid;
2-((4-((3-(3-methoxyphenyl)-3-phenylureido)methyl)cyclohexyl)methoxy)acetic acid;
2-((-4-((3-(4-methoxyphenyl)-3-phenylureido)methyl)cyclohexyl)methoxy)acetic acid;
2-((-4-((3-(4-methoxy-2-methylphenyl)-3-phenylureido)methyl)cyclohexyl)methoxy)acetic acid;
2-((-4-((3-phenyl-3-(3-trifluoromethyl)phenyl)ureido)methyl)cyclohexyl)methoxy)acetic acid;
2-((4-(((4-methoxyphenyl)(phenyl)carbamoyloxy)methyl)cyclohexyl)methoxy)acetic acid;
2-((-4-(((4-chlorophenyl)(phenyl)carbamoyloxy)methyl)cyclohexyl)methoxy)acetic acid;
2-((4-(((3-fluorophenyl)(phenyl)carbamoyloxy)methyl)cyclohexyl)methoxy)acetic acid;
2-((-4-((phenyl)(m-tolyl)carbamoyloxy)methyl)cyclohexyl)methoxy)acetic acid;
2-((-4-(((3-chlorophenyl)(phenyl)carbamoyloxy)methyl)cyclohexyl)methoxy)acetic acid;
2-((-4-((phenylcarbamoyloxy)methyl)cyclohexyl)methoxy)acetic acid;
2-((-4-(((2-methoxyphenyl)(phenyl)carbamoyloxy)methyl)cyclohexyl)methoxy)acetic acid;
2-((-4-((phenyl(p-tolyl)carbamoyloxy)methyl)cyclohexyl)methoxy)acetic acid;
2-((-4-(((4-fluorophenyl)(phenyl)carbamoyloxy)methyl)cyclohexyl)methoxy)acetic acid;
2-((-4-(((4-chloro-3-fluorophenyl)(phenyl)carbamoyloxy)methyl)cyclohexyl)methoxy)acetic acid;
2-((-4-(((3-chloro-4-fluorophenyl)(phenyl)carbamoyloxy)methyl)cyclohexyl)methoxy)acetic acid;
2-((-4-(((3-fluoro-4-methylphenyl)(phenyl)carbamoyloxy)methyl)cyclohexyl)methoxy)acetic acid;
2-((-4-(((3,5-difluorophenyl(phenyl)carbamoyloxy)methyl)cyclohexyl)methoxy)acetic acid;
2-((-4-(((3,4-difluorophenyl(phenyl)carbamoyloxy)methyl)cyclohexyl)methoxy)acetic acid;
2-((-4-((3-(2,3-difluorophenyl)-3-phenylureido)methyl)cyclohexyl)methoxy)acetic acid;
2-((-4-((3-(3,5-difluorophenyl)-3-phenylureido)methyl)cyclohexyl)methoxy)acetic acid;
2-((-4-((3-(3-chloro-2-fluorophenyl)-3-phenylureido)methyl)cyclohexyl)methoxy)acetic acid;
2-((-4-(((3-chloro-5-fluorophenyl(phenyl)carbamoyloxy)methyl)cyclohexyl)methoxy)acetic acid;
2-((-4-((3-(3-chloro-5-fluorophenyl)-3-phenylureido)methyl)cyclohexyl)methoxy)acetic acid;
2-((-4-((3-benzhydryl-3-methylureido)methyl)cyclohexyl)methoxy)acetic acid;
2-((-4-((phenyl(pyridin-3-yl)carbamoyloxy)methyl)cyclohexyl)methoxy)acetic acid;
2-((-4-(((5-methylthiophen-2-yl)phenyl)carbamoyloxy)methyl)cyclohexyl)methoxy)acetic acid;
2-((-4-(((2,3-diflurophenyl)(phenyl)carbamoyloxy)methyl)cyclohexyl)methoxy)acetic acid;
2-((4-((3-(4-chloro-3-fluorophenyl)-3-phenylureido)methyl)cyclohexyl)methoxy)acetic acid;
2-((-4-((3-(2-fluoro-3methoxyphenyl)-3-phenylureido)methyl)cyclohexyl)methoxy)acetic acid;
2-((-4-((3-(3,4-difluorophenyl)-3-phenylureido)methyl)cyclohexyl)methoxy)acetic acid;
2-((-4-(((3-fluorophenyl)(4-methoxyphenyl)carbamoyloxy)methyl)cyclohexyl)methoxy)acetic acid;
2-((-4-(((4-chlorophenyl)(3-fluorophenyl)carbamoyloxy)methyl)cyclohexyl)methoxy)acetic acid;
2-((-4-(((3-fluorophenyl)(4-fluorophenyl)carbamoyloxy)methyl)cyclohexyl)methoxy)acetic acid;
2-((-4-(((3-chlorophenyl)(3-fluorophenyl)carbamoyloxy)methyl)cyclohexyl)methoxy)acetic acid;
2-((-4-(((3-fluorophenyl)(m-tolyl)carbamoyloxy)methyl)cyclohexyl)methoxy)acetic acid;
2-((-4-(((4-chloro-3-fluorophenyl)(3-fluorophenyl)carbamoyloxy)methyl)cyclohexyl)methoxy)acetic acid;
2-((-4-(((3-chloro-4-fluorophenyl)(3-fluorophenyl)carbamoyloxy)methyl)cyclohexyl)methoxy)acetic acid;
2-((-4-(((3-fluoro-4-methylphenyl)(3-fluorophenyl)carbamoyloxy)methyl)cyclohexyl)methoxy)acetic acid;
2-((-4-((phenyl(pyridin-2-yl)carbamoyloxy)methyl)cyclohexyl)methoxy)acetic acid;
2-((4-(((3,5-difluorophenyl)(3-fluorophenyl)carbamoyloxy)methyl)cyclohexyl)methoxy)acetic acid;
2-((4-(((3,4-difluorophenyl)(3-fluorophenyl)carbamoyloxy)methyl)cyclohexyl)methoxy)acetic acid;
2-((4-((bis(3-fluorophenyl)carbamoyloxy)methyl)cyclohexyl)methoxy)acetic acid;
2-((-4-(((3-fluorophenyl)(3-methoxyphenyl)carbamoyloxy)methyl)cyclohexyl)methoxy)acetic acid;
2-((-4-(((3,5-dimethylphenyl)(3-fluorophenyl)carbamoyloxy)methyl)cyclohexyl)methoxy)acetic acid;
2-((-4-(((3-fluorophenyl)(p-tolyl)carbamoyloxy)methyl)cyclohexyl)methoxy)acetic acid;
2-((-4-(((3-fluorophenyl)(6-fluoropyridin-3-yl)carbamoyloxy)methyl)cyclohexyl)methoxy)acetic acid;
2-((-4-(((3-fluorophenyl)(5-methylthiophen-2-yl)carbamoyloxy)methyl)cyclohexyl)methoxy)acetic acid;
2-((-4-(((4-ethoxyphenyl)(3-fluorophenyl)carbamoyloxy)methyl)cyclohexyl)methoxy)acetic acid;
2-((-4-(((3-fluorophenyl)(3-(trifluoromethoxy)phenyl)carbamoyloxy)methyl)cyclohexyl)methoxy)acetic acid;
2-((-4-(((3-fluorophenyl)(pyridin-3-yl)carbamoyloxy)methyl)cyclohexyl)methoxy)acetic acid;
2-((-4-(((3-fluorophenyl)(pyrazin-2-yl)carbamoyloxy)methyl)cyclohexyl)methoxy)acetic acid;
2-((-4-(((4-chlorophenyl)(4-fluorophenyl)carbamoyloxy)methyl)cyclohexyl)methoxy)acetic acid;
2-((-4-(((4-fluorophenyl)(5-methylthiophenyl)-2-yl)carbamoyloxy)methyl)cyclohexyl)methoxy)acetic acid;
2-((-4-(((3-chlorophenyl)(4-fluorophenyl)carbamoyloxy)methyl)cyclohexyl)methoxy)acetic acid;
2-((-4-(((4-fluorophenyl)(pyridin-3-yl)carbamoyloxy)methyl)cyclohexyl)methoxy)acetic acid;
2-((-4-(((4-ethoxyphenyl)(4-fluorophenyl)carbamoyloxy)methyl)cyclohexyl)methoxy)acetic acid;
2-((-4-(((4-fluorophenyl)(4-(trifluoromethoxy)phenyl)carbamoyloxy)methyl)cyclohexyl)methoxy)acetic acid;

2-((-4-(((4-fluorophenyl)(m-tolyl)carbamoyloxy)methyl) cyclohexyl)methoxy)acetic acid;

2-((-4-((bis(4-fluorophenyl)carbamoyloxy)methyl)cyclohexyl)methoxy)acetic acid;

2-((4-(((6-fluoropyridin-3-yl)(phenyl)carbamoyloxy) methyl)cyclohexyl)methoxy)acetic acid;

2-((-4-((phenyl(pyrazin-2-yl)carbamoyloxy)methyl)cyclohexyl)methoxy)acetic acid;

2-((-4-((benzhydryl(methyl)carbamoyloxy)methyl)cyclohexyl)methoxy)acetic acid;

2-((-4-((3-benzhydryl-1,3-dimethylureido)methyl)cyclohexyl)methoxy)acetic acid;

2-((-4-(((4-ethoxyphenyl)(phenyl)carbamoyloxy)methyl) cyclohexyl)methoxy)acetic acid 2-((-4-(((2-fluoropyridin-4-yl)(phenyl)carbamoyloxy) methyl)cyclohexyl)methoxy)acetic acid;

2-((-4-(((5-methoxypyridin-3-yl)(phenyl)carbamoyloxy) methyl)cyclohexyl)methoxy)acetic acid;

2-((-4-(((5-fluoropyridin-2-yl)(phenyl)carbamoyloxy) methyl)cyclohexyl)methoxy)acetic acid;

2-((-4-((phenyl(5-(trifluoromethyl)pyridin-2-yl)carbamoyloxy)methyl)cyclohexyl)methoxy)acetic acid;

2-((-4-(((5-methylpyridin-3-yl)(phenyl)carbamoyloxy) methyl)cyclohexyl)methoxy)acetic acid;

2-((-4-(((5-chloropyridin-2-yl)(phenyl)carbamoyloxy) methyl)cyclohexyl)methoxy)acetic acid;

2-((-4-(((5-fluoropyridin-3-yl)(phenyl)carbamoyloxy) methyl)cyclohexyl)methoxy)acetic acid;

2-((-4-((benzhydryl(propyl)carbamoyloxy)methyl)cyclohexyl)methoxy)acetic acid; and 2-((-4-(((5-methylthiazol-2-yl)(phenyl)carbamoyloxy) methyl)cyclohexyl)methoxy)acetic acid.

The embodiments of the present invention include every combination of one or more compounds selected from the following group shown in TABLE A.

TABLE A

| Cmpd No. | Chemical Structure | Chemical Name |
|---|---|---|
| 1 | 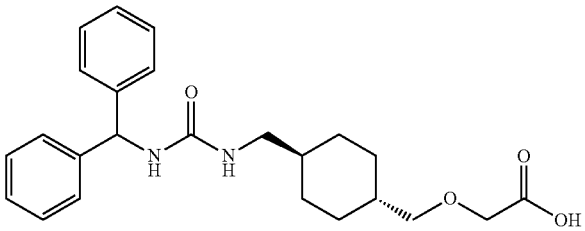 | 2-(((1r,4r)-4-((3-benzhydrylureido)methyl) cyclohexyl)methoxy)acetic acid |
| 2 | 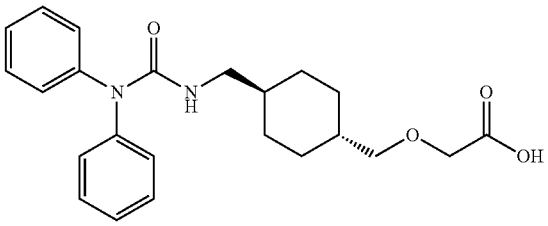 | 2-(((1r,4r)-4-((3,3-diphenylureido)methyl) cyclohexyl)methoxy)acetic acid |
| 3 | 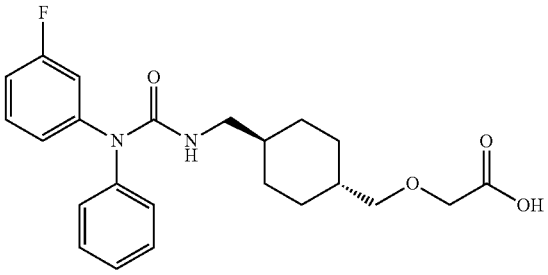 | 2-(((1r,4r)-4-((3-(3-fluorophenyl)-3-phenylureido)methyl) cyclohexyl)methoxy)acetic acid |
| 4 | 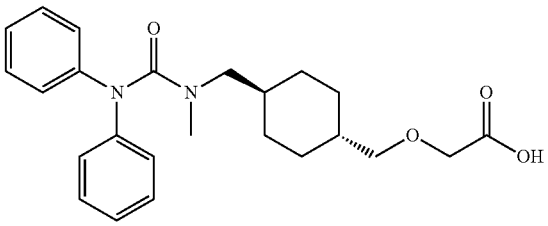 | 2-(((1r,4r)-4-((1-methyl-3,3-diphenylureido)methyl) cyclohexyl)methoxy)acetic acid |

TABLE A-continued

| Cmpd No. | Chemical Structure | Chemical Name |
|---|---|---|
| 5 | | 2-(((1r,4r)-4-((diphenylcarbamoyloxy)methyl) cyclohexyl)methoxy)acetic acid |
| 6 | | 2-(((1r,4r)-4-((3-(3-chlorophenyl)-3-phenylureido)methyl) cyclohexyl)methoxy)acetic acid |
| 7 | | 2-(((1s,4s)-4-((diphenylcarbamoyloxy)methyl) cyclohexyl)methoxy)acetic acid |
| 8 | | 2-(((1r,4r)-4-((3-(4-fluorophenyl)-3-phenylureido)methyl) cyclohexyl)methoxy)acetic acid |
| 9 | | 2-(((1s,4s)-4-((3,3-diphenylureido)methyl) cyclohexyl)methoxy)acetic acid |
| 10 | | 2-(((1r,4r)-4-((3-(2-fluorophenyl)-3-phenylureido)methyl) cyclohexyl)methoxy)acetic acid |

TABLE A-continued

| Cmpd No. | Chemical Structure | Chemical Name |
|---|---|---|
| 11 | 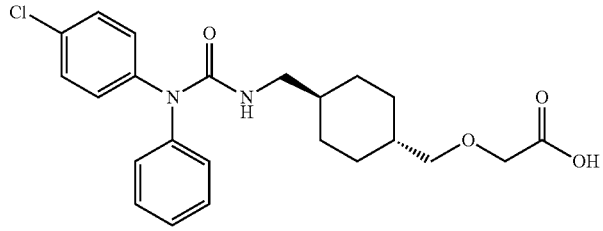 | 2-(((1r,4r)-4-((3-(4-chlorophenyl)-3-phenylureido)methyl) cyclohexyl)methoxy)acetic acid |
| 12 | 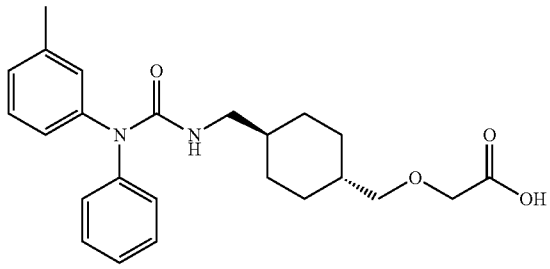 | 2-(((1r,4r)-4-((3-phenyl-3-m-tolylureido)methyl) cyclohexyl)methoxy)acetic acid |
| 13 | 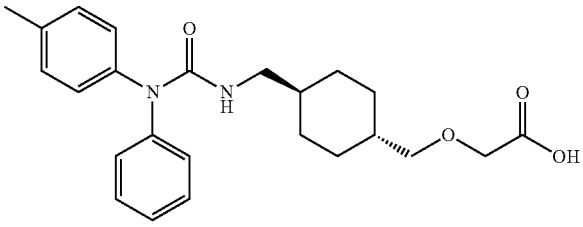 | 2-(((1r,4r)-4-((3-phenyl-3-p-tolylureido)methyl) cyclohexyl)methoxy)acetic acid |
| 14 | 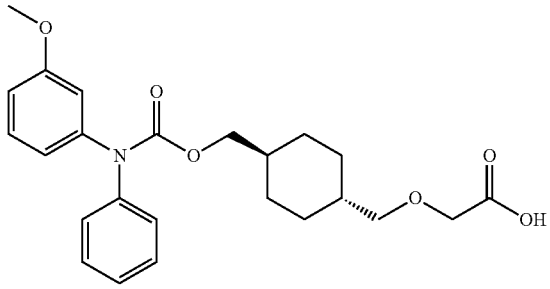 | 2-(((1r,4r)-4-(((3-methoxyphenyl)(phenyl) carbamoyloxy)methyl) cyclohexyl)methoxy)acetic acid |
| 15 | 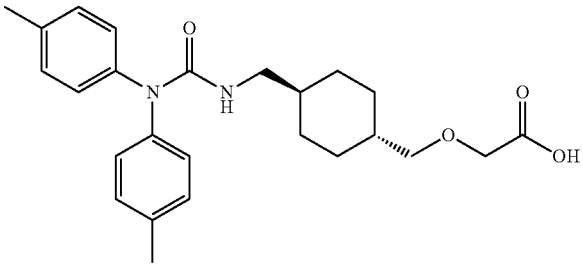 | 2-(((1r,4r)-4-((3,3-di p-tolylureido)methyl) cyclohexyl)methoxy)acetic acid |
| 16 | 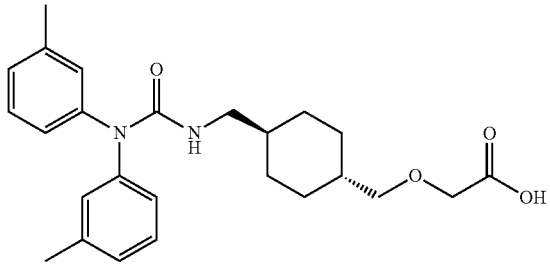 | 2-(((1r,4r)-4-((3,3-di m-tolylureido)methyl) cyclohexyl)methoxy)acetic acid |

TABLE A-continued

| Cmpd No. | Chemical Structure | Chemical Name |
|---|---|---|
| 17 | 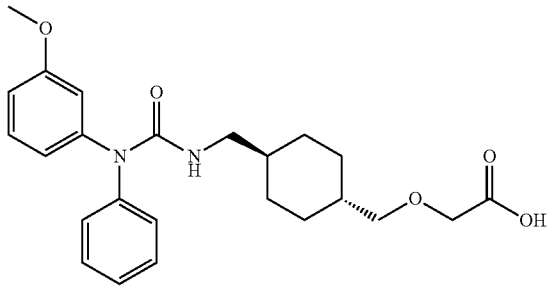 | 2-(((1r,4r)-4-((3-(3-methoxyphenyl)-3-phenylureido)methyl) cyclohexyl)methoxy)acetic acid |
| 18 | 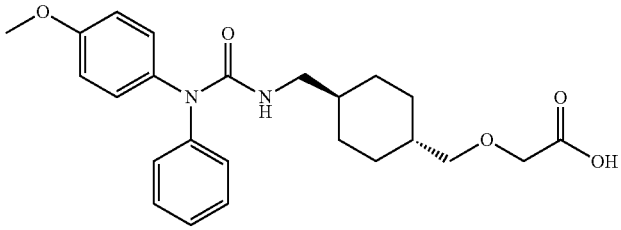 | 2-(((1r,4r)-4-((3-(4-methoxyphenyl)-3-phenylureido)methyl) cyclohexyl)methoxy)acetic acid |
| 19 | 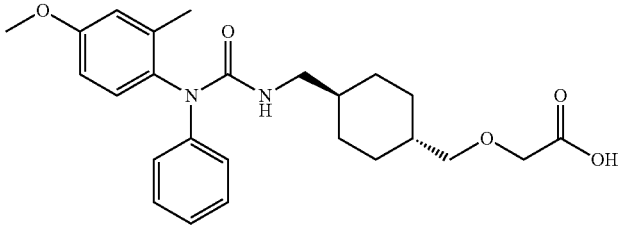 | 2-(((1r,4r)-4-((3-(4-methoxy-2-methylphenyl)-3-phenylureido)methyl) cyclohexyl)methoxy)acetic acid |
| 20 | 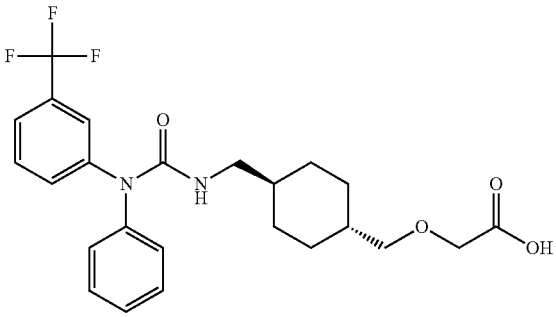 | 2-(((1r,4r)-4-((3-phenyl-3-(3-(trifluoromethyl)phenyl) ureido)methyl) cyclohexyl)methoxy)acetic acid |
| 21 | 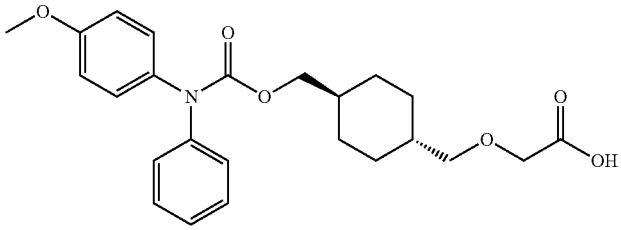 | 2-(((1r,4r)-4-(((4-methoxyphenyl)(phenyl) carbamoyloxy)methyl) cyclohexyl)methoxy)acetic acid |
| 22 | 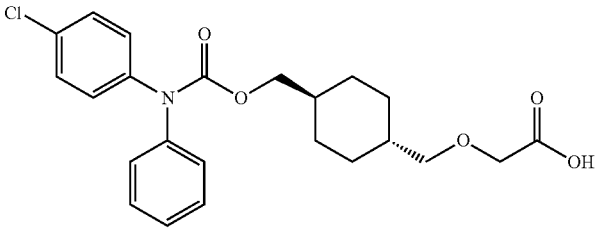 | 2-(((1r,4r)-4-(((4-chlorophenyl)(phenyl) carbamoyloxy)methyl) cyclohexyl)methoxy)acetic acid |

TABLE A-continued

| Cmpd No. | Chemical Structure | Chemical Name |
|---|---|---|
| 23 | 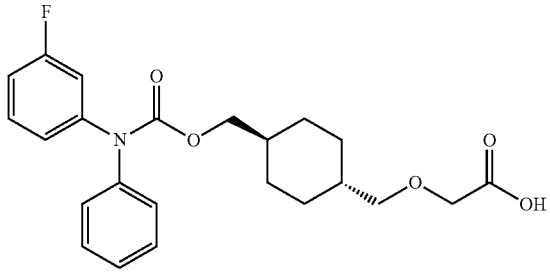 | 2-(((1r,4r)-4-(((3-fluorophenyl)(phenyl) carbamoyloxy)methyl) cyclohexyl)methoxy)acetic acid |
| 24 | 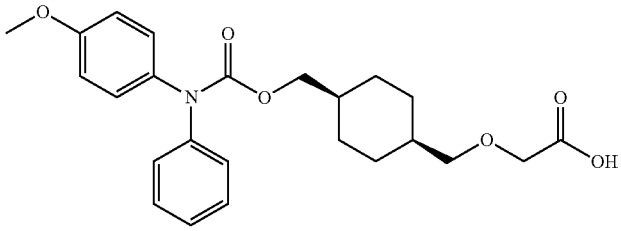 | 2-(((1s,4s)-4-(((4-methoxyphenyl)(phenyl) carbamoyloxy)methyl) cyclohexyl)methoxy)acetic acid |
| 25 | 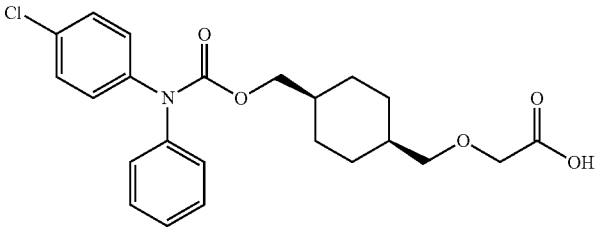 | 2-(((1s,4s)-4-(((4-chlorophenyl)(phenyl) carbamoyloxy)methyl) cyclohexyl)methoxy)acetic acid |
| 26 | 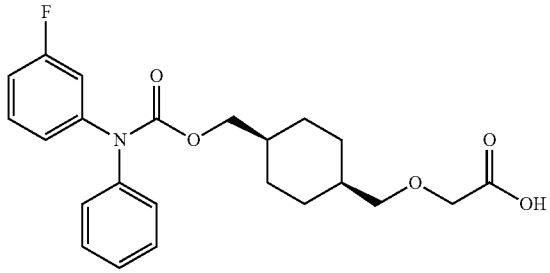 | 2-(((1s,4s)-4-(((3-fluorophenyl)(phenyl) carbamoyloxy)methyl) cyclohexyl)methoxy)acetic acid |
| 27 | 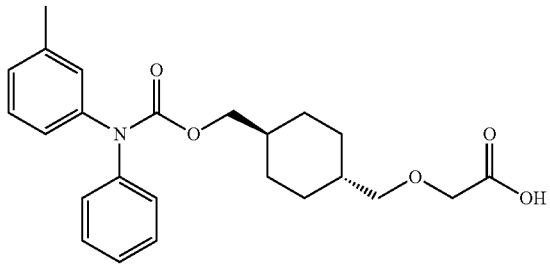 | 2-(((1r,4r)-4-((phenyl(m-tolyl)carbamoyloxy)methyl) cyclohexyl)methoxy)acetic acid |

TABLE A-continued

| Cmpd No. | Chemical Structure | Chemical Name |
|---|---|---|
| 28 | 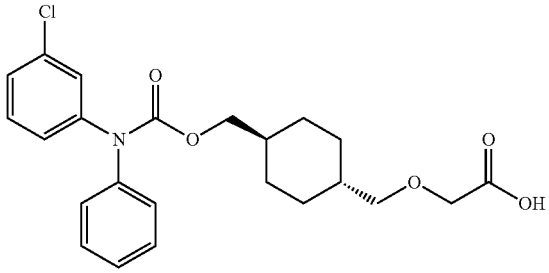 | 2-(((1r,4r)-4-(((3-chlorophenyl)(phenyl) carbamoyloxy)methyl) cyclohexyl)methoxy)acetic acid |
| 29 | 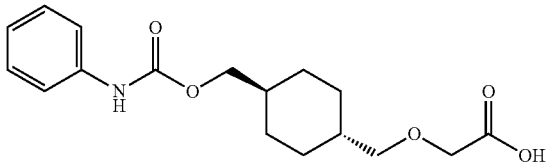 | 2-(((1r,4r)-4-((phenylcarbamoyloxy)methyl) cyclohexyl)methoxy)acetic acid |
| 30 | 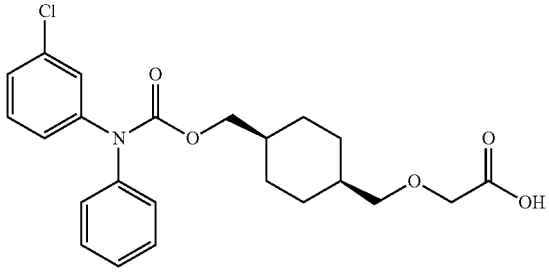 | 2-(((1s,4s)-4-(((3-chlorophenyl)(phenyl) carbamoyloxy)methyl) cyclohexyl)methoxy)acetic acid |
| 31 | 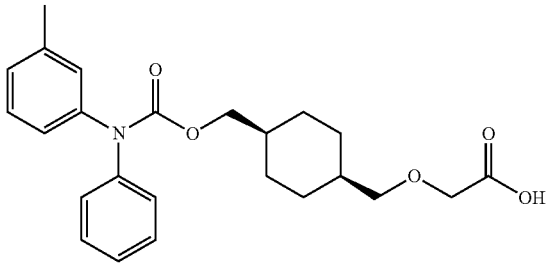 | 2-(((1s,4s)-4-((phenyl(m-tolyl)carbamoyloxy)methyl) cyclohexyl)methoxy)acetic acid |
| 32 | 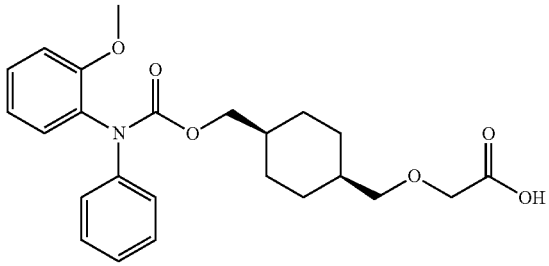 | 2-(((1s,4s)-4-(((2-methoxyphenyl)(phenyl) carbamoyloxy)methyl) cyclohexyl)methoxy)acetic acid |
| 33 | 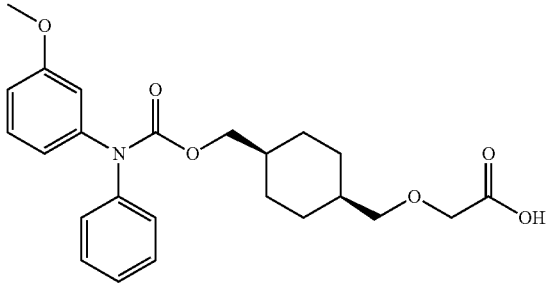 | 2-(((1s,4s)-4-(((3-methoxyphenyl)(phenyl) carbamoyloxy)methyl) cyclohexyl)methoxy)acetic acid |

TABLE A-continued

| Cmpd No. | Chemical Structure | Chemical Name |
|---|---|---|
| 34 | 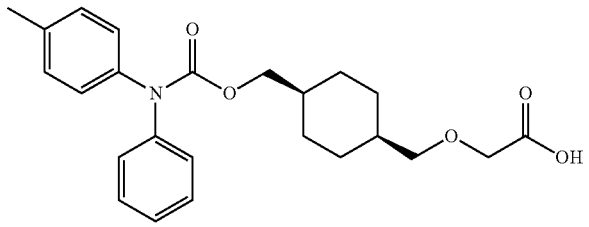 | 2-(((1s,4s)-4-((phenyl(p-tolyl)carbamoyloxy)methyl) cyclohexyl)methoxy)acetic acid |
| 35 | 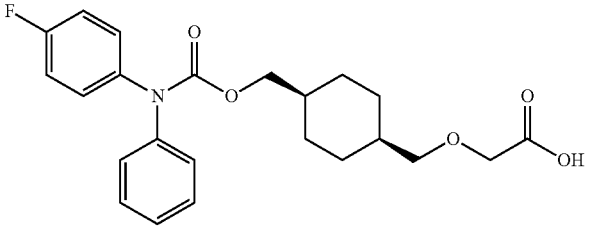 | 2-(((1s,4s)-4-(((4-fluorophenyl)(phenyl) carbamoyloxy)methyl) cyclohexyl)methoxy)acetic acid |
| 36 | 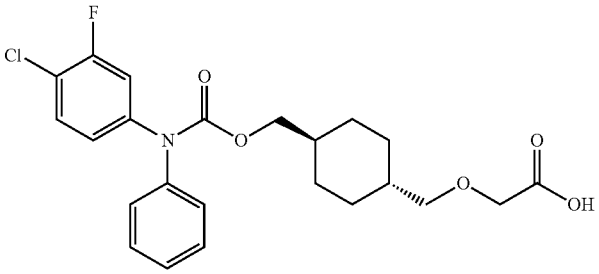 | 2-(((1r,4r)-4-(((4-chloro-3-fluorophenyl)(phenyl) carbamoyloxy)methyl) cyclohexyl)methoxy)acetic acid |
| 37 | 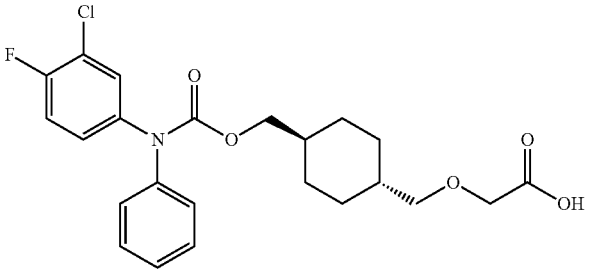 | 2-(((1r,4r)-4-(((3-chloro-4-fluorophenyl)(phenyl) carbamoyloxy)methyl) cyclohexyl)methoxy)acetic acid |
| 38 | 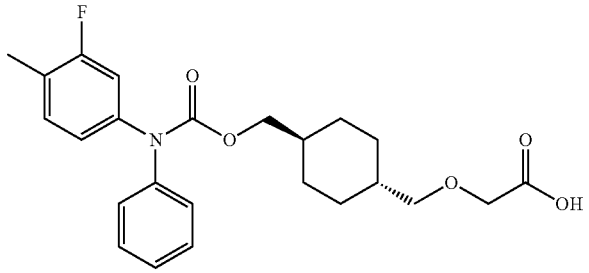 | 2-(((1r,4r)-4-(((3-fluoro-4-methylphenyl)(phenyl) carbamoyloxy)methyl) cyclohexyl)methoxy)acetic acid |

TABLE A-continued

| Cmpd No. | Chemical Structure | Chemical Name |
|---|---|---|
| 39 | 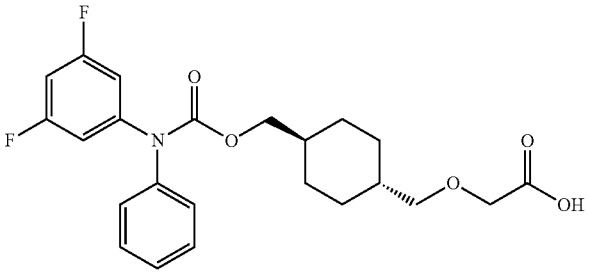 | 2-(((1r,4r)-4-(((3,5-difluorophenyl)(phenyl) carbamoyloxy)methyl) cyclohexyl)methoxy)acetic acid |
| 40 | 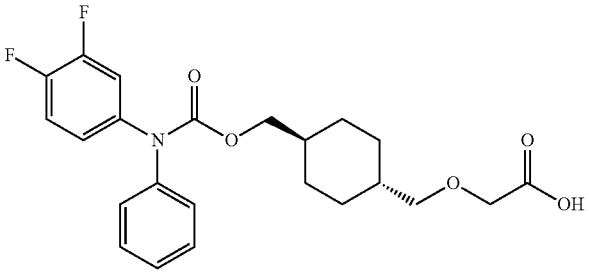 | 2-(((1r,4r)-4-(((3,4-difluorophenyl)(phenyl) carbamoyloxy)methyl) cyclohexyl)methoxy)acetic acid |
| 41 | 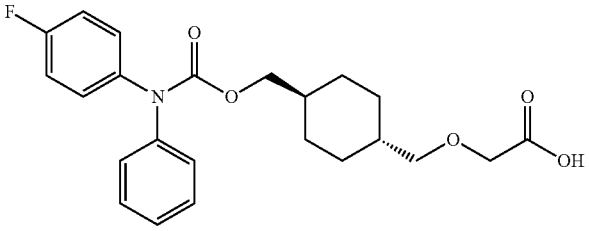 | 2-(((1r,4r)-4-(((4-fluorophenyl)(phenyl) carbamoyloxy)methyl) cyclohexyl)methoxy)acetic acid |
| 42 | 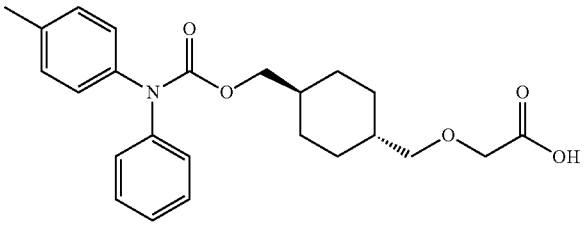 | 2-(((1r,4r)-4-((phenyl(p-tolyl)carbamoyloxy)methyl) cyclohexyl)methoxy)acetic acid |
| 43 | 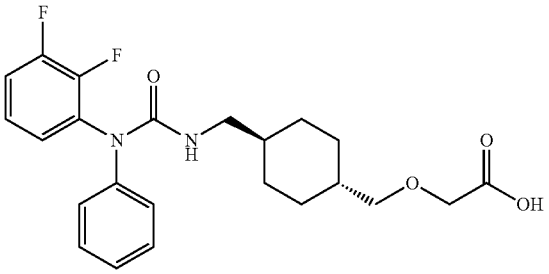 | 2-(((1r,4r)-4-((3-(2,3-difluorophenyl)-3-phenylureido)methyl) cyclohexyl)methoxy)acetic acid |
| 44 | 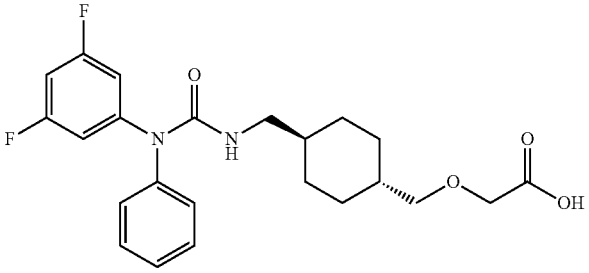 | 2-(((1r,4r)-4-((3-(3,5-difluorophenyl)-3-phenylureido)methyl) cyclohexyl)methoxy)acetic acid |

TABLE A-continued

| Cmpd No. | Chemical Structure | Chemical Name |
|---|---|---|
| 45 | 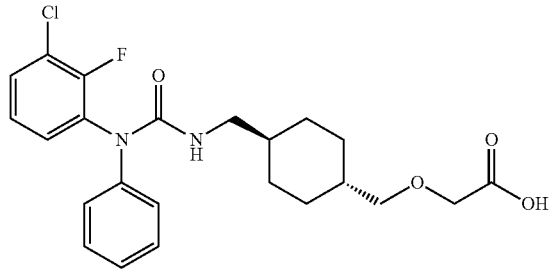 | 2-(((1r,4r)-4-((3-(3-chloro-2-fluorophenyl)-3-phenylureido)methyl) cyclohexyl)methoxy)acetic acid |
| 46 | 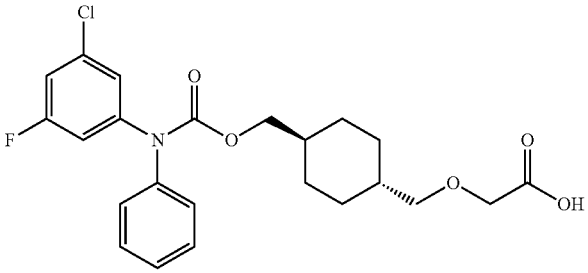 | 2-(((1r,4r)-4-(((3-chloro-5-fluorophenyl)(phenyl) carbamoyloxy)methyl) cyclohexyl)methoxy)acetic acid |
| 47 | 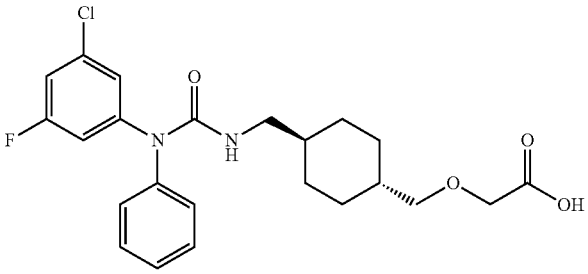 | 2-(((1r,4r)-4-((3-(3-chloro-5-fluorophenyl)-3-phenylureido)methyl) cyclohexyl)methoxy)acetic acid |
| 48 | 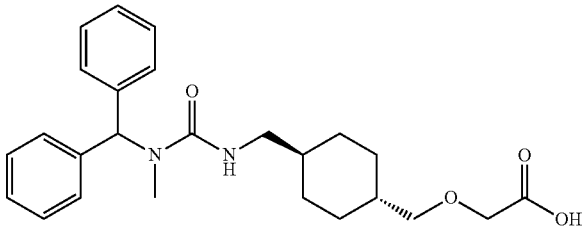 | 2-(((1r,4r)-4-((3-benzhydryl-3-methylureido)methyl) cyclohexyl)methoxy)acetic acid |
| 49 | 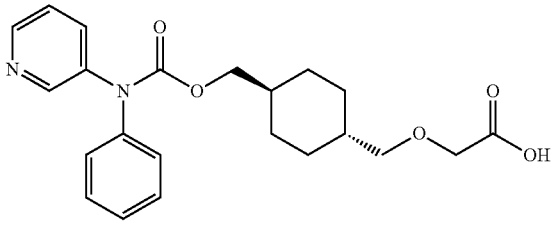 | 2-(((1r,4r)-4-(phenyl(pyridin-3-yl)carbamoyloxy)methyl) cyclohexyl)methoxy)acetic acid |
| 50 | 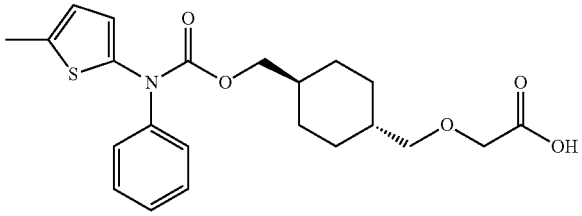 | 2-(((1r,4r)-4-(((5-methylthiophen-2-yl)(phenyl) carbamoyloxy)methyl) cyclohexyl)methoxy)acetic acid |

TABLE A-continued

| Cmpd No. | Chemical Structure | Chemical Name |
|---|---|---|
| 51 | 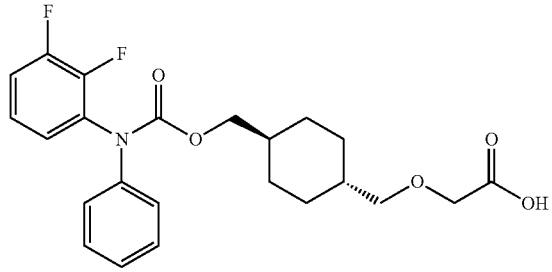 | 2-(((1r,4r)-4-(((2,3-difluorophenyl)(phenyl) carbamoyloxy)methyl) cyclohexyl)methoxy)acetic acid |
| 52 | 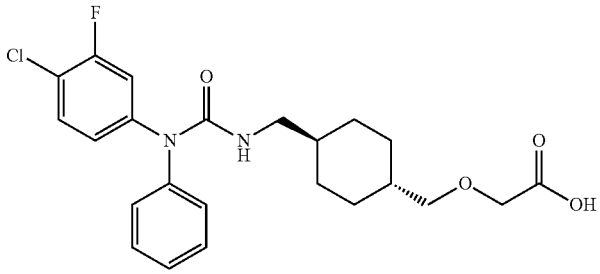 | 2-(((1r,4r)-4-((3-(4-chloro-3-fluorophenyl)-3-phenylureido)methyl) cyclohexyl)methoxy)acetic acid |
| 53 | 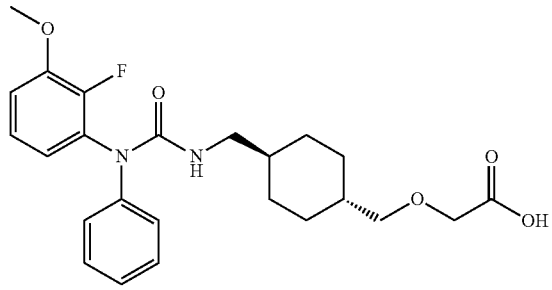 | 2-(((1r,4r)-4-((3-(2-fluoro-3-methoxyphenyl)-3-phenylureido)methyl) cyclohexyl)methoxy)acetic acid |
| 54 | 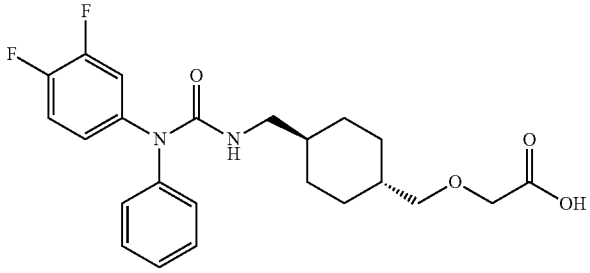 | 2-(((1r,4r)-4-((3-(3,4-difluorophenyl)-3-phenylureido)methyl) cyclohexyl)methoxy)acetic acid |
| 55 | 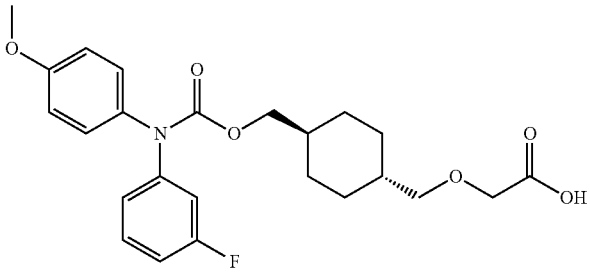 | 2-(((1r,4r)-4-(((3-fluorophenyl)(4-methoxyphenyl)carbamoyloxy) methyl)cyclohexyl) methoxy)acetic acid |

TABLE A-continued

| Cmpd No. | Chemical Structure | Chemical Name |
|---|---|---|
| 56 | 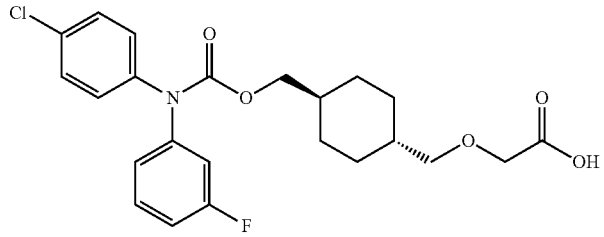 | 2-(((1r,4r)-4-(((4-chlorophenyl)(3-fluorophenyl)carbamoyloxy)methyl)cyclohexyl)methoxy)acetic acid |
| 57 | 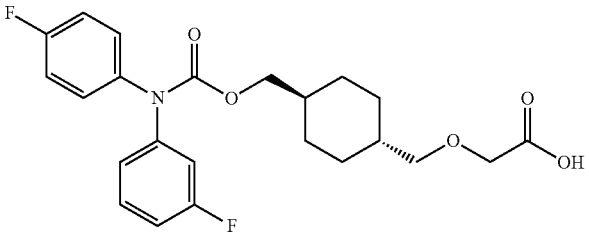 | 2-(((1r,4r)-4-(((3-fluorophenyl)(4-fluorophenyl)carbamoyloxy)methyl)cyclohexyl)methoxy)acetic acid |
| 58 | 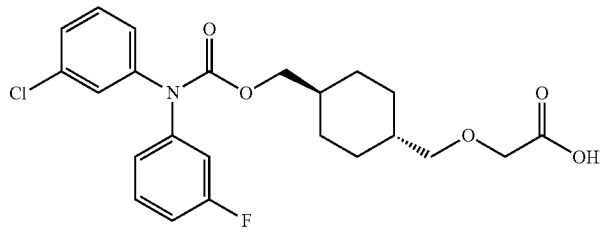 | 2-(((1r,4r)-4-(((3-chlorophenyl)(3-fluorophenyl)carbamoyloxy)methyl)cyclohexyl)methoxy)acetic acid |
| 59 | 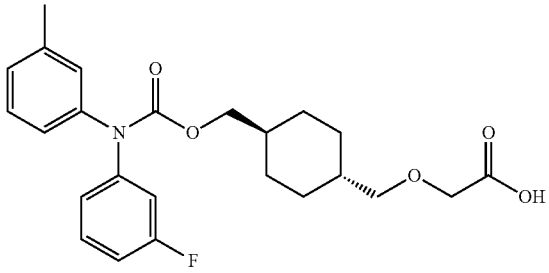 | 2-(((1r,4r)-4-(((3-fluorophenyl)(m-tolyl)carbamoyloxy)methyl)cyclohexyl)methoxy)acetic acid |
| 60 | 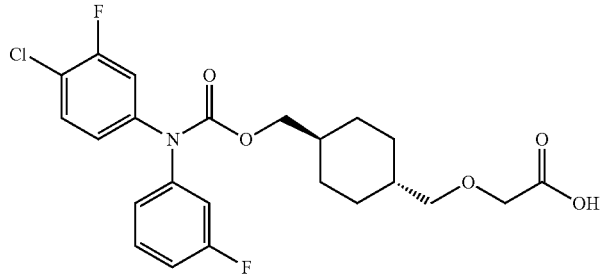 | 2-(((1r,4r)-4-(((4-chloro-3-fluorophenyl)(3-fluorophenyl)carbamoyloxy)methyl)cyclohexyl)methoxy)acetic acid |
| 61 | 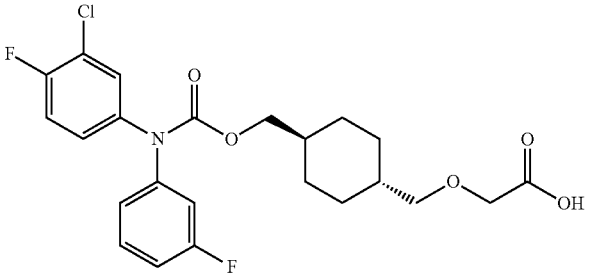 | 2-(((1r,4r)-4-(((3-chloro-4-fluorophenyl)(3-fluorophenyl)carbamoyloxy)methyl)cyclohexyl)methoxy)acetic acid |

TABLE A-continued

| Cmpd No. | Chemical Structure | Chemical Name |
|---|---|---|
| 62 | 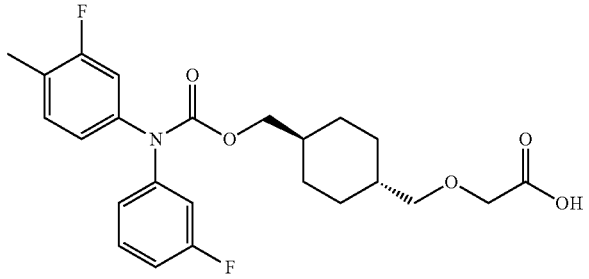 | 2-(((1r,4r)-4-(((3-fluoro-4-methylphenyl)(3-fluorophenyl)carbamoyloxy)methyl)cyclohexyl)methoxy)acetic acid |
| 63 | 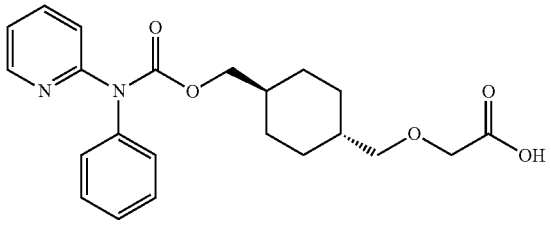 | 2-(((1r,4r)-4-((phenyl(pyridin-2-yl)carbamoyloxy)methyl)cyclohexyl)methoxy)acetic acid |
| 64 | 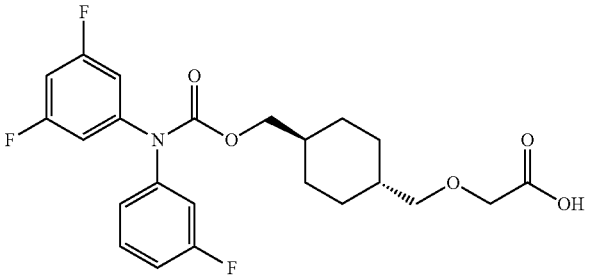 | 2-(((1r,4r)-4-(((3,5-difluorophenyl)(3-fluorophenyl)carbamoyloxy)methyl)cyclohexyl)methoxy)acetic acid |
| 65 | 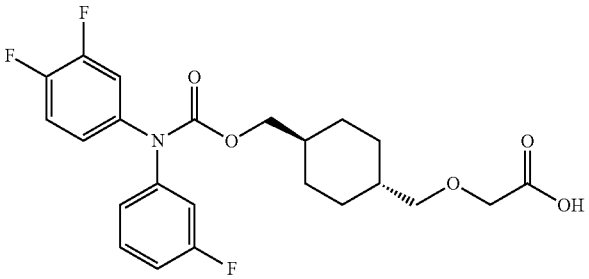 | 2-(((1r,4r)-4-(((3,4-difluorophenyl)(3-fluorophenyl)carbamoyloxy)methyl)cyclohexyl)methoxy)acetic acid |
| 66 | 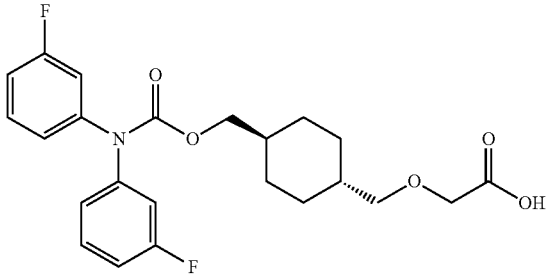 | 2-(((1r,4r)-4-((bis(3-fluorophenyl)carbamoyloxy)methyl)cyclohexyl)methoxy)acetic acid |

TABLE A-continued

| Cmpd No. | Chemical Structure | Chemical Name |
|---|---|---|
| 67 | 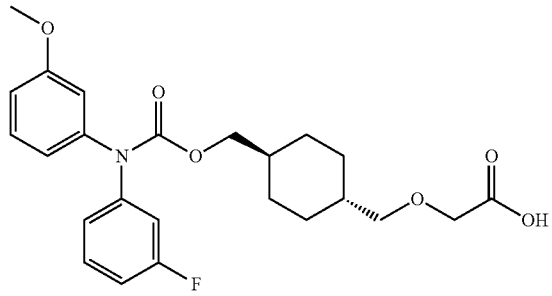 | 2-(((1r,4r)-4-(((3-fluorophenyl)(3-methoxyphenyl)carbamoyloxy)methyl)cyclohexyl)methoxy)acetic acid |
| 68 | 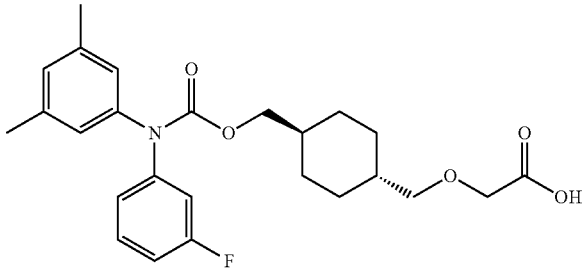 | 2-(((1r,4r)-4-(((3,5-dimethylphenyl)(3-fluorophenyl)carbamoyloxy)methyl)cyclohexyl)methoxy)acetic acid |
| 69 | 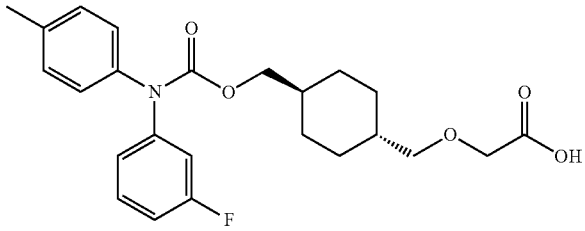 | 2-(((1r,4r)-4-(((3-fluorophenyl)(p-tolyl)carbamoyloxy)methyl)cyclohexyl)methoxy)acetic acid |
| 70 | 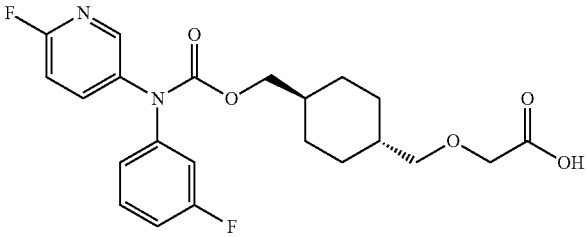 | 2-(((1r,4r)-4-(((3-fluorophenyl)(6-fluoropyridin-3-yl)carbamoyloxy)methyl)cyclohexyl)methoxy)acetic acid |
| 71 | 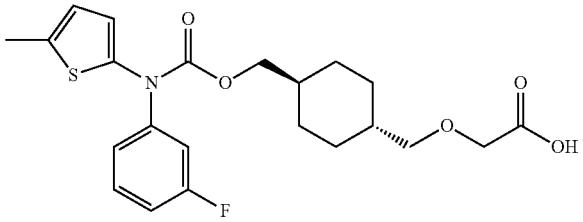 | 2-(((1r,4r)-4-(((3-fluorophenyl)(5-methylthiophen-2-yl)carbamoyloxy)methyl)cyclohexyl)methoxy)acetic acid |
| 72 | 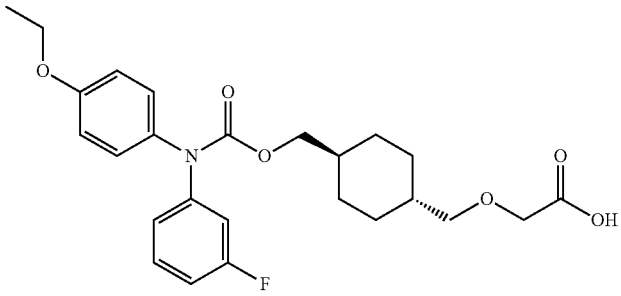 | 2-(((1r,4r)-4-(((4-ethoxyphenyl)(3-fluorophenyl)carbamoyloxy)methyl)cyclohexyl)methoxy)acetic acid |

TABLE A-continued

| Cmpd No. | Chemical Structure | Chemical Name |
|---|---|---|
| 73 | 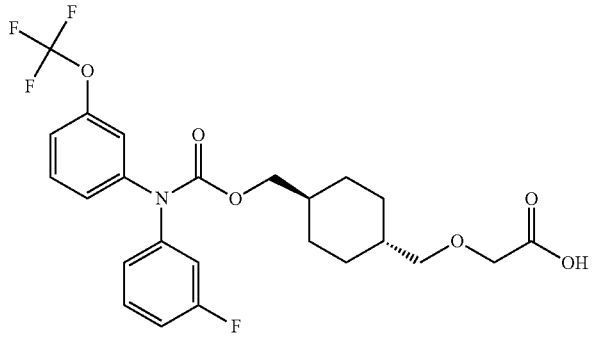 | 2-(((1r,4r)-4-(((3-fluorophenyl)(3-(trifluoromethoxy)phenyl) carbamoyloxy)methyl) cyclohexyl)methoxy)acetic acid |
| 74 | 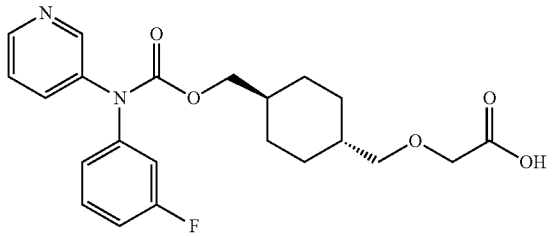 | 2-(((1r,4r)-4-(((3-fluorophenyl)(pyridin-3-yl)carbamoyloxy)methyl) cyclohexyl)methoxy)acetic acid |
| 75 | 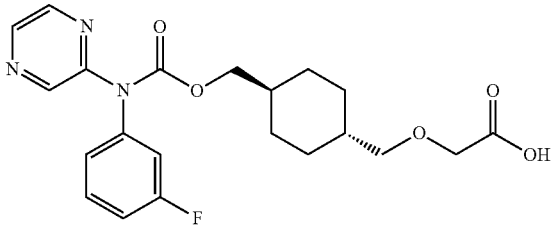 | 2-(((1r,4r)-4-(((3-fluorophenyl)(pyrazin-2-yl)carbamoyloxy)methyl) cyclohexyl)methoxy)acetic acid |
| 76 | 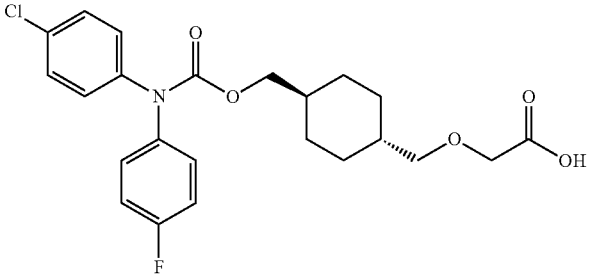 | 2-(((1r,4r)-4-(((4-chlorophenyl)(4-fluorophenyl)carbamoyloxy) methyl)cyclohexyl) methoxy)acetic acid |
| 77 | 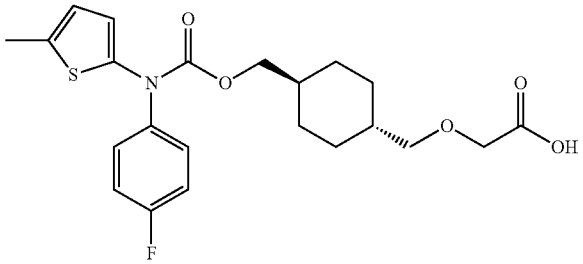 | 2-(((1r,4r)-4-(((4-fluorophenyl)(5-methylthiophen-2-yl)carbamoyloxy)methyl) cyclohexyl)methoxy)acetic acid |

TABLE A-continued

| Cmpd No. | Chemical Structure | Chemical Name |
|---|---|---|
| 78 | 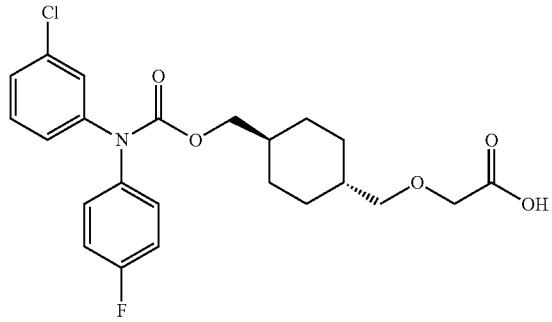 | 2-(((1r,4r)-4-(((3-chlorophenyl)(4-fluorophenyl)carbamoyloxy)methyl)cyclohexyl)methoxy)acetic acid |
| 79 | 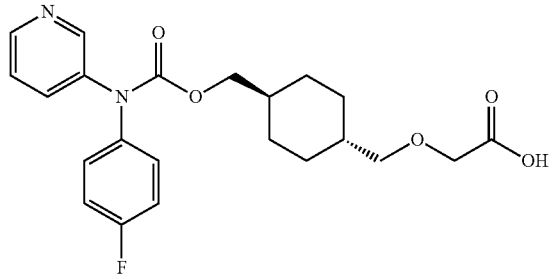 | 2-(((1r,4r)-4-(((4-fluorophenyl)(pyridin-3-yl)carbamoyloxy)methyl)cyclohexyl)methoxy)acetic acid |
| 80 | 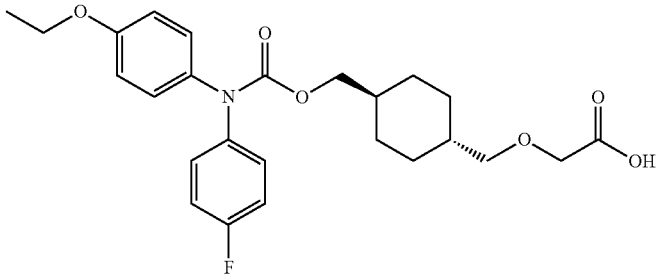 | 2-(((1r,4r)-4-(((4-ethoxyphenyl)(4-fluorophenyl)carbamoyloxy)methyl)cyclohexyl)methoxy)acetic acid |
| 81 | 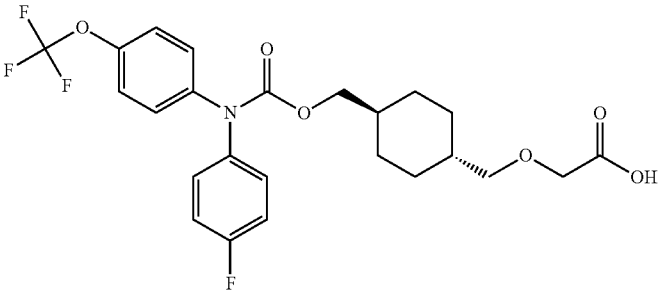 | 2-(((1r,4r)-4-(((4-fluorophenyl)(4-(trifluoromethoxy)phenyl)carbamoyloxy)methyl)cyclohexyl)methoxy)acetic acid |
| 82 | 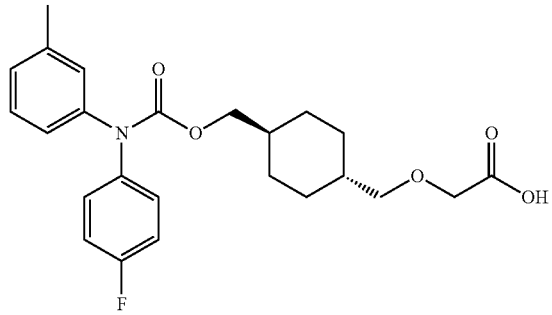 | 2-(((1r,4r)-4-(((4-fluorophenyl)(m-tolyl)carbamoyloxy)methyl)cyclohexyl)methoxy)acetic acid |

TABLE A-continued

| Cmpd No. | Chemical Structure | Chemical Name |
|---|---|---|
| 83 | 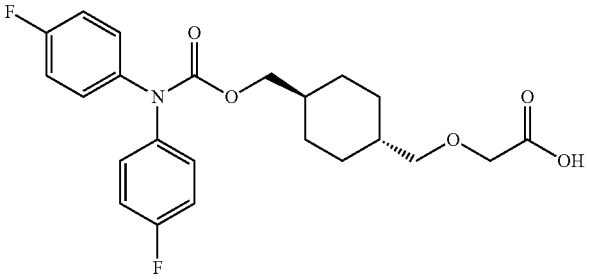 | 2-(((1r,4r)-4-((bis(4-fluorophenyl)carbamoyloxy)methyl)cyclohexyl)methoxy)acetic acid |
| 84 | 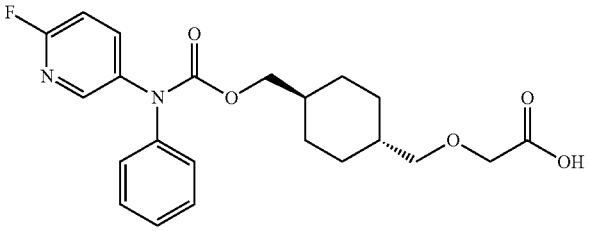 | 2-(((1r,4r)-4-(((6-fluoropyridin-3-yl)(phenyl)carbamoyloxy)methyl)cyclohexyl)methoxy)acetic acid |
| 85 | 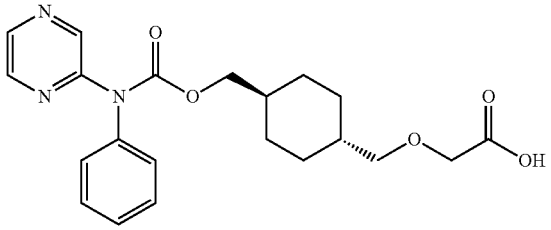 | 2-(((1r,4r)-4-((phenyl(pyrazin-2-yl)carbamoyloxy)methyl)cyclohexyl)methoxy)acetic acid |
| 86 | 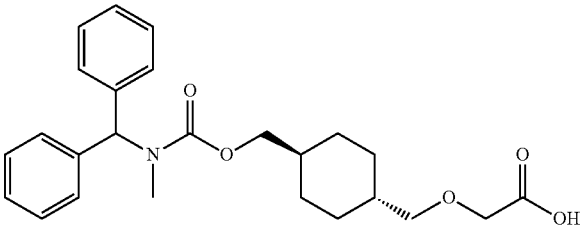 | 2-(((1r,4r)-4-((benzhydryl(methyl)carbamoyloxy)methyl)cyclohexyl)methoxy)acetic acid |
| 87 | 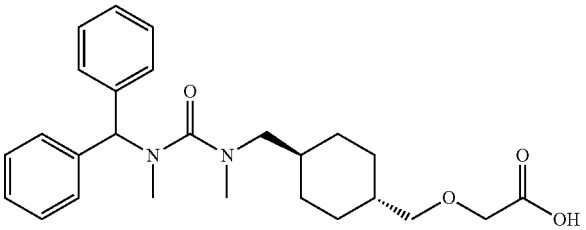 | 2-(((1r,4r)-4-((3-benzhydryl-1,3-dimethylureido)methyl)cyclohexyl)methoxy)acetic acid |
| 88 | 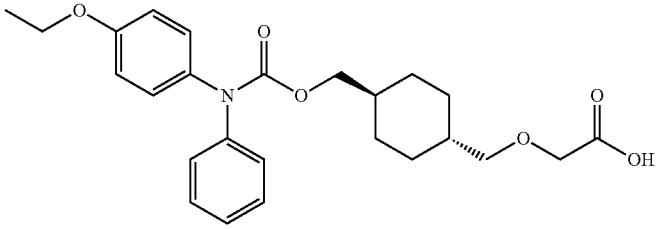 | 2-(((1r,4r)-4-(((4-ethoxyphenyl)(phenyl)carbamoyloxy)methyl)cyclohexyl)methoxy)acetic acid |

TABLE A-continued

| Cmpd No. | Chemical Structure | Chemical Name |
|---|---|---|
| 89 | 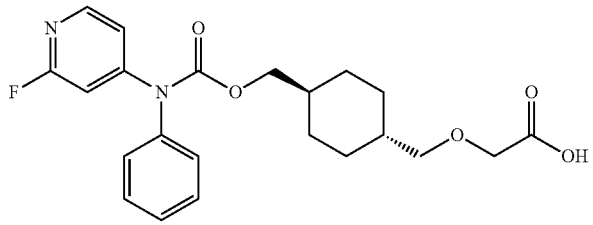 | 2-(((1r,4r)-4-(((2-fluoropyridin-4-yl)(phenyl)carbamoyloxy)methyl)cyclohexyl)methoxy)acetic acid |
| 90 | 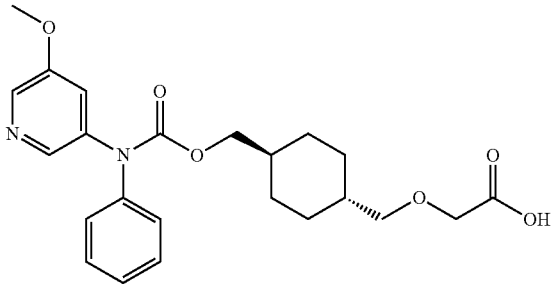 | 2-(((1r,4r)-4-(((5-methoxypyridin-3-yl)(phenyl)carbamoyloxy)methyl)cyclohexyl)methoxy)acetic acid |
| 91 | 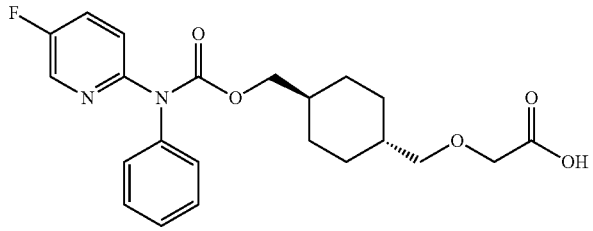 | 2-(((1r,4r)-4-(((5-fluoropyridin-2-yl)(phenyl)carbamoyloxy)methyl)cyclohexyl)methoxy)acetic acid |
| 92 | 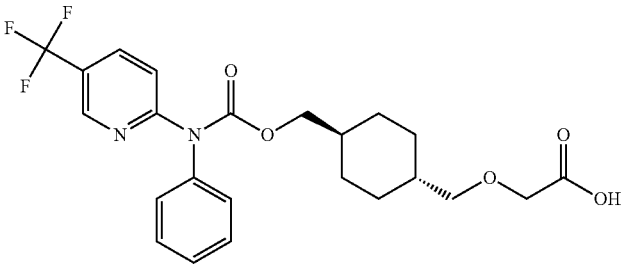 | 2-(((1r,4r)-4-((phenyl(5-(trifluoromethyl)pyridin-2-yl)carbamoyloxy)methyl)cyclohexyl)methoxy)acetic acid |
| 93 | 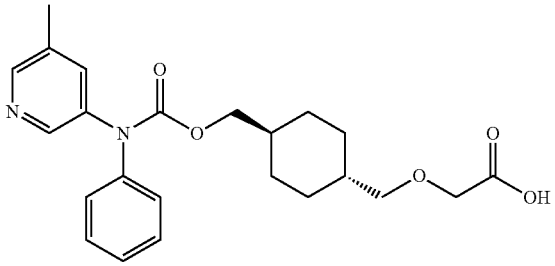 | 2-(((1r,4r)-4-(((5-methylpyridin-3-yl)(phenyl)carbamoyloxy)methyl)cyclohexyl)methoxy)acetic acid |
| 94 | 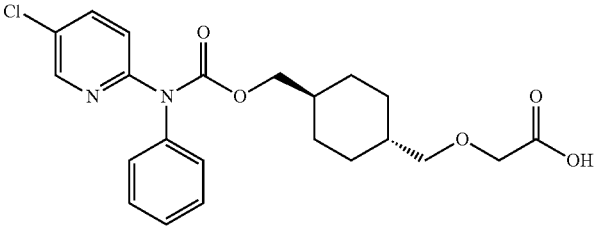 | 2-(((1r,4r)-4-(((5-chloropyridin-2-yl)(phenyl)carbamoyloxy)methyl)cyclohexyl)methoxy)acetic acid |

TABLE A-continued

| Cmpd No. | Chemical Structure | Chemical Name |
|---|---|---|
| 95 | 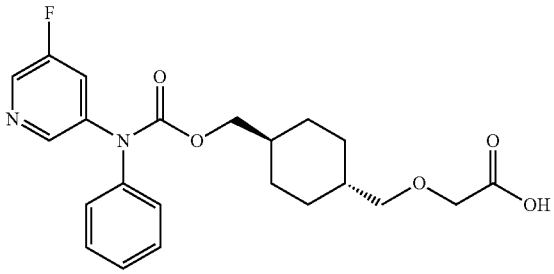 | 2-(((1r,4r)-4-(((5-fluoropyridin-3-yl)(phenyl)carbamoyloxy)methyl) cyclohexyl)methoxy)acetic acid |
| 96 | 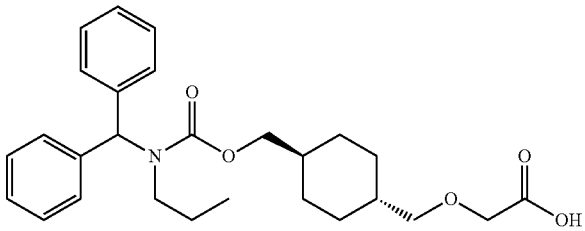 | 2-(((1r,4r)-4-((benzhydryl(propyl) carbamoyloxy)methyl) cyclohexyl)methoxy)acetic acid |
| 97 | 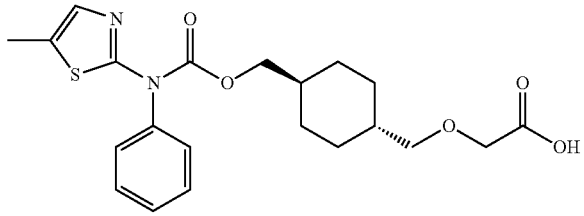 | 2-(((1r,4r)-4-(((5-methylthiazol-2-yl)(phenyl) carbamoyloxy)methyl) cyclohexyl)methoxy)acetic acid |
| 98 | 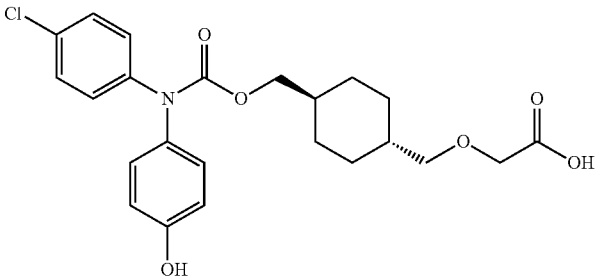 | 2-(((1r,4r)-4-(((4-chlorophenyl)(4-hydroxyphenyl)carbamoyloxy) methyl)cyclohexyl)methoxy) acetic acid |
| 99 | 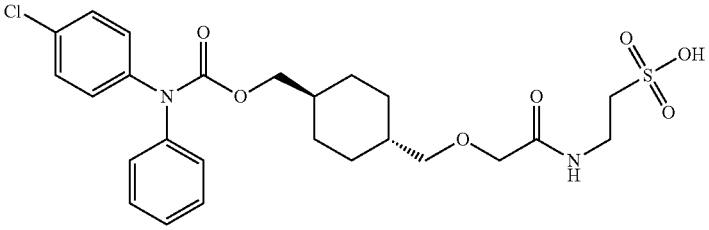 | 2-(2-(((1r,4r)-4-(((4-chlorophenyl)(phenyl) carbamoyloxy)methyl) cyclohexyl)methoxy)acetamido) ethanesulfonic acid |
| 100 | 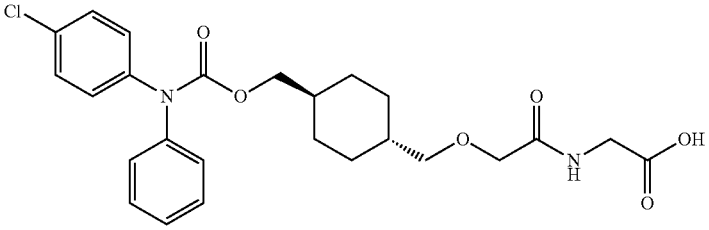 | 2-(2-(((1r,4r)-4-(((4-chlorophenyl)(phenyl) carbamoyloxy)methyl) cyclohexyl)methoxy)acetamido) acetic acid |

Additionally, individual compounds and chemical genera of the present invention, for example those compounds found in TABLE A including diastereoisomers and enantiomers thereof, encompass all pharmaceutically acceptable salts, solvates and particularly hydrates, thereof. Further, mesoisomers of individual compounds and chemical genera of the present invention, for example those compounds found in TABLE A, encompass all pharmaceutically acceptable salts, solvates and particularly hydrates, thereof. The compounds of the Formula (Ia) of the present invention may be prepared according to relevant published literature procedures that are used by one skilled in the art. Exemplary reagents and procedures for these reactions appear hereinafter in the working Examples.

The embodiments of the present invention include every combination of one or more salts selected from the following group and pharmaceutically acceptable solvates and hydrates thereof:

sodium 2-(((1r,4r)-4-((diphenylcarbamoyloxy)methyl)cyclohexyl)methoxy)acetate;

sodium 2-(((1r,4r)-4-(((4-chlorophenyl)(phenyl)carbamoyloxy)methyl)cyclohexyl)methoxy)acetate;

sodium 2-(((1r,4r)-4-(((4-fluorophenyl)(phenyl)carbamoyloxy)methyl)cyclohexyl)methoxy)acetate;

sodium 2-(((1r,4r)-4-(((3-fluorophenyl)(phenyl)carbamoyloxy)methyl)cyclohexyl)methoxy)acetate;

magnesium 2-(((1r,4r)-4-(((3-fluorophenyl)(phenyl)carbamoyloxy)methyl)cyclohexyl)methoxy)acetate;

potassium 2-(((1r,4r)-4-(((3-fluorophenyl)(phenyl)carbamoyloxy)methyl)cyclohexyl)methoxy)acetate; and calcium 2-(((1r,4r)-4-(((3-fluorophenyl)(phenyl)carbamoyloxy)methyl)cyclohexyl)methoxy)acetate.

It is understood that the present invention embraces each diastereoisomer, each enantiomer and mixtures thereof of each compound and generic formula disclosed herein just as if they were each individually disclosed with the specific stereochemical designation for each chiral carbon. Separation of the individual isomers (such as, by chiral HPLC, recrystallization of diastereoisomeric mixtures and the like) or selective synthesis (such as, by enantiomeric selective syntheses and the like) of the individual isomers is accomplished by application of various methods which are well known to practitioners in the art.

Indications and Methods of Prophylaxis and/or Treatment

In addition to the foregoing beneficial uses for the modulators of PGI2 receptor activity disclosed herein, the compounds disclosed herein are useful in the treatment of several additional diseases and disorders, and in the amelioration of symptoms thereof. Without limitation, these include the following:

1. Pulmonary Arterial Hypertension (PAH)

Pulmonary arterial hypertension (PAH) has a multifactorial pathobiology. Vasoconstriction, remodeling of the pulmonary vessel wall, and thrombosis contribute to increased pulmonary vascular resistance in PAH (Humbert et al., J. Am. Coll. Cardiol., 2004, 43:13S-24S).

The compounds of the present invention disclosed herein are useful in the treatment of pulmonary arterial hypertension (PAH) and symptoms thereof. PAH shall be understood to encompass the following forms of pulmonary arterial hypertension described in the 2003 World Health Organization (WHO) clinical classification of pulmonary arterial hypertension: idiopathic PAH (IPAH); familial PAH (FPAH); PAH associated with other conditions (APAH), such as PAH associated with collagen vascular disease, PAH associated with congenital systemic-to-pulmonary shunts, PAH associated with portal hypertension. PAH associated with HIV infection, PAH associated with drugs or toxins, or PAH associated with Other; and PAH associated significant venous or capillary involvement.

Idiopathic PAH refers to PAH of undetermined cause.

Familial PAH refers to PAH for which hereditary transmission is suspected or documented.

PAH associated with collagen vascular disease shall be understood to encompass PAH associated with scleroderma. PAH associated with CREST (calcinosis cutis, Raynaud's phenomenon, esophageal dysfunction, sclerodactyly, and telangiectasias) syndrome. PAH associated with systemic lupus erythematosus (SLE), PAH associated with rheumatoid arthritis, PAH associated with Takayasu's arteritis, PAH associated with polymyositis, and PAH associated with dermatomyositis.

PAH associated with congenital systemic-to-pulmonary shunts shall be understood to encompass PAH associated with atrial septic defect (ASD), PAH associated with ventricular septic defect (VSD) and PAH associated with patent ducts arteriosus.

PAH associated with drugs or toxins shall be understood to encompass PAH associated with ingestion of aminorex. PAH associated with ingestion of a fenfluramine compound (e.g., PAH associated with ingestion of fenfluramine or PAH associated with ingestion of dexfenfluramine), PAH associated with ingestion of certain toxic oils (e.g., PAH associated with ingestion of rapeseed oil). PAH associated with ingestion of pyrrolizidine alkaloids (e.g., PAH associated with ingestion of bush tea) and PAH associated with ingestion of monocrotaline.

PAH associated with Other shall be understood to encompass PAH associated with a thyroid disorder. PAH associated with glycogen storage disease, PAH associated with Gaucher disease. PAH associated with hereditary hemorrhagic telangiectasia. PAH associated with a hemoglobinopathy. PAH associated with a myeloproliferative disorder, and PAH associated with splenectomy.

PAH associated with significant venous or capillary involvement shall be understood to encompass PAH associated with pulmonary veno-occlusive disease (PVOD) and PAH associated with pulmonary capillary hemangiomatosis (PCH).

(See, e.g., Simonneau et al., J. Am. Coll. Cardiol. 2004, 43:5S-12S; McGoon et al., Chest, 2004, 126:14S-34S; Rabinovitch, Annu. Rev. Pathol. Mech. Dis., 2007, 2:369-399; McLaughlin et al., Circulation, 2006, 114:1417-1431; Strauss et al., Clin. Chest. Med., 2007, 28:127-142; Taichman et al., Clin. Chest. Med., 2007, 28:1-22).

Evidence for the association of PAH with scleroderma and the beneficial effect of an agonist of the PGI2 receptor on PAH is given by Badesch et al. (Badesch et al., Ann. Intern. Med., 2000, 132:425-434). Evidence for the association of PAH with the collagen vascular diseases mixed connective tissue disease (MCTD), systemic lupus, erythematosus (SLE), Sjögren's syndrome and CREST syndrome and the beneficial effect of an agonist of the PGI2 receptor on PAH is given by Humbert et al. (Eur. Respir. J., 1999, 13:1351-1356). Evidence for the association of PAH with CREST syndrome and the beneficial effect on an agonist of the PGI2 receptor on PAH is given by Miwa et al. (Int. Heart J., 2007, 48:417-422). Evidence for the association of PAH with SLE and the beneficial effect of an agonist of the PGI2 receptor on PAH is given by Robbins et al. (Chest, 2000, 117:14-18). Evidence for the association of PAH with HIV infection and the beneficial of an agonist of the PGI2 receptor on PAH is given by Aguilar et al. (Am. J. Respir. Crit. Care Med., 2000, 162:1846-1850). Evidence for the association of PAH with congenital heart defects (including ASD, VSD and patent ductus arteriosus) and the beneficial effect of an agonist of the PGI2 receptor on PAH is given by Rosenzweig et al. (Circulation, 1999, 99:1858-1865). Evidence for the association of PAH with fenfluramine and with dexfenfluramine, anorexigens, is given by Archer et al. (Am. J. Respir Crit. Care Med., 1998, 158:1061-1967). Evidence for the association of PAH with hereditary hemorrhagic telangiectasia is given by McGoon et al. (Chest, 2004, 126:14-34). Evidence for the association of PAH with splenectomy is given by Hoeper et al. (Ann. Intern. Med. 1999, 130:506-509). Evidence for the association of PAH with portal hypertension and the beneficial effect of an agonist of the PGI2 receptor on PAH is given by Hoeper et al. (Eur. Respir. J., 2005, 25:502-508).

Symptoms of PAH include dyspnea, angina, syncope and edema (McLaughlin et al., Circulation, 2006, 114:1417-1431). The compounds of the present invention disclosed herein are useful in the treatment of symptoms of PAH.

2. Antiplatelet Therapies (Conditions Related to Platelet Aggregation)

Antiplatelet agents (antiplatelets) are prescribed for a variety of conditions. For example, in coronary artery disease they are used to help prevent myocardial infarction or stroke in patients who are at risk of developing obstructive blood clots (e.g., coronary thrombosis).

In a myocardial infarction ("MI" or "heart attack"), the heart muscle does not receive enough oxygen-rich blood as a result of a blockage in the coronary blood vessels. If taken while an attack is in progress of immediately afterward (preferably within 30 min), antiplatelets can reduce the damage to the heart.

A transient ischemic attack ("TIA" or "mini-stroke") is a brief interruption of oxygen flow to the brain due to decreased blood flow through arteries, usually due to an obstructing blood clot. Antiplatelet drugs have been found to be effective in preventing TIAs.

Angina is a temporary and often recurring chest pain, pressure of discomfort caused by inadequate oxygen-rich blood flow (ischemia) in some parts of the heart. In patients with angina, antiplatelet therapy can reduce the effects of angina and the risk of myocardial infarction.

Stroke is an event in which the brain does not receive enough oxygen-rich blood, usually due to blockage of a cerebral blood vessel by a blood clot. In high-risk patients, taking antiplatelets regularly has been found to prevent the formation of blood clots that cause first or second strokes.

Angioplasty is a catheter based technique used to open arteries obstructed by a blood clot. Whether or not stenting is performed immediately after this procedure to keep the artery open, antiplatelets can reduce the risk of forming additional blood clots following the procedure(s).

Coronary bypass surgery is a surgical procedure in which an artery or vein is taken from elsewhere in the body and grafted to a blocked coronary artery, rerouting blood around the blockage and through the newly attached vessel. After the procedure, antiplatelets can reduce the risk of secondary blood clots.

Atrial fibrillation is the most common type of sustained irregular heart rhythm (arrhythmia). Atrial fibrillation affects about two million Americans every year. In atrial fibrillation, the atria (the heart's upper chambers) rapidly fire electrical signals that cause them to quiver rather than contract normally. The result is an abnormally fast and highly irregular heartbeat. When given after an episode of atrial fibrillation, antiplatelets can reduce the risk of blood clots forming in the heart and traveling to the brain (embolism).

There is evidence that a PGI2 receptor agonist will inhibit platelet aggregation and thus be a potential treatment as an antiplatelet therapy (see, e.g., Moncada et al., Lancet, 1977, 1:18-20). It has been shown that genetic deficiency of the PGI2 receptor in mice leads to an increased propensity towards thrombosis (Murata et al., Nature, 1997, 388:678-682).

PGI2 receptor agonists can be used to treat, for example, claudication or peripheral artery disease as well as cardiovascular complications, arterial thrombosis, atherosclerosis, vasoconstriction caused by serotonin, ischemia-reperfusion injury, and restenosis of arteries following angioplasty or stent placement. (See, e.g., Fetalvero et al., Prostaglandins Other Lipid Mediat., 2007, 82:109-118; Arehart et al., Curr. Med. Chem., 2007, 14:2161-2169: Davi et al., N. Engl. J. Med., 2007, 357:2482-2494; Fetalvero et al., Am. J. Physiol. Heart. Circ. Physiol., 2006, 290:111337-111346; Murata et al., Nature, 1997, 388:678-682; Wang et al., Proc. Natl. Acad. Sci. USA, 2006, 103:14507-14512; Xiao et al., Circulation, 2001, 104:2210-2215; McCormick et al., Biochem. Soc. Trans., 2007, 35:910-911; Arehart et al., Circ. Res., 2008, Mar. 6 Epub ahead of print.)

PGI2 receptor agonists can also be used alone or in combination with thrombolytic therapy, for example, tissue-type plasminogen activator (t-PA), to provide cardioprotection following MI or postischemic myocardial dysfunction or protection from ischemic injury during percutaneous coronary intervention, and the like, including complications resulting therefrom. PGI2 receptor agonists can also be used in antiplatelet therapies in combination with, for example, alpha-tocopherol (vitamin E), echistatin (a disintegrin) or, in states of hypercoagulability, heparin. (See, e.g., Chan., J. Nutr., 1998, 128:1593-1596; Mardla et al., Platelets, 2004, 18:319-324; Bernabei et al., Ann. Thorac. Surg., 1995, 59:149-153; Gainza et al., J. Nephrol., 2006, 19:48-655.)

The PGI2 receptor agonists disclosed herein provide beneficial improvement in microcirculation to patients in need of antiplatelet therapy by antagonizing the vasoconstrictive products of the aggregating platelets in, for example and not limited to the indications described above. Accordingly, in some embodiments, the present invention provides methods for reducing platelet aggregation in a patient in need thereof, comprising administering to the patient a composition comprising a PGI2 receptor agonist disclosed herein. In further embodiments, the present invention provides methods for treating coronary artery disease, myocardial infarction, transient ischemic attack, angina, stroke, atrial fibrillation, or a symptom of any of the foregoing in a patient in need of the treatment, comprising administering to the patient a composition comprising a PGI2 receptor agonist disclosed herein.

In further embodiments, the present invention provides methods for reducing risk of blood clot formation in an angioplasty or coronary bypass surgery patient, or a patient suffering from atrial fibrillation, comprising administering to the patient a composition comprising a PGI2 receptor agonist disclosed herein at a time where such risk exists.

3. Atherosclerosis

Atherosclerosis is a complex disease characterized by inflammation, lipid accumulation, cell death and fibrosis. It is the leading cause of mortality in many countries, including the United States. Atherosclerosis, as the term is used herein, shall be understood to encompass disorders of large and medium-sized arteries that result in the progressive accumulation within the intima of smooth muscle cells and lipids.

It has been shown that an agonist of the PGI2 receptor can confer protection from atherosclerosis, such as from atherothrombosis (Arehart et al., Curr. Med. Chem., 2007, 14:2161-2169: Stitham et al., Prostaglandins Other Lipid Mediat., 2007, 82:95-108; Fries et al., Hematology Am. Soc.

Hematol. Educ. Program. 2005, 445-451; Egan et al., Science, 2004, 306:1954-1957; Kobayashi et al., J. Clin. Invest., 2004, 114:784-794; Arehart et al., Circ. Res., 2008, Mar. 6 Epub ahead of print).

It has been shown that defective PGI2 receptor signaling appears to accelerate atherothrombosis in humans, i.e. that an agonist of the PGI2 receptor can confer protection from atherothrombosis in humans (Arehart et al., Circ. Res., 2008, Mar. 6 Epub ahead of print).

The compounds of the present invention disclosed herein are useful in the treatment of atherosclerosis, and the treatment of the symptoms thereof. Accordingly, in some embodiments, the present invention provides methods for treating atherosclerosis in a patient in need of the treatment, comprising administering to the patient a composition comprising a PGI2 receptor agonist disclosed herein. In further embodiments, methods are provided for treating a symptom of atherosclerosis in a patient in need of the treatment, comprising administering to the patient a composition comprising a PGI2 receptor agonist disclosed herein.

4. Asthma

Asthma is a lymphocyte-mediated inflammatory airway disorder characterized by airway eosinophilia, increased mucus production by goblet cells, and structural remodeling of the airway wall. The prevalence of asthma has dramatically increased worldwide in recent decades. It has been shown that genetic deficiency of the PGI2 receptor in mice augments allergic airway inflammation (Takahashi et al., Br J Pharmacol, 2002, 137:315-322). It has been shown that an agonist of the PGI2 receptor can suppress not only the development of asthma when given during the sensitization phase, but also the cardinal features of experimental asthma when given during the challenge phase (Idzko et al., J. Clin. Invest., 2007, 117:464-472; Nagao et al., Am. J. Respir. Cell Mol. Biol., 2003, 29:314-320), at least in part through markedly interfering with the function of antigen-presenting dendritic cells within the airways (Idzko et al., J. Clin. Invest., 2007, 117:464-472; Thou et al., J. Immunol., 2007, 178:702-710; Jaffar et al. J. Immunol., 2007, 179:6193-6203; Jozefowski et al., Int. Immunopharmacol., 2003, 3:865-878). These cells are crucial for both the initiation and the maintenance phases of allergic asthma, as depletion of airway dendritic cells during secondary challenge in sensitized mice abolished all characteristic features of asthma, an effect that could be completely restored by adoptive transfer of wild-type dendritic cells (van Rijt et al., J. Exp. Med., 2005, 201:981-991). It has also been shown that an agonist of the PGI2 receptor can inhibit proinflammatory cytokine secretion by human alveolar macrophages (Raychaudhuri et al., J. Biol. Chem., 2002, 277:33344-33348). The compounds of the present invention disclosed herein are useful in the treatment of asthma, and the treatment of the symptoms thereof. Accordingly, in some embodiments, the present invention provides methods for treating asthma in a patient in need of the treatment, comprising administering to the patient a composition comprising a PGI2 receptor agonist disclosed herein. In further embodiments, methods are provided for treating a symptom of asthma in a patient in need of the treatment, comprising administering to the patient a composition comprising a PGI2 receptor agonist disclosed herein.

5. Diabetic-Related Pathologies

Although hyperglycemia is the major cause for the pathogenesis of diabetic complications such as diabetic peripheral neuropathy (DPN), diabetic nephropathy (DN) and diabetic retinopathy (DR), enhanced vasoconstriction and platelet aggregation in diabetic patients has also been implicated to play a role in disease progression (Cameron at al., Naunyn Schmiedebergs Arch. Pharmacol., 2003, 367:607-614). Agonists of the PGI2 receptor promote vasodilation and inhibit platelet aggregation. Improving microvascular blood flow is able to benefit diabetic complications (Cameron, Diabetologia, 2001, 44:1973-1988).

It has been shown that an agonist of the PGI2 receptor can prevent and reverse motor and sensory peripheral nerve conduction abnormalities in streptozotocin-diabetic rats (Cotter et Naunyn Schmiedebergs Arch. Pharmacol., 1993, 347:534-540). Further evidence for the beneficial effect of an agonist of the PGI2 receptor in the treatment of diabetic peripheral neuropathy is given by Hotta et al. (Diabetes, 1996, 45:361-366). Ueno et al. (Jpn. J. Pharmacol., 1996, 70:177-182), Ueno et al, (Life Sci., 1996, 59:PI.105-PI.110). Hotta et al. (Prostaglandins, 1995, 49:339-349), Shindo et al. (Prostaglandins, 1991, 41:85-96), Okuda et al. (Prostaglandins, 1996, 52:375-384), and Koike et al. (FASEB J., 2003, 17:779-781). Evidence for the beneficial effect of an agonist of the PGI2 receptor in the treatment of diabetic nephropathy is given by Owada et al. (Nephron. 2002, 92:788-796) and Yamashita et al. (Diabetes Res. Clin. Pract., 2002, 57:149-161). Evidence for the beneficial effect of an agonist of the PGI2 receptor in the treatment of diabetic retinopathy is given by Yamagishi et al. (Mol. Med., 2002, 8:546-550). Burnette et al. (Exp. Eye Res., 2006, 83:1359-1365), and Hotta et al. (Diabetes, 1996, 45:361-366). It has been shown that an agonist of the PGI2 receptor can reduce increased tumor necrosis factor-α (TNF-α) levels in diabetic patients, implying that an agonist of the PGI2 receptor may contribute to the prevention of progression in diabetic complications (Fujiwara et al., Exp. Clin. Endocrinol. Diabetes, 2004, 112:390-394).

6. Glaucoma

Evidence that topical administration of an agonist of the PGI2 receptor can result in a decrease in intraocular pressure (IOP) in rabbits and dogs and thereby have beneficial effect in the treatment of glaucoma is given by Hoyng et al. (Hoyng et al., Invest. Ophthalmol. Vis. Sci., 1987, 28:470-476).

7. Hypertension

Agonists of the PGI2 receptor have been shown to have activity for regulation of vascular tone, for vasodilation, and for amelioration of pulmonary hypertension (see, e.g., Strauss et al., Clin Chest Med. 2007, 28:127-142; Driscoll et al., Expert Opin. Pharmacother., 2008, 9:65-81). Evidence for a beneficial effect of an agonist of the PGI2 receptor in the treatment of hypertension is given by Yamada et al. (Peptides, 2008, 29:412-418). Evidence that an agonist of the PGI2 receptor can protect against cerebral ischemia is given by Dogan et al. (Gen. Pharmacol., 1996, 27:1163-1166) and Fang et al. (J. Cereb. Blood Flow Metab., 2006, 26:491-501).

8. Anti-Inflammation Therapies

Anti-inflammation agents are prescribed for a variety of conditions. For example, in an inflammatory disease they are used to interfere with and thereby reduce an underlying deleterious There is evidence that a PGI2 receptor agonist can inhibit inflammation and thus be a potential treatment as an anti-inflammation therapy. It has been shown that an agonist of the PGI2 receptor can inhibit pro-inflammatory cytokine and chemokine (interleukin-12 (IL-12), tumor necrosis factor-α (TNF-α), IL-1α, IL-6, macrophage inflammatory protein-1alpha (MIP-1α), monocyte chemoattractant protein-1 (MCP-1)) production and T cell stimulatory function of dendrite cells (Jozefowski et al., Int. Immunopharmacol., 2003. 865-878; Thou et al., J. Immunol., 2007, 178:702-710; Nagao et al., Am. J. Respir. Cell Mol. Biol., 2003, 29:314-320; Idzko et al., J. Clin. Invest., 2007, 117:464-472). It has been shown that an agonist of the PGI2 receptor can inhibit pro-inflammatory cytokine (TNF-α, IL-1β, IL-6, granulocyte macrophage stimulating factor (GM-CSF)) production by macrophages (Raychaudhuri et al., J. Biol. Chem., 2002, 277:33344-33348; Czeslick et al., Eur. J. Clin. Invest., 2003, 33:1013-1017; Di Renzo et al., Prostaglandin Leukot. Essent. Fatty Acids, 2005, 73:405-410; Shinomiya et al., Biochem. Pharmacol., 2001, 61:1153-1160). It has been shown that an agonist of the PGI2 receptor can stimulate anti-inflammatory cytokine (IL-10) production by dendritic cells (Jozefowski et al., Int. Immunopharmacol., 2003, 865-878; Zhou et al., J. Immunol., 2007, 178:702-710). It has been shown that an agonist of the PGI2 receptor can stimulate anti-inflammatory cytokine (IL-10) production by macrophages (Shinomiya et al., Biochem. Pharmacol., 2001, 61:1153-1160). It has been shown that an agonist of the PGI2 receptor can inhibit a chemokine (CCL17)-induced chemotaxis of leukocytes ($CD4^+$ Th2 T cells) (Jaffar et al., J. Immunol., 2007, 179:6193-6203). It has been shown that an agonist of the PGI2 receptor can confer protection from atherosclerosis, such as from atherothrombosis (Arehart et al., Curr. Med. Chem., 2007, 14:2161-2169; Stitham et al., Prostaglandins Other Lipid Mediat., 2007, 82:95-108; Fries et al., Hematology Am. Soc. Hematol. Educ. Program, 2005, :445-451; Egan et al., Science, 2004, 306:1954-1957; Kobayashi et al., J. Clin. Invest., 2004, 114:784-794; Arehart et al., Circ. Res., 2008, Mar. 6 Epub ahead of print). It has been shown that an agonist of the PGI2 receptor can attenuate asthma (Idzko et al., J. Clin. Invest., 2007, 117:464-472; Jaffar et al., J. Immunol., 2007, 179:6193-6203; Nagao et al., Am. J. Respir. Cell. Mol. Biol., 2003, 29:314-320). It has been shown that an agonist of the PGI2 receptor can decrease TNF-α production in type 2 diabetes patients (Fujiwara et al., Exp. Clin. Endocrinol. Diabetes, 2004, 112:390-394; Goya et al., Metabolism, 2003, 52:192-198). It has been shown that an agonist of the PGI2 receptor can inhibit ischemia-reperfusion injury (Xiao et al., Circulation, 2001, 104:2210-2215). It has been shown that an agonist of the PGI2 receptor can inhibit restenosis (Cheng et al., Science, 2002, 296:539-541). It has been shown that an agonist of the PGI2 receptor can attenuate pulmonary vascular injury and shock in a rat model of septic shock (Harada et al., Shock, 2008, Feb. 21 Epub ahead of print). It has been shown that an agonist of the PGI2 receptor can reduce the serum levels of TNF-α in vivo in patients with rheumatoid arthritis, and this is associated with improvement in the clinical course of the disease (Gao et al., Rheumatol. Int., 2002, 22:45-51; Boehme et al., Rheumatol. Int., 2006, 26:340-347).

The compounds of the present invention disclosed herein provide beneficial reduction of inflammation. The compounds of the present invention disclosed herein provide beneficial reduction of a deleterious inflammatory response associated with an inflammatory disease. Accordingly, in some embodiments, the present invention provides methods for reducing inflammation in a patient in need thereof, comprising administering to the patient a composition comprising a PGI2 receptor agonist disclosed herein. In some embodiments, the present invention provides methods for decreasing IL-12, TNF-α, IL-1α, IL-1β, IL-6, MIP-1α or MCP-1 production in a patient in need thereof, comprising administering to the patient a composition comprising a PGI2 receptor agonist disclosed herein. In some embodiments, the present invention provides methods for decreasing TNF-α production in a patient in need thereof, comprising administering to the patient a composition comprising a PGI2 receptor agonist disclosed herein. In some embodiments, the present invention provides methods for increasing IL-10 production in a patient in need thereof, comprising administering to the patient a composition comprising a PGI2 receptor agonist disclosed herein. In some embodiments, the present invention provides methods for reducing a deleterious inflammatory response associated with an inflammatory disease in a patient in need thereof, comprising administering to the patient a composition comprising a PGI2 receptor agonist disclosed herein. In some embodiments, the present invention provides methods for treating an inflammatory disease or a symptom thereof in a patient in need of the treatment comprising administering to the patient a composition comprising a PGI2 receptor agonist disclosed herein. In some embodiments, the present invention provides methods for treating an inflammatory disease or a symptom thereof in a patient in need of the treatment comprising administering to the patient a composition comprising a PGI2 receptor agonist disclosed herein. In some embodiments, the present invention provides methods for treating an inflammatory disease or a symptom thereof in a patient in need of the treatment comprising administering to the patient a composition comprising a PGI2 receptor agonist disclosed herein, wherein the inflammatory disease is selected from the group consisting of psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, diabetes (including type 1 diabetes and type 2 diabetes), sepsis, chronic obstructive pulmonary disease (COPD), and asthma.

Pharmaceutical Compositions

A further aspect of the present invention pertains to pharmaceutical compositions comprising one or more compounds as described herein and one or more pharmaceutically acceptable carriers. The embodiments pertain to pharmaceutical compositions comprising a compound of the present invention and a pharmaceutically acceptable carrier.

The embodiments of the present invention include a method of producing a pharmaceutical composition comprising admixing at least one compound according to any of the compound embodiments disclosed herein and a pharmaceutically acceptable carrier.

Formulations may be prepared by any suitable method, typically by uniformly mixing the active compound(s) with liquids or finely divided solid carriers, or both, in the required proportions and then, if necessary, forming the resulting mixture into a desired shape.

Conventional excipients, such as binding agents, fillers, acceptable wetting agents, tabletting lubricants and disintegrants may be used in tablets and capsules for oral administration. Liquid preparations for oral administration may be in the form of solutions, emulsions, aqueous or oily suspensions and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives and flavorings and colorants may be added to the liquid preparations. Parenteral dosage forms may be prepared by dissolving the compound of the invention in a suitable liquid vehicle and filter sterilizing the solution before filling and sealing an appropriate vial or ampule. These are just a few examples of the many appropriate methods well known in the art for preparing dosage forms.

A compound of the present invention can be formulated into pharmaceutical compositions using techniques well known to those in the art. Suitable pharmaceutically-acceptable carriers, outside those mentioned herein, are known in the art; for example, see Remington, The Science and Practice of Pharmacy, 20$^{th}$ Edition, 2000, Lippincott Williams & Wilkins, (Editors: Gennaro et al.)

While it is possible that, for use in the prophylaxis or treatment, a compound of the invention may, in an alternative use, be administered as a raw or pure chemical, it is preferable however to present the compound or active ingredient as a pharmaceutical formulation or composition further comprising a pharmaceutically acceptable carrier.

The invention thus further provides pharmaceutical formulations comprising a compound of the invention or a pharmaceutically acceptable salt, solvent, hydrate or derivative thereof together with one or more pharmaceutically acceptable carriers thereof and/or prophylactic ingredients. The carrier(s) must be "acceptable" ii the sense of being compatible with the other ingredients of the formulation and not overlay deleterious to the recipient thereof. Typical procedures for making and identifying suitable hydrates and solvates, outside those mentioned herein, are well known to those in the art; see for example, pages 202-209 of K. J. Guillory, "Generation of Polymorphs, Hydrates, Solvates, and Amorphous Solids," in: Polymorphism in Pharmaceutical Solids, ed. Harry G. Brittan, Vol. 95, Marcel Dekker, Inc., New York, 1999, incorporated herein by reference in its entirety.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation, insufflation or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds of the invention, together with a conventional adjuvant, carrier, or diluent, may thus be placed into the form of pharmaceutical formulations and unit dosages thereof and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as tale or magnesium stearate. The active ingredient may also be administered by injection as a composition wherein, for example, saline, dextrose or water may be used as a suitable pharmaceutically acceptable carrier.

Compounds of the present invention or a solvate, hydrate or physiologically functional derivative thereof can be used as active ingredients in pharmaceutical compositions, specifically as PGI2 receptor modulators. By the term "active ingredient" is defined in the context of a "pharmaceutical composition" and is intended to mean a component of a pharmaceutical composition that provides the primary pharmacological effect, as opposed to an "inactive ingredient" which would generally be recognized as providing no pharmaceutical benefit.

The dose when using the compounds of the present invention can vary within wide limits and as is customary and is known to the physician, it is to be tailored to the individual conditions in each individual case. It depends, for example, on the nature and severity of the illness to be treated, on the condition of the patient, on the compound employed or on whether an acute of chronic diseases state is treated of prophylaxis is conducted or on whether further active compounds are administered in addition to the compounds of the present invention. Representative doses of the present invention include, but not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, about 0.001 mg to about 50 mg and about 0.001 mg to about 25 mg. Multiple doses may be administered during the day, especially when relatively large amounts are deemed to be needed, for example 2, 3 or 4 doses. Depending on the individual and as deemed appropriate from the patient's physician or caregiver it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis is conducted or on whether further active compounds are administered in addition to the compounds of the present invention and as part of a drug combination. The dosage regimen for treating a disease condition with the compounds and/or compositions of this invention is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods of this invention.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4 part administration. If appropriate, depending on individual behavior, it may be necessary to deviate upward or downward from the daily dose indicated.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt, solvate or hydrate of a compound of the invention.

For preparing pharmaceutical compositions from the compounds of the present invention, the selection of a suitable pharmaceutically acceptable carrier can be either solid, liquid or a mixture of both. Solid form preparations include powders, tablets, pills, capsules, cachets, suppositories and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desire shape and size.

The powders and tablets may contain varying percentage amounts of the active compound. A representative amount in a powder or tablet may contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving of suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations which are intended to be converted, shortly before use, to liquid form preparations for oral administration. Such liquid forms include solutions, suspensions and emulsions. These preparations may contain, in addition to the active component, colorants, flavors, stabilizers, buffers, artificial and natural sweeteners, dispersants, thickeners, solubilizing agents and the like.

For topical administration to the epidermis the compounds according to the invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one of more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions of suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds of the present invention or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds of the present inention as an aerosol can be prepared by processes well known to the person skilled in the art. For their preparation, for example, solutions or dispersions of the compounds of the present invention in water, water/alcohol mixtures or suitable saline solutions can be employed using customary additives, for example benzyl alcohol or other suitable preservatives, absorption enhancers for increasing the bioavailability, solubilizers, dispersants and others and, if appropriate, customary propellants, for example include carbon dioxide, CFCs, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the ingredient may be employed.

Alternatively the active ingredients may be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules of cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage can be a capsule, tablet, cachet, or lozenge itself, or it can be the appropriate number of any of these in packaged form.

Tablets or capsules for oral administration and liquids for intravenous administration are preferred compositions.

The compounds according to the invention may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfiric, tartaric, oxalic, p-toluenesulfonic and the like. Certain compounds of the present invention which contain a carboxylic acid functional group may optionally exist as pharmaceutically acceptable salts containing non-toxic, pharmaceutically acceptable metal cations and cations derived from organic bases. Representative metals include, but are not limited to, aluminium, calcium, lithium, magnesium, potassium, sodium, zinc and the like. In some embodiments the pharmaceutically acceptable metal is sodium. Representative organic bases include, but are not limited to, benzathine ($N^1$,$N^2$-dibenzylethane-1,2-diamine), chloroprocaine (2-(diethylamino)ethyl 4-(chloroamino)benzoate), choline, diethanolamine, ethylenediamine, meglumine ((2R,3R,4R,5S)-6-(methylamino) hexane-1,2,3,4,5-pentaol), procaine (2-(diethylamino)ethyl 4-aminobenzoate), and the like. Certain pharmaceutically acceptable salts are listed in Berge, et al., Journal of Pharmaceutical Sciences, 66:1-19 (1977), incorporated herein by reference in its entirety.

The embodiments of the present invention include every combination of one or more compounds selected from the following group and pharmaceutically acceptable solvates and hydrates thereof:

sodium 2-(((1r,4r)-4-((diphenylcarbamoyloxy)methyl)cyclohexyl)methoxy)acetate;

sodium 2-(((1r,4r)-4-(((4-chlorophenyl)(phenyl)carbamoyloxy)methyl)cyclohexyl)methoxy)acetate;

sodium 2-(((1r,4r)-4-(((4-fluorophenyl)(phenyl)carbamoyloxy)methyl)cyclohexyl)methoxy)acetate;

sodium 2-(((1r,4r)-4-(((3-fluorophenyl)(phenyl)carbamoyloxy)methyl)cyclohexyl)methoxy)acetate;

magnesium 2-(((1r,4r)-4-(((3-fluorophenyl)(phenyl)carbamoyloxy)methyl)cyclohexyl)methoxy)acetate;

potassium 2-(((1r,4r)-4-(((3-fluorophenyl)(phenyl)carbamoyloxy)methyl)cyclohexyl)methoxy)acetate; and calcium 2-(((1r,4r)-4-(((3-fluorophenyl)(phenyl)carbamoyloxy)methyl)cyclohexyl)methoxy)acetate.

The acid addition salts may be obtained as the direct products of compound synthesis. In the alternative, the free base may be dissolved in a suitable solvent containing the appropriate acid and the salt isolated by evaporating the solvent or otherwise separating the salt and solvent. The compounds of this invention may form solvates with standard low molecular weight solvents using methods known to the skilled artisan.

Compounds of the present invention can be converted to "pro-drugs." The term "pro-drugs" refers to compounds that have been modified with specific chemical groups known in the art and when administered into an individual these groups undergo biotransformation to give the parent compound. Pro-drugs can thus be viewed as compounds of the invention containing one or more specialized non-toxic protective groups used in a transient manner to alter or to eliminate a property of the compound. In one general aspect, the "pro-drug" approach is utilized to facilitate oral absorption. A thorough discussion is provided in T. Higuchi and V. Stella, Pro-drugs as Novel Delivery Systems Vol. 14 of the A.C.S. Symposium Series; and in Bioreversible Carriers in Drug Design, ed. Edward B. Roche, American Pharmaceutical Association and Pergamon Press, 1987, both of which are hereby incorporated by reference in their entirety.

The embodiments of the present invention include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

It is noted that when the PGI2 receptor modulators are utilized as active ingredients in a pharmaceutical composition, these are not intended for use only in humans, but in other non-human mammals as well. Indeed, recent advances in the area of animal health-care mandate that consideration be given for the use of active agents, such as PGI2 receptor modulators, for the treatment of an PGI2-associated disease or disorder in companionship animals (e.g., cats, dogs, etc.) and is livestock animals (e.g., cows, chickens, fish, etc.) Those of ordinary skill in the art are readily credited with understanding the utility of such compounds in such settings.

Hydrates and Solvates

It is understood that when the phrase "pharmaceutically acceptable salts, solvates and hydrates" is used in reference to a particular formula herein, it is intended to embrace solvates and/or hydrates of compounds of the particular formula, pharmaceutically acceptable salts of compounds of the particular formula as well as solvates and/or hydrates of pharmaceutically acceptable salts of compounds of the particular formula. It is also understood by a person of ordinary skill in the art that hydrates are a subgenus of solvates.

The compounds of the present invention can be administrated in a wide variety of oral and parenteral dosage forms. It will be apparent to those skilled in the ant that the following dosage forms may comprise, as the active component, either a compound of the invention of a pharmaceutically acceptable salt or as a solvate or hydrate thereof. Moreover, various hydrates and solvates of the compounds of the invention and their salts will find use as intermediates in the manufacture of pharmaceutical compositions. Typical procedures for making and identifying suitable hydrates and solvates, outside those mentioned herein, are well known to those in the art; see for example, pages 202-209 of K. J. Guillory, "Generation of Polymorphs, Hydrates, Solvates, and Amorphous Solids," in: Polymorphism in Pharmaceutical Solids, ed. Harry G. Brittan, Vol. 95, Marcel Dekker, Inc., New York, 1999, incorporated herein by reference in its entirety. Accordingly, one aspect of the present invention pertains to hydrates and solvates of compounds of the present invention and/or their pharmaceutical acceptable salts, as described herein, that can be isolated and characterized by methods known in the art, such as, thermogravimetric analysis (TGA), TGA-mass spectroscopy, TGA-Infrared spectroscopy, powder X-ray diffraction (PXRD), Karl Fisher titration, high resolution X-ray diffraction, and the like. There are several commercial entities that provide quick and efficient services for identifying solvates and hydrates on a routine basis. Example companies offering these services include Wilmington PharmaTech (Wilmington, Del.). Avantium Technologies (Amsterdam) and Aptuit (Greenwich, Conn.).

The embodiments of the present invention include every combination of one or more solvate or hydrate selected from the following group:

sodium 2-(((1r,4r)-4-(((4-chlorophenyl)(pheny)carbamoyloxy)methyl)cyclohexyl)methoxy)acetate hydrate;

sodium 2-(((1r,4r)-4-(((3-fluorophenyl)(phenyl)carbamoyloxy)methyl)cyclohexyl)methoxy)acetate hydrate;

magnesium 2-(((1r,4r)-4-(((3-fluorophenyl)(phenyl)carbamoyloxy)methyl)cyclohexyl)methoxy)acetate isopropanol solvate;

potassium 2-(((1r,4r)-4-(((3-fluorophenyl)(phenyl)carbamoyloxymethyl)methyl)cyclohexyl)methoxy)acetate isopropanol solvate; and calcium 2-(((1r,4r)-4-(((3-fluorophenyl)(phenyl)carbamoyloxy)methyl)cyclohexyl)methoxy)acetate isopropanol solvate.

Certain solvates and hydrates of compounds of the present invention are described in Examples 1.107 to 1.111.

Crystalline Forms

A further aspect of the present invention pertains to a crystalline form (Form 1) of sodium 2-(((1r,4r)-4-(((4-chlorophenyl)(phenyl)carbamoyloxy)methyl)cyclohexyl) methoxy)acetate (the sodium salt of Compound 22). Form 1 of the sodium salt of Compound 22 can be identified by its unique solid state signature with respect to, for example, differential scanning calorimetry (DSC), X-ray powder diffraction (PXRD), and other solid state methods. Further characterization with respect to water or solvent content of the crystalline form can be gauged by any of the following methods for example, thermogravimetric analysis (TGA), DSC and the like. For DSC, it is known that the temperatures observed will depend upon sample purity, the rate of temperature change, as well as sample preparation technique and the particular instrument employed. Thus, the values reported herein relating to DSC thermograms can vary by plus or minus about 6° C. The values reported herein relating to DSC thermograms can also vary by plus or minus about 20 joules per gram. For PXRD, the relative intensities of the peaks can vary, depending upon the sample preparation technique, the sample mounting procedure and the particular instrument employed. Moreover, instrument variation and other factors can often affect the 20 values. Therefore, the peak assignments of diffraction patterns can vary by plus or minus about 0.2°2θ. For TGA, the features reported herein can vary by plus or minus about 5° C. The TGA features reported herein can also vary by plus or minus about 2% weight change due to, for example, sample variations. Further characterization with respect to hygroscopicity of the crystalline form can be gauged by, for example, dynamic vapor sorption (DVS). The DVS features reported herein can vary by plus or minus about 5% relative humidity. The DVS features reported herein can also vary by plus or minus about 5% weight change. The physical properties of Form 1 of the sodium salt of Compound 22 are summarized in Table 1 below.

TABLE 1

| | Sodium Salt of Compound 22 (Form 1) |
|---|---|
| TGA | FIG. 11: <0.1% weight loss below about 200° C. |
| DSC | FIG. 11: extrapolated onset temperature: 243° C.; endotherm peak temperature: 245° C. (maximum); associated heat flow 105 J/g |
| PXRD | FIG. 9: Peaks of ≥10% relative intensity at 6.1, 7.5, 9.6, 12.3, 14.5, 19.4, 20.0, 22.1, 23.1 and 23.9 °2θ |
| DVS | FIG. 10: absorption of <0.25% at 90% relative humidity |

The small weight loss observed in the TGA data suggests that Form 1 of the sodium salt of Compound 22 is an anhydrous, non-solvated crystalline form. The DSC thermogram further reveals a melting endotherm with an onset at about 243° C.

DVS data for the crystalline form of the Form 1 of the sodium salt of Compound 22 reveals low hygroscopicity, with absorption of less than 0.25% at 90% relative humidity. Certain X-ray powder diffraction peaks for Form 1 of the sodium salt of Compound 22 are shown in Table 2 below.

TABLE 2

| Sodium Salt of Compound 22 (Form 1) PXRD Peaks with Relative Intensity of 10% or Higher (°2θ) | |
|---|---|
| Peak Position (°2θ) | Relative Intensity (%) |
| 6.1 | 65 |
| 7.5 | 32 |
| 9.6 | 11 |
| 12.3 | 14 |
| 14.5 | 15 |
| 19.4 | 27 |
| 20.0 | 100 |
| 22.1 | 29 |
| 23.1 | 16 |
| 23.9 | 31 |

One aspect of the present invention is directed to a crystalline form (Form 1) of sodium 2-(((1r,4r)-4-(((4-chlorophenyl)(phenyl)carbamoyloxy)methyl)cyclohexyl) methoxy)acetate having an X-ray powder diffraction pattern comprising a peak, in terms of 2θ, at about 20.0. In some embodiments, the crystalline form has an X-ray powder diffraction pattern comprising a peak, in terms of 2θ, at about 6.1°. In some embodiments, the crystalline form has an X-ray powder diffraction pattern comprising a peak, in terms of 20, at about 20.0° and about 6.1°. In some embodiments, the crystalline form has an X-ray powder diffraction pattern comprising a peak, in terms of 2θ, at about 20.0° and about 7.5°. In some embodiments, the crystalline form has an X-ray powder diffraction pattern comprising a peak, in terms of 20, at about 20.0°, about 6.1°, and about 7.5°. In some embodiments, the crystalline form has an X-ray powder diffraction pattern comprising a peak, in terms of 2θ, at about 20.0°, about 6.1°, about 7.5°, about 23.9°, about 22.1°, about 19.4°, about 23.1° and about 14.5. In some embodiments, the crystalline form has an X-ray powder diffraction pattern comprising a peak, in terms of 2θ, at about 20.0°, about 6.1°, about 7.5°, about 23.9°, about 22.1°, about 19.4°, about 23.1°, about 14.5°, about 12.3° and about 9.6°. In yet further embodiments, the crystalline form has an X-ray powder diffraction pattern substantially as shown in FIG. 9, wherein by "substantially" is meant that the reported peaks can vary by about ±0.2°2θ.

In some embodiments, the crystalline form (Form 1) of sodium 2-(((1r,4)-4-(((4-chlorophenyl)(phenyl)carbamoyloxy)methyl)cyclohexyl)methoxy)acetate has a differential scanning calorimetry thermogram comprising an endotherm with an extrapolated onset temperature between about 235° C. and about 250° C. In some embodiments, the crystalline form has a differential scanning calorimetry thermogram comprising an endotherm with an extrapolated onset temperature at about 243° C. In some embodiments, the crystalline form has a differential scanning colorimetry thermogram comprising an endotherm with a peak temperature between about 237° C. and about 252° C. In some embodiments, the crystalline form has a differential scanning calorimetry thermogram comprising an endotherm with a peak temperature at about 245° C. In some embodiments, the crystalline form has a differential scanning calorimetry thermogram comprising an endotherm with an associated heat flow of about 105 joules per gram. In further embodiments, the crystalline form has a differential scanning calorimetry thermogram substantially as shown in FIG. 11, wherein by "substantially" is meant that the reported DSC features can vary by about ±4° C.

In some embodiments, the crystalline form (Form 1) of sodium 2-(((1r,4r)-4-(((4-chlorophenyl)(phenyl)carbamoyloxy)methyl)cyclohexyl)methoxy)acetate has a dynamic vapor sorption profile substantially as shown in FIG. 10, wherein by "substantially" is meant that the reported DVS features can vary by about ±5% relative humidity.

In some embodiments, the crystalline form (Form 1) of sodium 2-(((1r,4r)-4-(((4-chlorophenyl)(phenyl)carbamoyloxy)methyl)cyclohexyl)methoxy)acetate has a thermogravimetric analysis profile substantially as shown in FIG. 11, wherein by "substantially" is meant that the reported TGA features can vary by about ±5° C.

The crystalline form (Form 1) of sodium 2-(((1r,4r)-4-(((4-chlorophenyl)(phenyl)carbamoyloxy)methyl)cyclohexyl)methoxy)acetate, the sodium salt of Compound 22 described herein, can be prepared by any of the suitable procedures known in the art for preparing crystalline polymorphs. In some embodiments Form 1 of the sodium salt of Compound 22 can be prepared as described in Example 1.106. In some embodiments, Form 1 of the sodium salt of Compound 22 can be prepared by heating crystalline sodium salt of Compound 22, containing one or more crystalline forms other than Form 1. In some embodiments, Form 1 of the sodium salt of Compound 22 can be prepared by recrystallizing crystalline sodium salt of Compound 22, containing one or more crystalline forms other than Form 1 of the sodium salt of Compound 22.

A further aspect of the present invention pertains to a crystalline form of 2-(((1r,4r)-4-(((4-chlorophenyl)(phenyl) carbamoyloxy)methyl)cyclohexyl)methoxy)acetic acid (Compound 22). The crystalline form of Compound 22 of the present invention can be identified by its unique solid state signature with respect to, for example, differential scanning calorimetry (DSC), X-ray powder diffraction (PXRD), and other solid state methods. Further characterization with respect to water or solvent content of the crystalline form can be gauged by any of the following methods for example, thermogravimetric analysis (TGA), DSC and the like. For DSC, it is known that the temperatures observed will depend upon sample purity, the rate of temperature change, as well as sample preparation technique and the particular instrument employed. Thus, the values reported herein relating to DSC thermograms can vary by plus or minus about 6°C. The values reported herein relating to DSC thermograms can also vary by plus or minus about 20 joules per gram. For PXRD, the relative intensities of the peaks can vary, depending upon the sample preparation technique, the sample mounting procedure and the particular instrument employed. Moreover, instrument variation and other factors can often affect the 20 values. Therefore the peak assignments of diffraction patterns can vary by plus or minus about 0.2°2θ. For TGA, the features reported herein can vary by plus or minus about 5° C. The TGA features reported herein can also vary by plus or minus about 2% weight change due to, for example, sample variation. Further characterization with respect to hygroscopicity of the crystalline form can be gauged by, for example, dynamic vapor sorption (DVS). The physical properties of the crystalline form of Compound 22 of the present invention are summarized in Table 3 below.

TABLE 3

| Crystalline form of Compound 22 | |
|---|---|
| TGA | FIG. 26: Insignificant weight loss below about 128° C. |

TABLE 3-continued

| | Crystalline form of Compound 22 |
|---|---|
| DSC | FIG. 26: extrapolated onset temperature: 128° C.; endotherm peak temperature: 129° C. (maximum); associated heat flow 109 J/g |
| PXRD | FIG. 27: Peaks of ≥8% relative intensity at 8.9, 10.8, 11.9, 15.2, 16.4, 16.9, 18.9, 20.3, 20.7 and 21.5 °2θ |

The insignificant weight loss observed in the TGA data suggests that the crystalline form of Compound 22 of the present invention is an anhydrous, non-solvated crystalline form. The DSC thermogram further reveals a melting endotherm with an onset at about 128° C.

Certain X-ray powder diffraction peaks for the crystalline form of Compound 22 of the present invention are shown in Table 4 below.

TABLE 4

| Compound 22 Crystalline Form PXRD Peaks with Relative Intensity of 8% or Higher (°2θ) | |
|---|---|
| Peak Position (°2θ) | Relative Intensity (%) |
| 8.9 | 8 |
| 10.8 | 19 |
| 11.9 | 29 |
| 15.2 | 9 |
| 16.4 | 49 |
| 16.8 | 63 |
| 18.9 | 84 |
| 20.3 | 34 |
| 20.7 | 62 |
| 21.5 | 100 |

One aspect of the present invention is directed to a crystalline form of 2-(((1r,4r)-4-(((4-chlorophenyl)(phenyl)carbamoyloxy)methyl)cyclohexyl)methoxy)acetic acid having an X-ray powder diffraction pattern comprising a peak, in terms of 2θ, at about 21.5. In some embodiments, the crystalline form has an X-ray powder diffraction pattern comprising a peak, in terms of 2θ, at about 18.9°. In some embodiments, the crystalline form has an X-ray powder diffraction pattern comprising a peak, in terms of 2θ, at about 21.5° and about 18.9°. In some embodiments, the crystalline form has an X-ray powder diffraction pattern comprising a peak, in terms of 2θ, at about 21.5° and about 20.7°. In some embodiments, the crystalline form has an X-ray powder diffraction pattern comprising a peak, in terms of 2θ, at about 21.5°, about 18.9°, and about 20.7°. In some embodiments, the crystalline form has an X-ray powder diffraction pattern comprising a peak, in terms of 2θ, at about 21.5°, about 18.9°, about 20.7°, about 16.9°, about 16.4°, about 20.3°, about 11.9° and about 10.8. In some embodiments, the crystalline form has an X-ray powder diffraction pattern comprising a peak, in terms of 2θ, at about 18.9°, about 20.7°, about 16.9°, about 16.4°, about 20.3°, about 11.9°, about 10.8°, about 15.2° and about 8.9°. In yet further embodiments, the crystalline form has an X-ray powder diffraction pattern substantially as shown in FIG. 27, wherein by "substantially" is meant that the reported peaks can vary by about ±0.2°2θ.

In some embodiments, the crystalline form of 2-(((1r,4r)-4-(((4-chlorophenyl)(phenyl)carbamoyloxy)methyl)cyclohexyl)methoxy)acetic acid has a differential scanning calorimetry thermogram comprising an endotherm with an extrapolated onset temperature between about 120° C. and about 135° C. In some embodiments, the crystalline form has a differential scanning calorimetry thermogram comprising an endotherm with an extrapolated onset temperature at about 128° C. In some embodiments, the crystalline form has a differential scanning calorimetry thermogram comprising an endotherm with a peak temperature between about 121° C. and about 136° C. In some embodiments, the crystalline form has a differential scanning calorimetry thermogram comprising an endotherm with a peak temperature at about 129° C. In some embodiments, the crystalline form has a differential scanning calorimetry thermogram comprising an endotherm with an associated heat flow of about 109 joules per gram. In further embodiments, the crystalline form has a differential scanning calorimetry thermogram substantially as shown in FIG. 26, wherein by "substantially" is meant that the reported DSC features can vary by about ±4° C.

In some embodiments, the crystalline form of 2-(((1r,4r)-4-(((4-chlorophenyl)(phenyl)carbamoyloxy)methyl)cyclohexyl)methoxy)acetic acid has a thermogravimetric analysis profile substantially as shown in FIG. 28, wherein by "substantially" is meant that the reported TGA features can vary by about ±5° C.

The crystalline form of 2-(((1r,4r)-4-(((4-chlorophenyl)(phenyl)carbamoyloxy)methyl)cyclohexyl)methoxy)acetic acid, Compound 22, described herein, can be prepared by any of the suitable procedures known in the art for preparing crystalline polymorphs. In some embodiments the crystalline form of Compound 22 of the present invention can be prepared as described in Example 1.115. In some embodiments, the crystalline form of Compound 22 of the present invention can be prepared by heating crystalline Compound 22, containing one or more crystalline forms other than the crystalline form of Compound 22 of the present invention. In some embodiments, the crystalline form of Compound 22 of the present invention can be prepared by recrystallizing crystalline Compound 22, containing one or more crystalline forms other than the crystalline form of Compound 22 of the present invention.

Compositions Containing Crystalline Forms of the Present Invention

The present invention further provides compositions containing the crystalline form (Form 1) of sodium 2-(((1r,4r)-4-(((4-chlorophenyl)(phenyl)carbamoyloxy)methyl)cyclohexyl)methoxy)acetate, the sodium salt of Compound 22 described herein.

In some embodiments, the compositions of the invention include at least about 1, about 5, about 10, about 20, about 30, or about 40% by weight of Form 1 of the sodium salt of Compound 22.

In some embodiments, the compositions of the invention include at least about 50, about 60, about 70, about 80, about 90, about 95, about 96, about 97, about 98, or about 99% by weight of Form 1 of the sodium salt of Compound 22.

In some embodiments, compositions of the invention include Form 1 of the sodium salt of Compound 22 and a pharmaceutically acceptable carrier.

The present invention further provides compositions containing the crystalline forms of 2-(((1r,4r)-4-(((4-chlorophenyl)(phenyl)carbamoyloxy)methyl)cyclohexyl)methoxy)acetic acid. Compound 22, described herein.

In some embodiments, the compositions of the invention include at least about 1, about 5, about 10, about 20, about 30, or about 40% by weight of the crystalline form of Compound 22 of the present invention.

In some embodiment, the compositions of the invention include at least about 50, about 60, about 70, about 80, about 90, about 95, about 96, about 97, about 98, or about 99% by weight of the crystalline form of Compound 22 of the present invention.

In some embodiments, compositions of the invention include the crystalline form of Compound 22 of the present invention and a pharmaceutically acceptable carrier.

Processes of the Present Invention

The present invention is directed, inter alia, to processes and intermediates for the preparation of cyclohexane derivatives that are useful in the treatment of: pulmonary arterial hypertension (PAH); idiopathic PAH; familial PAH; PAH associated with: a collagen vascular disease, a congenital heart disease, portal hypertension, HIV infection, ingestion of a drug or toxin, hereditary hemorrhagic telangiectasia, splenectomy, pulmonary veno-occlusive disease (PVOD) or pulmonary capillary hemangiomatosis (PCH); PAH with significant venous or capillary involvement; platelet aggregation; coronary artery disease; myocardial infarction; transient ischemic attack; angina; stroke; ischemia-reperfusion injury; restenosis; atrial fibrillation; blood clot formation in an angioplasty or coronary bypass surgery individual or in an individual suffering from atrial fibrillation; atherothrombosis; asthma or a symptom thereof; a diabetic-related disorder such as diabetic peripheral neuropathy, diabetic nephropathy or diabetic retinopathy; glaucoma or other disease of the eye with abnormal intraocular pressure; hypertension; inflammation; psoriasis; psoriatic arthritis; rheumatoid arthritis; Crohn's disease; transplant rejection; multiple sclerosis; systemic lupus erythematosus (SLE); ulcerative colitis; atherosclerosis; acne; type 1 diabetes; type 2 diabetes; sepsis; and chronic obstructive pulmonary disorder (COPD).

The processes described herein can be monitored according to any suitable method known in the art. For example, product formation can be monitored by spectroscopic means, such as nuclear magnetic resonance spectroscopy (e.g., $^{1}H$ or $^{13}C$), infrared spectroscopy, spectrophotometry (e.g., UV-visible), or mass spectrometry; or by chromatography such as high performance liquid chromatography (HPLC) or thin layer chromatography.

In some embodiments, preparation of compounds can involve the protection and deprotection of various chemical groups. The need for protection and deprotection, and the selection of appropriate protecting groups can be readily determined by one skilled in the art. The chemistry of protecting groups can be found, for example, in Greene and Wuts, Protective Groups in Organic Synthesis, 3rd Ed., Wiley & Sons, 1999, which is incorporated herein by reference in its entirety.

The reactions of the processes described herein can be carried out in suitable solvents which can be readily selected by one skilled in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include halogenated solvents such as carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, o-dichlorobenzene, chlorobenzene, fluorobenzene, fluorotrichloromethane, chlorotrifluoromethane, bromotrifluoromethane, carbon tetrafluoride, dichlorofluoromethane, chlorodifluoromethane, trifluoromethane, 1,2-dichlorotetrafluoroethane and hexafluoroethane.

Suitable ether solvents include: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, or t-butyl methyl ether.

Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol.

Suitable aprotic solvents can include, by way of example and without limitation, tetrahydrofuran, N,N-dimethylformamide, N-N-dimethylacetamide, 1,3-dimethyl-3,4,5,6-tetrahydro-2(1H)-pyrimidinone, 1,3-dimethyl-2-imidazolidinone; N-methylpyrrolidinone, formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable hydrocarbon solvents include benzene, cyclohexane, pentane, hexane, toluene, cycloheptane, methylcyclohexane, heptane, ethylbenzene, o, m-, or p-xylene, octane, indane, nonane, or naphthalene.

Supercritical carbon dioxide can also be used as a solvent.

The reactions of the processes described herein can be carried out at appropriate temperatures which can be readily determined by one skilled in the art. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures).

The reactions of the processes described herein can be carried out in air or under an inert atmosphere. Typically, reactions containing reagents or products that are substantially reactive with air can be carried out using air-sensitive synthetic techniques that are well known to one skilled in the art.

In some embodiments, preparation of compounds can involve the addition of acids or bases to effect, for example, catalysis of a desired reaction or formation of salt forms such as acid addition salts.

Example acids can be inorganic or organic acids. Inorganic acids include hydrochloric acid, hydrobromic acid, sulfuric acid, phosphoric acid, and nitric acid. Organic acids include formic acid, acetic acid, propionic acid, butanoic acid, methanesulfonic acid, p-toluene sulfonic acid, benzenesulfonic acid, propiolic acid, butyric acid, 2-butynoic acid, vinyl acetic acid, pentanoic acid, hexanoic acid, heptanoic acid, octanoic acid, nonanoic acid and decanoic acid.

Example bases include lithium hydroxide, sodium hydroxide, potassium hydroxide, lithium carbonate, sodium carbonate, and potassium carbonate. Some example strong bases include, but are not limited to, hydroxide, alkoxides, metal amides, metal hydrides, metal dialkylamides and arylamines, wherein: alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include sodium and potassium salts of methyl, ethyl, n-propyl, substituted amides.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis.

The processes described herein can be stereoselective such that any given reaction starting with one or more chiral reagents enriched in one stereoisomer forms a product that is also enriched in one stereoisomer. The reaction can be conducted such that the product of the reaction substantially retains one or more chiral centers present in the starting materials. The reaction can also be conducted such that the product of the reaction contains a chiral center that is substantially inverted relative to a corresponding chiral center present in the starting materials.

Resolution of racemic mixtures of compounds can be carried out by any of numerous methods known in the art. An example method includes fractional recrystallization (for example, diastereomeric salt resolution) using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisometrically pure forms of β-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention can also include all isotopes of atoms occurring in the intermediates or final compounds. Isotopes include those atoms having the same atomic number but different mass numbers. For example, isotopes of hydrogen include tritium and deuterium.

Compounds of the invention can also include tautomeric forms, such as keto-enol tautomers. Tautomeric forms can be in equilibrium or sterically locked into one form by appropriate substitution.

Upon carrying out preparation of compounds according to the processes described herein, the usual isolation and purification operations such as concentration, filtration, extraction, solid-phase extraction, recrystallization, chromatography, and the like may be used, to isolate the desired products.

Example processes and certain intermediates of the present invention, are shown in Scheme I below, wherein each substituent of the compounds depicted are defined herein.

Scheme 1

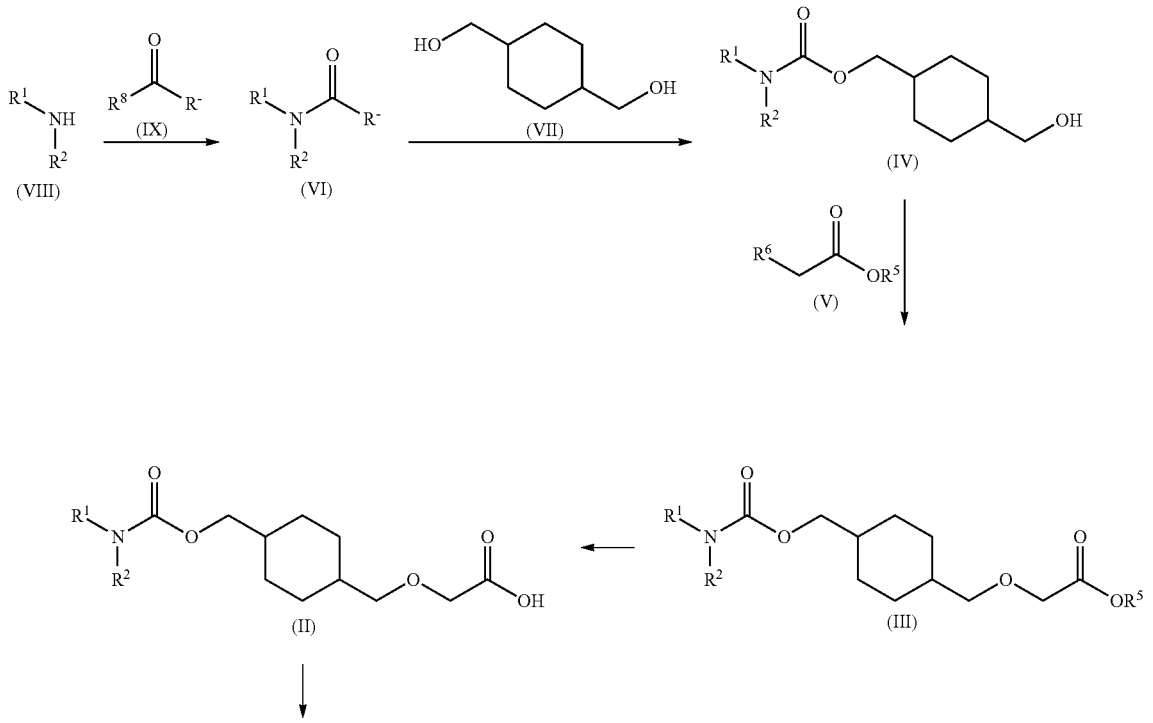

-continued

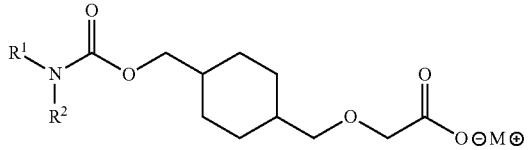

One aspect of the present invention pertains to processes, such as that exemplified by Scheme I (supra), that involve compounds of Formulae (II), (III), (IV), (V), (VI), (VII), (VIII) and (IX) or salt forms thereof, wherein:

$R^1$ is selected from $C_1$-$C_6$ alkyl, aryl and heteroaryl; each optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen; and $R^2$ is selected from: H, $C_1$-$C_6$ alkyl and aryl; wherein said aryl is optionally substituted with one or two substituents selected from: $C_1$-$C_6$ alkyl and halogen;

$R^5$ is $C_1$-$C_6$ alkyl;

$R^6$ is selected from: $C_1$-$C_6$ alkylarylsulfonate, $C_1$-$C_6$ alkylsulfonate, arylsulfonate, $C_1$-$C_6$ haloalkylsulfonate and halogen;

$R^7$ is a first leaving group;

$R^8$ is a second leaving group; and

M⊕ is a metal cation or a cation derived from an organic base.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables (e.g., $R^1$, $R^2$, $R^3$, $R^4$, $R^5$, $R^6$, $R^7$, $R^8$ and M) contained within the generic chemical formulae described herein, for example, (II), (III), (IV), (V), (VI), (VII), (VIII) and (IX) are specifically embraced by the present invention just as if each and every combination was individually explicitly recited, to the extent that such combinations embrace compounds that result in stable compounds (i.e., compounds that can be isolated, characterized and tested for biological activity).

Hydrolysis Step

The present invention provides, inter alfa, processes for preparing compounds of Formula (II):

(II)

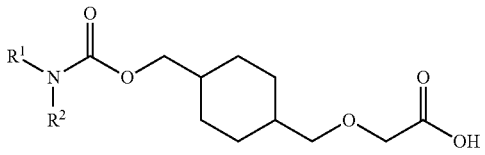

or a salt, solvate or hydrate thereof; comprising reacting a compound of Formula (III):

(III)

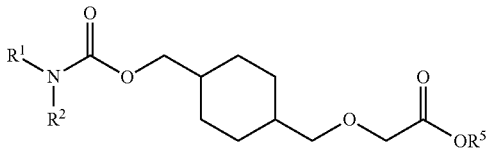

or a salt form thereof; with a hydrolyzing agent to form a compound of Formula (II) or a salt form thereof.

In some embodiments, $R^1$ is aryl, optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen.

In some embodiments, $R^1$ is aryl, optionally substituted with F or Cl.

In some embodiments, $R^1$ is 4-chlorophenyl.

In some embodiments, $R^1$ is 3-fluorophenyl.

In some embodiments, $R^2$ is aryl optionally substituted with one or two substituents selected from: $C_1$-$C_6$ alkyl and halogen.

In some embodiments, $R^2$ is phenyl.

In some embodiments, $R^5$ is tert-butyl.

In some embodiments, $R^1$ is 4-chlorophenyl; $R^2$ is phenyl; and $R^5$ is tert-butyl.

In some embodiments, $R^1$ is 3-fluorophenyl; $R^2$ is phenyl; and $R^5$ is tert-butyl.

The hydrolyzing agent can be any suitable reagent, readily selected by one skilled in the art. Examples of hydrolyzing agents include bases such as lithium hydroxide and sodium hydroxide; acids such as hydrochloric acid, trifluoroacetic acid and formic acid; lithium salts such as LiBr, LiCl, $LiBF_4$, $LiCF_3CO_2$, $LiSO_4$, $LiNO_3$, $LiCF_3SO_3$ and lithium propanethiolate; and electrophiles such as TMSI.

In some embodiments, the hydrolyzing agent is a base.

In some embodiments, the hydrolyzing agent is an alkali metal hydroxide.

In some embodiments, the hydrolyzing agent is sodium hydroxide.

The reacting of a compound of Formula (III) with a hydrolyzing agent can be optionally carried out in the presence of any suitable solvent, readily selected by one skilled in the art. Example solvents include polar to moderately polar solvents or high boiling solvents such as N,N-dimethylformamide (DMF), N,N-dimethylacetamide, toluene, acetonitrile, propionitrile, tetrahydrofuran and N-methylpyrrolidinone.

In some embodiments, the solvent comprises toluene.

In some embodiments, the solvent comprises a mixture of toluene and water.

In some embodiments, the solvent comprises a mixture of approximately equal parts by weight of toluene and water.

The reacting of a compound of Formula (III) with a hydrolyzing agent can be carried out at any suitable temperature, readily selected by one skilled in the art.

In some embodiments, the reacting is carried out at a temperature of about 20° C. to about 90° C.

In some embodiments, the reacting is carried out at a temperature of about 30° C. to about 80° C.

In some embodiments, the reacting is carried out at a temperature of about 40° C. to about 70° C.

In some embodiments, the reacting is carried out at a temperature of about 50° C. to about 60° C.

The reacting of a compound of Formula (III) with a hydrolyzing agent can be optionally carried out in situ following the reacting of a compound of Formula (IV) with a compound of Formula (V) in the presence of a base to form a compound of Formula (III), without substantial purification of the compound of Formula (III).

Alkylation Step

The present invention further provides processes for preparing compounds of Formula (III):

(III)

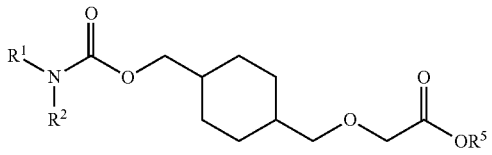

or a salt form thereof; wherein:

$R^1$ is selected from $C_1$-$C_6$ alkyl, aryl and heteroaryl; each optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen; and $R^2$ is selected from: H, $C_1$-$C_6$ alkyl and aryl; wherein said aryl is optionally substituted with one or two substituents selected from: $C_1$-$C_6$ alkyl and halogen; and $R^5$ is $C_1$-$c_6$ alkyl; comprising reacting a compound of Formula (IV):

(IV)

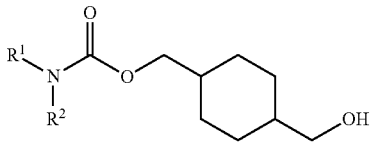

or a salt form thereof; with a compound of Formula (V):

(V)

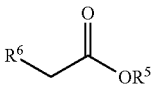

wherein:

$R^6$ is selected from: $C_1$-$C_6$ alkylarylsulfonate, $C_1$-$C_6$ alkylsulfonate, arylsulfonate, $C_1$-$C_6$ haloalkylsulfonate and halogen;

in the presence of a base to form a compound of Formula (III) or a salt form thereof.

In some embodiments, $R^1$ is aryl, optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen.

In some embodiments, $R^1$ is aryl, optionally substituted with F or Cl.

In some embodiments, $R^1$ is 4-chlorophenyl.

In some embodiments, $R^1$ is 3-fluorophenyl.

In some embodiments, $R^2$ is aryl optionally substituted with one or two substituents selected from: $C_1$-$C_6$ alkyl and halogen.

In some embodiments, $R^2$ is phenyl.

In some embodiments, $R^5$ is tert-butyl.

In some embodiments, $R^6$ is halogen.

In some embodiments, $R^6$ is bromo.

In some embodiments, $R^1$ is 4-chlorophenyl; $R^2$ is phenyl; $R^5$ is tert-butyl; and $R^6$ is bromo.

In some embodiments, $R^1$ is 3-fluorophenyl; $R^2$ is phenyl; $R^5$ is tert-butyl; and $R^6$ is bromo.

The base can be any suitable base, readily selected by one skilled in the art. Examples of suitable bases include inorganic bases such as ammonia and carbonates, hydroxides and hydrogen carbonates of metals such as sodium, potassium, magnesium, calcium, cesium and the like; and organic bases such as methylamine, triethylamine, N-ethyldiisopropylamine, benzylamine, dibenzylamine, morpholine and pyridine.

In some embodiments, the base is an alkali metal hydroxide.

In some embodiments, the base is sodium hydroxide.

The reacting of a compound of Formula (IV) with a compound of Formula (V) can be optionally carried out in the presence of a catalyst.

In some embodiments, the catalyst is a phase-transfer catalyst.

In some embodiments, the catalyst is a tetraallcylammonium salt.

In some embodiments, the catalyst is a tetra-n-butylammonium bromide.

In some embodiments the molar ratio of the compound of Formula (IV) to the catalyst is about 20:1 to about 0.5:1.

In some embodiments the molar ratio of the compound of Formula (IV) to the catalyst is about 10:1 to about 1:1.

In some embodiments the molar ratio of the compound of Formula (IV) to the catalyst is about 5:1 to about 2:1.

In some embodiments the molar ratio of the compound of Formula (IV) to the catalyst is about 4:1 to about 3:1.

The reacting of a compound of Formula (IV) with a compound of Formula (V) can be optionally carried out in the presence of any suitable solvent, readily selected by one skilled in the art. Example solvents include polar to moderately polar solvents or high boiling solvents such as N,N-dimethylformamide (DMF), N,N-dimethylacetamide, toluene, acetonitrile, propionitrile, tetrahydrofuran and N-methylpyrrolidinone.

In some embodiments, the solvent comprises toluene.

In some embodiments, the solvent comprises a mixture of toluene and water.

In some embodiments, the solvent comprises a mixture of approximately equal parts by weight of toluene and water.

The reacting of a compound of Formula (IV) with a compound of Formula (V) can be carried out at any suitable temperature, readily selected by one skilled in the art.

In some embodiments, the reacting is carried out at a temperature of about −10° C. to about 20° C.

In some embodiments, the reacting is carried out at a temperature of about −5° C. to about 15° C.

In some embodiments, the reacting is carried out at a temperature of about 0° C. to about 15° C.

In some embodiments, the reacting is carried out at a temperature of about 5° C. to about 15° C.

Carbamate Formation Step

The present invention further provides processes for preparing compounds of Formula (IV).

(IV)

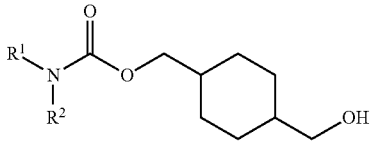

or a salt form thereof; wherein:

$R^1$ is selected from $C_1$-$C_6$ alkyl, aryl and heteroaryl; each optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen; and $R^2$ is selected from: H, $C_1$-$C_6$ alkyl and aryl; wherein said aryl is optionally substituted with one or two substituents selected from: $C_1$-$C_6$ alkyl and halogen;

comprising reacting a compound of Formula (VI):

(VI)

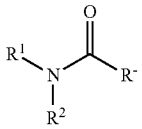

or a salt form thereof; wherein:

$R^7$ is a first leaving group;

with a compound of formula (VII):

(VII)

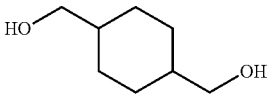

to form a compound of Formula (IV) or a salt form thereof.

In some embodiments, $R^1$ is aryl, optionally substituted with one or two substituents selected from: $C_1$-$C_6$ alkoxy; $C_1$-$C_6$ alkyl, aryl, $C_1$-$C_6$ haloalkoxy, $C_1$-$C_6$ haloalkyl and halogen.

In some embodiments, $R^1$ is aryl, optionally substituted with F or Cl.

In some embodiments, $R^1$ is 4-chlorophenyl.

In some embodiments, $R^1$ is 3-fluorophenyl.

In some embodiments, $R^2$ is aryl optionally substituted with one or two substituents selected from: $C_1$-$C_6$ alkyl and halogen.

In some embodiments, $R^2$ is phenyl.

In some embodiments, $R^7$ is halogen.

In some embodiments, $R^7$ is chlorine.

In some embodiments, $R^7$ is heteroaryl.

In some embodiments, $R^7$ is benzotriazol-1-yl)

In some embodiments, $R^7$ is imidazol-1-yl.

In some embodiments, $R^1$ is 4-chlorophenyl; $R^2$ is phenyl; and $R^7$ is imidazol-1-yl.

In some embodiments, $R^1$ is 3-fluorophenyl; $R^2$ is phenyl; and $R^7$ is imidazol-1-yl.

The reacting of a compound of Formula (VI) with a compound of Formula (VII) can be optionally carried out in the presence of any suitable solvent, readily selected by one skilled in the art. Example solvents include polar to moderately polar solvents or high boiling solvents, such as N,N-dimethylformamide (DMF), N,N-dimethylacetamide, toluene, acetonitrile, propionitrile, tetrahydrofuran and N-methylpyrrolidinone.

In some embodiments, the solvent comprises acetonitrile.

The reacting of a compound of Formula (VI) with a compound of Formula (VII) can be carried out at any suitable temperature, readily selected by one skilled in the art.

In some embodiments, the reacting is carried out at a temperature of about 35° C. to about 105° C.

In some embodiments, the reacting is carried out at a temperature of about 45° C. to about 95° C.

In some embodiments, the reacting is carried out at a temperature of about 55° C. to about 85° C.

In some embodiments, the reacting is carried out at a temperature of about 65° C. to about 70° C.

The reacting of a compound of Formula (VI) with a compound of Formula (VII) can be optionally carried out in situ following the reacting of a compound of Formula (VIII) with a compound of Formula (IX) in the presence of a base to form a compound of Formula (VI), without substantial purification of the compound of Formula (VI).

Acylation Step

The present invention further provides processes for preparing compounds of Formula (VI):

(VI)

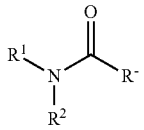

or a salt form thereof; wherein:

$R^1$ is selected from $C_1$-$C_6$ alkyl, aryl and heteroaryl; each optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen; and $R^2$ is selected from: H, $C_1$-$C_6$ alkyl and aryl; wherein said aryl is optionally substituted with one or two substituents selected from: $C_1$-$C_6$ alkyl and halogen; and $R^7$ is a first leaving group;

comprising reacting a compound of Formula (VII):

(VIII)

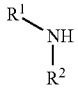

or a salt form thereof; with a compound of formula (IX):

(IX)

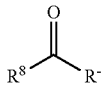

wherein:

$R^8$ is a second leaving group;

to form a compound of Formula (VI) or a salt form thereof.

In some embodiments, $R^1$ is aryl, optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen.

In some embodiments, $R^1$ is aryl, optionally substituted with F or Cl.

In some embodiments, $R^1$ is 4-chlorophenyl.

In some embodiments, $R^1$ is 3-fluorophenyl.

In some embodiments, $R^2$ is aryl optionally substituted with one or two substituents selected from: $C_1$-$C_6$ alkyl and halogen.

In some embodiments, $R^2$ is phenyl.

In some embodiments, $R^7$ and $R^8$ are both halogen.

In some embodiments, $R^7$ and $R^8$ are both chlorine.

In some embodiments, $R^7$ and $R^8$ are both heteroaryl.

In some embodiments, $R^7$ and $R^8$ are both benzotriazol-1-yl

In some embodiments, $R^7$ and $R^8$ are both imidazol-1-yl.

In some embodiments, $R^1$ is 4-chlorophenyl; $R^2$ is phenyl; and $R^7$ and $R^8$ are both imidazol-1-yl.

In some embodiments, $R^1$ is 3-fluorophenyl; $R^2$ is phenyl; and $R^7$ and $R^8$ are both imidazol-1- yl.

The reacting of a compound of Formula (VI) with a compound of Formula (VII) can be optionally carried out in the presence of any suitable solvent, readily selected by one skilled in the art. Example solvents include polar to moderately polar solvents or high boiling solvents such as N,N-dimethylformamide (DMF), N,N-dimethylacetamide, toluene, acetonitrile, propionitrile, tetrahydrofuran and N-methylpyrrolidinone.

In some embodiment, the solvent comprises acetonitrile.

The reacting of a compound of Formula (VI) with a compound of Formula (VII) can be carried out at any suitable temperature, readily selected by one skilled in the art.

In some embodiments, the reacting is carried out at a temperature of about 35° C. to about 105° C.

In some embodiments, the reacting is carried out at a temperature of about 45° C. to about 95° C.

In some embodiments, the reacting is carried out at a temperature of about 55° C. to about 85° C.

In some embodiments, the reacting is carried out at a temperature of about 65° C. to about 70° C.

Salt Formation

The present invention further provides processes for preparing salts of compounds of Formula (II):

(II)

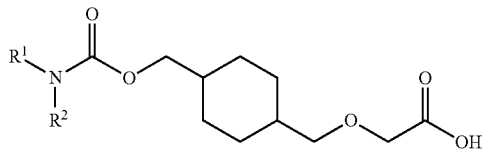

and solvates and hydrates thereof;

comprising reacting a compound of Formula (II) with a salt-forming reagent to form a salt of a compound of formula (II).

In some embodiments, $R^1$ is aryl, optionally substituted with one or two substituents selected from: $C_1$-$C_6$ alkoxy, $C_1$-$C_6$ alkyl, aryl, $C_1$-$C_6$ haloalkoxy; $C_1$-$C_6$ haloalkyl and halogen.

In some embodiments, $R^1$ is aryl, optionally substituted with F or Cl.

In some embodiments, $R^1$ is 4-chlorophenyl.

In some embodiments, $R^1$ is 3-fluorophenyl.

In some embodiments, $R^2$ is aryl optionally substituted with one or two substituents selected from: $C_1$-$C_6$ alkyl and halogen.

In some embodiments, $R^2$ is phenyl.

In some embodiments, $R^1$ is 4-chlorophenyl and $R^2$ is phenyl.

In some embodiments, $R^1$ is 3-fluorophenyl and $R^2$ is phenyl.

In some embodiments, the salt forming reagent is an alkali metal hydroxide.

In some embodiments, the salt forming reagent is sodium hydroxide.

The reacting a compound of Formula (II) with a salt-forming reagent to form a salt of a compound of formula (II) can be optionally carried out in the presence of any suitable solvent, readily selected by one skilled in the art.

In some embodiments, the solvent comprises an alcohol such as ethanol, n-propanol, isopropanol, n-butanol and the like.

In some embodiments, the solvent comprises isopropanol.

In some embodiments, the solvent comprises a mixture of isopropanol and water.

The reacting a compound of Formula (II) with a salt-forming reagent to form a salt of a compound of formula (II) can be carried out at any suitable temperature, readily selected by one skilled in the art.

In some embodiments, the reacting is carried out at a temperature of about 10° C. to about 70° C.

In some embodiments, the reacting is carried out at a temperature of about 20° C. to about 60° C.

In some embodiments, the reacting is carried out at a temperature of about 30° C. to about 50° C.

In some embodiments, the reacting is carried out at a temperature of about 40° C.

Pharmaceutically Acceptable Salts

Some embodiments of the present invention pertain to pharmaceutically acceptable salts of compounds of Formula (II):

(II)

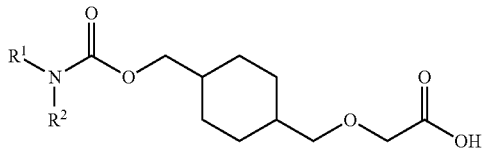

In some embodiments, $R^1$ is aryl, optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen.

In some embodiments, $R^1$ is aryl, optionally substituted with F or Cl.

In some embodiments, $R^1$ is 4-chlorophenyl.

In some embodiments, $R^1$ is 3-fluorophenyl.

In some embodiments, $R^2$ is aryl optionally substituted with one or two substituents selected from: $C_1$-$C_6$ alkyl and halogen.

In some embodiments, $R^2$ is phenyl.

In some embodiments, $R^1$ is 4-chlorophenyl and $R^2$ is phenyl.

In some embodiments, $R^1$ is 3-fluorophenyl and $R^2$ is phenyl.

In some embodiments, the pharmaceutically acceptable salt has a purity of 80% or greater.

In some embodiments, the pharmaceutically acceptable salt has a purity of 90% or greater.

In some embodiments, the pharmaceutically acceptable salt has a purity of 95% or greater.

In some embodiments, the pharmaceutically acceptable salt has a purity of 99% or greater.

In some embodiments, the pharmaceutically acceptable salt has a purity of 99.5% or greater.

In some embodiments, the pharmaceutically acceptable salt comprises a pharmaceutically acceptable salt of a compound of Formula (II) and a compound of Formula (II) in a ratio of about 4:1 or greater.

In some embodiments, the pharmaceutically acceptable salt comprises a pharmaceutically acceptable salt of a compound of Formula (II) and a compound of Formula (II) in a ratio of about 9:1 or greater.

In some embodiments, the pharmaceutically acceptable salt comprises a pharmaceutically acceptable salt of a compound of Formula (II) and a compound of Formula (II) in a ratio of about 19:1 or greater.

In some embodiments, the pharmaceutically acceptable salt comprises a pharmaceutically acceptable salt of a compound of Formula (II) and a compound of Formula (II) in a ratio of about 99:1 or greater.

In some embodiments, the pharmaceutically acceptable salt is a sodium salt.

Intermediates

The present invention further provides intermediates that are useful in the preparation of compounds of Formula (II) and salts thereof.

Some embodiments pertain to compounds of Formula (III) or a salt form thereof:

(III)

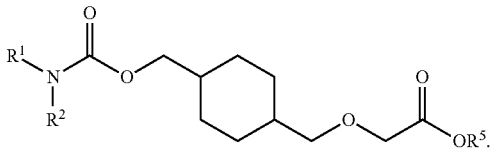

In some embodiments, $R^1$ is aryl, optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen.

In some embodiments, $R^1$ is aryl, optionally substituted with F or Cl.

In some embodiments, $R^1$ is 4-chlorophenyl.

In some embodiments, $R^1$ is 3-fluorophenyl.

In some embodiments, $R^2$ is aryl optionally substituted with one or two substituents selected from: $C_1$-$C_6$ alkyl and halogen.

In some embodiments, $R^2$ is phenyl.

In some embodiments, $R^5$ is tert-butyl.

In some embodiments, $R^1$ is 4-chlorophenyl; $R^2$ is phenyl; and $R^5$ is tert-butyl.

In some embodiments, $R^1$ is 3-fluorophenyl; $R^2$ is phenyl; and $R^5$ is tert-butyl.

Some embodiments pertain to compounds of Formula (IV) or a salt form thereof:

(IV)

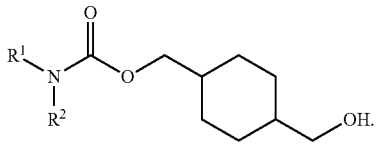

In some embodiments, $R^1$ is aryl, optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen.

In some embodiments, $R^1$ aryl, optionally substituted with F or Cl.

In some embodiments, $R^1$ is 4-chlorophenyl.

In some embodiments, $R^1$ is 3-fluorophenyl.

In some embodiments, $R^2$ is aryl optionally substituted with one or two substituents selected from: $C_1$-$C_6$ alkyl and halogen.

In some embodiments, $R^2$ is phenyl.

In some embodiments, $R^1$ is 4-chlorophenyl; $R^2$ is phenyl.

In some embodiments, $R^1$ is 3-fluorophenyl; $R^2$ is phenyl.

Some embodiments pertain to compounds of Formula (IV) or a salt form thereof:

(VI)

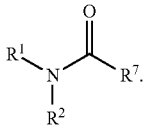

In some embodiments, $R^1$ is aryl, optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen.

In some embodiments, $R^1$ is aryl, optionally substituted with F or Cl.

In some embodiments, $R^1$ is 4-chlorophenyl.

In some embodiments, $R^1$ is 3-fluorophenyl.

In some embodiments, $R^2$ is aryl optionally substituted with one or two substituents selected from: $C_1$ -$C_6$ alkyl and halogen.

In some embodiments, $R^2$ is phenyl.

In some embodiments, $R^7$ is halogen.

In some embodiments, $R^7$ is chlorine.

In some embodiments, $R^7$ is heteroaryl.

In some embodiments, $R^7$ is benzotriazol-1-yl

In some embodiments, $R^7$ is imidazol-1-yl.

In some embodiments, $R^1$ is 4-chlorophenyl; $R^2$ is phenyl; and $R^7$ is imidazol-1-yl.

In some embodiments, $R^1$ is 3-fluorophenyl; $R^2$ is phenyl; and $R^7$ is imidazol-1-yl.

Pro-Drugs of the Present Invention

The compounds of the Formula (Ia) may be administered in the form of a pro-drug which is broken down in the human or animal body to give a compound of the Formula (Ia). Pro-drugs of the present invention may employ any pro-drug strategy known in the art. A pro-drug may be used to alter or improve the physical and/or pharmacokinetic profile of the parent compound and can be formed when the parent compound contains a suitable group or substituent which can be derivatized to form a pro-drug. Examples of pro-drugs include in-vivo hydrolyzable amides of a compound of the Forumla (Ia) or pharmaceutically-acceptable salts thereof.

One aspect of the present invention pertains to compounds of Formula (X) useful as pro-drugs for the delivery of compounds of Formula (Ia):

(X)

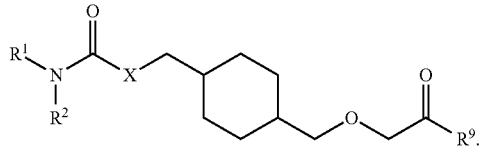

wherein:

$R^1$ and $R^2$ are each independently selected from: H, $C_1$-$C_6$ alkyl, aryl and heteroaryl; wherein $C_1$-$C_6$ alkyl, aryl and heteroaryl are each optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen;

X is O or $NR^3$;

$R^3$ is selected from: H and $C_1$-$C_6$ alkyl; and $R^9$ is a radical derived from any natural or unnatural amino acid, upon the loss of a hydrogen atom from the α-amino group of said natural or unnatural amino acid; or $R^9$ is —$NHCH_2CH_2SO_3H$.

One aspect of the present invention pertains to compounds of Formula (Xa) useful as pro-drugs for the delivery of compounds of Formula (Ia):

(Xa)

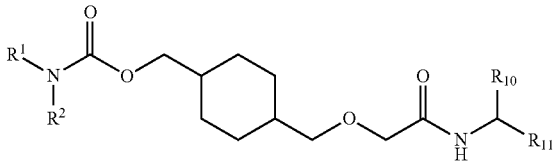

$R^1$ and $R^2$ are each independently selected from: H, $C_1$-$C_6$ alkyl, aryl and heteroaryl; wherein $C_1$-$C_6$ alkyl, aryl and heteroaryl are each optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen;

$R^{10}$ is selected from: H and carboxyl; and $R^{11}$ is selected from: H and $C_1$-$C_6$ alkyl; wherein $C_1$-$C_6$ alkyl is optionally substituted with 4-hydroxyphenyl, amino, carboxamide, carboxyl, guanidino, hydroxyl, imidazolyl, indolyl, methylthio, phenyl, pyrrolidinyl, sulfo and thiol.

In some embodiments, $R^1$ is aryl, optionally substituted with one or two substituents selected from: $C_1$-$C_6$ alkoxy, $C_1$-$C_6$ alkyl, aryl, $C_1$-$C_6$ haloalkoxy, $C_1$-$C_6$ haloalkyl and halogen.

In some embodiments, $R^1$ is aryl, optionally substituted with F or Cl.

In some embodiments, $R^1$ is 4-chlorophenyl.

In some embodiments, $R^1$ is 3-fluorophenyl.

In some embodiments, $R^1$ is aryl optionally substituted with one or two substituents selected from: $C_1$-$C_6$ alkyl and halogen.

In some embodiments, $R^2$ is phenyl.

In some embodiments, $R^{10}$ is H and $R^{11}$ is —$CH_2SO_3H$.

In some embodiments, $R^{10}$ is carboxyl and $R^{11}$ is H.

In some embodiments, $R^1$ is 4-chlorophenyl; $R^2$ is phenyl; $R^{10}$ is H and $R^{11}$ is —$CH_2SO_3H$.

In some embodiments: $R^1$ is 4-chlorophenyl; $R^2$ is phenyl; $R^{10}$ is carboxyl and $R^{11}$ is H.

In some embodiments: $R^1$ is 3-fluorophenyl; $R^2$ is phenyl; $R^{10}$ is H and $R^{11}$ is —$CH_2SO_3H$.

In some embodiments: $R^1$ is 3-fluorophenyl; $R^2$ is phenyl; $R^{10}$ is carboxyl and $R^{11}$ is H.

Certain pro-drugs of compounds of the present invention are described in Examples 1.112, 1.113 and 9-11.

Other Utilities

Another object of the present invention relates to radio-labeled compounds of the present invention that would be useful not only in radio-imaging but also in assays, both in vitro and in vivo, for localizing and quantitating the PGI2 receptor in tissue samples, including human and for identifying PGI2 receptor ligands by inhibition binding of a radio-labeled compound. It is a further object of this invention to develop novel PGI2 receptor assays of which comprise such radio-labeled compounds.

The present invention embraces isotopically-labeled compounds of the present invention. Isotopically or radio-labeled compounds are those which are identical to compounds disclosed herein, but for the fact that one or more atoms are replaced or substituted by an atom having an atomic mass or mass number different from the atomic mass or mass number most commonly found in nature. Suitable radionuclides that may be incorporated in compounds of the present invention include but are not limited to $^2H$ (also written as D for deuterium). $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{35}Cl$, $^{75}Br$, $^{76}Br$, $^{77}Br$, $^{82}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro PGI2 receptor labeling and competition assays, compounds that incorporate $^3H$, $^{14}C$, $^{82}Br$, $^{125}I$, $^{131}I$ or $^{35}S$ will generally be most useful. For radio-imaging applications $^{11}C$, $^{18}F$, $^{125}I$, $^{123}I$, $^{124}I$, $^{131}I$, $^{75}Br$, $^{76}Br$, or $^{77}$ Br will generally be most useful.

It is understood that a "radio-labeled" or "labeled compound" is a compound of Formula (Ia), (Ic), (Ie), (Ig), (Ii), (Ik), (Im) or (II) that has incorporated at least one radionuclide; in some embodiments the radionuclide is selected from the group consisting of $^3H$, $^{14}C$, $^{125}I$, $^{35}S$ and $^{82}Br$.

Certain isotopically-labeled compounds of the present invention are useful in compound and/or substrate tissue distribution assays. In some embodiments the radionuclide $^3H$ and/or $^{14}C$ isotopes are useful in these studies. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the present invention can generally be prepared by following procedures analogous to those disclosed in the Drawings and Examples infra, by substituting an isotopically labeled reagent for a non-isotopically labeled reagent. Other synthetic methods that are useful are discussed infra. Moreover, it should be understood that all of the atoms represented in the compounds of the invention can be either the most commonly occurring isotope of such atoms or the scarcer radio-isotope or nonradioactive isotope.

Synthetic methods for incorporating radio-isotopes into organic compounds are applicable to compounds of the invention and are well known in the art. These synthetic methods, for example, incorporating activity levels of tritium into target molecules, are as follows:

A. Catalytic Reduction with Tritium Gas: This procedure normally yields high specific activity products and requires halogenated or unsaturated precursors.

B. Reduction with Sodium Borohydride [$^3H$]: This procedure is rather inexpensive and requires precursors containing reducible functional groups such as aldehydes, ketones, lactones, esters and the like.

C. Reduction with Lithium Aluminum Hydride [$^3$H]: This procedure offers products at almost theoretical specific activities. It also requires precursors containing reducible functional groups such as aldehydes, ketones, lactones, esters and the like.

D. Tritium Gas Exposure Labeling: This procedure involves exposing precursors containing exchangeable protons to tritium gas in the presence of a suitable catalyst.

E. N-Methylation using Methyl Iodide [$^3$H]: This procedure is usually employed to prepare O-methyl or N-methyl ($^3$H) products by treating appropriate precursors with high specific activity methyl iodide ($^3$H). This method in general allows for higher specific activity, such as for example, about 70-90 Ci/mmol.

Synthetic methods for incorporating activity levels of $^{125}$I into target molecules include:

A. Sandmeyer and like reactions: This procedure transforms an aryl amine or a heteroaryl amine into a diazonium salt, such as a diazonium tetrafluoroborate salt and subsequently to $^{125}$I-labeled compound using Na$^{125}$I. A represented procedure was reported by Zhu, (i-I), and co-workers in J. Org. Chem., 2002, 67, 943-948.

B. Ortho $^{125}$Iodination phenols: This procedure allows for the incorporation of $^{125}$I at the ortho position of a phenol as reported by Collier, T. L. and co-workers in J. Labelled Compd. Radiopharm., 1999, 42, S264-S266.

C. Aryl and heteroaryl bromide exchange with $^{125}$I: This method is generally a two step process. This first step is the conversion of the aryl or heteroaryl bromide to the corresponding tri-alkyltin intermediate using for example, a Pd catalyzed reaction [i.e. Pd($Ph_3P_4$] or through an aryl or heteroaryl lithium, in the presence of a tri-alkyltinhalide or hexaalkylditin [e.g., $(CH_3)_3SnSn(CH_3)_3$]. A representative procedure was reported by Le Bas, M.-D, and co-workers in J. Labelled Compd. Radiopharm. 2001, 44, S280-S282.

A radiolabeled PGI2 receptor compound of formula (Ia) can be used in a screening assay to identify/evaluate compounds. In general terms, a newly synthesized or identified compound (i.e., test compound) can be evaluated for its ability to reduce binding of the "radio-labeled compound of Formula (Ia)" to the PGI2 receptor. Accordingly, the ability of a test compound to compete with the "radio-labeled compound of Formula (IA)" for the binding to the PGI2 receptor directly correlates to its binding affinity.

The labeled compounds of the present invention bind to the PGI2 receptor. In one embodiment the labeled compound has an $IC_{50}$ less than about 500 μM in another embodiment the labeled compound has an $IC_{50}$ less than about 100 μM, in yet another embodiment the labeled compound has an $IC_{50}$ less than about 100 μM, in yet another embodiment the labeled compound has an $IC_{50}$ less than about 1 μM and in still yet another embodiment the labeled inhibitor has an $IC_{50}$ less than about 0.1 μM.

Other uses of the disclosed receptors and methods will become apparent to those skilled in the art based upon, inter alia, a review of this disclosure.

As will be recognized, the steps of the methods of the present invention need not be performed any particular number of times or in any particular sequence. Additional objects, advantages and novel features of this invention will become apparent to these skilled in the art upon examination of the following examples thereof, which are intended to be illustrative and not intended to be limiting.

EXAMPLES

Example 1: Syntheses of Compounds of the Present Invention

Illustrated syntheses for compounds of the present invention are shown in FIGS 1 through 6 where the symbols have the same definitions as used throughout this disclosure.

The compounds of the invention and their syntheses are further illustrated by the following examples. The following examples are provided to further define the invention without, however, limiting the invention so the particulars of these examples. The compounds described herein, supra and infra, are named according to the CS ChemDraw Ultra Version 7.0.1. AutoNom version 2.2, or CS ChemDraw Ultra Version 9.0.7. In certain instances common names are used and it is understood that these common names would be recognized by those skilled in the art.

Chemistry: Proton nuclear magnetic resonance ($^1$H NMR) spectra were recorded on a Bruker Avance-400 equipped with a QNP (Quad Nucleus Probe) or a BBI (Broad Band Inverse) and z-gradient. Chemical shifts are given in parts per million (ppm) with the residual solvent signal used as reference. NMR abbreviations are used follows: s=singlet, d=doublet, dd=doublet of doublets, ddd=doublet of doublet of doublets, dt=doublet of triplets, t=triplet, td=triplet of doublet, tt=triplet of triplets, q=quartet, m=multiplet, bs=broad singlet, bt=broad triplet. Microwave irradiations were carried out using a Smith Synthesizer™ or an Emrys Optimizer™ (Biotage). Thin-layer chromatography (TLC) was performed on silica gel 60 $F_{254}$ (Merck), preparatory thin-layer chromatography (prep TLC) was preformed on PK6F silica gel 60 A 1 mm plates (Whatman) and column chromatography was carried out on a silica gel column using Kieselgel 60, 0.063-0.200 mm (Merck). Evaporation was done under reduced pressure on a Buchi rotary evaporator.

LCMS spec: HPLC-pumps: LC-10AD VP. Shimadzu Inc.; HPLC system controller: SCL-10A VP, Shimadzu Inc: UV-Detector: SPD-10A VP, Shimadzu Inc: Autosampler: (TC HTS, PAL, Leap Scientific: Mass spectrometer: API 150EX with Turbo Ion Spray source, AB/MDS Sciex; Software: Analyst 1.2.

Example 1.1: Preparation of tert-Butyl 2-(((1s,4s)-4-((Phenylcarbamoyloxy)methyl)cyclohexyl)methoxy)acetate

Step A: Preparation of (1s,4s)-Diethyl Cyclohexane-1,4-dicarboxylate

To a solution of (1s,4s)-cyclohexane-1,4-dicarboxylic acid (25 g, 145 mmol) in ethanol (150 mL) was added concentrated $H_2SO_4$ (98%, 1 mL). The reaction was heated to reflex for 16 h, cooled to room temperature and concentrated. The residue was extracted with EtOAc and saturated $NaHCO_3$, washed with brine, dried over $MgSO_4$, and filtered. The filtrate was concentrated to provide the title compound as colorless oil (30.5 g). $^1$H NMR (400 MHz, $CDCl_3$) δ ppm 1.25 (t, J=7.14 Hz, 6H), 1.62-1.75 (m, 4H), 1.84-1.97 (m, 4H), 2.40-2.50 (m, 2H), 4.13 (q, J=7.12 Hz, 4H).

Step B: Preparation of (1s,4s)-Cyclohexane-1,4-diyldimethanol

To a solution of (1s,4s)-diethyl cyclohexane-1,4-dicarboxylate (13.0 g, 56.9 mmol) in THF (500 mL) was added lithium aluminum hydride (4.54 g, 120 mmol) in portions at 0° C. The mixture was stirred at that temperature for 2 h and quenched with cold water, filtered and concentrated to give the title compound as colorless oil (8.2 g). $^1$H NMR (400 MHz, DMSO-$d_6$) δ ppm 1.25-1.44 (m, 8H), 1.45-1.56 (m, 2H), 3.24-3.33 (m, 4H), 4.29 (t, J=5.31 Hz, 2H).

Step C: Preparation of ((1s,4s)-4-(Hydroxymethyl)cyclohexyl)methyl Phenylcarbamate To a solution of (1s,4s)-cyclohexane-1,4-diyldimethanol (3.0 g, 20.80 mmol) in pyridine (100 mL) were added phenyl isocyanate (2.478 g, 20.80 mmol). The reaction was stirred overnight at room temperature. The mixture was concentrated and purified via silica gel column chromatography to provide the title compound as colorless oil (2.55 g). LCMS m/z=264.1 [M+H]$^+$; $^1$H NMR (400 MHz, $CDCl_3$) δ ppm 1.37-1.61 (m, 8H), 1.63-1.76 (m, 1H), 1.85-1.97 (m, 1H), 3.54 (d, J=6.95 Hz, 2H), 4.10 (d, J=7.20 Hz, 2H), 6.72 (s, 1H), 7.02-7.08 (m, 1H), 7.25-7.33 (m, 2H), 7.34-7.41 (m, 2H).

Step D: Preparation of tert-Butyl 2-(((1s,4s)-4-((Phenylcarbamoyloxy)methyl)cyclohexyl)methoxy) acetate To a solution of ((1s4s(-4-(hydroxymethyl)cyclohexyl) methyl phenylcarbamate (1.55 g, 5.89 mmol) in $CH_2Cl_2$ (100 mL) was added diacetoxyrhodium (0.15 g, 0.399 mmol) and tert-butyl 2-diazoacetate (0.837 g, 5.89 mmol) and the mixture was stirred for 2 h at 0° C. The mixture was concentrated and purified via silica gel column chromatography to provide the title compound as colorless oil (1.85 g). LCMS m/z=378.2 [M+H]$^+$; $^1$H NMR (400 MHz, $CDCl_3$) δ ppm 1.40-1.64 (m, 8H), 1.48 (s, 9H), 1.79-1.95 (m, 2H), 3.42 (d, J=6.95 Hz, 2H), 3.94 (s, 2H), 4.09 (d J=7.20 Hz, 2H), 6.63 (s, 1H), 7.02-7.08 (m, 1H), 7.25-7.33 (m, 2H), 7.35-7.41 (m, 2H).

Example 1.2: Preparation of 2-(((1s,4s)-4-(((4-Methoxyphenyl)(phenyl)carbamoyloxy)methyl)cyclohexyl)methoxy)acetic Acid (Compound 24)

To a solution of tert-butyl 2-(((1s,4s)-4-((phenylcarbamoyloxy)methyl)cyclohexyl)methoxy)acetate (0.1 g, 0.265 mmol) in dioxane (2 mL) were added 1-iodo-4-methoxybenzene (0.062 g, 0.265 mmol), (1R,2R)-cyclohexane-1,2-diamine (0.030 g, 0.265 mmol), CuI (0.02 g, 0.158 mmol), and $K_3PO_4$ (0.1 g, 0.471 mmol) at room temperature. The reaction mixture was sealed in a reaction vial and heated to 150° C. under microwave irradiation for 4 h. The mixture was filtered and the filtrate was concentrated. The residue was treated with HCl (4.0 N in dioxane, 5 mL) for 16 h. The resulting mixture was concentrated and purified by preparative HPLC LCMS m/z=428.2 [M+H]$^+$; $^1$H NMR (400 MHz, DMSO-$d_6$) δ ppm 1.34-1.56 (m, 8H), 1.70-1.88 (m, 2H), 3.31 (s, 3H), 3.39 (d, J=7.07 Hz, 2H), 4.00 (d, J=7.20 Hz, 2H), 4.11 (s, 2H), 6.94-7.01 (m, 2H), 7.23.7.31 (m, 4H), 7.42-7.49 (m, 3H).

Example: 13: Preparation of 2-(((1s,4s)-4-(((4-Chlorophenyl)(phenyl)carbamoyloxy)methyl)cyclohexyl)methoxy)acetic Acid (Compound 25)

From tert-butyl 2-4(1s,4s)-4-((phenylcarbamoyloxy) methyl)cyclohexyl)methoxy)acetate and 1-chloro-4-iodobenzene, using a similar method to the one described in Example 1.2, the title compound was obtained. LCMS m/z=432.1 [M+H]$^+$; $^1$H NMR (400 MHz, DMSO-$d_6$) δ ppm 1.28-1.53 (m, 8H), 1.60-1.81 (m, 2H), 3.29 (d, J=7.07 Hz, 2H), 3.96 (s, 2H), 3.98 (d, J=6.69 Hz, 2H), 7.24-7.33 (m, 5H), 7.36-7.48 (m, 4H).

Example 1.4: Preparation of 2-(((1s,4s)-4-(((3-Fluorophenyl)(phenyl)carbamoyloxy)methyl)cyclohexyl) methoxy)acetic Acid (Compound 26)

From tert-butyl 2-(((1s,4s)-4-((phenylcarbamoyloxy) methyl)cyclohexyl)methoxy)acetate and 1-fluoro-3-iodobenzene, using a similar method to the one described in Example 1.2, the title compound was obtained. LCMS m/z=416.4 [M+H]$^+$: $^1$H NMR (400 MHz, DMSO-$d_6$) δ ppm 1.28-1.42 (m, 8H), 1.71 (s, 2H), 3.28 (d, J=7.07 Hz, 2H), 3.96 (s, 2H), 3.99 (d, J=6.44 Hz, 2H), 7.03-7.11 (m, 2H), 7.20-7.33 (m, 4H), 7.37-7.43 (m, 3H).

Example 1.5: Preparation of 2-(((1s,4s)-4-(((3-Chlorophenyl)(phenyl)carbamoyloxy)methyl)cyclohexyl) methoxy)acetic Acid (Compound 30)

From tert-butyl 20(((1s,4s)-4-((phenylcarbamoyloxy) methyl)cyclohexyl)methoxy)acetate and 1-chloro-3-iodobenzene, using a similar method to the one described in Example 1.2, the title compound was obtained. LCMS m/z=432.1 [M+H]$^+$: $^1$H NMR (400 MHz, DMSO-$d_6$) δ ppm 1.27-1.55 (m, 8H), 1.60-1.87 (m, 2H), 3.29 (d, J=7.07 Hz, 2H), 3.96 (s, 2H), 3.99 (d, J=6.57 Hz, 2H), 7.18-7.34 (m, 5H), 7.35-7.48 (m, 4H).

Example 1.6: Preparation of 2-(((1s,4s)-4-(Phenyl (m-tolyl)carbamoyloxy)methyl)cyclohexyl)methoxy) acetic Acid (Compound 31)

From tert-butyl 2-(((1s,4s)-4-((phenylcarbamoyloxy) methyl)cyclohexyl)methoxy)acetate and 1-iodo-3-methylbenzene, using a similar method to the one described in Example 1.2, the title compound was obtained. LCMS m/z=412.2 [M+H]$^+$; $^1$H NMR (400 MHz, DMSO-$d_6$) δ ppm 1.28-1.53 (m, 8H), 1.60-1.76 (m, 2H), 2.27 (s, 3H), 3.28 (d, J=6.95 Hz, 2H), 3.95 (s, 2H), 4.00 (d, J=7.20 Hz, 2H), 7.02-7.11 (m, 3H), 7.19-7.29 (m, 4H) 7.33-7.39 (m, 2H).

Example 1.7: Preparation of 2-(((1s,4s)-4-(((2-Methoxyphenyl)(phenyl)carbamoyloxy)methyl)cyclohexyl)methoxy)acetic Acid (Compound 32)

From tert-butyl 2-(((1,s,4s)-4-((phenylcarbamoyloxy) methyl)cyclohexyl)methoxy)acetate and 1-iodo-2-methoxybenzene, using a similar method to the one described in Example 1.2, the title compound was obtained. LCMS m/z=428.3 [M+H]$^+$; $^1$H NMR (400 MHz, DMSO-$d_6$) δ ppm 1.34-1.56 (m, 8H), 1.70-1.88 (m, 2H) 3.32 (s, 3H), 3.40 (d, J=7.07 Hz, 2H), 4.00 (d, J=7.33 Hz, 2H), 4.11 (s, 2H), 6.93-7.02 (m, 2H), 7.23-7.31 (m, 4H), 7.42-7.49 (m, 3H).

Example 1.8: Preparation of 2-(((1s,4s)-4-(((3-Methoxyphenyl)(phenyl)carbamoyloxy)methyl)cyclohexyl)methoxy)acetic Acid (Compound 33)

From tert-butyl 2-(((1s,4s)-4-((phenylcarbamoyloxy) methyl)cyclohexyl)methoxy)acetate and 1-iodo-3-methoxybenzene, using a similar method to the one described in Example 1.2, the title compound was obtained. LCMS m/z=428.3 [M+]$^+$; $^1$H NMR (400 MHz, DMSO-$d_6$) δ ppm 1.34-1.56 (m, 8H), 1.71-1.88 (m, 2H), 3.32 (s, 3H), 3.40 (d, J=7.07 Hz, 2H), 4.00 (d, J=7.33 Hz, 2H), 4.11 (s, 2H), 6.94-7.01 (m, 2H), 7.23-7.30 (m, 4H), 7.43-7.48 (m, 3H).

Example 1.9: Preparation of 2-(((1s,4s)-4-((Phenyl (p-tolyl)carbamoyloxy)methyl)cyclohexyl)methoxy) acetic acetic Acid (Compound 34)

From tert-butyl 2-(((1s,4s)-4-((phenylcarbamoyloxy) methyl)cyclohexyl)methoxy)acetate and 1-iodo-4-methyl-benzene, using a similar method to the one described in Example 1.2, the title compound was obtained. LCMS m/z=412.2 [M+H]$^+$; $^1$H NMR (400 MHz, DMSO-$d_6$) δ ppm 1.28-1.53 (m, 8H), 1.59-1.80 (m, 2H), 2.29 (s, 3H), 3.38 (d, J=7.07 Hz, 2H), 3.96 (s, 2H), 4.00 (d, J=7.20 Hz, 2H), 7.13-7.21 (m, 2H), 7.21-7.30 (m, 4H), 7.32-7.39 (m, 3H).

Example 1.10: Preparation of 2-(((1s,4s)-4-4(((4-Fluorophenyl)(phenyl)carbamoyloxy)methyl)cyclo-hexyl)methoxy)acetic Acid (Compound 35)

From tert-butyl 2-(((1s,4s)-4-((phenylcarbamoyloxy) methyl)cyclohexyl)methoxy)acetate and 1-fluoro-4-iodo-benzene, using a similar method to the one described in Example 1.2, the title compound was obtained. LCMS m/z=416.3 [M+H]$^+$; $^1$H NMR (400 MHz, DMSO-$d_6$) δ ppm 1.28-1.54 (m, 8H), 1.60-1.75 (m, 2H), 3.29 (d, J=7.07 Hz, 2H), 3.96 (s, 2H), 3.97 (d, J=6.69 Hz, 2H), 7.17-7.31 (m, 5H), 7.31-7.41 (m, 4H).

Example 1.11: Preparation of 2-(((1s,4s)-4-((Diphenylcarbamoyloxy)methyl)cyclohexyl)methoxy)acetic Acid (Compound 7)

Step A: Preparation of ((1s,4s)-4-(Hydroxymethyl)cyclohexyl)methyl diphenylcarbamate To a solution of (1s,4s)-cyclohexane-1,4-diyldimethanol (0.560 g, 3.88 mmol) in pyridine (5 mL) was added diphenylcarbamic chloride (0.9 g, 3.88 mmol) at room temperature. The reaction was refluxed for 5 h, cooled to room temperature, and concentrated under reduced pressure. The residue was poured into water. The organic material was extracted with ethyl acetate and washed with 1.0 M HCl. The extract was dried over $MgSO_4$ and concentrated under reduced pressure. The residue was purified by silica gel column chromatography to provide the title compound (0.870 g). LCMS m/z=340.23 [M+H]$^+$.

Step B: Preparation of 2-(((1s,4s)-4-((Diphenylcarbamoyloxy)methyl)cyclohexyl)methoxy acetic Acid To a solution of ((1s,4s)-4-(hydroxymethyl)cyclohexyl) methyl diphenylcarbamate (300 mg, 0.884 mmol) and diacetoxyrhodium (19.53 mg, 0.044 mmol) in $CH_2Cl_2$ (3 mL), was added dropwise a solution of tert-butyl 2-diazoacetate (188 mg, 1.326 mmol) in $CH_2Cl_2$ (1 mL) at 0° C. After stirring for 1 h at room temperature, the reaction was filtered and concentrated under reduced pressure. The residue was treated with HCl (4.0 M in dioxane, 2 mL). After stirring for 8 h, the reaction was concentrated under reduced pressure and the residue was purified by HPLC to provide the title compound (198 mg). LCMS m/z=398.45 [M+H]$^+$; $^1$H NMR (400 MHz, DMSO-$d_6$) δ 1.15-1.40 (m, 8H), 1.50-1.62 (m, 2H), 1.75-1.81 (m, 2H), 3.90-3.92 (d, J=4.3 Hz, 2H), 3.96 (s, 2H), 7.21-7.32 (m, 6H), 7.35-7.39 (m, 4H).

Example 1.12: Preparation of Sodium 2-(((1r,4r)-4-((Diphenylcarbamoyloxy)methyl)cyclohexyl) methoxy)acetate To a solution of 2-(((1r,4r)-4-((diphenylcarbamoyloxy) methyl)cyclohexyl)methoxy) acetic acid (25 mg, 0.063 mmol) in MeOH (1 mL), was added sodium methanolate (0.126 mL, 0.063 mmol) at −10° C. After stirring for 30 min, the reaction was concentrated under reduced pressure to provide the title compound as a white solid (26.1 mg). LCMS m/z=398.41 [M+H]$^+$.

Example 1.13: Preparation of 2-(((1r,4r)-4-(((3-Methoxyphenyl)(phenyl)carbamoyloxy)methyl)cy-clohexyl)methoxy)acetic Acid (Compound 14)

Step A: Preparation of ((1r,4r)-4-(Hydroxymethyl)cyclohexyl)methyl Phenylcarbamate To a solution of (1r,4r)-cyclohexane-1,4-diyldimethanol (5 g, 34.7 mmol) in pyridine, was added phenyl isocyanate (4.13 g, 34.7 mmol) at room temperature. The reaction was stirred for 5 h, concentrated and extracted with ethyl acetate. The extract was dried over $MgSO_4$ and concentrated. The residue was purified by silica gel column chromatography to give the title compound (4.69 g). LCMS m/z=264.43 [M+H]$^+$; $^1$H NMR (400 MHz, DMSO-$d_6$) δ ppm 0.81-1.09 (m, 4H), 1.30-1.39 (m, 1H), 1.51-1.62 (m, 1H), 1.75-1.88 (m, 4H), 3.15-3.25 (d, J=5.8 Hz, 2H), 3.82-3.95 (d, J=6.56 Hz, 2H), 4.52 (t, J=5.31 Hz, 1H), 6.29 (m, 1H), 7.30 (m, 2H), 7.48 (m, 2H), 9.62 (s, 1H).

Step B: Preparation of tert-Butyl 2-(((1r,4r)-4-((phenylcarbamoyloxy)methyl)cyclohexyl)methoxy) Acetate To a solution of ((1r,4r)-4-(hydroxymethyl)cyclohexyl) methyl phenylcarbamate (2.5 g, 9.49 mmol) and diacetoxyrhodium (0.210 g, 0.475 mmol) in dichloromethane (50 mL) was added dropwise a solution of tert-butyl 2-diazoacetate (1.350 g, 9.49 mmol) in dichloromethane (5 mL) at 0° C. for 20 min. After stirring for 30 min at room temperature, the solid was filtered off and the filtrate was concentrated under reduced pressure. The residue was purified by silica gel column chromatography to give the title compound (3.32 g). LCMS m/z=378.43 [M+H]$^+$; $^1$H NMR (400 MHz, DMSO-$d_6$) δ ppm 0.85-1.08 (m, 4H), 1.42 (s, 9H), 1.41-1.62 (m, 2H), 1.78-1.81 (m, 4H), 3.25 (d, J=6.3 Hz, 2H), 3.92 (d, J=4.6 Hz, 2H), 6.29 (m, 1H), 7.31 (m, 2H), 7.48 (m, 2H), 9.62 (s, 1H).

Step C: Preparation of 2-(((1r,4r)-4-(((3-Methoxyphenyl(phenyl)carbamoyloxy)methyl)cyclohexyl) methoxy)acetic Acid To a solution of tert-butyl 2-(((1r,4r)-4-((phenylcarbamoyloxy)methyl)cyclohexyl)methoxy) acetate (0.2 g, 0.530 mmol) in dioxane (95 mL) were added 1-bromo-3-methoxybenzene (0.099 g, 0.530 mmol), (1R,2R)-cyclohexane-1,2-diamine (0.012 g, 0.106 mmol), copper(I) iodide (10.09 mg, 0.053 mmol), and $K_3PO_4$ (0.225 g, 1.060 mmol) at room temperature. The reaction was irradiated under microwave for 4 h at 150° C. The reaction mixture was filtered and concentrated under reduced pressure. The residue was treated with HCl (4.0 M in dioxane, 5 mL). After stirring for 10 h, the reaction was concentrated under reduced pressure and the residue was purified by preparative HPLC to provide the title compound (0.123 g). LCMS m/z=428.52 $[M+H]^+$; $^1H$ NMR (400 MHz, DMSO-$d_6$) δ 0.85-1.90 (m, 4H), 1.35-1.50 (s, 2H), 1.51-1.72 (m, 4H), 3.25 (d, J=6.4 Hz, 2H), 3.72 (s, 3H), 3.92 (d, J=6.1 Hz, 2H), 6.81-6.89 (m, 3H), 7.21-7.45 (m, 6H).

Example 1.14: Preparation of 2-(((1r,4r)-4-((1-Methyl-3,3-diphenylureido)methyl)cyclohexyl)methoxy)acetic Acid (Compound 4)

Step A: Preparation 1-(((1r,4r)-4-(Hydroxymethyl)cyclohexyl)methyl)-1-methyl-3,3-diphenylurea To a solution of ((1r,4r)-4-((methylamino)methyl)cyclohexyl)methanol (0.339 g, 2.158 mmol) in pyridine (3 mL) was added diphenylcarbamic chloride (0.5 g, 2.158 mmol) at room temperature. The reaction was refused for 5 h. The mixture was cooled to room temperature and poured into water. The organic material was extracted and washed with 10 M HCl. The extract was dried over $MgSO_4$ and concentrated under reduced pressure. The residue was purified by silica gel column chromatography to provide the title compound (0.685 g). LCMS m/z=353.16 $[M+H]^+$.

Step B: Preparation of 2-(((1r,4r)-4-((1-Methyl-3,3-diphenylureido)methyl)cyclohexyl)methoxy)acetic Acid To a solution of 1-(((1r,4r)-4-(hydroxymethyl)cyclohexyl)methyl)-1-methyl-3,3-diphenylurea (0.1 g, 0.284 mmol) in $CH_2Cl_2$ (5 mL), was added rhodium (II) acetate dimer (6.27 mg, 0.014 mmol) followed by tert-butyl 2-diazoacetate (0.040 g, 0.284 mmol) at 0° C. The reaction was stirred for 1 h and concentrated under reduced pressure. The residue was treated with 4.0 M HCl in dioxane and stirred overnight. The mixture was concentrated under reduced pressure and the residue was purified by preparative HPLC to provide the title compound (58 mg). LCMS m/z=411.32 $[M+H]^+$; $^1H$ NMR (400 MHz, DMSO-$d_6$) δ ppm 1.35-1.41 (m, 2H), 1.81-1.92 (m, 1H), 2.21-2.51 (m, 4H), 2.62-2.86 (m, 2H), 3.21 (m, 2H), 4.62 (s, 3H), 7.15-7.38 (m, 10H).

Example 1.15: Preparation of 2-(((1r,4r)-4-((Diphenylcarbamoyloxy)methyl)cyclohexyl)methoxy)acetic Acid (Compound 5)

From (1r,4r)-cyclohexane-1,4-diyldimethanol, the title compound was obtained using a similar method to the one described in Example 1.11. LCMS m/z=398.10 $[M+H]^+$; $^1H$ NMR (400 MHz, DMSO-$d_6$) δ 1.10-1.42 (m, 8H), 1.53-1.60 (m, 2H), 1.70-1.87 (m, 2H), 3.91-3.93 (d, J=4.2 Hz, 2H), 3.98 (s, 2H), 7.20-7.31 (m, 6H), 7.30-7.50 (m, 4H).

Example 1.16: Preparation of 2-(((1s,4s)-4-((3,3-Diphenylureido)methyl)cyclohexyl)methoxy)acetic Acid (Compound 9)

Step A: Preparation of (1s,4s)-Cyclohexane-1,4-diyldimethanol

To a mixture of (1s,4s)-cyclohexane-1,4-dicarboxylic acid (4 g, 23.23 mmol) in THF (30 mL) was added lithium aluminum hydride (1 M, 93 mL, 93 mmol) dropwise at 0° C. The mixture was stirred at room temperature overnight. The reaction was quenched with water, extracted with EtOAc (3×40 mL), and dried over anhydrous $MgSO_4$. The mixture was filtered and the filtrate was concentrated under reduced pressure to provide the title compound as colorless oil (3.3 g). $^1H$ NMR (400 MHz, $CDCl_3$) δ ppm 1.64-1.38 (m, 8H), 1.70 (m, 2H), 3.56 (d, J=4 Hz, 4H).

Step B: Preparation of tert-Butyl 2-(((1s,4s)-4-(Hydroxymethyl)cyclohexyl)methoxy)acetate To a mixture of (1s,4s)-cyclohexane-1,4-diyldimethanol (1.0 g, 6.93 mmol) and rhodium(II) acetate dimer (0.184 g, 0.416 mmol) in DCM (10 mL) was added tert-butyl 2-diazoacetate (1.281 g, 9.01 mmol) dropwise at room temperature over 1 h period. The mixture was stirred overnight. The mixture was purified via column chromatography to provide the title compound as pale yellow oil (0.89 g). $^1H$ NMR (400 MHz, $CDCl_3$) δ ppm 1.42 (m, 4H), 1.48 (s, 9H), 1.54 (m, 4H), 1.68 (m, 1H), 1.86 (m, 1H), 3.43 (d, 2H, J=8 Hz), 3.55 (d, 2H, J=8 Hz), 3.94 (s, 2H).

Step C: Preparation of tert-Butyl 2-(((1s,4s)-4-((Methylsulfonyloxy)methyl)cyclohexyl)methoxy)acetate To a mixture of tert-butyl 2-(((1s,4s)-4-(hydroxymethyl)cyclohexyl)methoxy)acetate (0.87 g, 3.37 mmol) and triethylamine (1.408 mL, 10.10 mmol) in DCM (10 mL) was added methanesulfonyl chloride (0.579 g, 5.05 mmol) at 0° C. The mixture was stirred at 0° C. for 5 hr. The reaction was quenched with water and extracted with DCM (3×20 mL) and dried over anhydrous $MgSO_4$. The mixture was filtered and concentrated under reduced pressure to provide the title compound as pale yellow oil (1.1 g).

Step D: Preparation of tert-Butyl 2-(((1s,4s)-4-(Aminomethyl)cyclohexyl)methoxy)acetate A mixture of tert-butyl 2-(((1s,4s)-4-((methylsulfonyl)methyl)cyclohexyl)methoxy)acetate (0.25 g, 0.743 mmol) and sodium azide (0.097 g, 1.486 mmol) in DMF (5 mL) was stirred for 48 h. The reaction was diluted with EtOAc (20 mL) and washed with water. The organic layer was dried over anhydrous $MgSO_4$ and concentrated under reduced pressure. The residue was dissolved into MeOH (5.00 mL) and added Pd/C (3.95 mg, 0.037 mmol). The mixture was stirred under $H_2$ atmosphere overnight. The mixture was filtered through a celite column and concentrated under reduced pressure to provide the title compound as yellow oil (0.164 g) without further purification. LCMS m/z=258.2 $[M+H]^+$.

Step E: Preparation of 2-((1s,4s)-4-((3,3-Diphenylureido)methyl)cyclohexyl)methoxy)acetic Acid To a mixture of tert-butyl 2-(((1s,4s)-4-(aminomethyl)cyclohexyl)methoxy)acetate (50 mg, 0.194 mmol) in THF (5 mL) was added potassium tert-butoxide (65.4 mg, 0.583 mmol) at room temperature. After stirring for 10 min. diphenylcarbamic chloride (45.0 mg, 0.194 mmol) was added. The reaction mixture was stirred at room temperature overnight. The reaction was quenched with water and the mixture was purified by preparative HPLC to provide the title compound as a white solid (6 mg). LCMS m/z=397.2 $[M+H]^+$; $^1H$ NMR (400 MHz, $CDCl_3$) δ ppm: 0.93 (m, 4H), 1.44 (m, 1H), 1.58 (m, 1H), 1.74 (d, J=11 Hz, 2H), 1.83 (d, J=11 Hz, 2H), 3.10 (t, J=6.3 Hz, 2H), 3.38 (d, J=6.3 Hz, 2H), 4.06 (s, 2H), 4.59 (t, J=5.8 Hz, 1H), 7.21 (dd, $J_1$, $J_2$=7.2 Hz, 2H), 7.26 (m, 4H), 7.35 (m, 4H).

Example 1.17: Preparation of 2-(((1r,4r)-4-((3-Benzhydryl-3-methylureido)methyl)cyclohexyl) methoxy)acetic Acid (Compound 48)

A solution of N-methyl-1,1-diphenylmethanamine (25 mg, 0.127 mmol), triphosgene (41.4 mg, 0.139 mmol), triethylamine (0.088 mL, 0.634 mmol) in DCM (5 mL) was refluxed at 40° C. for 3 h. tert-Butyl 2-(((1r,4r)-4-(aminomethyl)cyclohexyl)methoxy)acetate (48.9 mg. 0.190 mmol) was added. The reaction mixture was refluxed overnight, quenched with $H_2O$, and extracted with DCM. The organic layer was washed with brine, dried over $MgSO_4$ and concentrated. The residue was purified by preparative LCMS to provide the title compound as a white solid (7.6 mg). LCMS m/z=425.2 $[M+H]^+$; $^1H$ NMR (400 MHz, $CDCl_3$) δ ppm 0.82-1.02 (m, 4H), 1.41 (m, 1H), 1.57 (m, 1H), 1.70 (d, J=10.36 Hz, 2H), 1.80 (d, J=10.36 Hz, 2H), 2.72 (s, 3H), 3.11 (t, J=5.68 Hz, 2H), 3.36 (d, J=6.32 Hz, 2H), 4.06 (s, 2H), 4.53 (m, 1H), 6.64 (s, 1H), 7.19 (d, J=7.07 Hz, 4H), 7.27-7.38 (m, 6H).

Example 1.18: Preparation of 2-(((1r,4r)-4-(((2,3-Difluorophenyl)(phenyl)carbamoyloxy)methyl)cyclohexyl)methoxy)acetic Acid (Compound 51)

Step A: Preparation of 2,3-Difluoro-N-phenylaniline

A mixture of 1-bromo-2,3-difluorobenzene (0.232 mL, 2.073 mmol), aniline (0.208 mL, 2.280 mmol), $Pd_2(dba)_3$ (95 mg, 0.104 mmol), BINAP (194 mg, 0.311 mmol), sodium tert-butoxide (299 mg, 3.11 mmol), and toluene (3 mL) in a sealed vessel under argon was heated in an oil bath at 110° C. overnight. The reaction mixture was filtered through a plug of celite. The filtrate was concentrated and the residue was purified by silica gel column chromatography to give the title compound as a light brown oil (411 mg). LCMS m/z=206.1 $[M+H]^+$; $^1H$ NMR (400 MHz, Methanol-$d_4$) δ ppm 6.53-6.64 (m, 1H), 6.80-6.88 (m, 2H), 6.88-6.95 (m, 1H), 6.95-7.03 (m, 2H), 7.11-7.19 (m, 2H).

Step B: Preparation of 2,3-Difluorophenyl(phenyl)carbamic Chloride 2,3-Difluoro-N-phenylaniline (100 mg, 0.487 mmol) and triphosgene (159 mg, 0.536 mmol) were dissolved in $CH_2Cl_2$ (1 mL). The solution was cooled in an ice bath, and pyridine (79 μL, 0.975 mmol) was added slowly. Upon complete addition, the reaction was warmed to room temperature and stirred for 1 h. Then, it was cooled in an ice bath and quenched by the slow addition of $H_2$ O (1 mL). The reaction mixture was extracted with $H_2O$ (5 mL) and $CH_2Cl_2$ (5 mL). The aqueous layer was extracted again with $CH_2Cl_2$ (5 mL). The organic layers were combined and washed once with $H_2O$ (10 mL), dried over $MgSO_4$, and concentrated. The residue was purified by silica gel column chromatography to yield the title compound as a light brown oil (114.7 mg).

Step C: Preparation of 2-(((1r,4r)-4-(((2,3-Difluorophenyl)(phenyl)carbamoyloxy)methyl)cyclohexyl) methoxy)acetic Acid 2,3-Difluorophenyl(phenyl)carbamic chloride (50 mg, 0.187 mmol) and tert-butyl 2-(((1r,4r)-4-(hydroxymethyl) cyclohexyl)methoxy)acetate (48.3 mg, 0.187 mmol) were dissolved in pyridine (1 mL). The reaction mixture was heated to 100° C. and stirred overnight. The solvent was removed from the mixture and the residue was purified by silica gel column chromatography to provide an oil, which was redissolved in HCl (4 M in dioxane) (500 μL, 1.999 mmol). The reaction mixture was stirred at room temperature for 5 h. After removal of the solvent, the residue was purified by preparative LCMS to provide the title compound as a white solid (12.3 mg). LCMS m/z=434.2 $[M+H]^+$; $^1H$ NMR (400 MHz, Methanol-$d_4$) δ ppm 0.78-0.94 (m, 4H), 1.32-1.49 (m, 2H), 1.51-1.62 (m, 2H), 1.63-1.77 (m, J=7.33 Hz, 2H), 3.20-3.22 (m, 2H), 3.89 (d, J=6.06 Hz, 2H), 3.92 (s, 2H), 6.99-7.10 (m, 2H), 7.11-7.22 (m, 4H), 7.22-7.31 (m, 2H).

Example 1.19: Preparation of Sodium 2-(((1r,4r)-4-(((4-Chlorophenyl)(phenyl)carbamoyloxy)methyl) cyclohexyl)methoxy)acetate Step A. Preparation of 4-Chlorophenyl(phenyl)carbamic Chloride From 4-choro-N-phenylaniline, using a similar method to the one described in Example 1.18, Step B, the title compound was obtained as a light yellow oil. $^1H$ NMR (400 MHz, DMSO-$d_6$) δ ppm 7.31-7.81 (m, 9H).

Step B: Preparation of ((1r,4r)-4-(Hydroxymethyl) cyclohexyl)methyl 4-chlorophenyl(phenyl)carbamate 4-Chlorophenyl(phenyl)carbamic chloride (12.34 g, 46.4 mmol) and (1r,4r)-cyclohexane-1,4-diyldimethanol (6.69 g, 46.4 mmol) were dissolved in pyridine (50 mL, 618 mmol). The reaction mixture was heated to reflux overnight, cooled and concentrated under reduced pressure. The residue was resuspended in $Et_2O$/EtOAc (50:50), filtered and washed with EtOAc and $Et_2O$. The filtrate was extracted with 1 M HCl (200 mL) and EtOAc (200 mL). The aqueous layer was extracted again with EtOAc (100 mL). The organic layers were combined and washed with $H_2O$ (200 mL), dried, and concentrated. The residue was purified by silica gel column chromatography to provide the title compound as a light pink colored solid (10.4 g). LCMS m/z=374.1 $[M+H]^+$; $^1H$ NMR (400 MHz, DMSO-$d_6$) δ 0.73-0.92 (m, 4H), 1.13-1.27 (m, 1H), 1.36-1.50 (m, 1H), 1.53-1.62 (m, 2H), 1.62-1.73 (m, 2H), 3.17 (d, J=6.19 Hz, 2H), 3.89 (d, J=6.06 Hz, 2H), 4.29 (bs, 1H), 7.23-7.32 (m, 5H), 7.34-7.45 (m, 4H).

Step C: Preparation of tert-Butyl 2-(((1r,4r)-4-(((4-Chlorophenyl)(phenyl)carbamoyloxy)methyl)cyclohexyl)methoxy)acetate ((1r,4r)-4-(Hydroxymethyl)cyclohexyl)methy) 4-chlorophenyl(phenyl)carbamate (8.9 g, 23.80 mmol) was dissolved in $CH_2Cl_2$ (30 mL). Diacetoxyrhodium (0.526 g, 1.190 mmol) was added and the reaction was cooled on an ice bath. tert-Butyl 2-diazoacetate (3.63 mL, 26.2 mmol) pre-dissolved in $CH_2Cl_2$ (10 mL) was added slowly to the reaction via an addition funnel. The reaction was stirred in an ice bath for 1 h, warmed to room temperature and stirred for an additional 1 h. After removal of the solvent, the residue was purified by silica gel column chromatography to provide the title compound as a colorless oil (8.8 g). LCMS m/z=432.6 [M-tert-butyl group+H]$^+$; $^1H$ NMR (400 MHz, DMSO-$d_6$) δ ppm 0.77-0.95 (m, 4H), 1.33-1.50 (m, 2H), 1.42 (s, 9H), 1.52-1.62 (m, 2H), 1.63-1.75 (m, 2H), 3.22 (d, J=6.32 Hz, 2H), 3.83-3.93 (m, 4H), 7.23-7.32 (m, 5H), 7.35-7.44 (m, 4H).

Step D: Preparation of Sodium 2-(((1r,4r)-4-(((4-Chlorophenyl)(phenyl)carbamoyloxy)methyl)cyclohexyl)methoxy)acetate tert-Butyl 2-(((1r,4r)-4-(((4-chlorophenyl)(phenyl)carbamoyloxy)methyl)cyclohexyl)methoxy)acetate (8.8 g, 18.03 mmol) was dissolved in HCl (4 M in dioxane, 100 mL, 400 mmol). The reaction was stirred at room temperature overnight and concentrated under reduced pressure to provide an oil. The oil was extracted with $H_2O$ (100 mL) and EtOAc (100 mL). The aqueous layer was extracted again with EtOAc (100 mL). The combined organic layer was washed with $H_2O$ (150 mL), dried, and concentrated to yield a light yellow oil. The oil was dissolved in a minimal amount of MeOH (10-20 mL) and cooled in an ice bath. NaOH (1 M, 27.0 mL, 27.0 mmol) was added with stirring. A white solid precipitate was formed. The mixture was diluted with $H_2O$ (20 mL). The solid was filtered and washed with cold $H_2O$ (20 mL). The solid was dried in a vacuum oven (60° C. overnight) to provide the title compound as a white solid (7.7 g). LCMS m/z=432.5 $[M+H]^+$; $^1H$ NMR (400 MHz, DMSO-$d_6$) δ ppm 0.73-0.93 (m, 4H), 1.28-1.40 (bs, 1H), 1.40-1.50 (bs, 1H), 1.50-1.61 (m, 2H), 1.63-1.77 (m, 2H), 3.16 (d, J=6.57 Hz, 2H), 3.47 (s, 2H), 3.89 (d, J=6.06 Hz, 2H), 7.23-7.32 (m, 5H), 7.35-7.44 (m, 4H).

Example 1.20: Preparation of Sodium 2-(((1r,4r)-4-(((4-Fluorophenyl)(phenyl)carbamoyloxy)methyl)cyclohexyl)methoxy)acetate From 4-fluoro-N-phenylaniline, using a similar method to the one described in Example 1.19, the title compound was obtained as a white solid. LCMS m/z=416.4 $[M+H]^+$; $^1H$ NMR (400 MHz, DMSO-$d_6$) δ ppm 0.72-0.94 (m, 4H), 1.28-1.39 (m, 1H), 1.39-1.49 (m, 1H), 1.50-1.61 (m, 2H), 1.62-1.76 (m, 2H), 3.15 (d, J=6.44 Hz, 2H), 3.45 (s, 2H), 3.88 (d, J=6.06 Hz, 2H), 7.16-7.41 (m, 9H).

Example 1.21: Preparation of 2-(((1r,4r)-4-(((4-Methoxyphenyl)(phenyl)carbamoyloxy)methyl)cyclohexyl)methoxy)acetic Acid (Compound 21)

tert-Butyl 2-(((1r,4r)-4-((phenylcarbamoyloxy)methyl)cyclohexyl)methoxy)acetate (50.0 mg, 0.132 mmol), copper (I) Iodide (12.61 mg, 0.066 mmol), $K_3PO_4$ (56.2 mg, 0.265 mmol), 4-methoxyphenyl iodide (3.10 mg, 0.132 mmol) and dioxane (1.6 mL) were added to a vial. The reaction was heated under microwave irradiation at 150° C. for 4-5 h. The reaction mixture was filtered through a plug of $MgSO_4$. The solvent was evaporated and the resulting oil was redissolved in HCl (4 M in dioxane, 497 μL, 1.987 mmol). The mixture was stirred overnight. After removal of the solvent, the residue was purified by preparative LCMS to provide the title compound as a white solid (12.2 mg). LCMS m/z=428.4 $[M+H]^+$.

Example 1.22: Preparation of 2-(((1r,4r)-4-(((4-Chlorophenyl)(phenyl)carbamoyloxy)methyl)cyclohexyl)methoxy)acetic Acid (Compound 22)

From tert-butyl 2-(((1r,4r)-4-((phenylcarbamoyloxy)methyl)cyclohexyl)methoxy)acetate and 1-chloro-4-iodobenzene, using a similar method to the one described in Example 1.21, the title compound was obtained as a white solid. LCMS m/z=432.5 $[M+H]^+$.

Example 1.23: Preparation of 2-(((1r,4r)-4-(((3-Fluorophenyl)(phenyl)carbamoyloxy)methyl)cyclohexyl)methoxy)acetic Acid (Compound 23)

From tert-butyl 2-(((1r,4r)-4-((phenylcarbamoyloxy)methyl)cyclohexyl)methoxy)acetate and 1-fluoro-3-iodobenzene, using a similar method to the one described in Example 1.21, the title compound was obtained as a white solid. LCMS m/z=416.5 $[M+H]^+$.

Example 1.24: Preparation of 2-(((1r,4r)-4-((Phenyl(m-tolyl)carbamoyloxy)methyl)cyclohexyl)methoxy)acetic Acid (Compound 27)

From tert-butyl 2-(((1r,4r)-4-((phenylcarbamoyloxy)methyl)cyclohexyl)methoxy)acetate and 1-iodo-3-methylbenzene, using a similar method to the one described in Example 1.21, the title compound was obtained as a white solid. LCMS m/z=412.2 $[M+H]^+$.

Example 1.25: Preparation of 2-(((1r,4r)-4-(((3-Chlorophenyl)(phenyl)carbamoyloxy)methyl)cyclohexyl)methoxy)acetic Acid (Compound 28)

From tert-butyl 2-(((1r,4r)-4-((phenylcarbamoyloxy)methyl)cyclohexyl)methoxy)acetate and 1-chloro-3-iodobenzene, using a similar method to the one described in Example 1.21, the title compound was obtained as a white solid. LCMS m/z=432.6 $[M+H]^+$.

Example 1.26: Preparation of 2-(((1r,4r)-4-(((4-Chloro-3-fluorophenyl)(phenyl)carbamoyloxy)methyl)cyclohexyl)methoxy)acetic Acid (Compound 36)

From tert-butyl 2-(((1r,4r)-4-((phenylcarbamoyloxy)methyl)cyclohexyl)methoxy)acetate and 1-chloro-2-fluoro-4-iodobenzene, using a similar method to the one described in Example 1.21, the title compound was obtained as a white solid. LCMS m/z=450.1 $[M+H]^+$; $^1H$ NMR (400 MHz, Methanol-$d_4$) δ ppm 0.69-0.91 (m, 4H), 1.08-1.31 (m, 1H), 1.32-1.48 (m, 1H), 1.48-1.64 (m, 2H), 1.64-1.81 (m, 2H), 3.17 (d, J=6.57 Hz, 2H), 3.71 (s, 2H), 3.87 (d, J=6.06 Hz, 22H), 6.94 (ddd, J=8.75, 2.43, 1.20 Hz, 1H), 7.14-7.24 (m, 4H), 7.27-7.34 (m, 3H).

Example 1.27: Preparation of 2-(((1r,4r)-4-(((3-Chloro-4-fluorophenyl)(phenyl)carbamoyloxy)methyl)cyclohexyl)methoxy)acetic Acid (Compound 37)

From tert-butyl 2-(((1r,4r)-4-((phenylcarbamoyloxy)methyl)cyclohexyl)methoxy)acetate and 2-chloro-1-fluoro-4-iodobenzene, using a similar method to the one described in Example 1.21, the title compound was obtained as a white solid. LCMS m/z=450.2 $[M+H]^+$.

Example 1.28: Preparation of 2-(((1r,4r)-4-(((3-Fluoro-4-methylphenyl)(phenyl)carbamoyloxy)methyl)cyclohexyl)methoxy)acetic Acid (Compound 38)

From tert-butyl 2-(((1r,4r)-4-((phenylcarbamoyloxy)methyl)cyclohexyl)methoxy)acetate and 2-fluoro-4-iodo-1-methylbenzene, using a similar method to the one described in Example 1.21, the title compound was obtained as a white solid. LCMS m/z=430.2 $[M+H]^+$.

Example 1.29: Preparation of 2-(((1r,4r)-4-(((3,5-Difluorophenyl)(phenyl)carbamoyloxy)methyl)cyclohexyl)methoxy)acetic Acid (Compound 39)

From tert-butyl 2-(((1r,4r)-4-((phenylcarbamoyloxy)methyl)cyclohexyl)methoxy)acetate and 1,3-difluoro-5-iodobenzene, using a similar method to the one described in Example 1.21, the title compound was obtained as a white solid. LCMS m/z=434.3 $[M+H]^+$; $^1H$ NMR (400 MHz, Methanol-$d_4$) δ ppm 0.85-1.02 (m, 4H), 1.46-1.58 (m, 2H), 1.59-1.70 (m, 2H), 1.79-1.87 (m, 2H), 3.28 (d, J=6.44 Hz, 2H), 3.82 (s, 2H), 3.99 (d, J=6.19 Hz, 2H), 6.79 (tt, J=9.02, 2.23 Hz, 1H), 6.88-6.95 (m, 2H), 7.25-7.32 (m, 2H), 7.33-7.41 (m, 1H), 7.41-7.50 (m, 2H).

Example 1.30: Preparation of 2-(((1r,4r)-4-(((3,4-Difluorophenyl)(phenyl)carbamoyloxy)methyl)cyclohexyl)methoxy)acetic Acid (Compound 40)

From tert-butyl 2-(((1r,4r)-4-((phenylcarbamoyloxy)methyl)cyclohexyl)methoxy)acetate and 1,2-difluoro-4-iodobenzene, using a similar method to the one described in Example 1.21, the title compound was obtained as a white solid, LCMS m/z=434.5 $[M+H]^+$; $^1H$ NMR (400 MHz, Methanol-$d_4$) δ ppm 0.93-1.11 (m, 4H), 1.52-1.68 (m, 2H), 1.67-1.81 (m, 2H), 1.84-1.98 (m, 2H), 3.36 (d, J=6.44 Hz, 2H), 3.90 (s, 2H), 4.05 (d, J=6.06 Hz, 2H), 7.10-7.18 (m, 1H), 7.27-7.42 (m, 5H), 7.45-7.53 (m, 2H).

Example 1.31: Preparation of 2-(((1r,4r)-4-(((4-Fluorophenyl)(phenyl)carbamoyloxy)methyl)cyclohexyl)methoxy)acetic Acid (Compound 41)

From tert-butyl 2-(((1r,4r)-4-((phenylcarbamoyloxy)methyl)cyclohexyl)methoxy)acetate and 1-fluoro-4-iodobenzene, using a similar method to the one described in Example 1.21, the title compound was obtained as a white solid. LCMS m/z=416.5 $[M+H]^+$; $^1H$ NMR (400 MHz, Methanol-$d_4$) δ ppm 0.79-1.08 (m, 4H), 1.45-1.60 (m, 2H), 1.61-1.73 (m, 2H), 1.77-1.89 (m, 2H), 3.29 (d, J=6.57 Hz, 2H), 3.83 (s, 2H), 3.97 (d, J=6.06 Hz, 2H), 7.07-7.14 (m, 2H), 7.21-7.34 (m, 5H), 7.35-7.41 (m, 2H).

Example 1.32: Preparation of 2-(((1r,4r)-4-((Phenyl(p-tolyl)carbamoyloxy)methyl)cyclohexyl)methoxy)acetic Acid (Compound 42)

From tert-butyl 2-(((1r,4r)-4-((phenylcarbamoyloxy)methyl)cyclohexyl)methoxy)acetate and 1-iodo-4-methylbenzene, using a similar method to the one described in Example 1.21, the title compound was obtained as a white solid. LCMS m/z=412.2 $[M+H]^+$.

Example: 1.33: Preparation of 2-(((1r,4r)-4-(Phenyl(pyridin-3-yl)carbamoyloxy)methyl)cyclohexyl)methoxy)acetic Acid (Compound 49)

From tert-butyl 2-(((1r,4r)-4-((phenylcarbamoyloxy)methyl)cyclohexyl)methoxy)acetate and 3-iodopyridine, using a similar method to the one described in Example 1.21, the title compound was obtained as a white solid. LCMS m/z=399.2 $[M+H]^+$; $^1H$ NMR (400 MHz, $CDCl_3$) δ ppm 0.67-0.91 (m, 4H), 1.31-1.47 (m, 2H), 1.47-1.58 (m, 2H), 1.62-1.76 (m, 2H), 3.21-3.27 (m, 2H), 3.93 (d, J=6.06 Hz, 2H), 3.96 (s, 2H), 7.12 (d, J=7.58 Hz, 2H), 7.26-7.45 (m, 3H), 7.56 (dd, J=7.96, 5.43 Hz, 1H), 8.13 (d, J=8.08 Hz, 1H), 8.36 (d, J=4.29 Hz, 1H), 8.56 (s, 1H).

Example 1.34: Preparation of 2-(((1r,4r)-4-(((5-Methylthiophen-2-yl)(phenyl)carbamoyloxy)methyl)cyclohexyl)methoxy)acetic Acid (Compound 50)

From tert-butyl 2-(((1r,4r)-4-((phenylcarbamoyloxy)methyl)cyclohexyl)methoxy)acetate and 2-iodo-5-methylthiophene, using a similar method to the one described in Example 1.21, the title compound was obtained as a white solid. LCMS m/z=418.4 $[M+H]^+$.

Example 1.35: Preparation of 2-(((1r,4r)-4-(((6-Fluoropyridin-3-yl)(phenyl)carbamoyloxy)methyl)cyclohexyl)methoxy)acetic Acid (Compound 84)

From tert-butyl 2-(((1r,4r)-4-((phenylcarbamoyloxy)methyl)cyclohexyl)methoxy)acetate and 2-fluoro-5-iodopyridine, using a similar method to the one described in Example 1.21, the title compound was obtained as a white solid. LCMS m/z=417.6 $[M+H]^+$.

Example 1.36: Preparation of 2-(((1r,4r)-4-((Phenyl(pyrazin-2-yl)carbamoyloxy)methyl)cyclohexyl)methoxy)acetic Acid (Compound 85)

From tert-butyl 2-(((1r,4r)-4-((phenylcarbamoyloxy)methyl)cyclohexyl)methoxy)acetate and the 2-iodopyrazine, using a similar method to the one described in Example 1.21, the title compound was obtained as a white solid. LCMS m/z=400.2 $[M+H]^+$.

Example 1.37: Preparation of 2-(((1r,4r)-4-(((4-Ethoxyphenyl)(phenyl)carbamoyloxy)methyl(cyclohexyl)methoxy)acetic Acid (Compound 88)

From tert-butyl 2-(((1r,4r)-4-((phenylcarbamoyloxy)methyl)cyclohexyl)methoxy)acetate and 1-ethoxy-4-iodobenzene, using a similar method to the one described in Example 1.21, the title compound was obtained as a white solid. LCMS m/z=442.1 $[M+H]^+$.

Example 1.38: Preparation of 2-(((1r,4r)-4-(((2-Fluoropyridin-4-yl)(phenyl)carbamoyloxy)methyl)cyclohexyl)methoxy)acetic Acid (Compound 89)

From tert-butyl 2-(((1r,4r)-4-((phenylcarbamoyloxy)methyl)cyclohexyl)methoxy)acetate and 2-fluoro-4-iodopyridine, using a similar method to the one described in Example 1.21, the title compound was obtained as a white solid. LCMS m/z=417.6 $[M+H]^+$.

Example 1.39: Preparation of 2-(((1r,4r)-4-(((5-Methoxypyridin-3-yl)(phenyl)carbamoyloxy)methyl)cyclohexyl)methoxy)acetic Acid (Compound 90)

From tert-butyl 2-(((1r,4r)-4-((phenylcarbamoyloxy)methyl)cyclohexyl)methoxy)acetate and 3-iodo-5-methoxypyridine, using a similar method to the one described in Example 1.21, the title compound was obtained as a white solid. LCMS m/z=429.4 $[M+H]^+$.

Example 1.40: Preparation of 2-(((1r,4r)-(((5-Fluoropyridin-2-yl)(phenyl)carbamoyloxy)methyl)cyclohexyl)methoxy)acetic Acid (Compound 91)

From tert-butyl 2-(((1r,4r)-4-(phenylcarbamoyloxy)methyl)cyclohexyl)methoxy)acetate and 5-fluoro-2-iodopyridine, using a similar method to the one described in Example 1.21, the title compound was obtained as a white solid. LCMS m/z=417.6 $[M+H]^+$.

Example 1.41: Preparation of 2-(((1r,4r)-4-((Phenyl(5-(trifluoromethyl)pyridin-2-yl)carbamoyloxy)methyl)cyclohexyl)methoxy)acetic Acid (Compound 92)

From tert-butyl 2-(((1r,4r)-4-((phenylcarbamoyloxy)methyl)cyclohexyl)methoxy)acetic and 2-iodo-5-(trifluoromethyl)pyridine, using a similar method to the one described in Example 1.21, the title compound was obtained as a white solid. LCMS m/z=467.5 $[M+H]^+$.

Example 1.42: Preparation of 2-(((1r,4r)-4-(((5-Methylpyridin-3-yl)(phenyl)carbamoyloxy)methyl)cyclohexyl)methoxy)acetic Acid (Compound 93)

From tert-butyl 2-(((1r,4r)-4-((phenylcarbamoyloxy)methyl)cyclohexyl)methoxy)acetate and 3-iodo-5-methylpyridine, using a similar method to the one described in Example 1.21, the title compound was obtained as a white solid. LCMS m/z=413.2 $[M+H]^+$.

Example 1.43: Preparation of 2-(((1r,4r)-4-(((5-Chloropyridin-2-yl)(phenyl)carbamoyloxy)methyl)cyclohexyl)methoxy)acetic Acid (Compound 94)

From tert-butyl 2-(((1r,4r)-4-((phenylcarbamoyloxy)methyl)cyclohexyl)methoxy)acetate and 5-chloro-2-iodopyridine, using a similar method to the one described in Example 1.21, the title compound was obtained as a white solid. LCMS m/z=433.3 $[M+H]^+$; $^1H$ NMR (400 MHz, DMSO-$d_6$) δ ppm 0.77-0.95 (m, 4H), 1.32-1.41 (m, 1H), 1.41-1.50 (m, 1H), 1.51-1.61 (m, 2H), 1.63-1.75 (m, 2H), 3.22 (d, J=6.44 Hz, 2H), 3.93 (d, J=6.06 Hz, 2H), 3.94 (s, 2H) 7.21-7.32 (m, 3H), 7.36-7.44 (m, 2H), 7.70-7.75 (m, 1H), 7.97-8.02 (m, 1H), 8.33-8.41 (m, 1H), 12.52 (bs, 1H).

Example 1.44: Preparation of 2-(((1r,4r)-4-(((5-Fluoropyridin-3-yl)(phenyl)carbamoyloxy)methyl)cyclohexyl)methoxy)acetic Acid (Compound 95)

From tert-butyl 2-(((1r,4r)-4-((phenylcarbamoyloxy)methyl)cyclohexyl)methoxy)acetate and 5-fluoro-3-iodopyridine, using a similar method to the one described in Example 1.21, the title compound was obtained as a white solid. LCMS m/z=417.5 $[M+H]^+$.

Example 1.45: Preparation of 2-(((1r,4r)-4-(((3-Fluorophenyl)(4-methoxyphenyl)carbamoyloxy)methyl)cyclohexyl)methoxy)acetic Acid (Compound 55)

Step A: Preparation of tert-Butyl 2-(((1r,4r)-4-(Hydroxymethyl)cyclohexyl)methoxy)acetate To a solution of (1r,4r)-cyclohexane-1,4-diyldimethanol (5.0 g, 34.7 mmol) in benzene (20 mL) was added tetrabutylammonium iodide (6.40 g, 17.34 mmol) and 50% aqueous NaOH (10 mL, 34.7 mmol) at room temperature. The reaction was stirred vigorously for 5 min and then tert-butyl 2-bromoacetate (5.63 mL, 38.1 mmol) was added. The reaction was stirred vigorously for 2 h. The mixture was extracted with $H_2O$/NaOH (100 mL) and EtOAc/benzene (100 mL). The aqueous layer was extracted again with EtOAc (100 mL). The combined organic layer was dried and concentrated. The residue was purified by silica gel column chromatography to provide the title compound as a colorless oil (3.96 g). LCMS m/z=259.3 $[M+H]^+$; $^1H$ NMR (400 MHz, $CDCl_3$) δ ppm 0.89-1.06 (m, 4H), 1.47 (s, 9H), 1.55-1.68 (m, 2H), 1.76-1.98 (m, 4H), 3.32 (d, J=6.57 Hz, 2H), 3.45 (d, J=6.32 Hz, 2H), 3.93 (s, 2H).

Step B: Preparation of tert-Butyl 2-(((1r,4r)-4-((3-Fluorophenylcarbamoyloxy)methyl)cyclohexyl)methoxy)acetate To a solution of tert-butyl 2-(((1r,4r)-4-(hydroxymethyl)cyclohexyl)methoxy)acetate (1.0 g, 3.87 mmol) and pyridine (0.438 mL, 5.42 mmol) in $CH_2Cl_2$ (10 mL) was added 3-fluorophenyl isocyanate (0.480 mL, 4.26 mmol) and the reaction was stirred at room temperature overnight. The reaction was then heated to reflux for 5 h. After removal of the solvent, the residue was purified by silica gel column chromatography to yield the title compound as a white solid (1.12 g). LCMS m/z=340.4 $[M-tert\text{-}butyl+H]^+$; $^1H$ NMR (400 MHz, $CDCl_3$) δ ppm 0.85-1.04 (m, 4H), 1.41 (s, 9H), 1.51-1.64 (m, 2H), 1.69-1.87 (m, 4H), 3.26 (d, J=6.32 Hz, 2H), 3.87 (s, 2H), 3.92 (d, J=6.57 Hz, 2H), 6.57 (s, 1H), 6.68 (dt, J=8.34, 2.53 Hz, 1H), 6.94 (d, J=8.59 Hz, 1H), 7.13-7.18 (m, 1H), 7.20-7.28 (m, 1H).

Step C: Preparation of 2-(((1r,4r)-4-(((3-Fluorophenyl)(4-methoxyphenyl)carbamoyloxy)methyl)cyclohexyl)methoxy)acetic Acid From 1-iodo-4-methoxybenzene and tert-butyl 2-(((1r,4r)-4-((3-fluorophenyl-carbamoyloxy)methyl)cyclohexyl)methoxy)acetate, using a similar method to the one described in Example 1.21, the title compound was obtained as a white solid. LCMS m/z=446.5 $[M+H]^+$; $^1H$ NMR (400 MHz, DMSO-$d_6$) δ ppm: 0.86 (t, J=10.11 Hz, 4H), 1.39 (s, 2H), 1.54-1.62 (m, 2H), 1.64-1.74 (m, 2H), 3.23 (d, J-=6.32 Hz, 2H), 3.76 (s, 3H), 3.89 (d, J=6.19 Hz, 2H), 3.94 (s, 2H). 6.91-6.98 (m, 2H), 6.99-7.07 (m, 2H), 7.17-7.26 (m, 3H), 7.36 (dt, J=8.18, 6.88 Hz, 1H), 12.52 (bs, 1H).

Example 1.46: Preparation of 2-(((1r,4r)-4-(((4-Chlorophenyl)(3-fluorophenyl)carbamoyloxy)methyl)cyclohexyl)methoxy)acetic Acid (Compound 56)

From 1-chloro-4-iodobenzene and tert-butyl 2-(((1r,4r)-4-((3-fluorophenyl-carbamoyloxy)methyl)cyclohexyl))methoxy)acetate, using a similar method to the one described in Example 1.21, the title compound was obtained as a white solid. LCMS m/z=450.2 $[M+H]^+$; $^1H$ NMR (400 MHz, DMSO-$d_6$) δ ppm 0.77-0.98 (m, 4H), 1.34-1.42 (m, 1H), 1.42-1.52 (m, 1H), 1.53-1.63 (m, 2H), 1.63-1.75 (m, 2H), 3.23 (d, J=6.44 Hz, 2H), 3.91 (d, J=6.06 Hz, 2H), 3.94 (s, 2H), 7.04-7.14 (m, 21-1), 7.23-7.28 (m, 1H), 7.29-7.36 (m, 2H), 7.36-7.42 (m, 1H), 7.42-7.49 (m, 2H), 12.52 (bs, 1H).

Example 1.47 Preparation of 2-(((1r,4r)-4-(((3-Fluorophenyl)(4-fluorophenyl)carbamoyloxy)methyl)cyclohexyl)methoxy)acetic Acid (Compound 57)

From 1-fluoro-4-iodobenzene and tert-butyl 2-(((1r,4r)-4-((3fluorophenyl-carbamoyloxy)methyl)cyclohexyl)

methoxy)acetate, using a similar method to the one described in Example 1.21, the title compound was obtained as a white sold. LCMS m/z=434.4 [M+H]$^+$.

Example 1.48: Preparation of 2-(((1r,4r)-4-(((3-Chlorophenyl)(3-fluorophenyl)carbamoyloxy)methyl)cyclohexyl)methoxy)acetic Acid (Compound 58)

From tert-butyl 2-(((1r,4r)-4-((3-fluorophenylcarbamoyloxy)methyl)cyclohexyl)methoxy)acetate and 1-chloro-3-iodobenzene, using a similar method to the one described in Example 1.21, the title compound was obtained as a white solid. LCMS m/z=450.2 [M+H]$^+$.

Example 1.49: Preparation of 2-(((1r,4r)-4-(((3-Fluorophenyl)(m-tolyl)carbamoyloxy)methyl)cyclohexyl)methoxy)acetic Acid (Compound 59)

From tert-butyl 2-(((1r,4r)-4-((3-fluorophenylcarbamoyloxy)methyl)cyclohexyl)methoxy)acetate and 1-iodo-3-methylbenzene, using a similar method to the one described in Example 1.21, the title compound was obtained as a white solid. LCMS m/z=430.5 [M+H]$^+$.

Example 1.50: Preparation of 2-(((1r,4r)-4-(((4-Chloro-3-fluorophenyl)(3-fluorophenyl)carbamoyloxy)methyl)cyclohexyl)methoxy)acetic Acid (Compound 60)

From tert-butyl 2-(((1r,4r)-4-((3-fluorophenylcarbamoyloxy)methyl)cyclohexyl)methoxy)acetate and 1-chloro-2-fluoro-4-iodobenzene, using a similar method to the one described in Example 1.21, the title compound was obtained as a white solid. LCMS m/z=468.5 [M+H]$^+$.

Example 1.51: Preparation of 2-(((1r,4r)-4-(((3-Chloro-4-fluorophenyl)(3-fluorophenyl)carbamoyloxy)methyl)cyclohexyl)methoxy)acetic Acid (Compound 61)

From tert-butyl 2-(((1r,4r)-4-((3-fluorophenylcarbamoyloxy)methyl)cyclohexyl)methoxy)acetate and 2-chloro-1-fluoro-4-iodobenzene, using a similar method to the one described in Example 1.21, the title compound was obtained as a white solid. LCMS m/z=468.4 [M+H]$^+$.

Example 1.52

Preparation of 2-(((1r,4r)-4-(((3-Fluoro-4-methylphenyl)(3-fluorophenyl)carbamoyloxy)methyl)cyclohexyl)methoxy)acetic Acid (Compound 62)

From tert-butyl 2-(((1r,4r)-4-((3-fluorophenylcarbamoyloxy)methyl)cyclohexyl)methoxy)acetate and 2-fluoro-4-iodo-4-methylbenzene, using a similar method to the one described in Example 1.21, the title compound was obtained as a white solid (17.4 mg). LCMS m/z=448.2 [M+H]$^+$.

Example 1.53: Preparation of 2-(((1r,4r)-4-(((3,5-Difluorophenyl)(3-fluorophenyl)carbamoyloxy)methyl)cyclohexyl)methoxy)acetic Acid (Compound 64)

From tert-butyl 2-(((1r,4r)-4-((3-fluorophenylcarbamoyloxy)methyl)cyclohexyl)methoxy)acetate and 1,3-difluoro-5-iodobenzene, using a similar method to the one described in Example 1.21, the title compound was obtained as a white solid. LCMS m/z=452.3 [M+H]$^+$; $^1$H NMR (400 MHz, DMSO-$d_6$) δ ppm 0.77-0.94 (m, 4H), 1.32-1.42 (m, J=3.41 Hz, 1H), 1.42-1.52 (m, 1H), 1.52-1.60 (m, 2H), 1.64-1.76 (m, 2H), 3.23 (d, J=6.32 Hz, 2H), 3.92 (d, J=5.94 Hz, 2H), 3.94 (s, 2H), 7.07-7.21 (m, 5H), 7.32 (dt, J=10.36, 2.27 Hz, 1H), 7.45 (td, J=8.18, 6.76 Hz, 1H), 12.53 (bs, 1H).

Example 1.54: Preparation of 2-(((1r,4r)-4-(((3,4-Difluorophenyl)(3-fluorophenyl)carbamoyloxy)methyl)cyclohexyl)methoxy)acetic Acid (Compound 65)

From tert-butyl 2-(((1r,4r)-4-((3-fluorophenylcarbamoyloxy)methyl)cyclohexyl)methoxy)acetate and 1,2-difluoro-4-iodobenzene, using a similar method to the one described in Example 1.21, the title compound was obtained as a white solid. LCMS m/z=452.1 [M+H]$^+$.

Example 1.55: Preparation of 2-(((1r,4r)-4-((Bis(3-fluorophenyl)carbamoyloxy)methyl)cyclohexyl)methoxy)acetic Acid (Compound 66)

From tert-butyl 2-(((1r,4r)-4-((3-fluorophenylcarbamoyloxy)methyl)cyclohexyl)methoxy)acetate and 1-fluoro-3-iodobenzene, using a similar method to the one described in Example 1.21, the title compound was obtained as a white solid. LCMS m/z=434.4 [M+H]$^+$.

Example 1.56: Preparation of 2-(((1r,4r)-4-(((3-Fluorophenyl)(3-methoxyphenyl)carbamoyloxy)methyl)cyclohexyl)methoxy)acetic Acid (Compound 67)

From tert-butyl 2-(((1r,4r)-4-((3-fluorophenylcarbamoyloxy)methyl)cyclohexyl)methoxy)acetate and 1-iodo-3-methoxybenzene, using a similar method to the one described in Example 1.21, the title compound was obtained as a white solid. LCMS m/z=446.4 [M+H]$^+$.

Example 1.57: Preparation of 2-(((1r,4r)-4-(((3,5-Dimethylphenyl)(3-fluorophenyl)carbamoyloxy)methyl)cyclohexyl)methoxy)acetic Acid (Compound 68)

From tert-butyl 2-(((1r,4r)-4-((3-fluorophenylcarbamoyloxy)methyl)cyclohexyl)methoxy)acetate and 1-iodo-3,5-dimethylbenzene, using similar method to the one described in Example 1.21, the title compound was obtained as a while solid. LCMS m/z=444.7 [M+H]$^+$.

Example 1.58: Preparation of 2-(((1r,4r)-4-(((3-Fluorophenyl)(p-tolyl)carbamoyloxy)methyl)cyclohexyl)methoxy)acetic Acid (Compound 69)

From tert-butyl 2-(((1r,4r)-4-((3-fluorophenylcarbamoyloxy)methyl)cyclohexyl)methoxy)acetate and 1-iodo-4-methylbenzene, using a similar method to the one described in Example 1.21, the title compound was obtained as a white solid. LCMS m/z=430.3 [M+H]$^+$.

Example 1.59: Preparation of 2-(((1r,4r)-4-((3-Fluorophenyl)(6-fluoropyridin-3-yl)carbamoyloxy)methyl)cyclohexyl)methoxy)acetic Acid (Compound 70)

From tert-butyl 2-(((1r,4r)-4-((3-fluorophenylcarbamoyloxy)methyl)cyclohexyl)methoxy)acetate and 5-fluoro-2-iodopyridine, using a similar method to the one described in Example 1.21, the title compound was obtained as a white solid. LCMS m/z=435.3 $[M+H]^+$.

Example 1.60: Preparation of 2-(((1r,4r)-4-(((3-Fluorophenyl)(5-methylthiophen-2-yl)carbamoyloxy)methyl)cyclohexyl)methoxy)acetic Acid (Compound 71)

From tert-butyl 2-(((1r,4r)-4-((3-fluorophenylcarbamoyloxy)methyl)cyclohexyl)methoxy)acetate and 2-iodo-5-methylthiophene, using a similar method to the one described in Example 1.21, the title compound was obtained as a white solid. LCMS m/z=436.3 $[M+H]^+$.

Example 1.61. Preparation of 2-(((1r,4r)-4-(((4-Ethoxyphenyl)(3-fluorophenyl)carbamoyloxy)methyl)cyclohexyl)methoxy)acetic Acid (Compound 72)

From tert-butyl 2-(((1r,4r)-4-((3-fluorophenylcarbamoyloxy)methyl)cyclohexyl)methoxy)acetate and 1-ethoxy-4-iodobenzene, using a similar method to the one described in Example 1.21, the title compound was obtained as a white solid. LCMS m/z=460.5 $[M+H]^+$.

Example 1.62: Preparation of 2-(((1r,4r)-4-(((3-Fluorophenyl)(3-(trifluoromethoxy)phenyl)carbamoyloxy)methyl)cyclohexyl)methoxy)acetic Acid (Compound 73)

From tert-butyl 2-(((1r,4r)-4-((3-fluorophenylcarbamoyloxy)methyl)cyclohexyl)methoxy)acetate and 1-iodo-3-(trifluoromethoxy)benzene, using a similar method to the one described in Example 1.21, the title compound was obtained as a white solid. LCMS m/z=500.5 $[M+H]^+$.

Experiment 1.63: Preparation of 2-(((1r,4r)-4-(((3-Fluorophenyl)(pyridin-3-yl)carbamoyloxy)methyl)cyclohexyl)methoxy)acetic Acid (Compound 74)

From tert-butyl 2-(((1r,4r)-4-((3-fluorophenylcarbamoyloxy)methyl)cyclohexyl)methoxy)acetate and 3-iodopyridine, using a similar method to the one described in Example 1.21, the title compound was obtained as a white solid. LCMS m/z=417.4 $[M+H]^+$.

Experiment 1.64: Preparation of 2-(((1r,4r)-4-(((3-Fluorophenyl)(pyrazin-2-yl)carbamoyloxy)methyl)cyclohexyl)methoxy)acetic Acid (Compound 75)

From tert-butyl 2-(((1r,4r)-4-((3-fluorophenylcarbamoyloxy)methyl)cyclohexyl)methoxy)acetate and 2-iodopyrazine, using a similar method to the one described in Example 1.21, the title compound was obtained as a white solid. LCMS m/z=418.5 $[M+H]^+$.

Example 1.65: Preparation of 2-(((1r,4r)-4-(((4-Chlorophenyl)(4-fluorophenyl)carbamoyloxy)methyl)cyclohexyl)methoxy)acetic (Compound 76)

Step A: Preparation of Methyl 4-Fluoro-2-((1r,4r)-4-(hydroxymethyl)cyclohexyl)phenylcarbamate 4-Fluorophenyl isocyanate (4.75 g, 34.7 mmol), (1r,4r)-cyclohexane-1,4-diyldimethanol (5.0 g, 34.7 mmol), and pyridine (3.93 mL, 48.5 mmol) were dissolved in $CH_2Cl_2$ (30 mL). The reaction mixture was stirred at room temperature overnight. After removal of the solvent, the residue was purified by silica gel column chromatography to yield the title compound as a white solid (4.92 g). LCMS m/z=282.4 $[M+H]^+$; $^1H$ NMR (400 MHz, DMSO-$d_6$) δ ppm 0.81-1.07 (m, 4H), 1.25-1.38 (m, 1H), 1.49-1.64 (m, 1H), 1.72-1.82 (m, 4H), 3.19-3.24 (m, 2H), 3.89 (d, J=6.57 Hz, 2H), 4.34 (t, J=5.31 Hz, 1H), 7.04-7.15 (m, 2H), 7.46 (dd, J=8.97, 4.93 Hz, 2H), 9.61 (s, 1H).

Step B: Preparation of tert-Butyl 2-(((1r,4r)-4-((4-Fluorophenylcarbamoyloxy)methyl)cyclohexyl)methoxy)acetate To a solution of methyl 4-fluoro-2-(1r,4r)-4(-hydroxymethyl)cyclohexyl)phenylcarbamate (2.0 g, 7.11 mmol) and rhodium(II) acetate dimer (0.157 g, 0.355 mmol) in $CH_2Cl_2$ (10 mL) was added slowly tert-butyl 2-diazoacetate (1.084 mL, 7.82 mmol) pre-dissolved in $CH_2Cl_2$ (5 mL) via an addition funnel at 0° C. The reaction was stirred at 0° C. for 1 h and stirred at room temperature for another 1 h. After removal of the solvent, the residue was purified by silica gel column chromatography to yield the title compound as a tan solid (1.9 g). LCMS m/z=340.4 $[M-\text{tert-butyl}+H]^+$, 396.2 $[M+H]^+$; $^1H$ NMR (400 MHz, DMSO-$d_6$) δ ppm 0.97 (d, J=10.36 Hz, 4H), 1.42 (s, 9H), 1.44-1.53 (m, 1H), 1.54-1.64 (m, 1H), 1.72-1.82 (m, 4H), 3.26 (d, J=6.32 Hz, 2H), 3.90 (d, J=6.57 Hz, 2H) 3.92 (s, 2H), 7.06-7.15 (m, 2H), 7.46 (dd, J=8.84, 4.93 Hz, 2H), 9.61 (s, 1H).

Step C: Preparation of 2-(((1r,4r)-4-(((4-Chlorophenyl)(4-fluorophenyl)carbamoyloxy)methyl)cyclohexyl)methoxy)acetic Acid From tert-butyl 2-(((1r,4r)-4-((4-fluorophenylcarbamoyloxy)methyl)cyclohexyl)methoxy)acetate and 1-chloro-4-iodobenzene, using a similar method to the one described in Example 1.21, the title compound was obtained as a white solid. LCMS m/z=450.1 $[M+H]^+$; $^1H$ NMR (400 MHz, DMSO-$d_6$), δ ppm 0.78-0.94 (m, 4H), 1.33-1.52 (m, J=29.68 Hz, 2H), 1.53-1.62 (m, 2H), 1.64-1.74 (m, 2H), 3.23 (d, J=6.32 Hz, 2H), 3.89 (d, J=6.06 Hz, 2H), 3.93 (s, 2H), 7.17-7.27 (m, 2H), 7.27-7.39 (m, 4H), 7.39-7.50 (m, 2H), 12.51 (bs, 1H).

Example 1.66: Preparation of 2-(((1r,4r)-4-(((4-Fluorophenyl)(5-methylthiophen-2-yl)carbamoyloxy)methyl)cyclohexyl)methoxy)acetic Acid (Compound 77)

From tert-butyl 2-(((1r,4r)-4-((4-fluorophenylcarbamoyloxy)methyl)cyclohexyl)methoxy)acetate and 2-iodo-5-methylthiophene, using a similar method to the one described in Example 1.21, the title compound was obtained as a white solid. LCMS m/z=436.4 $[M+H]^+$.

Example 1.67: Preparation of 2-(((1r,4r)-4-(((3-Clorophenyl)(4-fluorophenyl)carbamoyloxy)methyl)cyclohexyl)methoxy)acetic Acid (Compound 78)

From tert-butyl 2-(((1r,4r)-4-((4-fluorophenylcarbamoyloxy)methyl)cyclohexyl)methoxy)acetate and 1-chloro-3-iodobenzene, using a similar method to the one described in Example 1.21, the title compound was obtained as a white solid. LCMS m/z=450.0 $[M+H]^+$.

Example 1.68: Preparation of 2-(((1r,4r)-4-(((4-Fluorophenyl)(pyridine-3-yl)carbamoyloxy)methyl) cyclohexyl)methoxy)acetic Acid (Compound 79)

From tert-butyl 2-(((1r,4r)-4-((4-fluorophenylcarbamoyloxy)methyl)cyclohexyl)methoxy)acetate and and 3-iodopyridine, using a similar method to the one described in Example 1.21, the title compound was obtained as a white solid. LCMS m/z=417.3 $[M+H]^+$; $^1H$ NMR (400 MHz, DMSO-$d_6$) δ ppm: 0.79-0.94 (m, J=10.57, 10.57, 10.57 Hz, 4H), 1.31-1.43 (m, 1H), 1.42-1.52 (m, 1H), 1.52-1.63 (m, 2H), 1.64-1.78 (m, 2H), 3.23 (d, J=6.44 Hz, 2H), 3.92 (d, J=5.94 Hz, 2H), 3.95 (s, 2H), 7.20-7.30 (m, 2H), 7.39-7.46 (m, 2H), 7.49 (dd, J=8.27, 4.86 Hz, 1H), 7.77-7.84 (m, 1H), 8.46 (dd, J=4.86, 1.45 Hz, 1H), 8.62 (d, J=2.15 Hz, 1H).

Example 1.69: Preparation of 2-(((1r,4r)-4-(((4-Ethoxyphenyl)(4-fluorophenyl)carbamoyloxy) methyl)cyclohexyl)methoxy)acetic Acid (Compound 80)

From tert-butyl 2-(((1r,4r)-4-((4-fluorophenylcarbamoyloxy)methyl)cyclohexyl)methoxy)acetate and 1-ethoxy-4-iodobenzene, using a similar method to the one described in Example 1.21, the title compound was obtained as a white solid. LCMS m/z=460.3 $[M+H]^+$; $^1H$ NMR (400 MHz, DMSO-$d_6$) δ ppm 0.79-0.94 (m, 4H), 1.31 (t, J=6.95 Hz, 3H), 1.34-1.50 (m, 2H), 1.51-1.64 (m, 2H), 1.64-1.76 (m, 2H), 3.23 (d, J=6.44 Hz, 2H), 3.86 (d, J=6.19 Hz, 2H), 3.94 (s, 2H), 4.00 (q, J=6.95 Hz, 2H), 6.85-6.95 (m, 2H), 7.11-7.25 (m, 4H), 7.28-7.36 (m, 2H), 12.53 (s, 1H).

Example 1.70: Preparation of 2-(((1r,4r)-4-(((4-Fluorophenyl)(4-(trifluoromethoxy)phenyl)carbamoyloxy)methyl)cyclohexyl)methoxy)acetic Acid (Compound 81)

From tert-butyl 2-(((1r,4r)-4-((4-fluorophenylcarbamoyloxy)methyl)cyclohexyl)methoxy)acetate and 1-iodo-4-(trifluoromethoxy)benzene, using a similar method to the one described in Example 1.21, the title compound was obtained as a white solid. LCMS m/z=500.5 $[M+H]^+$.

Example 1.71: Preparation of 2-(((1r,4r)-4-(((4-Fluorophenyl)(m-tolyl)carbamoyloxy)methyl)cyclohexyl)methoxy)acetic Acid (Compound 82)

From tert-butyl 2-(((1r,4r)-4-((4-fluorophenylcarbamoyloxy)methyl)cyclohexyl)methoxy)acetate and 1-iodo-3-methylbenzene, using a similar method to the one described in Example 1.21, the title compound was obtained as a white solid. LCMS m/z=430.5 $[M+H]^+$.

Example 1.72: Preparation of 2-(((1r,4r)-4-(Bis(4-fluorophenyl)carbamoyloxy)methyl)cyclohexyl) methoxy)acetic Acid (Compound 83)

From tert-butyl 2-(((1r,4r)-4-((4-fluorophenylcarbamoyloxy)methyl)cyclohexyl)methoxy)acetate and 1-fluoro-4-iodobenzene, using a similar method to the one described in Example 1.21, the title compound was obtained as a white solid. LCMS m/z=434.5 $[M+H]^+$.

Example 1.73: Preparation of 2-(((1r,4r)-4-((Phenylcarbamoyloxy)methyl)cyclohexyl)methoxy)acetic Acid (Compound 29)

tert-Butyl 2-(((1r,4r)-4-((phenylcarbamoyloxy)methyl) cyclohexyl)methoxy)acetate (20.0 mg, 0.053 mmol) was dissolved in HCl (4 M in dioxane) (397 μL, 1.590 mmol). The reaction was stirred at room temperature overnight. The solvent was removed and the residue was purified by preparative LCMS to yield the title compound as a white solid (9.2 mg). LCMS m/z=322.4 $[M+H]^+$.

Example 1.74: Preparation of 2-(((1r,4r)-4-(((3-Chloro-5-fluorophenyl)(phenyl)carbamoyloxy) methyl)cyclohexyl)methoxy)acetic Acid (Compound 46)

From 1-bromo-3-chloro-5-fluorobenzene, using a similar method to the one described in Example 1.18, the title compound was obtained as a light brown oil. LCMS m/z=450.2 $[M+H]^+$.

Example 1.75: Preparation of 2-(((1r,4r)-4-((Phenyl (pyridine-2-yl)carbamoyloxy)methyl)cyclohexyl) methoxy)acetic Acid (Compound 63)

From N-phenylpyridin-2-amine, using a similar method to the one described in Example 1.18 (Steps B and C), the title compound was obtained as a colorless oil. LCMS m/z=399.2 $[M+H]^+$; $^1H$ NMR (400 MHz, DMSO-$d_6$) δ ppm 0.77-0.93 (m, 4H), 1.32-1.41 (m, 1H), 1.41-1.49 (m, J=3.28 Hz, 1H). 1.50-1.63 (m, J=7.20 Hz, 2H), 1.62-1.77 (m, J=7.33 Hz, 2H), 3.22 (d, J=6.32 Hz, 2H), 3.92 (d, J=6.06 Hz, 2H), 3.94 (s, 2H), 7.19-7.29 (m, 4H), 7.33-7.41 (m, 2H), 7.60 (d, J=8.21 Hz, 1H) 7.83-7.91 (m, 1H), 8.31-8.38 (m, 1H).

Example 1.76: Preparation of 2-(((1r,4r)-4-(((5-Methylthiazol-2-yl)(phenyl)carbamoyloxy)methyl) cyclohexyl)methoxy)acetic Acid (Compound 97)

Step A: Preparation of 2-Iodo-5-methylthiazole

5-Methylthiazole (179 μL, 2.017 mmol) was dissolved in THF (5 mL). The solution was cooled in a dry ice/acetone bath (−70° C.) and LDA (1.8 M in heptane/THF/ethylbenzene, 1233 μL, 2.219 mmol) was added slowly via syringe. The reaction was stirred at −70° C. for 30 min. Iodine (614 mg, 2.420 mmol) pre-dissolved in THF (2 mL) was added slowly via syringe. The reaction was warmed to room temperature, stirred for 1 h, and quenched with $H_2O$ (5 mL). The mixture was extracted with $H_2O$ (20 mL) and EtOAc (20 mL). The aqueous layer was extracted again with EtOAc (20 mL). The combined organic layers were dried, concentrated, and the residue was purified by silica gel column chromatography to provide the title compound as a light brown oil (61 mg). LCMS m/z=226.1 $[M+H]^+$.

Step B: Preparation of 2-(((1r,4r)-4-(((5-Methylthiazol-2-yl)(phenyl)carbamoyloxy)methyl)cyclohexyl) methoxy)acetic Acid From 2-iodo-5-methylthiazole and tert-butyl 2-(((1r,4r)-4-((phenylcarbamoyloxy)methyl)cyclohexyl)methoxy)acetate, using a similar method to the one described in Example 1.21, the title compound was obtained as a light brown oil. LCMS m/z=419.5 $[M+H]^+$.

Example 1.77: Preparation of Sodium 2-(((1r,4r)-4-(((3-Fluorphenyl)(phenyl)carbamoyloxy)methyl) cyclohexyl)methoxy)acetate From 3-fluoro-N-phenylaniline, using a similar method to the one described in Example 1.19, the sodium salt of the title compound was obtained as a white solid. LCMS m/z=416.5 $[M+H]^+$; $^1H$ NMR (400 MHz, DMSO-$_6$) δ ppm 0.71-0.93 (m, 4H), 1.34 (bs, 1H), 1.44 (bs, 1H), 1.54-1.57 (m, 2H), 1.65-1.69 (m, 2H), 3.15 (d, J=6.57 Hz, 2H), 3.44 (s, 2H), 3.90 (d, J=5.94 Hz, 2H) 7.02-7.11 (m, 2H), 7.22 (dt, J=10.67, 2.24 Hz, 1H), 7.25-7.33 (m, 3H), 7.34-7.44 (m, 3H).

Example 1.78: Preparation of 2-(((1r,4r)-4-((3,3-Diphenylureido)methyl)cyclohexyl)methoxy)acetic Acid (Compound 2)

Step A: Preparation of tert-Butyl 2-(((1r,4r)-4-((tert-Butoxycarbonylamino)methyl)cyclohexyl)methoxy) acetate A cooled solution of tert-butyl ((1r,4r)-4-(hydroxymethyl) cyclohexyl)methylcarbamate (2.0 g, 8.22 mmol) in THF (30 mL) was treated with NaH (60% dispersion in mineral oil, 1.315 g, 32.9 mmol). The resulting suspension was stirred at room temperature for 1 h then tert-butyl 2-bromoacetate (1.822 mL, 12.33 mmol) was added. The reaction was heated in the microwave to 60° C. for 1 h and then left stirring overnight at room temperature. Additional tert-butyl 2-bromoacetate (975 μL) was added and the reaction was heated to 60° C. and stirred for 2 h. The reaction was quenched with water and extracted with DCM. The combined DCM extract was washed with water; dried over $MgSO_4$ and concentrated. The resulting residue was purified by preparative LCMS to provide the title compound as a white solid (0.250 g). LCMS m/z=380.4 $[M+Na]^+$; $^1H$ NMR (400 MHz, DMSO-$d_6$) δ ppm 0.78-0.96 (m, 4H), 1.29 (bs, 1H), 1.39 (s, 9H), 1.44 (s, 9H), 1.66-1.79 (m, 4H), 2.78 (t, J=6.32 Hz, 2H), 3.26 (d, J=6.32 Hz, 2H), 3.94 (s, 2H), 6.80 (t, J=5.68 Hz, 1H).

Step B: Preparation of 2-(((1r,4r)-4-(Aminomethyl) cyclohexyl)methoxy)acetic Acid tert-Butyl 2-(((1r,4r)-4-((tert-butoxycarbonylamino) methyl)cyclohexyl)methoxy)acetate (61 mg, 0.171 mmol) was treated with 4.0 M HCl in dioxane (5.00 mL, 165 mmol) at room temperature for 1 h, followed by heating at 60° C. for 45 min. The solvent was evaporated and the resulting residue was washed 3× with DCM and concentrated to yield the title compound as an off white solid (40 mg) without further purification. LCMS m/z=202.4 $[M+H]^+$.

Step C: Preparation of 2-(1r,4r)-4-((3,3-Diphenylureido)methyl)cyclohexyl)methoxy)acetic (Compound 2)

A solution of 2-(((1r,4r)-4-(aminomethyl)cyclohexyl) methoxy)acetic acid (39.1 mg, 0.194 mmol) in THF (2 mL) was treated with potassium tert-butoxide (0.583 mL, 0.583 mmol). Diphenylcarbamic chloride (45 mg, 0.194 mmol) was added and the resulting solution was stirred at room temperature for 45 min. The reaction was quenched with water. The water layer was concentrated under reduced pressure. The residue was purified by preparative LCMS. The appropriate fractions were collected. After removal of the solvent, the residue was dissolved in MeOH (2.0 mL) and to this mixture was added 0.5 M sodium methoxide in MeOH (0.388 mL, 0.194 mmol). The solution was stirred at room temperature for 1 h. After removal of the solvent, the residue was dissolved in minimal amount of 1:1 $H_2O$/The solution, frozen and lyophilized to provide the title compound (32 mg). LCMS m/z=397.3 $[M+H]^+$; $^1H$ NMR (400 MHz, DMSO-$d_6$) δ ppm 0.69-0.87 (m, 4H), 1.25-1.43 (m, 2H), 1.53-1.70 (m, 4H), 2.83 (t, J=6.19 Hz, 2H), 3.18 (d, J=6.32 Hz, 2H), 3.89 (s, 2H), 5.88 (t, J=5.68 Hz, 1H), 7.05-7.14 (m, 6H), 7.28 (t, J=7.83 Hz, 4H).

Example 1.79: Preparation of 2-(((1r,4r)-4-((3-Benzhydrylureido)methyl)cyclohexyl)methoxy)acetic Acid (Compound 1)

A solution of 2-(((1r,4r)-4-(aminomethyl)cyclohexyl) methoxy)acetic acid (20.0 mg, 0.099 mmol) in DMF was treated with TEA (0.021 mL, 0.149 mmol) followed by (isocyanatomethylene)dibenzene (0.019 mL, 0.099 mmol); the resulting solution was stirred at room temperature for 1.0 h. The reaction was stopped and the reaction mixture was purified by preparative LCMS to provide the title compound as a white solid (9.0 mg). LCMS m/z=411.4 $[M+H]^+$; $^1H$ NMR (400 MHz, DMSO-$d_6$) δ ppm 0.80-0.97 (m, 4H), 1.27 (bs, 1H), 1.47 (bs, 1H), 1.66-1.79 (m, 4H), 2.89 (t, J=6.06 Hz, 2H), 3.27 (d, J=6.32 Hz, 2H), 3.98 (s, 2H), 5.89 (d, J=8.34 Hz, 1H), 5.96 (t, J=5.68 Hz, 1H), 6.80 (d, J=8.59 Hz, 1H), 7.21-7.29 (m, 6H), 7.31-7.37 (m, 4H), 12.57 (bs, 1H).

Example 1.80: Preparation of 2-(((1r,4r)-4-((3-(3-Methoxyphenyl)-3-phenylureido)methyl)cyclohexyl) methoxy)acetic acid (Compound 17)

Step A: Preparation of 3-Methoxyphenyl(phenyl)carbamic Chloride

To a cooled solution of 3-methoxy-N-phenylaniline (100.0 mg, 0.502 mmol) and pyridine (0.102 mL, 1.267 mmol) in DCM (500 mL) was added triphosgene (120.0 mg, 0.406 mmol). The solution was allowed to warm up to room temperature and stirred overnight. The organic solvent was evaporated. The residue was dissolved in ethyl acetate, washed with water, brine, dried over $MgSO_2$ and concentrated to provide the title compound (105.0 mg). LCMS m/z=261.9 $[M+H]^+$; $^1H$ NMR (400 MHz, DMSO-$d_6$) δ ppm 3.79 (s, 3H), 6.90-7.31 (m, 3H), 7.32-7.52 (m, 4H), 7.52-7.70 (m, 2H).

Step B: Preparation of tert-Butyl 2-(((1r,4r)-4-((tert-Butoxy carbonylamino)methyl)cyclohexyl)methoxy) acetate To a solution of tert-butyl ((1r,4r)-4-(hydroxymethyl) cyclohexyl)methylcarbamate (1.0 g, 4.11 mmol) and rhodium(II) acetate (0.091 g, 0.205 mmol) in dichloromethane (10 mL) was added dropwise a solution of tert-butyl 2-diazoacetate (0.584 g, 4.11 mmol) in dichloromethane (10 mL). The resulting solution was stirred at room temperature overnight. The reaction was quenched with water; the organic layer was subsequently washed with water (twice) and brine; dried over MgSO4 and concentrated. The residue was purified by preparative LCMS to provide the title compound as a white solid (571 mg). LCMS m/z=380.4 $[M+Na]^+$; $^1H$ NMR (400 MHz, DMSO-$d_6$) δ ppm 0.78-0.97 (m, 4H), 1.29 (bs, 1H), 1.39 s, 9H), 1.44 (s, 9H), 1.66-1.79 (m, 4H), 2.78 (t, J=6.32 Hz, 2H), 3.26 (d, J=6.32 Hz, 2H), 3.94 (s, 2H), 6.80 (t, J=5.68 Hz, 1H).

Step C: Preparation of tert-Butyl 2-(((1r,4r)-4-(aminomethyl)cyclohexyl)methoxy)acetate tert-Butyl 2-(((1r,4r)-4-((tert-butoxycarbonylamino) methyl)cyclohexyl)methoxy)acetate (61.0 mg; 0.17 mmol)

was treated with HCl (4.0 M in dioxane, 3.0 mL) and stirred at room temperature for 1 h. The mixture was concentrated to provide the title compound without further purification. LCMS m/z=258.4 $[M+H]^{30}$ .

Step D: Preparation of 2-(((1r,4r)-4-((3-(3-Methoxyphenyl)-3-phenylureido)methyl)cyclohexyl) methoxy)acetic Acid (Compound 17)

To tert-butyl 2-(((1r,4r)-4-(aminomethyl)cyclohexyl) methoxy)acetate (25.3 mg, 0.098 mmol) in a 5 mL microwave reaction vial were added DCM (1.0 mL) and TEA (0.036 mL, 0.262 mmol). The solution was stirred briefly then 3-methoxyphenyl(phenyl)carbamic chloride (17.0 mg, 0.065 mmol) was added in three portions. The resulting solution was heated under microwave irradiation at 80° C. 2 h. The reaction mixture was concentrated and the residue was treated with HCl (4.0 M in dioxane, 3 mL) at 60° C. for 1 h. The mixture was concentrated and the residue was purified by preparative LCMS to provide the title compound as a white solid (8.0 mg). LCMS m/z=427.4 $[M+H]^+$; $^1H$ NMR (400 MHZ, DMSO-$d_6$) δ ppm 0.68-0.88 (m, 4H), 1.25-1.43 (m, 2H), 1.54-1.70 (m, 4H), 2.83 (t, J=6.19 Hz, 2H), 3.17 (d, J=6.57 Hz, 2H), 3.65 (s, 3H), 3.89 (s, 2H), 5.96 (t, J=5.81 Hz, H4), 6.63 (dd, J=7.83, 1.52 Hz, 1H), 6.68 (t, J=2.15 Hz, 1H), 6.72 (dd, J=8.21, 2.40 Hz, 1H), 7.06-7.13 (m, 3H), 7.19 (t, J=8.08 Hz, 1H), 7.27 (t, J=7.71 Hz, 2H), 12.50 (bs, 1H).

Example: 1.81: Preparation of 2-(((1r,4r)-4-((3,3-dip-Tolylureido)methyl)cyclohexyl)methoxy)acetic Acid (Compound 15)

From dip-tolyl carbamic chloride and tert-butyl 2-(((1r, 4r)-4-(aminomethyl)cyclohexyl)methoxy)acetate, using a similar method to the one described in Example 1.80, Step D, the title compound was obtained as a white solid. LCMS m/z=425.3 $[M+H]^+$; $^1H$ NMR (400 MHz, DMSO-$d_6$) δ ppm 0.66-0.88 (m, 4H), 1.23-1.43 (m, 2H), 1.52-1.72 (m, 4H), 2.20 (s, 6H), 2.81 (t, J=6.32 Hz, 2H), 3.17 (d, J=6.32 Hz, 2H), 3.89 (s, 2H), 5.76 (t, J=5.81 Hz, 1H), 6.96 (d, J=8.34 Hz, 4H), 7.07 (d, J=8.08 Hz, 4H) 12.50 (bs, 1H).

Example 1.82: Preparation of 2-(((1r,4r)-4-((3,3-di-m-Tolylureido)methyl)cyclohexyl)methoxy)acetic Acid (Compound 16)

From di-m-tolyl carbamic chloride and tert-butyl 2-(((1r, 4r)-4-(aminomethyl)cyclohexyl)methoxy)acetate, using a similar method to the one described in Example 1.80, Step D, the title compound was obtained as a white solid. LCMS m/z=425.3 $[M+H]^+$.

Example 1.83: Preparation of 2-(((1r,4r)-4-((3-(4-Methoxyphenyl)-3-phenylureido)methyl)cyclohexyl) methoxy)acetic Acid (Compound 18)

From 4-methoxyphenyl(phenyl)carbamic chloride and tert-butyl 2-(((1r,4r)-4-(aminomethyl)cyclohexyl)methoxy) acetate, using a similar method to the one described in Example 1.80, Step D, the title compound was obtained as a white solid. LCMS m/z=427.4 $[M+H]^+$. $^1H$ NMR (400 MHz, DMSO-$d_6$) δ ppm 0.66-0.87 (m, 4H), 1.23-1.43 (m, 2H), 1.51-1.70 (m, 4H), 2.81 (t, J=6.19 Hz, 2H), 3.17 (d, J=6.32 Hz, 2H), 3.68 (s, 3H, 3.89 (s, 2H), 5.77 (t, J=5.68 Hz, 1H), 6.88 (d, J=8.84 Hz, 2H), 7.00-7.10 (m, 5H), 7.22 (t, J=7.83 Hz, 2H), 12.50 (bs, 1H).

Example 1.84: Preparation of 2-(((1r,4r)-4-((3-(4-Methoxy-2-methylphenyl)-3-phenylureido)methyl) cyclohexyl)methoxy)acetic Acid (Compound 19)

From 4-methoxy-2-methylphenyl(phenyl)carbamic chloride and tert-butyl 2-(((1r,4r)-4-(aminomethyl)cyclohexyl) methoxy)acetate, using a similar method to the one described in Example 1.80, Step D, the title compound was obtained as a white solid. LCMS m/z=441.3 $[M+H]^+$.

Example 1.85: Preparation of 2-(((1r,4r)-4((3-Phenyl-3-(3-(trifluoromethyl)phenyl)ureido)methyl) cyclohexyl)methoxy)acetic Acid (Compound 20)

From phenyl(3-(trifluoromethyl)phenyl)carbamic chloride and tert-butyl 2-(((1r,4r)-4-(aminomethyl)cyclohexyl) methoxy)acetate, using a similar method to the one described in Example 1.80, Step D, the title compound was obtained as a white solid. LCMS m/z=465.3 $[M+H]^+$. $^1H$ NMR (400 MHz, DMSO-$d_6$) δ ppm 0.68-0.87 (m, 4H), 1.26-1.43 (m, 2H), 1.54-1.71 (m, 4H), 2.84 (t, J=6.19 Hz, 2H), 3.18 (d, J=6.32 Hz, 2H), 3.89 (s, 2H), 6.23 (t, J=5.68 Hz, 1H), 7.16 (d, J=7.58 Hz, 2H), 7.21-7.27 (m, 2H), 7.33-7.49 (m, 5H), 12.50 (bs, 1H).

Example 1.86: Preparation of 2-(((1r,4r)-4-((3-(3-Fluorophenyl)-3-phenylureido)methyl)cyclohexyl) methoxy)acetic Acid (Compound 3)

Step A: Preparation of 3-Fluoro-N-phenylaniline

In a round bottom flask equipped with a condenser was placed N-phenylacetamide (1.0 g, 7.40 mmol), copper (I) chloride (0.146 g, 1.480 mmol), potassium carbonate (1.329 g, 9.62 mmol), 1-bromo-3-fluorobenzene (1.942 g, 11.10 mmol) and xylene (5 mL). The suspension was heated to 180° C. and refluxed for 66 h. The suspension was filtered; and the filtrate was concentrated. The dark brown residue was dissolved in ether; filtered; and the filtrate was concentrated. The dark brown residue was dissolved in ethanol (10.00 mL), treated with potassium hydroxide (1.909 g, 34.0 mmol) and refluxed for 2 h. The solution was poured into of water (80 mL) and extracted with DCM. The combined DCM extract was washed with water (6×), dried over $MgSO_4$ and concentrated to afford the title compound as a dark brown solid (0.669 g). LCMS m/z=188.2 $[M+H]^+$.

Step B: Preparation of 3-Fluorophenyl(phenyl)carbamic Chloride

From 3-fluoro-N-phenylaniline, using a similar method to the one described in Example 1.80, Step A, the title compound was obtained as a brown oil. LCMS m/z=250.2 $[M+H]^+$.

Step C: Preparation of 2-(((1r,4r)-4-((3-(3-Fluorophenyl)-3-phenylureido)methyl)cyclohexyl) methoxy)acetic Acid (Compound 3)

From 3-fluorophenyl(phenyl)carbamic chloride and tert-butyl 2-(((1r,4r)-4-(aminomethyl)cyclohexyl)methoxy)acetate, using a similar method to the one described in Example 1.80, Step D, the title compound was obtained as a white solid. LCMS m/z=415.5 $[M+H]^+$; $^1H$ NMR (400

MHz, DMSO-$d_6$) δ ppm 0.78-0.97 (m, 4H), 0.89-0.96 (m, 2H), 1.34-1.54 (m, 2H), 1.64-1.80 (m, 4H), 2.93 (t, J=6.25 Hz, 2H), 3.27 (d, J=6.44 Hz, 2H), 3.98 (s, 2H), 6.12 (t, J=5.81 Hz, 1H), 6.91 (ddd, J=8.08, 1.96, 0.82 Hz, 1H), 6.96-7.05 (m, 2H), 7.22 (dd, J=8.46, 1.14 Hz, 2H), 7.26-7.39 (m, 2H), 7.43 (t, J=7.83 Hz, 2H), 12.55 (bs, 1H).

Example 1.87: Preparation of 2-(((1r,4r)-4-((3-(3-Chlorophenyl)-3-phenylureido)methyl)cyclohexyl) methoxy)acetic Acid (Compound 6)

To a solution of 2-(((1r,4r)-4-(aminomethyl)cyclohexyl) methoxy)acetic acid (24.96 mg, 0.124 mmol) in THF (1.5 mL) was added potassium tert-butoxide (50.6 mg, 0.451 mmol). The solution was stirred briefly then 3-chlorophenyl (phenyl)carbamic chloride (30 mg, 0.113 mmol) was added. The resulting solution was stirred at room temperature for 1 h. The reaction was quenched with water. The aqueous layer was concentrated under vacuum. The residue was purified by preparative LCMS to provide the title compound as a white solid (5.0 mg). LCMS m/z=431.3 $[M+H]^+$.

Example 1.88: Preparation of 2-(((1r,4r)-4-((3-(4-Fluorophenyl)-3-phenylureido)methyl)cyclohexyl) methoxy)acetic acid (Compound 8)

From 4-fluorophenyl(phenyl)carbamic chloride and 2-(((1r,4r)-4-(aminomethyl)cyclohexyl)methoxy)acetic acid, using a similar method to the one described in Example 1.87, the title compound was obtained as a white solid. LCMS m/z=415.5 $[M+H]^+$; $^1$H NMR (400 MHz, DMSO-$d_6$) δ ppm 0.66-0.88 (m, 4H), 1.24-1.43 (m, 2H), 1.54-1.71 (m, 4H), 2.83 (t, J=6.25 Hz, 2H), 3.18 (d, J=6.44 Hz, 2H), 3.88 (s, 2H), 5.88 (t, J=5.75 Hz, 1H), 7.06-7.17 (m, 7H), 7.28 (t, J=7.77 Hz, 2H), 12.41 (bs, 1H).

Example 1.89: Preparation of 2-(((1r,4r)-4-((3-(2-Fluorophenyl)-3-phenylureido)methyl)cyclohexyl) methoxy)acetic Acid (Compound 10)

From 2-fluorophenyl(phenyl)carbamic chloride and 2-(((1r,4r)-4-(aminomethyl)cyclohexyl)methoxy)acetic acid, using a similar method to the one described in Example 1.87, the title compound was obtained as a white solid. LCMS m/z=415.5 $[M+H]^+$.

Example 1.90: Preparation of 2-(((1r,4r)-4-((3-(4-Chlorophenyl)-3-phenylureido)methyl)cyclohexyl) methoxy)acetic Acid (Compound 11)

From 4-chlorophenyl(phenyl)carbamic chloride and 2-(((1r,4r)-4-(aminomethyl)cyclohexyl)methoxy)acetic acid, using a similar method to the one described in Example 1.87, the tile compound was obtained as a white solid. LCMS m/z=431.2 $[M+H]^+$; $^1$H NMR (400 MHz, DMSO-$d_6$) δ ppm 0.77-1.01 (m, 4H), 1.34-1.55 (m, 2H), 1.63-1.85 (m, 4H), 2.92 (t, J=5.87 Hz, 2H), 3.28 (d, J=6.44 Hz, 2H),3.98 (s, 2H), 5.88 (t, J=5.75 Hz, 1H), 7.13-7.29 (m, 5H), 7.36-7.45 (m, 4H).

Example 1.91: Preparation of 2-(((1r,4r)-4-((3-Phenyl-3-m-tolylureido)methyl)cyclohexyl)methoxy) acetic Acid (Compound 12)

From phenyl(m-tolyl)carbamic chloride and 2-(((1r,4r)-4-(aminomethyl)cyclohexyl)methoxy)acetic acid, using a similar method to the one described in Example 1.87, the title compound was obtained as a white solid. LCMS m/z=411.5 $[M+H]^+$; $^1$H NMR (400 MHz, DMSO-$d_6$) δ ppm 0.77-0.98 (m, 4H), 1.34-1.54 (m, 2H), 1.63-1.81 (m, 4H), 2.29 (s 3H), 2.93 (t, J=6.32 Hz, 2H), 3.28 (d, J=6.44 Hz, 2H), 3.98 (s, 2H), 5.89 (t, J=5.81 Hz, 1H), 6.98 (d, J=7.96 Hz, 1H), 7.05 (d, J=8.21 Hz, 2H), 7.13-7.22 (m, 3H), 7.27 (t, J=7.71 Hz, 1H), 7.33-7.39 (m, 2H), 12.51 (bs, 1H).

Example 1.92: Preparation of 2-(((1r,4r)-4-((3-Phenyl-3-p-tolylureido)methyl)cyclohexyl)methoxy) acetic Acid (Compound 13)

From phenyl(p-tolyl)carbamic chloride and 2-(((1r,4r)-4-(aminomethyl)cyclohexyl)methoxy)acetic acid, using a similar method to the one described in Example 1.87, the title compound was obtained as a white sold. LCMS m/z=411.5 $[M+H]^+$.

Example 1.93: Preparation of 2-(((1r,4r)-4-((3-(3,5-Difluorophenyl)-3-phenylureido)methyl)cyclohexyl) methoxy)acetic Acid (Compound 44)

Step A: Preparation of 3,5-Difluoro-N-phenylaniline

In a 5 mL microwave reaction vial was placed aniline (0.298 g, 3.20 mmol) and 1,3-difluoro-5-iodobenzene (0.768 g, 3.20 mmol) in toluene (3 mL). KOH (0.323 g, 5.76 mmol) in water (650 μL) and N,N,N-trimethylhexadecan-1-aminium bromide (6.30 mg, 0.017 mmol) were added to the vial with stirring. After the reaction was warmed to 90° C., bis[tri(t-butylphosphine]palladium[0] (0.016 g, 0.032 mmol) was added and the reaction was stirred at 150° C. for 4 h and then 160° C. for 2 h. The mixture was diluted with water and brine, and extracted with toluene. The toluene extract was subsequently washed with water, dried over $MgSO_4$ and concentrated. The residue was purified by flash column chromatography to provide the title compound as a brown oil (0.132 g). LCMS m/z=206.2 $[M+H]^+$; $^1$H NMR (400 MHz, DMSO-$d_6$) δ ppm 6.54 (tt, J=9.35, 2.27 Hz, 1H), 6.63 (dd, J=10.48, 2.15 Hz, 2H), 7.01 (dt, J=14.65, 1.14 Hz, 1H), 7.17 (dd, J=8.59, 1.01 Hz, 2H), 7.34 (t, J=7.83 Hz, 2H), 8.69 (s, 1H).

Step B: Preparation of 3,5-Difluorophenyl(phenyl)carbamic Chloride

From 3,5-difluoro-N-phenylaniline, using a similar method to the one described in Example 1.80, Step A, the title component was obtained as a brown oil. LCMS m/z=268.7 $[M+H]^+$.

Step C: Preparation of 2-(((1r,4r)-4-((3-(3,5-Difluorophenyl)-3-phenylureido)methyl)cyclohexyl) methoxy)acetic acid (Compound 44)

From 3,5-difluorophenyl(phenyl)carbamic chloride and tert-butyl 2-(((1r,4r)-4-(aminomethyl)cyclohexyl)methoxy) acetate, using a similar method to the one described in Example 1.80, Step D, the title compound was obtained as a white solid. LCMS m/z=433.4 $[M+H]^+$; $^1$H NMR (400 MHz, DMSO-$d_6$) δ ppm 0.77-0.97 (m, 4H), 1.35-1.53 (m, 2H), 1.62-1.79 (m, 4H), 2.92 (t, J=6.19 Hz, 2H), 3.27 (d, J=6.32 Hz, 2H), 3.98 (s, 2H), 6.32 (t, J=5.56 Hz, 1H), 6.76-6.84 (m, 2H), 6.96-7.04 (m, 1H), 7.26 (d, J=7.33 Hz, 2H), 7.33-7.40 (m, 1H), 7.48 (t, J=7.71 Hz, 2H).

Example 1.94: Preparation of 2-(((1r,4r)-4-((3-(2,3-Difluorophenyl)-3-phenylureido)methyl)cyclohexyl)methoxy)acetic acid (Compound 43)

From 2,3-difluorophenyl(phenyl)carbamic chloride and tert-butyl 2-(((1r,4r)-4-(aminomethyl)cyclohexyl)methoxy)acetate, using a similar method to the one described in Example 1.80, Step D, the title compound was obtained as a white solid. LCMS m/z=433.4 $[M+H]^+$.

Example 1.95: Preparation of 2-(((1r,4r)-4-((3-(3-Chloro-2-fluorophenyl-3-phenylureido)methyl)cyclohexyl)methoxy)acetic Acid (Compound 45)

From 3-chloro-2-fluorophenyl(phenyl)carbamic chloride and tert-butyl 2-(((1r,4r)-4-(aminomethyl)cyclohexyl)methoxy)acetate, using a similar method to the one described in Example 1.80, Step D, the title compound was obtained as a white solid. LCMS m/z=449.2 $[M+H]^+$; $^1H$ NMR (400 MHz, DMSO-$d_6$) δ ppm: 0.78-0.97 (m, 4H), 1.34-1.53 (m, 2H), 1.64-1.80 (m, 4H), 2.92 (t, J=5.94 Hz, 2H), 3.27 (d, J=6.32 Hz, 2H), 3.98 (s, 2H), 6.51 (t, J=5.56 Hz, 1H), 7.16-7.30 (m, 5H), 7.38 (t, J=7.20 Hz, 2H), 7.50-7.56 (m, 1H).

Example 1.96: Preparation of 2-(((1r,4r)-4-((3-(3-Chloro-5-fluorophenyl)-3-phenylureido)methyl)cyclohexyl)methoxy)acetic Acid (Compound 47)

From 3-chloro-5-fluorophenyl(phenyl)carbamic chloride and tert-butyl 2-(1r,4r)-4-(aminomethyl)cyclohexyl)methoxy)acetate, using a similar method to the one described in Example 1.80, Step D, the title compound was obtained as a white solid. LCMS m/z 449.2 $[M+H]^+$.

Example 1.97: Preparation of 2-(((1r,4r)-4-((3-(2-Fluoro-3-methoxyphenyl)-3-phenylureido)methyl)cyclohexyl)methoxy)acetic Acid (Compound 53)

Step A: Preparation of 2-Fluoro-3-methoxy-N-phenylaniline

In a reaction vial were placed aniline (0.200 g, 2.182mmol); 2-fluoro-1-iodo-3-methoxybenzene (0.500 g, 1.984 mmol), $Pd_2$(dba), (0.091 g, 0.099 mmol), BINAP (0.185 g, 0.298 mmol), NaOtBu (0.286 g, 2.98 mmol), and toluene (3 ml). The reaction was stirred at 80° C. overnight and quenched with water. The organic layer was separated and concentrated. The residue was purified by flash column chromatography to provide the title compound as a brown oil (0.313 g). LCMS m/z=218.4 $[M+H]^+$; $^1H$ NMR (400 MHz, DMSO-$d_6$) δ ppm 3.82 (s, 3H), 6.73 (ddd, J=10.93, 8.15, 1.64 Hz, 1H), 6.88-7.05 (m, 3H), 7.15 (d, J=7.33 Hz, 2H), 7.25-7.31 (m, 2H), 7.80 (s, 1H).

Step B: Preparation of 2-Fluoro-3-methoxyphenyl(phenyl)carbamic Chloride

From 2-fluoro-3-methoxy-N-phenylaniline, using a similar method to the one described in Example 1.80, Step A, the title compound was obtained as a brown oil. LCMS m/z=280.5 $[M+H]^+$; $^1H$ NMR (400 MHz, DMSO-$d_6$) δ ppm 3.98 (s, 3H), 7.12-7.24 (m, 1H), 7.33-7.53 (m, 6H, 7.59 (d, J=7.33 Hz, 1H).

C: Preparation of Ethyl 2-(((1r,4r)-4-((tert-Butoxycarbonylamino)methyl)cyclohexyl)methoxy)acetate To a solution of tert-butyl ((1r,4r)-4-(hydroxymethyl)cyclohexyl)methylcarbamate (500 mg, 2.055 mmol) and rhodium(II) acetate (45.4 mg, 0.103 mmol) in DCM (5.0 mL) was added dropwise a solution of ethyl 2-diazoacetate (0.213 mL, 2.055 mmol) in DCM (10 mL). The resulting solution was stirred at room temperature overnight. The reaction was quenched with water; the organic layer was washed with water (twice) and brine, dried over $MgSO_4$ and concentrated. The residue was purified by preparative LCMS to provide the title compound as a white solid, (244 mg). LCMS m/z=330.2 $[M+H]^+$; $^1H$ NMR (400 MHz, DMSO-$d_6$) δ ppm 0.78-0.97 (m, 4H), 1.22 (t, J=7.07 Hz, 3H), 1.29 (bs, 1H), 1.39 (s, 9H), 1.48 (bs, 1H), 1.66-1.79 (m, 4H), 2.78 (t, J=6.32 Hz, 2H), 3.28 (d, J=6.57 Hz, 2H), 4.07(s, 2H), 4.13 (q, J=7.07 Hz, 2H), 6.81 (t, J=5.81 Hz, 1H).

Step D: Preparation of Ethyl 2-(((1r,4r)-4-(Aminomethyl)cyclohexyl)methoxy)acetate In a round-bottomed false ethyl 2-(((1r,4r)-4-((tert-butoxycarbonylamino)methyl)cyclohexyl)methoxy)acetate (2.44 mg, 0.741 mmol) was treated with HCl (4.0 M in dioxane, 4.0 mL) and the mixture was stirred for 30 min at room temperature. The mixture was concentrated under reduced pressure and the residue was dried in a vacuum oven overnight to afford the title compound (110 mg) without further purification. LCMS m/z=230.4 $[M+H]^+$.

Step E: Preparation of 2-(((1r,4r)-4-((3-(2-Fluoro-3-methoxyphenyl)-3-phenylureido)methyl)cyclohexyl)methoxy)acetic Acid (Compound 53)

To tert-butyl 2-(((1r,4r)-4-(aminomethyl)cyclohexyl)methoxy)acetate (36.9 mg, 0.161 mmol) in a 5 mL microwave reaction vial were added DCM (1.0 mL) and TEA (0.045 mL, 0.322 mmol). The solution was stirred briefly and 2-fluoro-3-methoxyphenyl(phenyl)carbamic chloride (30.0 mg, 0.107 mmol) was added. The reaction mixture was heated under microwave irradiation at 80° C. and stirred for 2 h. After removal of the solvent the residue was treated with 1.0 M LiOH (2.145 mL, 2.145 mmol) and the solution was stirred overnight at room temperature. The reaction mixture was acidified to pH 4 by dropwise addition of 1 M HCl and extracted with ethyl acetate. After evaporation of the ethyl acetate, the residue was purified by preparative LCMS to provide the title compound as a white solid (22.8 mg). LCMS m/z=445.3 $[M+H]^+$; $^1H$ NMR (400 MHz, DMSO-$_6$) δ ppm 0.79-1.02 (m, 4H), 1.35-1.54 (m, 2H), 1.66-1.81 (m, 4H), 2.93 (t, J=6.00 Hz, 2H), 3.28 (d, J=6.32 Hz, 2H), 3.75 (s, 3H), 3.98 (s, 2H), 6.18 (t, J=5.75 Hz, 1H), 7.02-7.07 (m, 1H) 7.08-7.18 (m, 4H), 7.21-7.27 (m, 1H), 7.33 (t, J=7.83 Hz, 2H).

Example 1.98: Preparation of 2-(((1r,4r)-4-((3-(4-Chloro-3-fluorophenyl)-3-phenylureido)methyl)cyclohexyl)methoxy)acetic Acid (Compound 52)

From ethyl 2-(((1r,4r)-4-(aminomethyl)cyclohexyl)methoxy)acetate and 4-chloro-3-fluorophenyl)phenyl)carbamic chloride, using a similar method to the one described in Example 1.97, Step F, the title compound was obtained as a white solid. LCMS m/z=449.2 $[M+H]^+$; $^1H$ NMR (400 MHz, DMSO-$d_6$) δ ppm 0.76-0.99 (m, 4H), 1.35-1.54 (m, 2H), 1.66-1.81 (m, 4H), 2.93 (t, J=6.25 Hz, 2H), 3.27 (d, J=6.32 Hz, 2H), 3.98 (s, 2H), 6.24 (t, J=5.68 Hz, 1H), 6.91 (dd, J=9.98, 1.26 Hz, 1H), 7.21-7.35 (m, 4H), 7.40-7.56 (m, 3H).

Example 1.99: Preparation of 2-((1r,4r)-4-((3-(3,4-Difluorophenyl)-3-phenylureido)methyl)cyclohexyl) methoxy)acetic Acid (Compound 54)

From ethyl 2-(((1r,4r)-4-(aminomethyl)cyclohexyl) methoxy)acetate and 3,4-difluorophenyl(phenyl)carbamic chloride, using a similar method to the one described in Example 1.97, Step E, the title compound was obtained as a white solid. LCMS m/z=433.4 $[M+H]^+$; $^1H$ NMR (400 MHz, DMSO-$d_6$) δ ppm 0.76-0.98 (m, 4H), 1.35-1.53 (m, 2H), 1.64-1.80 (m, 4H), 2.92 (t, J=6.13 Hz, 2H), 3.28 (d, J=6.44 Hz, 2H), 3.98 (s, 2H), 6.12 (t, J=5.68 Hz, 1H), 6.96 (d, J=4.17 Hz, 1H), 7.20-7.37 (m, 4H), 7.38-7.45 (m, 3H).

Example 1.100: Preparation of 2-((1r,4r)-4-((Benzhydryl(methyl)carbamoyloxy)methyl)cyclohexyl) methoxy)acetic Acid (Compound 86)

To tert-butyl 2-(((1r,4r)-4-(hydroxymethyl)cyclohexyl) methoxy)acetate (15 mg, 0.058 mmol) in DCM (0.5 mL) was added bis(2,5-dioxopyrrolidin-1-yl)carbonate (15.62 mg, 0.061 mmol) followed by TEA (0.016 mL, 0.116 mmol). The suspension was heated until the solution turned clear. The reaction was then stirred for 2 h at room temperature, followed by 2 h at 80° C. N-methyl-1,1-diphenylmethanamine (17.18 mg, 0.087 mmol) and TEA (0.016 mL, 0.116 mmol) were added to the reaction mixture and the resulting solution was heated under microwave irradiation at 60° C. for 2 h. The organic solvent was evaporated and the residue was purified by preparative LCMS to provide an intermediate which was treated with 4.0 M HCl in dioxane for 1 hr at 60° C. The acid solution was evaporated and the residue was purified by preparative LCMS to provide the title compound as an oil (1.0 mg). LCMS m/z=426.3 $[M+H]^+$.

Example 1.101: Preparation 2-(((1r,4r)-4-((3-Benzhydryl-1,3-dimethylureido)methyl)cyclohexyl) methoxy)acetic Acid (Compound 87)

Step A: Preparation of 1-Benzhydryl-3-(((1r,4r)-4-(hydroxymethyl)cyclohexyl)methyl)-1,3-dimethylurea A solution of ((1r,4r)-4-((methylamino)methyl)cyclohexyl)methanol (40.7 mg, 0.259 mmol) in DCM (0.5 mL) was treated with TEA (0.090 mL, 0.647 mmol) and benzhydryl(methyl)carbamide chloride (56 mg, 0.216 mmol). The reaction was heated under microwave irradiation at 80° C. for 2 hr. The reaction mixture was concentrated and the residue was purified by preparative LCMS to provide the title compound as an oil (26 mg). LCMS m/z=381.2 $[M+H]^+$.

Step B: Preparation of 2-(((1r,4r)-4-((3-Benzhydryl-1,3-dimethylureido)methyl)cyclohexyl)methoxy) acetic Acid (Compound 87)

To 1-benzhydryl-3-(((1r,4r)-4-(hydroxymethyl)cyclohexyl)methyl)-1,3-dimethylurea (26 mg, 0.068 mmol) and rhodium(II) acetate (6.04 mg, 0.014 mmol) in dichloromethane (2.0 mL) was added dropwise a solution of ethyl 2-diazoacetate (9.36 mg, 0.082 mmol) in DCM (2 mL). The reaction was stirred at room temperature for 4 days. The mixture was diluted with DCM, washed with water (five time), 1 M HCl (twice), saturated $NaHCO_3$ (twice); and brine (twice). The combined organic layers were dried over $MgSO_4$ and concentrated. To the residue was added 1.0 M LiOH (2 mL), and the mixture was stirred at 65° C. for 2 h and acidified to pH 4 with 1.0 M HCl. The mixture was extracted into ethyl acetate which was subsequently evaporated and the residue was purified by preparative LCMS to provide the title compound as an oil (1.0 mg). LCMS m/z=439.6 $[M+H]^+$.

Example 1.102: Preparation of 2-(((1r,4r)-4-((Benzhydryl(propyl)carbamoyloxy)methyl)cyclohexyl) methoxy)acetic Acid (Compound 96)

To tert-butyl 2-(((1r,4r)-4-(hydroxymethyl)cyclohexyl) methoxy)acetate (200 mg, 0.774 mmol) in DCM (2.0 mL) were added bis(2,5-dioxopyrrolidin-1-yl)carbonate (397 mg, 1.548 mmol) and TEA (0.324 ml, 2.322 mmol). The reaction was heated under microwave irradiation at 80° C. for 2 h. N-Benzhydrylpropan-1-amine (174 mg, 0.774 mmol) was added and the resulting solution was again heated under microwave irradiation at 60° C. for 1 h. The reaction mixture was concentrated and the residue was purified by flash column chromatography to provide 210 mg of the t-butyl ester intermediate. 102 mg of which was treated with HCl (4.0 M in dioxane, 1.161 mL, 4.64 mmol) for 3 h at room temperature. The reaction mixture was concentrated and the resulting residue was purified by preparative LCMS to provide the title compound as an oil (17.8 mg). LCMS m/z=454.4 $[M+H]^+$; $^1H$ NMR (400 MHz, DMSO-$d_6$) δ ppm 0.54 (t, J=7.39 Hz, 3H), 0.82-1.05 (m, 6H), 1.44 (bs, 2H), 1.56-1.78 (m, 4H), 3.17 (t, J=7.96 Hz, 2H), 3.26 (d, J=6.32 Hz, 2H), 3.87 (d, J=5.81 Hz, 2H), 3.97 (s, 2H), 6.43 (bs, 1H), 7.18 (d, J=7.20 Hz, 4H), 7.29-7.43 (m, 6H).

Example 1.103: Preparation of Sodium 2-(((1r,4r)-4-(((3-Fluorophenyl)(phenyl)carbamoyloxy)methyl) cyclohexyl)methoxy)acetate Step A: Preparation of 3-Fluoro-N-phenylaniline In a 3 liter, three-neck flask equipped with mechanical stirring, a solution of 3-fluoroaniline (75 g, 675 mol), bromobenzene (73 mL, 690 mol), and dichloro[1,1'-bis (diphenylphosphine)-ferrocene]palladium(II) dichloromethane adduct (15 g, 18 mmol) in anhydrous toluene (13 L) containing sodium tert-butoxide (130 g, 1.35 mol) was heated at 105° C. for 3 h. The reaction mixture was then cooled to 80° C., and then quenched by gradually pouring the reaction mixture into ice water (1 L). The aqueous layer was removed, and was then extracted with an additional volume of toluene (300 mL). The organic extracts were combined, rinsed with brine, dried over $MgSO_4$, and passed through a silica plug (1.3 kg), eluting with toluene. The solvent was removed to give a dark amber oil (86 g). LCMS m/z (%)=188.0 $[M+H]^+$; $^1H$ NMR (400 MHz, $CDCl_3$) δ 6.45 (t, J=8.5 Hz, 1H), 6.62-6.66 (m, 2H), 6.87 (t, J=7.2 Hz, 1H), 6.98 (d, J=7.6 Hz, 2H), 7.05 (q, J=7.5 Hz, 1H), 7.17 (t, J=8.6 Hz, 2H).

Step B: Preparation of 3-Fluorophenyl(phenyl)carbamic Chloride

A 3 liter three-neck mechanically stirred flask under $N_2$ containing a solution of 3-fluoro-N-phenylaniline (86 g, 460 mmol) in 1.2 L dichloromethane was cooled in an ice bath to 0° C., and then triphosgene (150 g, 505 mmol) was added. A solution of pyridine (52 mL, 640 mmol) in dichloromethane (200 mL) was added in a dropwise fashion. Initial addition resulted in a temperature spike to 25° C. after the first 10 mL had been added over 10 min. The addition was paused, and the reaction mixture was stirred for 1 h while cooling to 5° C. Addition of the pyridine solution was again commenced at a rate of 5 mL/min, at which a reaction temperature of 5-10° C. was maintained. After addition was complete (about 1 h), the reaction had proceeded to completion, and was quenched by the slow addition of ice water (500 g). Gas formation from the quench was controlled by adjusting the stirring speed, as decomposition was largely a function of the mixing of the two immiscible layers. Gas effluent was passed through a 20% sodium hydroxide trap, until all gas evolution had ceased (about 3 h). The aqueous layer was removed, and was then extracted with an additional 300 mL of dichloromethane. The organic extracts were combined, dried over $MgSO_4$, and the solvent was removed. Clean product was readily isolated as a viscous, pink oil, which gradually formed a pale pink solid upon seeding with crystals. LCMS m/z (%) 250.0 $[M+H]^+$; $^1H$ NMR ($CDCl_3$, 400 MHz) δ 7.00-7.07 (m, 1H), 7.10 (d, J=9.6 Hz, 1H), 7.15 (d, J=8.1 Hz, 1H), 7.35 (d, J=7.7 Hz, 2H), 7.35-7.41 (m, 2H), 7.42-7.48 (m, 2H).

Step C: Preparation of 4-(Dimethylamino)-1-((3-fluorophenyl)(phenyl)carbamoyl)pyridinium Chloride To a solution of 3-fluorophenyl(phenyl)carbamic chloride (62.4 g, 250 mmol) in acetonitrile (500 mL) in a 2 liter mechanically stirred three-neck flask was added a solution of 4-dimethylaminopyridine (30.5 g, 250 mmol) in 500 mL acetonitrile. The flask warmed slightly as crystallization began to occur, and then cooled again to ambient temperature. The resulting suspension was stirred overnight, cooled to 10° C. in an ice bath and filtered, rinsing with cold acetonitrile (100 mL) to provide the title compound as a fine, white solid (88.27 g). LCMS m/z=336.4 $[M+H]^+$; $^1H$ NMR (400 MHz, Methanol-$d_4$) δ 3.29 (s, 6H), 6.92 (d, J=8.1 Hz, 2H), 7.11 t, J=8.6 Hz, 1H), 7.16 (d, J=8.8 Hz, 1H), 7.21 (d, J=9.5 Hz, 1H), 7.33-7.38 (m, 3H), 7.41-7.47 (m, 3H), 8.37 d, J=8.1 Hz, 2H).

Step D: Preparation of ((1r,4r)-4-(Hydroxymethy) cyclohexyl)methyl-3-fluorophenyl(phenyl)carbamate A suspension of 4-(dimethylamino)-1-((3-fluorophenyl)(phenyl)carbamoyl)-pyridinium chloride (88.25 g, 237 mmol), (1r,4r)-cyclohexane-1,4-diyldimethanol (137 g, 950 mmol) and 4-dimethylaminopyridine (29.0 g, 237 mmol) in acetonitrile (1 L) was heated at 53° C. for 18 h. Upon cooling, the solvent was removed, and the residue was taken up in isopropyl acetate (500 mL) and 1 N HCl (500 mL), heated to suspend all solids, and then filtered through glass fiber filter paper to remove the insoluble bis-carbamate impurity. The aqueous filtrate was discarded, and the organic filtrate was washed with an additional 500 mL of 1 N HCl, followed by water (5×500 mL). Heptane (100 mL) was added to the organic phase, which was further washed with water (2×500 mL) and brine (100 mL), dried over $MgSO_4$, and concentrated to dryness. The residue was taken up in isopropyl acetate (100 mL) and heptane (300 mL) was added. Crystals gradually formed over 1 h. forming a white precipitate, which was collected by filtration, rinsing with 25% isopropyl acetate/heptane (100 mL). The filtrate was concentrated to dryness, and the hot residue was taken up in 25% isopropyl acetate/heptane (100 mL) and filtered hot. As the filtrate cooled, more solids precipitated, which were collected by filtration and combined with the first crop. This material still contained about 5% bis-carbamate by-product, which could not be readily removed by filtration. The solid was then taken up in dichloromethane (200 mL) and subjected to plug filtration over 1.6 kg of silica gel, eluting the remaining bis-carbamate with dichloromethane and the product with 20% ethyl acetate/dichloromethane to provide the title compound as a white solid (71 g). LCMS m/z=358.2 $[M+H]^+$; $^1H$ NMR ($CDCl_3$, 400 MHz) δ 0.91-0.98 (m, 4H), 1.35-1.44 (m, 1H), 1.54-1.60 (m, 1H), 1.68-1.73 (m, 2H), 1.79-1.83 (m, 2H), 3.45 (d, J=6.4 Hz, 2H), 4.01 (d, J=6.4 Hz, 2H), 6.91 (t, J=7.6 Hz, 1H), 7.04 (d, J=8.6 Hz, 2H), 7.22-7.30 (m, 4H), 7.38 (t, J=7.8 Hz, 2H).

Step E: Preparation of Ethyl-2-(((1r,4r)-4-(((3-fluorophenyl)(phenyl)carbamoyloxy)methyl)cyclohexyl) methoxy)acetate In a 250 mL three-neck reactor equipped with a stirrer, a thermocouple, a cooling bath, an addition funnel and a nitrogen inlet was placed ((1r,4r)-4-(hydroxymethyl)cyclohexyl)methyl-3-fluorophenyl(phenyl)carbamate (8 g, 22.38 mmol). This was dissolved in dichloromethane (150 mL). The mixture was cooled and stirred well at 4° C. in an isopropanol/ice bath. Diacetoxyrhodium (0.5 g, 1.12 mmol) was added. After the addition was complete, ethyl diazoacetate (3.69 g, 32.34 mmol) was dissolved in dichloromethane (30 mL) and added to the reaction mixture keeping the temperature below 10° C. After addition, the reaction mixture was warmed to 30° C. and the progress of the reaction was followed by LCMS. Based on the LCMS ethyl diazoacetate (0.63 g, 5.52 mmol) was added, followed by more ethyl diazoacetate (0.710 g, 6.22 mmol) dissolved in dichloromethane (15 mL) separately at 25° C. The reaction mixture was stirred at 30° C. until LCMS showed complete consumption of the starting material. The reaction mixture was diluted with water (100 mL) and the mixture was filtered through a bed of celite (35 g) to remove the catalyst. The organic layer was then separated and dried over magnesium sulfate (15 g) and filtered. The solvent was removed to provide the title compound as an oil (9.9 g), which still contained a small amount of ethyl diazoacetate and was used without further purification. LCMS m/z=444.5 $[M+H]^+$; $^1H$ NMR (400 MHz, DMSO-$d_6$) δ ppm 0.82-0.96 (m, 4H), 1.22 (t, J=7.07 Hz, 3H), 1.27 (t, J=7.14 Hz, 1H), 1.37-1.53 (m, 2H), 1.57-1.78 (m, 4H), 3.26 (d, J=6.32 Hz, 2H), 3.94 (d, J=6.06 Hz, 2H), 4.06 (s, 2H), 4.14 (q, J=7.07 Hz, 3H), 4.23 (q, J=7.07 Hz, 1H), 7.05-7.11 (m, 2H), 7.24 (dt, J=10.64, 2.26 Hz, 1H), 7.28-7.35 (m, 3H), 7.36-7.45 (m, 3H).

Step F: Preparation of 2-((1r,4r)-4-(((3-Fluorophenyl)(phenyl)carbamoyloxy)methyl)cyclohexyl) methoxy)acetic Acid p In a 500 mL, three-neck reactor equipped with a stirrer, a thermocouple, a heating oil bath, an addition funnel and a nitrogen inlet was placed ethyl-2-(((1r,4r)-4-(((3-fluorophenyl)(phenyl)carbamoyloxy)methyl)cyclohexyl) methoxy)acetate (9.9 g, 22.32 mmol), which was dissolved in acetonitrile (150 mL). To this mixture lithium bromide (19.58 g, 225.00 mmol) was added. After the addition was complete, triethylamine (6.84 g, 67.6 mmol) was added and the reaction mixture was heated at 70° C. The progress of the reaction was followed by LCMS. Based on the LCMS the starting material was consumed in 2 h. Solvent was removed and the reaction mixture was diluted with water (200 mL) and made acidic with hydrochloric acid (3 M, 7.8 mL). The precipitated solids were filtered and the wet solid was dissolved in isopropyl acetate (200 mL). Isopropyl acetate layer was dried over magnesium sulfate (15 g), filtered and the solvent was removed. The residue was dried in a vacuum oven to provide the title compound (9.2 g). LCMS m/z=416.4 $[M+H]^+$; NMR (400 MHz, DMSO-$d_6$) δ ppm 0.81-0.96 (m, 4H), 1.36-1.53 (m, 2H), 1.55-1.77 (m, 4H), 3.25 (d, J=6.44 Hz, 2H), 3.93 (d, J=5.94 Hz, 2H), 3.97 (s, 2H), 7.05-7.13 (m, 2H), 7.24 (dt, J=10.64, 2.26 Hz, 1H), 7.28-7.36 (m, 3H), 7.37-7.46 (m, 3H), 12.53 (bs, 1H)

Step G: Preparation of 2-(((1r,4r)-4-(((3-Fluorophenyl(phenyl)carbamoyloxy)methyl)cyclohexyl) methoxy)acetic Acid Sodium Salt In a 500 mL, three-neck reactor equipped with a stirrer, a thermocouple, a heating oil bath, an addition funnel and a nitrogen inlet was placed 2-(((1r,4r)-4-(((3-fluorophenyl)(phenyl)carbamoyloxy)methyl)cyclohexyl)methoxy)acetic acid (9.2 g, 22.83 mmol) and 2-propanol (100 mL). The reaction mixture was heated of 30° C. (bath temperature), until all of the acid was dissolved completely. To the orange solution, sodium hydroxide (1 M, 22 mL, 22 mmol) was added slowly keeping the temperature and 25° C. The sodium salt separated out as crystals. The thick slurry was stirred at 25° C. for 2 h and then cooled in an ice water bath for 40 min. The solids were filtered and dried in a vacuum oven at 40' C. overnight until most of the residual 2-propanol was removed to provide the title compound (7.4 g). LCMS m/z=416.5 $[M+H]^+$; $^1H$ NMR (400 MHz, DMSO-$d_6$) δ ppm 0.77-0.95 (m, 4H), 1.34-1.53 (m, 2H), 1.55-1.75 (m, 4H), 3.19 (d, J=6.44 Hz, 2H), 3.52 (s, 2H), 3.93 (d, J=5.94 Hz, 2H), 7.05-7.13 (m, 2H), 7.24 (dt, J=10.64, 2.26 Hz, 1H), 7.28-7.35 (m, 3H), 7.37-7.46 (m, 3H).

Example 1.104: Preparation of Sodium 2-(((1r,4r)-4-(((3-Fluorophenyl)(phenyl)carbamoyloxy)methyl) cyclohexyl)methoxy)acetate To 5.0 g of ((1r,4r)-4-(hydroxymethyl)cyclohexyl)methyl 3-fluorophenyl(phenyl)carbamate was added toluene (30 mL), 50% NaOH (28 mL), tetrabutylammonium bromide (2.3 g) and tert-butyl bromoacetic (10.3 mL). The reaction mixture was stirred at room temperature for about 7 h and monitored by LC-MS to give tert-butyl 2-(((1r,4r)-4-(((3-fluorophenyl)(phenyl)carbamoyloxy)methyl)cyclohexyl) methoxy)acetate. The mixture was then heated at 50-60° C. for about 4 hours and monitored by LC-MS in give 2-(((1r,4r)-4-(((3-fluoromethyl)(phenyl)carbamoyloxy)methyl)cyclohexy)methoxy)acetic acid (Compound 23). The mixture was then acidified with 12 N HCl and the phases separated. The organic layer was concentrated and the residue suspended in isopropyl alcohol (20 mL). Thereafter, 50% sodium hydroxy (~1 mL) and water (4 mL) were added at 50-60° C. The mixture was stirred at 40-50° C. for 1 hr and then cooled to room temperature. The mixture was filtered and washed with isopropyl alcohol (10 mL). The solid was dried under reduced pressure at 50° C. to leave the title compound (4.0 g, 66%). LCMS m/z=416.5 $[M-Na+H]^+$.

Example 1.105: Preparation of 4-Chloro-N-phenylaniline

Method 1.

A solution of 4-chloroaniline (25.5 g, 200 mmol), bromobenzene (31.4 g, 200 mmol), and dichloro[1.1'bis(diphenylphosphino)ferrocene]palladium(II) dichloromethane adduct (4.9 g, 6.0 mmol) in anhydrous toluene (500 mL) containing sodium tert-butoxide (38.4 g, 400 mmol) was refluxed under $N_2$ for 90 min. The reaction mixture was cooled until it began to solidify, and then water (400 mL) was added, and the aqueous layer was removed. The organic layer was rinsed with brine, dried over $MgSO_4$, and passed through a silica plug, eluting with toluene. The solvent was removed to give a pale reddish amber solid (35.3 g). LCMS m/z=204.4 $[M+H]^+$; $^1H$ NMR (400 MHz, $CDCl_3$) δ ppm 7.00 (t, J=7.6 Hz, 1H), 7.04 (d, J=8.8 Hz, 2H), 7.10 (d, J=7.6 Hz, 2H), 7.24 (d, J=8.6 Hz, 2H), 7.31 (t, J=7.7 Hz, 2H).

Method 2.

A solution of 4-bromochlorobenzene (38.3 g, 2.00 mmol), aniline (18.6 g, 200 mmol), and dichloro[1,1'bis(diphenylphosphino)ferrocene]palladium(II) dichloromethane adduct (4.9 g, 6.0 mmol) in anhydrous toluene (500 mL) containing sodium tert-butoxide (38.4 g, 400 mmol) was refluxed under $N_2$ for 90 min. The reaction mixture was cooled under it began to solidify, and then water (400 mL) was added, and the aqueous layer was removed. The organic layer was rinsed with brine, dried over $MgSO_4$, and passed through a silica plug, eluting with toluene. The solvent was removed to give a reddish amber solid (37.2 g). LCMS m/z=204.4 $[M+H]^+$; $^1H$ NMR (400 MHz, $CDCl_3$) δ ppm 7.00 (t, J=7.6 Hz, 1H), 7.04 (d, J=8.8 Hz, 2H), 7.10 (d, J=7.6 Hz, 2H), 7.24 (d, J=8.6 Hz, 2H), 7.31 (t, J=7.7 Hz, 2H).

Example 1.106: Preparation of Sodium 2-(((1r,4r)-4-(((4-Chlorophenyl)phenyl)carbamoyloxy)methyl) cyclohexyl)methoxy)acetate Method 1.

Step A: Preparation of ((1r,4r)-4-(hydroxymethyl) cyclohexyl)methyl-4-chlorophenyl(phenyl)carbamate 4-Chloro-N-phenylaniline (15.0 g, 73.6 mmol), tribasic potassium phosphate, (fine powder, 4.69 g, 22.1 mmol), N,N-carbonyldiimidazole (13.14 g, 81 mmol) and acetonitrile (75 mL) were changed to a 500-mL jacketed, four-necked cylindrical reaction flask equipped with a mechanical stirrer and a condenser. The reaction mixture was heated at 65° C. under nitrogen and monitored by HPLC. After about 2.5 h HPLC showed >98% conversion to the intermediate N-(4-chlorophenyl)-N-phenyl-1H-imidazole-1-carboxamide. After about 5.5 h a solution of (1r,4r)-cyclohexane-1,4-diyldimethanol (37.2 g, 258 mmol) in acetonitrile (150 mL) at 65° C., was added to the reaction mixture over 20 min. The resulting mixture was heated at 65° C. overnight. HPLC showed about 98% conversion to the required product. The mixture was filtered, and the cake was rinsed with acetonitrile (2×25 mL). The filtrate was concentrated under reduced pressure (40° C., 32 torr) 124.125 g of distillate was collected. The residue was diluted with water (50 mL) and this mixture was concentrated under reduced pressure (40° C., 32 torr) and 35.184 g of distillate was collected. The residue was diluted with water (50 mL) and the resulting mixture was allowed to stir overnight to give a white paste. The mixture was filtered, and the cake was rinsed with 25% acetonitrile/water (2×75 mL). The solid was dried in a vacuum oven to leave a white solid (22.271 g); 94.8% purity by HPLC peak area. LCMS m/z=374.3 $[M+H]^+$; $^1$NMR (400 MHz, DMSO-$d_6$) δ ppm 0.77-0.93 (m, 4H) 1.23 (dd, J=6.22, 3.51 Hz, 1H) 1.47 (dd, J=6.32, 2.91 Hz, 1H) 1.56-1.76 (m, 4H) 3.20 (t, J=5.78 Hz, 2H) 3.92 (d, J=6.13 Hz, 2H) 4.33 (t, J=5.31 Hz, 1H) 7.28-7.35 (m, 5H) 7.38-7.47 (m, 4H).

Step B: Preparation of Sodium 2-(((1r,4r)-4-(((4-Chlorophenyl)(phenyl)carbamoyloxy)methyl)cyclohexyl)methoxy)acetate In a 1 L 3-neck flask fitted with an overhead stirrer was placed ((1r,4r)-4-(hydroxymethyl)cyclohexyl)methyl 4-chlorophenyl(phenyl)carbamate (30 g). TBAB (7.8 g) and toluene (180 mL) and the mixture stirred at room temperature. To this mixture was added 50% NaOH (180 mL) followed by addition of tert-butyl bromoacetate (17.8 mL). The mixture was stirred at room temperature for 7 hr. The mixture was then heated at 50-60° C. for 4 h. The mixture was then neutralized with concentrated HCl (300 mL). The mixture was filtered and the resulting filtrate was separated into two phases. The aqueous layer was extracted with toluene (80 mL). The combined organic layers were washed with water and the solvent was evaporated. The residue was azeotroped with isopropyl alcohol (150 mL) to remove the remaining toluene. Isopropyl alcohol (150 mL) was added to dissolve the residue and to this solution was added 12.5% NaOH solution (17 mL) to give a pH of 7-8. The resulting precipitate was collected by filtration and the filter cake was dissolved in water/acetone (280 mL; 1:1) at 55-60° C. The solution was filtered and the filtrate was diluted with acetone (320 mL) and stirred at room temperature overnight. The resulting slurry was cooled to 0-5° C. and then filtered. The filter cake was suspended in acetonitrile (400 mL), stirred at room temperature for 16 h and then filtered. The filter cake was dried at 60-70° C. under reduced pressure to leave the desired product (21.1 g): >90% purity by HPLC peak area. LCMS m/z=432.3 $[M-Na+H]^+$.

Method 2.

Step A: Preparation of ((1r,4r)-4-(Hydroxymethyl)cyclohexyl)methyl 4-chlorophenyl(phenyl)carbamate A 50-liter glass-lined reactor equipped with overhead agitation, jacket temperature control, and a nitrogen atmosphere was charged with (1r,4r)-cyclohexane-1,4-diyldimethanol (3.97 kg) and acetonitrile (12.71 kg). The reactor contents were stirred at 130 rpm and heated to 63° C. for 1.2 h to achieve dissolution. The mixture was cooled to <40° C. and then filtered. The filtrate was stored in a carboy. 4-Chloro-N-phenylaniline (1.60 kg), $K_3PO_4$ (0.50 kg), CDI (1.41 kg) and acetonitrile (6.29 kg) were charged to a 50-liter glass-lined reactor equipped with overhead agitation, jacket temperature control, and a nitrogen atmosphere. The reactor contents were stirred at 130 rpm and heated to 65° C. to 70° C. for 3 h, after which conversion of 4-chloro-N-phenylaniline to N-(4-chlorophenyl)-N-phenyl-1H-imidazole-1-carboxamide was 98.0% by HPLC peak area. The reaction mixture was cooled to less than 40° C. and the solution of (1r,4r)-cyclohexane-1,4-diyldimethanol in acetonitrile prepared earlier was added to the mixture. The reactor contents were stirred at 130 rpm and heated at 65 to 70° C. for 19 h, after which conversion of N-(4-chlorophenyl)-N-phenyl-1H-imidazole-1-carboxamide to ((1r,4r)-4-(hydroxymethyl)cyclohexyl)methyl 4-chlorophenyl(phenyl) carbamate was verified to be 98.0% by HPLC peak area. The reactor contents were filtered and the filter cake was rinsed with acetonitrile (2.00 kg). The filtrate was transferred back to the reactor and most of the acetonitrile (18.48 kg) was then removed at 22° C. by vacuum distillation at 80 mm Hg. Water (5.34 kg) was added to the reactor and 1.55 kg of water/acetonitrile mixture was then removed by vacuum distillation at 29° C. and 70 mm Hg. Water (5.34 kg) was added to the reactor and the product precipitated during the addition. The resulting mixture was stirred at 20° C. to 25° C. for 13 h. The precipitated product was filtered and washed with aqueous acetonitrile in two portions (1.59 kg acetonitrile dissolved in 6.00 kg water). The product was dried under reduced pressure at 60° C. (until loss-on-drying was ≤2 wt %) to give the title compound as an off-while solid (2.29 kg, 78% yield; 97% purity by HPLC peak area.)

Step B: Preparation of Sodium 2-(((1r,4r)-4-(((4-Chlorophenyl)(phenyl)carbamoyloxy)methyl)cyclohexyl)methoxy)acetate ((1r,4r)-4-(Hydroxymethyl)cyclohexyl)methyl 4-chlorophenyl(phenyl)carbamate (1.70 kg), tetrabutylammonium bromide (0.44 kg) and toluene (7.36 kg) were charged to a 50-liter glass-lined reactor equipped with overhead agitation, jacket temperature control, and a nitrogen atmosphere. The mixture was stirred for 1 h at 20° C. To the resulting solution was added 50 wt % aqueous sodium hydroxide (15.34 kg) and the jacket temperature was set to 10° C. Then tert-butyl bromoacetate (1.33 kg was added sufficiently slowly to maintain the stirred reaction mixture at 5-15° C. with reactor jacket cooling. The mixture was stirred at 5-15° C. for 8.1 h. Conversion of ((1r,4r)-4-(hydroxymethyl)cyclohexyl)methyl 4-chlorophenyl(phenyl)carbamate to tert-butyl 2-(((1r,4r)-4-(((4-chlorophenyl)(phenyl)carbamoyloxy)methyl)cyclohexyl)methoxy)acetate was >90.0% by HPLC peak area. The reactor contents were heated at 50-60° C. for 7.2 h. Conversion of tert-butyl (((1r,4r)-4-(((4-chlorophenyl)(phenyl)carbamoyloxy)methyl)cyclohexyl) methoxy)acetate to 2-(((1,4r)-4-(((4-chlorophenyl)(phenyl) carbamoyloxy)methyl)cyclohexyl)methoxy)acetic acid was >90.0% by HPLC peak area. The reactor contents were then cooled to 15° C. and concentrated hydrochloric acid (18.87 kg) was added to the mixture at a rate sufficiently slow to maintain an internal temperature <50° C. The mixture was filtered to remove the solid sodium chloride from the reactor. The filtrate separated into two phases and the organic phase was removed. The aqueous layer was extracted with toluene (4.55 kg). The organic phases were combined and the mixture was distilled at 30° C. and 40 mm Hg to remove most of the toluene. Then, IPA (6.75 kg) was charged to the reactor and the resulting solution was distilled at 28° C. and 40 mm Hg to remove solvent (5.05 Kg). IPA (6.68 kg) was charged a second time to the reactor and the resulting mixture was vacuum distilled at 37° C. and 40 mm Hg to remove solvent (4.98 kg). Then, IPA (6.77 kg) was charged to the reactor for the third time and the reactor contents were heated to 40° C. Sodium hydroxide (12.5%, 0.87 kg) was added to the reactor. The resulting mixture had a pH of 7. The mixture was agitated at 155 rpm for 2 h at 40° C. The product precipitated, and the solid was filtered. The filter cake was washed with IPA (3.01 kg). The filter cake was transferred to a reactor using acetone (6.27 kg) and water (7.95 kg) and the mixture was heated at 59° C. for 3 h. The resulting mixture was filtered through a sintered glass filter and the filtrate was transferred to a reactor. Acetone (15.82 kg) was added and the mixture stirred for 66 h at 20° C. The reactor contents were further stirred at 0° C. for 2 hours, filtered and the filter cake was washed with acetone (3.2 kg). The filter cake was then transferred back to the reactor with the aid of acetonitrile (17.79 kg). The reactor contents were stirred at 100 rpm and 20° C. for 18.5 h. The slurry was filtered and the cake was washed with two portions of acetonitrile (10.26 kg total). The solid was dried at 65° C. to 70° C. under reduced pressure for 27 h. and then sieved through a 1.18 mm mesh screen. The product was further dried under reduced pressure at ≤70° C. to an acetonitrile level of ≤2000 ppm, to leave the title compound as a white to off-white solid (0.65 kg, 32% yield; 98.8% purity by HPLC peak area.)

Example: 1.107: Preparation of Sodium 2-(((1r,4r)-4-(((4-Chlorophenyl)(phenyl)carbamoyloxy)methyl)cyclohexyl)methoxy)acetate Hydrate Sodium 2-(((1r,4r)-4-(((4-chlorophenyl)(phenyl)carbamoyloxy)methyl)cyclohexyl)methoxy)acetate was slurried in water for 3 days at 40° C., and then filtered to give the title compound as a solid. The TGA thermogram of the title compound (FIG. 12) shows a weight loss of about 13%, indicating that the compound is a hydrate. The PXRD pattern for the hydrate is shown in FIG. 13.

Example 1.108: Preparation of Sodium 2-(((1r,4r)-4-(((3-Fluorophenyl)(phenyl)carbamoyloxy)methyl)cyclohexyl)methoxy)acetate Hydrate Crude sodium 2-(((1r,4r)-4-(((3-fluorophenyl)(phenyl)carbamoyloxy)methyl)cyclohexyl)methoxy)acetate (0.422 g) was suspended in water (10 volumes) and heated to 85° C. (bath). The sodium 2-(((1r,4r)-4-(((3-fluorophenyl)(phenyl)carbamoyloxy)methyl)cyclohexyl)methoxy)acetate did not dissolve. Ethanol (8.5 volume) was added and a solution formed. The solution was hot-filtered, the solvate crystallized, and the suspension was stirred at room temperature for 1 h and filtered. The solids were dried in a vacuum oven at 45° C. overnight. The TGA thermogram of the title compound (FIG. 14) shows a weight loss of about 4.3%, indicating that the compound is a mono-hydrate. The PXRD pattern is shown in FIG. 15.

Example 1.109: Preparation of Magnesium 2-(((1r,4r)-4-(((3-Fluorophenyl)(phenyl)carbamoyloxy)methyl)cyclohexyl)methoxy)acetate Solvate $Mg(OAc)_2$ (aqueous solution, 2.13 M) was added to a solution of 2-(((1r,4r)-4-(((3-fluorophenyl)(phenyl)carbamoyloxy)methyl)cyclohexyl)methoxy)acetic acid in EPA (64.456 mg/mL) at room temperature to achieve a 1:2 ratio of magnesium 2-(((1r,4r)-4-(((3-fluorophenyl)(phenyl)carbamoyloxy)methyl)cyclohexy)methoxy)acetic acid. No precipitation occurred so the solution was allowed to evaporate to dryness to produce a crystalline solid. The TGA thermogram of the title compound (FIG. 16) shows a weight loss of about 18.9%, indicating that the compound is a solvate. The PXRD pattern for the solvate shown in FIG. 17.

Example 1.110: Preparation of Potassium 2-(((1r,4r)-4-(((3-Fluorophenyl)(phenyl)carbamoyloxy)methyl)cyclohexyl)methoxy)acetate Solvate Potassium carbonate (aqueous solution, 2.19M) was added to a solution of 2-(((1r,4r)-4-(((3-fluorophenyl)(phenyl)carbamoyloxy)methyl)cyclohexyl)methoxy)acetic acid in IPA (64.456 mg/mL) at room temperature to achieve a 1:1 ratio of potassium to 2-(1r,4r)-4-(((3-fluoropheny)(phenyl)carbamoyloxy)methyl)cyclohexyl)methoxy)acetic acid. A precipitate formed after ~15 min and the solid was isolated by filtration. The TGA thermogram of the title compound (FIG. 18) shows weight losses of about 2.0% below about 93° C. and about a further 3.8% below about 177° C., indicating that the compound is a solvate. The PXRD pattern for the solvate is shown in FIG. 19.

Example 1.111: Preparation of Calcium 2-(((1r,4r)-4-(((3-Fluorophenyl)(phenyl)carbamoyloxy)methyl)cyclohexyl)methoxy)acetate Solvate $Ca(OAc)_2$ (aqueous solution, 2.13M) was added to a solution of 2-(((1r,4r)-4-(((3-fluorophenyl)(phenyl)carbamoyloxy)methyl)cyclohexyl)methoxy)acetic acid in IPA (64.456 mg/mL) at room temperature to achieve a 1:2 ratio of calcium to 2-(((1r,4r)-4-(((3-fluorophenyl)(phenyl)carbamoyloxy)methyl)cyclohexyl)methoxy)acetic acid. A white precipitate formed immediately. The solid was isolated by filtration. The TGA thermogram of the title compound (FIG. 20) shows a weight loss of about 8.2%, indicating that the compound is a solvate. The PXRD pattern for the solvate is shown in FIG. 21.

Example 1.112: Preparation of 2-(2-(((1r,4r)-4-(((4-Chlorophenyl)(phenyl)carbamoyloxy)methyl)cyclohexyl)methoxy)acetamido)ethanesulfonic Acid (Compound 99)

Method 1.

2-(((1r,4r)-4-(((4-Chlorophenyl)(phenyl)carbamoyloxy)methyl)cyclohexyl)methoxy)acetic acid (0.30 g, 0.695 mmol) was dissolved in $SOCl_2$ (5.0 mL, 68.5 mmol) (bubbling was observed). The reaction was heated to reflux and stirred for 2 h, and then concentrated and dried overnight under reduced pressure. The resulting ((1r,4r)-4-((2-chloro-2-oxoethoxy)methyl)cyclohexyl)methyl 4-chlorophenyl (phenyl)carbamate was dissolved in THF (2 mL) with gentle heating. To this was added a solution of 2-aminoethanesulfonic acid (0.113 g, 0.903 mmol) and sodium hydroxide (0.038 g, 0.938 mmol) in water (0.6 mL). The reaction was vigorously stirred at room temperature for 1 h. The solvent was removed under reduced pressure and the residue was dissolved in DMSO (3 mL) and filtered. The filtrate was purified by HPLC to yield the title compound as a white solid (70.1 mg, 18.35%). Exact mass calculated for $C_{25}H_{31}ClN_2O_7S$: 538.2, found: LCMS m/z=539.2 $[M+H]^+$; $^1H$ NMR (400 MHz, DMSO-$d_6$) δ ppm 0.78-0.97 (m, 4H) 1.37-1.52 (m, 2H) 1.52-1.62 (m, J=7.83 Hz, 2H) 1.67-1.77 (m, 2H) 2.54 (t, J=6.44 Hz, 2H) 3.21 (d, J=6.32 Hz, 2H) 3.37

(q, J=5.81 Hz, 2H) 3.76 (s, 2H) 3.90 (d, J=6.06 Hz, 2H) 7.22-7.34 (m, 51H) 7.35-7.48 (m, 4H) 7.91 (bs, 1H).

Method 2.

To a solution of sodium 2-(((1r,4r)-4-(((4-chlorophenyl)(phenyl)carbamoyloxy)methyl)cyclohexyl)methoxy)acetate (50 mg, 0.11 mmol) in DMF (5 ml) and $H_2O$ (2.5 ml), was added 1H-benzo[d][1,2,3]triazol-1-ol hydrate (16.87 mg, 0.11 mmol) followed by 2-aminoethanesulfonic acid (13.79 mg, 0.11 mmol) at ambient temperature. The reaction was heated to 120° C. for 10 h. After cooling to room temperature, the reaction was poured into water, extracted with ethyl acetate, and then dried with $MgSO_4$. The organic layer was concentrated under reduced pressure and the resulting residue was purified by HPLC to afford the title compound as a white solid (12 mg). Exact mass calculated for $C_{25}H_{31}ClN_2O_7S$: 538.2, found: LCMS m/z=539.3 $[M+H]^+$; $^1H$ NMR (400 MHz, DMSO-$d_6$) δ ppm: 1.73-1.85 (m, 4H), 1.35-1.41 (m, 2H), 1.50-1.52 (m, 2H), 1.65-1.69 (m, 2H), 2.50 (m, 2H), 3.15 (d, J=6.4 Hz, 2H), 3.36 (m, 2H), 3.72 (s, 2H), 3.89 (d, J=6.2 Hz, 2H), 7.12-7.25 (m, 5H), 7.27-7.49 (m, 4H), 7.85 (br, 1H).

Example 1.113: Preparation of 2-(2-(((1r,4r)-4-(((4-Chlorophenyl)(phenyl)carbamoyloxy)methyl)cyclohexyl)methoxy)acetamido)acetic Acid (Compound 100)

2-(((1r,4r)-4-(((4-Chlorphenyl)(phenyl)carbamoyloxy)methyl)cyclohexyl)methoxy)acetic acid (0.30 g, 0.695 mmol) was dissolved in $SOCl_2$ (5.0 mL, 68.5 mmol) (bubbling was observed). The reaction was heated to reflux and stirred for 2 h, and then concentrated and dried overnight under reduced pressure. The resulting ((1r,4r)-4-((2-chloro-2-oxoethoxy)methyl)cyclohexyl)methyl 4-chlorophenyl (phenyl)carbamate was dissolved in THF (2 mL) with gentle heating. To the resulting solution was added a solution of glycine (0.052 g, 0.688 mmol) and sodium hydroxide (0.030 g, 0.757 mmol) in water (0.6 mL). The reaction was vigorously stirred at room temperature for 1 h. The solvent was removed under reduced pressure and the residue was dissolved in DMSO (3 mL) and filtered. The filtrate was purified by HPLC to yield the title compound as a white solid (20.0 mg, 5.88%). Exact mass calculated for $C_{25}H_{29}ClN_2O_6$: 488.2, found: LCMS m/z=489.2 $[M+H]^+$; $^1H$ NMR (400 MHz, DMSO-$d_6$) δ ppm 0.80-0.97 (m, 4H) 1.40-1.53 (m, 2H) 1.55-1.63 (m, 2H) 1.69-1.80 (m, 2H) 3.25 (d, J=6.57 Hz, 2H) 3.78 (d, J=6.06 Hz, 2H) 3.84 (s, 2H) 3.90 (d, J=6.06 Hz, 2H) 7.22-7.33 (m, 5H) 7.34-7.46 (m, 4H) 7.80 (bs, J=5.81, 5.81 Hz, 1H).

Example 1.114: Preparation of 2-(((1r,4r)-4-(((4-Chlorophenyl)(4-hydroxyphenyl)carbamoyloxy)methyl)cyclohexyl)methoxy)acetic Acid (Compound 98)

Step A: Preparation of tert-Butyl(4-iodophenoxy)dimethylsilane

4-Iodophenol (1.0 g, 4.55 mmol) was dissolved in dichloromethane (5 mL). tert-Butyldimethylsilyl chloride (0.685 g, 4.55 mmol) and imidazole (0.309 g, 4.55 mmol) were added. The reaction was stirred overnight at room temperature. The reaction mixture was partitioned between water (30 mL) and dichloromethane (30 mL). The organic layer was removed and the aqueous layer was extracted with dichloromethane (30 mL). The organic layers were combined, dried and concentrated, and the residue was purified by chromatography (0-10% EtOAc/hexanes) to give the title compound as a light yellow oil (1.45 g, 94%).

Step B: Preparation of tert-Butyl 2-(((1r,4r)-4-((4-chlorophenylcarbamoyloxy)methyl)cyclohexyl)methoxy)acetate tert-Butyl 2-(((1r,4r)-4-(hydroxymethyl)cyclohexyl)methoxy)acetate (2.4 g 9.29 mmol) and 4-chlorophenylisocyanate (1.712 g, 11.15 mmol) were dissolved in dichloromethane (20 mL). Then, pyridine (1.503 mL, 18.58 mmol) was added. The reaction was heated to reflux and stirred overnight. The solvents were removed under reduced pressure and the residue was purified by column chromatography (0-10% EtOAc/hexanes) to yield the title compound as a light yellow solid (1.45 g, 36.4%).

Step C. Preparation of 2-(((1r,4r)-4-(((4-Chlorophenyl)(4-hydroxyphenyl)carbamoyloxy)methyl)cyclohexyl)methoxy)acetic Acid tert-Butyl 2-(((1r,4r)-4-((4-chlorophenylcarbamoyloxy)methyl)cyclohexyl)methoxy)acetate (100 mg, 0.243 mmol), tert-butyl(4-iodophenoxy)dimethylsilane (81 mg, 0.243 mmol), potassium phosphate (103 mg, 0.486 mmol), copper (I) iodide (23.12 mg, 0.121 mmol), and trans-1,2-diaminocyclohexane (29.2 μL, 0.243 mmol) in dioxane (1.6 mL) were heated as 150° C. for 5 h under microwave irradiation. The reaction mixture was filtered through a plug of $MgSO_4$, the solvent was removed under reduced pressure, and the residue was purified by column chromatography (0-10% EtOAc/hexanes). The purified material was dissolved in HCl (4 M in Dioxane; 0.5 mL) and the mixture was stirred at room temperature overnight. The solvent was removed under reduced pressure and the title compound was isolated by preparative HPLC: (30-85% MeOH/$H_2O$, 30 min).

Example 1.115. 2-(((1r,4r)-4-(((4-Chlorophenyl)(phenyl)carbamoyloxy)methyl)cyclohexyl)methoxy)acetic Acid (Compound 22)

In a 1 L 3-neck flask fitted with an overhead stirrer was added ((1r,4r)-4-(hydroxymethyl)cyclohexyl)methyl 4-chlorophenyl(phenyl)carbamate (30 g), TBAB (7.8 g) and toluene (150 mL). To the resulting solution was added tert-butyl bromoacetate (17.8 mL). The mixture was cooled to 5-10° C. before slowly adding 50% sodium hydroxide (180 mL). The mixture was stirred at 3-10° C. for 7 h, allowed to sit at 18-24° C. overnight, and then heated at 45-50° C. for 4 h. The mixture was then acidified with conc. HCl (~260 mL) to pH 2. The mixture was filtered and the filtrate was transferred to a seperatory funnel. The phases were separated and the aqueous layer extracted once again with toluene (30 mL). The combined toluene layer was evaporated to an oil. To the oil was added 25% aqueous acetone (90 mL) and 12.5% sodium hydroxide solution (14 mL). The resulting solid was filtered and the filter cake was recrystallized from water (60 mL) and acetone (300 mL). The recrystallized material was suspended in water (100 mL) and 2 N HCl (30 mL) was added to pH 3. The mixture was allowed to stir overnight. The suspension was filtered and the filter cake was resuspended in water (150 mL). The mixture was stirred and filtered and the filter cake was dried at 65° C. in a vacuum oven to give the title compound as a white solid (19.33 g, HPLC purity: 97.4% by weight). $^1H$ NMR (400 MHz, DMSO-$d_6$) δ ppm 0.82-0.99 (m, 4H), 1.38-1.52 (m, 2H), 1.52-1.80 (m, 4H), 3.26 (d, J=3.0 Hz, 2H), 3.93 (d, J=3.0 Hz, 2H), 3.97 (s, 1H), 7.25-7.38 (m, 5H), 7.39-7.50 (m, 4H), 12.51 (bs, 1H).

Example 2: Homogeneous Time-Resolved Fluorescence (HTRF®) Assay for Direct cAMP Measurement Compounds were screened for agonists of the human prostacyclin (PGI2) receptor using the HTRF® assay for direct cAMP measurement (Gabriel et al., ASSAY and Drug Development Technologies, 1:291-303, 2003) and recombinant CHO-K1 cells stably transfected with human prostacyclin receptor. CHO-K1 cells were obtained from ATCC® (Manassas, Va.; Catalog # CCL-61). An agonist of the prostacyclin receptor was detected in HTRF® assay for direct cAMP measurement as a compound which increased cAMP concentration. HTRF® assay also was used to determine $EC_{50}$ values for prostacyclin receptor agonists.

Principle of the Assay:

The HTRF® assay kit was purchased from Cisbio-US, Inc. (Bedford, Mass., Catalog #62AM4PEC). The HTRF® assay supported by the kit is a competitive immunoassay between endogenous cAMP produced by the CHO-K1 cells and tracer cAMP labeled with the dye d2. The tracer binding is visualized by a monoclonal anti-cAMP antibody labeled with Cryptate. The specific signal (i.e., fluorescence resonance energy transfer, FRET) is inversely proportional to the concentration of unlabeled cAMP in the standard or sample.

Standard Curve:

The fluorescence ratio (665 nm/620 nm) of the standards (0.17 to 712 nM cAMP) included in the assay was calculated and used to generate a cAMP standard curve according to the kit manufacturer's instructions. The fluorescence ratio of the samples (test compound or compound buffer) was calculated and used to deduce respective cAMP concentrations by reference to the cAMP standard curve.

Setup of the Assay:

The HTRF® assay was carried out using a two-step protocol essentially according to the kit manufacturer's instructions, in 20 μL total volume per well in 384-well plate format (ProxiPlates; PerkinElmer, Fremont, Calif.; catalog #6008280). To each of the experimental wells was transferred 3000 recombinant CHO-K1 cells in 5 μL assay buffer (phosphate buffered saline containing calcium chloride and magnesium chloride (Invitrogen, Carlsbad, Calif.; catalog #14040) supplemented with IBMX (100 μM) and rolipram (10 μM) (phosphodiesterase inhibitors; Sigma-Aldrich, St. Louis, Mo.: catalog #15879 and catalog # R6520, respectively) and 0.1% bovine serum albumin (BSA) fraction V (Sigma-Aldrich; catalog #A3059)), followed by test compound in 5 μL assay buffer or 5 μL assay buffer. The plate was then incubated at room temperature for 1 h. To each well was then added 5 μL cAMP-d2 conjugate in lysis buffer and 5 μL Cryptate conjugate in lysis buffer according to the kit manufacturer's instructions. The plate was then further incubated at room temperature for 1 h, after which the assay plate was read.

Assay Readout:

The HTRF® readout was accomplished using a PHERAstar (BMG LABTECH Inc., Durham, N.C.) or EnVision™ (PerkinElmer, Fremont Calif.) microplate reader.

Certain compounds of the present invention and their corresponding activity values are showing in TABLE B.

TABLE B

| Compound No. | human PGI2 receptor $EC_{50}$ (nM) (HTRF ®) |
|---|---|
| 6 | 61.09 |
| 35 | 56.89 |
| 55 | 5.14 |
| 71 | 19.10 |

Certain other compounds of the invention had activity values ranging from about 2.7 nM to about 2.65 μM in this assay.

Example 3: Human Platelet Aggregation Inhibition Test

Blood collected from healthy human volunteers in aqueous trisodium citrate solution was centrifuged at 150 g for 15 min and the upper layer was recovered to obtain platelet-rich plasma (PRP). The residual blood was centrifuged at 3000 g for 10 min and the supernatant was collected as platelet-poor plasma (PPP). Platelet concentration in the PRP was determined using the Z series Beckman Coulter particle counter (Beckman, Fullerton, Calif.) and adjusted to 250,000 platelets/μL using PPP. 480 μL of PRP was pre-incubated at 37° C. and stirred as 1200 rpm with 10 μL aqueous test compound solution for 1 min prior to induction of aggregation by the addition of 10 μL of aqueous adenosine diphosphate (ADP) solution to adjust the final ADP concentration in the PRP to $1\times10^{-5}$ M. The maximal amplitude of aggregation response within 3 min was determined and measured in triplicate using the Chronolog model 490 aggregometer (Chrono-log Corp., Havertown, Pa.). Percent inhibition of aggregation was calculated from the maximum decrease in optical density of the control (addition of water in place of the test compound solution) sample and of the samples containing test compound. The test compound was added to adjust the final concentration to the range $10^{-9}$ to $10^{-4}$ M, and $IC_{50}$ values were determined by inhibition percentage of aggregation at each concentration. The results are shown in Table C.

TABLE C

| Compound No. | human PRP $IC_{50}$ (nM) |
|---|---|
| 2 | 73 |
| 30 | 210 |
| 50 | 12.6 |
| 88 | 70 |

Certain other compounds of the invention had activity values ranging from about 10.5 nM to about 1.59 μM in this assay.

It is apparent that the compounds of the present invention markedly inhibit platelet aggregation in human PRP.

Example 4: Rat Model of Pulmonary Arterial Hypertension

Animals.

Male Wistar rats (100-150 g at start of study) (Charles River Laboratories, Wilmington, Mass.) were housed two per cage and maintained in a humidity (40-60%) and temperature (68-72° F.) controlled facility on a 12 hr:12 hr light/dark cycle (lights on at 6:30 am) with free access to food (Harlan Teklad, Orange Calif., Rodent Diet 8604) and water. Rats were allowed one week of habitation to the animal facility before testing.

Rat Monocrotaline Model:

The rat monocrotaline (MCT) model is a standard and well-accepted model of pulmonary arterial hypertension. MCT induces acute pulmonary endothelial damage associated with pulmonary vascular inflammation. Subsequently, pulmonary artery smooth muscle cells proliferate, occluding small pulmonary vessels and leading to severe pulmonary arterial hypertension including right ventricular hypertrophy. (See, e.g., Schermuly et al., Circ. Res., 2004, 94:1101-1108).

Rats were randomly given a single subcutaneous injection of either 60 mg/kg MCT (Sigma, St. Louis, Mo.) or 0.9% saline (sham) and assigned to receive oral administration of 20% hydroxypropyl beta-cyclodextrin (vehicle) or test compound (30 mg/kg; FIGS. 7 and 8). 10-11 rats were used per treatment group. 24 h following MCT administration, test compound or vehicle was administered by oral gavage twice a day for 21 consecutive days. Heart chamber weights were measured on Day 22. Rats were anesthetized with intraperitoneal pentobarbital (50 mg/kg), the chest cavity was opened and the heart was excited. The right ventricle was dissected free from the septum and felt ventricle and both parts were weighed. The ratio of right ventricular (RV) weight to left ventricle plus septum (LV+S) weight (this ratio is indicated as "RV/(LV+S)" in FIGS. 7 and 8) was calculated as an index of the hypertrophic response to the induced pulmonary arterial hypertension and, as such, as an index of a test compound's therapeutic efficacy for pulmonary arterial hypertension.

It is apparent from inspection of FIGS. 7 and 8 that oral administration of Compounds 23 and 22 inhibited the hypertrophic response to the induced pulmonary arterial hypertension and, as such, evidenced therapeutic efficacy for pulmonary arterial hypertension.

Example 5: Powder X-ray Diffraction

Powder X-ray Diffraction (PXRD) data were collected on an X'Pert PRO MPD powder diffractometer (PANalytical, Inc.) with a Cu source set at 45 kV and 40 mA, a Ni-filter to remove Cu Kβ radiation, and an X'Celerator detector. The instrument was calibrated by the vendor using a silicon powder standard NIST #640c. The calibration was found to be correct when it was tested with NIST #675 low-angle diffraction standard. Samples were prepared for PXRD scanning by placing several milligrams of as-is compound onto a sample holder and smoothing as flat as possible by pressing weigh paper down on the sample with a flat object. The samples were analyzed using a spinning-sample stage. Scans covered the range of 5 to 40° 2θ. A continuous scan mode was used with a step size of 0.0170° 2θ. Diffraction data were viewed and analyzed with the X'Pert Data Viewer Software, version 1.0a and X'Pert HighScore Software, version 1.0b. The PXRD pattern for the crystalline form of sodium 2-(((1r,4r)-4-(((4-chlorophenyl)(phenyl)carbamoyloxy)methyl)cyclohexyl)methoxy)acetate is shown in FIG. 9. The PXRD pattern for a sodium 2-(((1r,4r)-4-(((4-chlorophenyl)(phenyl)carbamoyloxy)methyl)cyclohexyl) methoxy)acetate hydrate is shown in FIG. 13. The PXRD pattern for a sodium 2-(((1r,4r)-4-(((3-fluorophenyl)(phenyl)carbamoyloxy)methyl)cyclohexyl)methoxy)acetate hydrate is shown in FIG. 15. The PXRD pattern for a magnesium 2-(((1r,4r)-4-(((3-fluorophenyl)(phenyl)carbamoyloxy)methyl)cyclohexyl)methoxy)acetate solvate is shown in FIG. 17. The PXRD pattern for a potassium 2-(((1r,4r)-4-(((3-fluorophenyl)(phenyl)carbamoyloxy) methyl)cyclohexyl)methoxy)acetate solvate is shown in FIG. 19. The PXRD pattern for a calcium 2-(((1r,4r)-4-(((3-fluorophenyl)(phenyl)carbamoyloxy)methyl)cyclohexyl) methoxy)acetate solvate is shown in FIG. 21.

Example 6: Differential Scanning Calorimetry

Differential Scanning calorimetry (DSC) was performed on a TA instruments, Inc. DSC Q1000 or Q2000 at 10° C./min. The instrument was calibrated at this scan rate by the vendor for temperature and energy using the melting point and enthalpy of fusion of an indium standard. Samples were prepared by taring a sample-pan lid along with a sample-pan bottom on a Mettler Toldeo MX5 balance. Sample was placed in the bottom of the tared sample pan. The sample-pan lid fitted snuggly in the sample-pan bottom. The sample and pan were reweighted to get the sample weight. Thermal events (for example, onset temperature, enthalpy of fusion) are calculated using the Universal Analysis 2000 software, version 4.1D, Build 4.1.0.16. The DSC thermogram for the crystalline form of sodium 2-(((1r,4r)-4-(((4-chlorophenyl)(phenyl)carbamoyloxy)methyl)cyclohexyl)methoxy)acetate is shown in FIG. 11 overlaid with the TGA trace.

Example 7: Thermal Gravimetric Analysis

Thermal Gravimetric Analysis (TGA) was performed on the TA Instruments, Inc. TGA Q500 or Q5000. The instrument is calibrated by the vendor at 10 ° C./min. for temperature using the curie point of a ferromagnetic standard. The balance is calibrated with a standard weight. Sample is placed into an open sample pan, previously tared on the TGA balance. Thermal events such as weight-loss are calculated using the Universal Analysis 2000 software, version 4.1D, Build 4.1.0.16. The TGA thermogram for the crystalline form of sodium 2-(((1r,4r)-4-(((4-chlorpheny)(phenyl)carbamoyloxy)methyl)cyclohexyl)methoxy)acetate is shown in FIG. 11 overlaid with the DSC trace. The TGA thermogram for a sodium 2-(((1r,4r)-4-(((4-chlorophenyl)(phenyl)carbamoyloxy)methyl)cyclohexyl)methoxy)acetate hydrate is shown in FIG. 12. The TGA thermogram for a sodium 2-(((1r,4r)-4-(((3-fluorophenyl)(phenyl)carbamoyloxy)methyl)cyclohexyl)methoxy)acetate hydrate is shown in FIG. 14. The TGA thermogram for a magnesium 2-(((1r,4r)-4-(((3-fluorophenyl)(phenyl)carbamoyloxy)methyl)cyclohexyl)methoxy)acetate solvate is shown in FIG. 16. The TGA thermogram for potassium 2-(((1r,4r)-4-(((3-fluorophenyl)(phenyl)carbamoyloxy)methyl)cyclohexyl) methoxy)acetate solvate is shown in FIG. 18. The TGA thermogram for calcium 2-(((1r,4r)-4-(((3-fluorophenyl)(phenyl)carbamoyloxy)methyl)cyclohexyl)methoxy)acetate solvate is shown in FIG. 20.

Example 8: Dynamic Vapor Sorption (DVS)

Hygroscopicity was measured using a dynamic moisture-sorption analyzer, VTI Corporation, SGA-100. The sample was placed as-is in a tared sample holder on the VTI balance. A drying step was run at 40° C. and ~1% RH for 60 to 120 min. The isotherm conditions are 25° C. with steps of 20% RH from 10% RH up to 90% RH and back to 10% RH. The weight was checked every 2 min. Percent weight change of <0.01% in 20 min or 2 h, whichever occurs first, is required before continuing to the next step. The DVS profile for the crystalline form of sodium 2-(((1r,4r)-4-(((4-chloropheny)(phenyl)carbamoyloxy)methyl)cyclohexyl)methoxy)acetate is shown in FIG. 10.

Example 9: Interspecies Comparison of Hepatocyte Metabolism of Sodium 2-(((1r,4r)-4-(((4-Chlorophenyl)(phenyl)carbamoyloxy)methyl)cyclohexyl)methoxy)acetate All cryopreserved hepatocytes were thawed and diluted to a desired cell density ($1\times10^6$ cell/mL) according to the supplier's (Xenotech) guidelines using hepatocytes isolation kit. Cell viability was determined by trypan blue exclusion using a hemacytometer. A typical incubation mixture contained human, cynomolgus monkey, beagle dog or Sprague-Dawley rat hepatocytes (200,000 cell/199 μL) in designated wells of a 48-well plate containing incubation medium (Phenol red-free Waymouth's medium). The incubation mixture plate was incubated at 37° C., 5% $CO_2$, for 5 min before starting the reaction with 1 μL of sodium 2-(((1r,4r)-4-(((4-chlorophenyl)(phenyl)carbamoyloxy)methyl)cyclohexyl)methoxy)acetate (Compound 22 sodium salt)(100 μM final concentration). One incubation plate was prepared for each time point (i.e., 0, 60, 120, and 240 min) with samples being prepared in duplicate. Incubations were conducted at 37° C., 5% $CO_2$ and 100% relative humidity in an incubator. At each time point, one incubation plate was revived form the incubator, and reaction was terminated by adding 400 μL of acetonitrile containing an internal standard. For the 0 min time point, the reactions were kept on ice before adding Compound 22 sodium salt. After 5 min on ice, the reaction mixture was terminated by adding 400 82 L of acetonitrile containing an internal standard. Supernatants were transferred to labeled strip tubes with caps, which were vortexed for 3 min, and then sonicated for an additional 3 min. The samples were centrifuged for 10 min at 4000 rpm and the supernatants were used for metabolite identification.

Two major metabolites of sodium Compound 22 sodium salt were identified in hepatocytes. The taurine conjugate (Compound 99), was detected in human, monkey, dog and rat. The glycine conjugate (Compound 100), was only detected in human and monkey.

MS/MS fragmentation was used to identify the metabolites. The identity of the taurine conjugate of Compound 22 was confirmed by the characteristic m/z=202 peak, corresponding to the (4-chlorophenyl)(phenyl)amino group and the m/z=290 peak, corresponding to the (4-((2-oxo-2-(2-sulfonatoethylamino)ethoxy)methyl)cyclohexyl)methyl group. See FIG. 22. The identity of the glycine conjugate of Compound 22 was confirmed by the characteristic, m/z=487 consistent with an addition of glycine moiety. Furthermore, the fragmentation pattern also showed the characteristic m/z=202 peak, indicating the (4-chlorophenyl)(phenyl) amino group moiety was intact. See FIG. 23.

Example 10: In Vivo Metabolism of Sodium 2-(((1r,4r)-4-(((4-Chlorophenyl)(phenyl)carbamoyloxy)methyl)cyclohexyl)methoxy)acetate in Rats Three bile-duct cannulated male Sprague-Dawley rats were dosed intravenously (IV) at 2.00 mg/kg. In addition to plasma samples, bile and urine were collected from 0 to 48 hours post-dose.

2-(2-(((1r,4r)-4-(((4-Chlorophenyl)(phenyl)carbamoyloxy)methyl)cyclohexyl)methoxy)acetamido)ethanesulfonic acid (the taurine conjugate of Compound 22) (Compound 99) is a major metabolite of sodium 2-(((1r,4r)-4-(((4-chlorophenyl)(phenyl)carbamoyloxy)methyl)cyclohexyl)methoxy)acetate in rats. The taurine conjugate of Compound 22 was observed in bile but not observed in urine.

Example 11: Pharmacokinetics in Rats after an Oran Administration of 2-(2-(((1r,4r)-4-(((4-Chlorophenyl)(phenyl)carbamoyloxy)methyl)cyclohexyl)methoxy)acetamido)ethanesulfonic Acid (Compound 99)

Male Sprague-Dawley rats (N=3) were given a 1.25 mg/kg oral (PO) administration of 2-(2-(((1r,4r)-4-(((4-chlorophenyl)(phenyl)carbamoyloxy)methyl)cyclohexyl)methoxy)acetamido)ethanesulfonic acid (the taurine conjugate of Compound 22) (Compound 99) formulated in 20% hydroxypropyl cyclodextrin (HPCD) and dosed at 1.00 mL/kg. Blood samples were obtained from: 0.100 to 21.0 h post-dose for plasma drug concentration measurements. Plasma levels of the taurine conjugate of Compound 22 and 2-(((1r,4r)-4-(((4-chlorophenyl)(phenyl)carbamoyloxy)methyl)cyclohexyl)methoxy)acetic acid (Compound 22) were determined using a selective LC/MS/MS method. Pharmacokinetic parameters were estimated using non-compartmental pharmacokinetic analysis.

The taurine conjugate of Compound 22 showed minimal exposure and was converted to Compound 22 after a 1.25 mg/kg oral dose in rats. The terminal phase half-lives ($T_{1/2}$ of Compound 22 and the taurine conjugate of Compound 22 were 3.51 and 3.24 hr, respectively. The $C_{max}$ of Compound 22 and the taurine conjugate of Compound 22 were 0.214 μg/mL at 2.67 hr and 0.00193 μg/mL at 3.33 hr, respectively. The $AUC_{last}$ values of Compound 22 and the taurine conjugate of Compound 22 were 0.935 and 0.0119 hr·μg/mL, respectively. See FIG. 24.

The time to $T_{max}$ (3 h) for the taurine conjugate of Compound 22 was extended compared to the $T_{max}$ (1.5 h) after a 10 mg/kg oral dose of Compound 22. See FIG. 25

It is apparent from these data that the taurine conjugate of Compound 22 can act as a pro-drug for Compound 22.

Example 12: Excipient Solubility and Compatibility Study of 2-(((1r,4r)-4-(((4-Chlorophenyl)(phenyl)carbamoyloxy)methyl)cyclohexyl)methoxy)acetic acid (Compound 22) and Sodium 2-(((1r,4r)-4-(((4-Chlorophenyl)(phenyl)carbamoyloxy)methyl)cyclohexyl)methoxy)acetate (Compound 22 Sodium Salt)

The solubility of 2-(((1r,4r)-4-(((4-chlorophenyl)(phenyl)carbamoyloxy)methyl)cyclohexyl)methoxy)acetic acid (Compound 22) and sodium 2-(((1r,4r)-4-(((4-chlorophenyl)(phenyl)carbamoyloxy)methyl)cyclohexyl)methoxy)acetate (Compound 22 sodium salt) in various excipients was measured. The results of the solubility study are presented in the following table.

| | Solubility (mg/mL) | |
|---|---|---|
| Solvents | Sodium Salt of Compound 22 | Compound 22 |
| Corn Oil | <0.10 | 0.93 |
| Safflower oil | <0.10 | 0.82 |
| Labrasol | 12.98 | 54.1 |
| Cremophor RH 40 | 7.82 | 44.8 |
| Imwitor 742 | 16.20 | 37.4 |
| TPGS 1000 | 2.55 | 35.0 |

-continued

| Solvents | Solubility (mg/mL) Sodium Salt of Compound 22 | Compound 22 |
|---|---|---|
| Gelucire 44/14 | 1.61 | 43.4 |
| PEG400 | 4.85 | 44.6 |
| Lauroglycol 90 | 0.26 | 46.6 |
| PEG6000 | <10 | >20 |
| Gelucire 50/13 | <10 | >20 |

As can be seen from the preceding table, Compound 22 was observed to be generally more soluble than Compound 22 sodium salt in the excipients tested.

Compound 22 was tested for stability in three of the excipients. Solutions of Compound 22 in Cremophor RH40, Imwitor 742 and TPGS 10000 showed no observable degradation or API assay loss after four weeks in a glass vial at 50° C.

Based in part of the foregoing solubility and stability data, it is apparent that Compound 22 is suitable for formulation in liquid media.

Those skilled in the art will recognize that various modifications, additions, substitutions and variations to the illustrative examples set forth herein can be made without departing from the spirit of the invention and are, therefore, considered within the scope of the invention. All documents referenced above, including, but not limited to, printed publications and provisional and regular patent applications, are incorporated herein by reference in their entirety.

What is claimed is:

1. A method for modulating a prostacyclin (PGI2) receptor in an individual, comprising administering to said individual [in need thereof, a therapeutically effective amount of a prostacyclin receptor modulator] *a* compound selected from compounds of Formula [(XIIIa)] (*Xa*) and pharmaceutically acceptable salts, solvates and hydrates thereof:

(XIIIa)

[

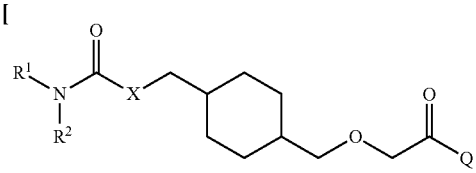

]

(*Xa*)

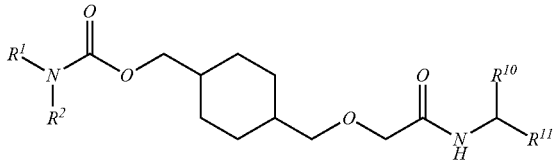

wherein:

$R^1$ and $R^2$ are each independently selected from: H, $C_1$-$C_6$ alkyl, [aryl] and heteroaryl; wherein $C_1$-$C_6$ alkyl, [aryl] and heteroaryl are each optionally substituted with one or two substituents selected from: [$C_1$-$C_6$ alkoxy, $C_1$-$C_6$ alkyl, aryl, $C_1$-$C_6$haloalkoxy, $C_1$-$C_6$haloakoalkyl and] halogen;

[X is O or $NR^3$;]

[$R^3$ is selected from H and $C_1$-$C_6$ alkyl; and]

[Q is selected from: OH, —$NHCH_2CH_2SO_3H$, 1-carboxyethylamino, 1-carboxy-4-guanidinobutylamino, 3-amino-1-carboxy-3-oxopropylamino, 1,2-dicarboxyethylamino, 1-carboxy-2-mercaptoethylamino, 4-amino-1-carboxy-4-oxobutylamino, 3-carboxy-1-carboxylatopropylamino, carboxymethylamino, 1-carboxy-2-(1H-imidazol-4-yl)ethylamino, 1-carboxy-2-methylbutylamino, 1-carboxy-3-methylbutylamino, 5-amino-1-carboxypentylamino, 1-carboxy-3-(methylthio)propylamino, 1-carboxy-2-phenylethylamino, 2-carboxypyrrolidin-1-yl, 1-carboxy-2-hydroxyethylamino, 1-carboxy-2-hydroxypropylamino, 1-carboxy-2-(1H-indol-3-yl)ethylamino, 1-carboxy-2-(4-hydroxyphenyl)ethylamino and 1-carboxy-2-methylpropylamino]

*$R^{10}$ is H; and*

*$R^{11}$ is selected from: H and $C_1$-$C_6$ alkyl; and*

*performing radio-imaging to localize and quantitate the PGI2 receptor in tissues in the individual;*

*wherein the individual has a disorder that is diabetic neuropathy, diabetic peripheral neuropathy, diabetic retinopathy, glaucoma, psoriasis, psoriatic arthritis, rheumatoid arthritis, Crohn's disease, ulcerative colitis, acne, type 1 diabetes, or type 2 diabetes;*

*wherein the compound of Formula (Xa) is radio-labeled with $^{18}F$, $^{125}I$, $^{123}I$, $^{124}I$, $^{131}I$, $^{75}Br$, $^{76}Br$ or $^{77}Br$.*

[2. The method according to claim 1, wherein $R^1$ and $R^2$ are each independently selected from: H, diphenylmethyl, 2,3-difluorophenyl, 2-fluoro-3-methoxyphenyl, 2-fluorophenyl, 2-fluoropyridin-4-yl, 2-methoxyphenyl, 3-(trifluoromethoxy)phenyl, 3,4-difluorophenyl, 3,5-difluorophenyl, 3,5-dimethylphenyl, 3-chloro-2-fluorophenyl, 3-chloro-4-fluorophenyl, 3-chloro-5-fluorophenyl, 3-chlorophenyl, 3-fluoro-4-methylphenyl, 3-fluorophenyl, 3-methoxyphenyl, 3-tolyl, 3-(trifluoromethyl)phenyl, 4-(trifluoromethoxy)phenyl, 4-chloro-3-fluorophenyl, 4-chlorophenyl, 4-ethoxyphenyl, 4-fluorophenyl, 4-methoxy-2-methylphenyl, 4-methoxyphenyl, 4-tolyl, 5-(trifluoromethyl)pyridin-2-yl, 5-chloropyridin-2-yl, 5-fluoropyridin-2-yl, 5-fluoropyridin-3-yl, 5-methoxypyridin-3-yl, 5methylpyridin-3-yl, 5-methylthiazol-2-yl, 5-methylthiophen-2-yl, 6-fluoropyridin-3-yl, methyl, phenyl, n-propyl, pyrazin-2-yl, pyridin-2-yl and pyridin-3-yl.]

[3. The method according to claim 1, wherein $R^1$ is selected from: diphenylmethyl, 2,3-difluorophenyl, 2-fluoro-3-methoxyphenyl, 2-fluorophenyl, 2-fluoropyridin-4-yl, 2-methoxyphenyl, 3-(trifluoromethoxy)phenyl, 3,4-difluorophenyl, 3,5-difluorophenyl, 3,5-dimethylphenyl, 3-chloro-2-fluorophenyl, 3-chloro-4-fluorophenyl, 3-chloro-5-fluorophenyl, 3-chlorophenyl, 3-fluoro-4-methylphenyl, 3-fluorophenyl, 3-methoxyphenyl, 3-tolyl, 3-(trifluoromethyl)phenyl, 4-(trifluoromethoxy)phenyl, 4-chloro-3-fluorophenyl, 4-chlorophenyl, 4-ethoxyphenyl, 4-fluorophenyl, 4-methoxy-2-methylphenyl, 4-methoxyphenyl, 4-tolyl, 5-(trifluoromethyl)pyridin-2-yl, 5-chloropyridin-2-yl, 5-fluoropyridin-2-yl, 5-fluoropyridin-3-yl, 5-methoxypyridin-3-yl, 5-methylpyridin-3-yl, 5-methylthiazol-2-yl, 5-methylthiophen-2-yl, 6-fluoropyridin-3-yl, phenyl, pyrazin-2-yl, pyridin-2-yl and pyridin-3-yl; and $R^2$ is selected from: H, methyl, n-propyl, phenyl, 3-tolyl, 4-tolyl, 3-fluorophenyl and 4-fluorophenyl.]

[4. The method according to claim 1, wherein X is O; and Q is OH.]

[5. The method according to claim 1, wherein the compound is selected from compounds of Formula (XIIIc) and pharmaceutically acceptable salts, solvates and hydrates thereof:

(XIIIc)

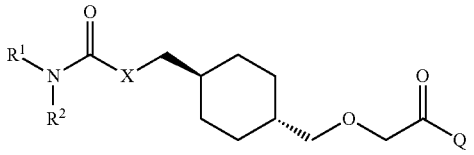

wherein:

$R^1$ and $R^2$ are each independently selected from: H, $C_1$-$C_6$ alkyl, aryl and heteroaryl; wherein $C_1$-$C_6$ alkyl, aryl and heteroaryl are each optionally substituted with one or two substituents selected from: $C_1$-$C_6$alkoxy, $C_1$-$C_6$ alkyl, aryl, $C_1$-$C_6$haloalkoxy, $C_1$-$C_6$haloalkyl and halogen;

X is O or $NR^3$;

$R^3$ is selected from H and $C_1$-$C_6$ alkyl; and

Q is selected from: OH, —$NHCH_2CH_2SO_3H$, 1-carboxyethylamino, 1-carboxy-4-guanidinobutylamino, 3-amino-1-carboxy-3-oxopropylamino, 1,2-dicarboxyethylamino, 1-carboxy-2-mercaptoethylamino, 4-amino-1-carboxy-4-oxobutylamine, 3-carboxy-1-carboxylatopropylamino, carboxymethylamino, 1-carboxy-2-(1H-imidazol-4-yl)ethylamino, 1-carboxy-2-methylbutylamino, 1-carboxy-3-methylbutylamino, 5-amino-1-carboxypentylamino, 1-carboxy-3-(methylthio)propylamino, 1-carboxy-2-phenylethylamino, 2-carboxypyrrolidin-1-yl, 1-carboxy-2-hydroxyethylamino, 1-carboxy-2-hydroxypropylamino, 1-carboxy-2(1H-indol-3-yl)ethylamino, 1-carboxy-2-(4-hydroxyphenyl)ethylamino and 1-carboxy-2-methylpropylamino.]

[6. The method according to claim 1, wherein the compound is selected from compounds of Formula (XIIIc) and pharmaceutically acceptable salts, solvate and hydrates thereof:

(XIIIc)

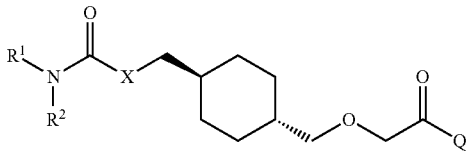

wherein:

$R^1$ is selected from: diphenylmethyl, 2,3-difluorophenyl, 2-fluoro-3-methoxyphenyl, 2-fluorophenyl, 2-fluoropyridin-4-yl, 2-methoxyphenyl, 3-(trifluoromethoxy)phenyl, 3,4-difluorophenyl, 3,5-difluorophenyl, 3,5-dimethylphenyl, 3-chloro-2-fluorophenyl, 3-chloro-4-fluorophenyl, 3-chloro-5-fluorophenyl, 3-chlorophenyl, 3-fluoro-4-methylphenyl, 3-fluorophenyl, 3-methoxyphenyl, 3-tolyl, 3-(trifluoromethyl)phenyl, 4-trifluoromethoxy)phenyl, 4-chloro-3-fluorophenyl, 4-chlorophenyl, 4-ethoxyphenyl, 4-fluorophenyl, 4-methoxy-2-methylphenyl, 4-methoxyphenyl, 4-tolyl, 5-(trifluoromethyl)pyridin-2-yl, 5-chloropyridin-2-yl, 5-fluoropyridin-2-yl, 5-fluoropyridin-3-yl, 5-methoxypyridin-3-yl, 5-methylpyridin-3-yl, 5-methylthiazol-2-yl, 5-methylthiophen-2-yl, 6-fluoropyridin-3-yl, phenyl, pyrazin-2-yl, pyridin-2-yl and pyridin-3-yl;

$R^2$ is selected from: H, methyl, n-propyl, phenyl, 3-tolyl, 4-tolyl, 3-fluorophenyl and 4-fluorophenyl;

X is O or $NR^3$;

$R^3$ is selected from H and methyl; and

Q is selected from: OH, —$NHCH_2CH_2SO_3H$ and carboxymethylamino.]

[7. The method according to claim 1, wherein the compound is selected from compounds of Formula (Ia) and pharmaceutically acceptable salts, solvates and hydrates thereof:

(Ia)

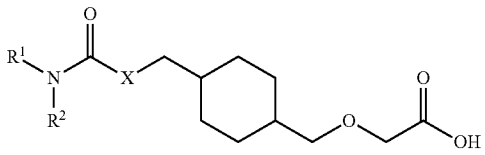

wherein:

$R^1$ and $R^2$ are each independently selected from: H, $C_1$-$C_6$ alkyl, aryl and heteroaryl;

wherein $C_1$-$C_6$ alkyl, aryl and heteroaryl are each optionally substituted with one or two substituents selected from: $C_1$-$C_6$alkoxy, $C_1$-$C_6$ alkyl, aryl, $C_1$-$C_6$ haloalkoxy, $C_1$-$C_6$haloalkyl and halogen;

X is O or $NR^3$; and $R^3$ is selected from H and $C_1$-$C_6$ alkyl.]

[8. The method according to claim 1, wherein the compound is selected from compounds of Formula (Ic) and pharmaceutically acceptable salts, solvates and hydrates thereof:

(Ic)

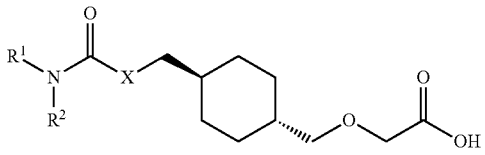

wherein:

$R^1$ and $R^2$ are each independently selected from: H, $C_1$-$C_6$ alkyl, aryl and heteroaryl;

wherein $C_1$-$C_6$ alkyl, aryl and heteroaryl are each optionally substituted with one or two substituents selected from: $C_1$-$C_6$alkoxy, $C_1$-$C_6$ alkyl, aryl, $C_1$-$C_6$haloalkoxy; $C_1$-$C_6$haloalkyl and halogen;

X is O or $NR^3$; and $R^3$ is selected from H and $C_1$-$C_6$ alkyl.]

[9. The method according to claim 1, wherein the compound is selected from compounds of Formula (Ic) and pharmaceutically acceptable salt, solvates and hydrates thereof:

(Ic)

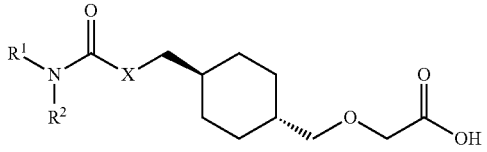

wherein:

$R^1$ is selected from: diphenylmethyl, 2,3-difluorophenyl, 2-fluoro-3-methoxyphenyl, 2-fluorophenyl, 2-fluoropyridin-4-yl, 2-methoxyphenyl, 3-(trifluoromethoxy)phenyl, 3,4-difluorophenyl, 3,5-difluorophenyl, 3,5-dimethylphenyl, 3-chloro-2-fluorophenyl, 3-chloro-4-fluorophenyl, 3-chloro-5-fluorophenyl, 3-chlorophenyl, 3-fluoro-4-methylphenyl, 3-fluorophenyl, 3-methoxyphenyl, 3-tolyl, 3-(trifluoromethyl)phenyl, 4-trifluoromethoxy)phenyl, 4-chloro-3-fluorophenyl, 4-chlorophenyl, 4-ethoxyphenyl, 4-fluorophenyl, 4-methoxy-2-methylphenyl, 4-methoxyphenyl, 4-tolyl, 5-(trifluoromethyl)pyridin-2-yl, 5-chloropyridin-2-yl, 5-fluoropyridin-2-yl, 5-fluoropyridin-3-yl, 5-methoxypyridin-3-yl, 5-methylpyridin-3-yl, 5-methylthiazol-2-yl, 5-methylthiophen-2-yl, 6-fluoropyridin-3-yl, phenyl, pyrazin-2-yl, pyridin-2-yl and pyridin-3-yl;

$R^2$ is selected from: H, methyl, n-propyl, phenyl, 3-tolyl, 4-tolyl, 3-fluorophenyl and 4-fluorophenyl;

X is O or $NR^3$; and $R^3$ is selected from H and methyl.]

[10. The method according to claim 1, wherein the compound is selected from compounds of Formula (Ik) and pharmaceutically acceptable salts, solvates and hydrates thereof:

(Ik)

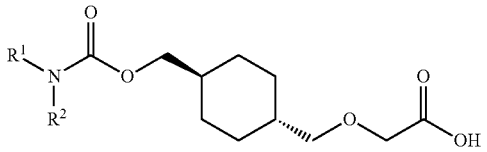

wherein:

$R^1$ and $R^2$ are each independently selected from: H, $C_1$-$C_6$ alkyl, aryl and heteroaryl; wherein $C_1$-$C_6$ alkyl, aryl and heteroaryl are each optionally substituted with one or two substituents selected from: $C_1$-$C_6$alkoxy, $C_1$-$C_6$ alkyl, aryl, $C_1$-$C_6$haloalkoxy; $C_1$-$C_6$haloalkyl and halogen.]

[11. The method according to claim 1, wherein the compound is selected from compounds of Formula (Ik) and pharmaceutically acceptable salts, solvates and hydrates thereof:

(Ik)

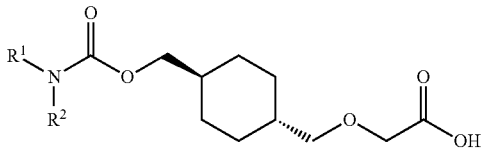

wherein:

$R^1$ is selected from: diphenylmethyl, 2,3-difluorophenyl, 2-fluoro-3-methoxyphenyl, 2-fluorophenyl, 2-fluoropyridin-4-yl, 2-methoxyphenyl, 3-(trifluoromethoxy)phenyl, 3,4-difluorophenyl, 3,5-difluorophenyl, 3,5-dimethylphenyl, 3-chloro-2-fluorophenyl, 3-chloro-4-fluorophenyl, 3-chloro-5-fluorophenyl, 3-chlorophenyl, 3-fluoro-4-methylphenyl, 3-fluorophenyl, 3-methoxyphenyl, 3-tolyl, 3-(trifluoromethyl)phenyl, 4-trifluoromethoxy)phenyl, 4-chloro-3-fluorophenyl, 4-chlorophenyl, 4-ethoxyphenyl, 4-fluorophenyl, 4-methoxy-2-methylphenyl, 4-methoxyphenyl, 4-tolyl, 5-(trifluoromethyl)pyridin-2-yl, 5-chloropyridin-2-yl, 5-fluoropyridin-2-yl, 5-fluoropyridin-3-yl, 5-methoxypyridin-3-yl, 5-methylpyridin-3-yl, 5-methylthiazol-2-yl, 5-methylthiophen-2-yl, 6-fluoropyridin-3-yl, phenyl, pyrazin-2-yl, pyridin-2-yl and pyridin-3-yl;

$R^2$ is selected from: H, methyl, n-propyl, phenyl, 3-tolyl, 4-tolyl, 3-fluorophenyl and 4-fluorophenyl.]

[12. The method according to claim 1, wherein the compound is selected from the following compounds and pharmaceutically acceptable salts, solvates and hydrates thereof:

2-(((1r,4r)-4-((3-benzhydrylureido)methyl)cyclohexyl)methoxy)acetic acid;

2-(((1r,4r)-4-((3,3-diphenylureido)methyl)cyclohexyl)methoxy)acetic acid;

2-(((1r,4r)-4-((3-(3-fluorophenyl)-3-phenylureido)methyl)cyclohexyl)methoxy)acetic acid;

2-(((1r,4r)-4-((1-methyl-3,3-diphenylureido)methyl)cyclohexyl)methoxy)acetic acid;

2-(((1r,4r)-4-((diphenylcarbamoyloxy)methyl)cyclohexyl)methoxy)acetic acid;

2-(((1r,4r)-4-((3-(3-chlorophenyl)-3-phenylureido)methyl)cyclohexyl)methoxy)acetic acid;

2-(((1s,4s)-4-((diphenylcarbamoyloxy)methyl)cyclohexyl)methoxy)acetic acid;

2-(((1r,4r)-4-((3-(4-fluorophenyl)-3-phenylureido)methyl)cyclohexyl)methoxy)acetic acid;

2-(((1s,4s)-4-((3,3-diphenylureido)methyl)cyclohexyl)methoxy)acetic acid;

2-(((1r,4r)-4-((3-(2-fluorophenyl)-3-phenylureido)methyl)cyclohexyl)methoxy)acetic acid;

2-(((1r,4r)-4-((3-(4-chlorophenyl)-3-phenylureido)methyl)cyclohexyl)methoxy)acetic acid;

2-(((1r,4r)-4-((3-phenyl-3-m-tolylureido)methyl)cyclohexyl)methoxy)acetic acid;

2-(((1r,4r)-4-((3-phenyl-3-p-tolylureido)methyl)cyclohexyl)methoxy)acetic acid;

2-(((1r,4r)-4-(((3-methoxyphenyl)(phenyl)carbamoyloxy)methyl)cyclohexyl)methoxy)acetic acid;

2-(((1r,4r)-4-((3,3-di p-tolylureido)methyl)cyclohexyl)methoxy)acetic acid;

2-(((1r,4r)-4-((3,3-di m-tolylureido)methyl)cyclohexyl)methoxy)acetic acid;

2-(((1r,4r)-4-((3-(3-methoxyphenyl)-3-phenylureido)methyl)cyclohexyl)methoxy)acetic acid;

2-(((1r,4r)-4-((3-(4-methoxyphenyl)-3-phenylureido)methyl)cyclohexyl)methoxy)acetic acid;

2-(((1r,4r)-4-((3-(4-methoxy-2-methylphenyl)-3-phenylureido)methyl)cyclohexyl)methoxy)acetic acid;

2-(((1r,4r)-4-((3-phenyl-3-(3-trifluoromethyl)phenyl)ureido)methyl)cyclohexyl)methoxy)acetic acid;

2-(((1r,4r)-4-(((4-methoxyphenyl)(phenyl)carbamoyloxy)methyl)cyclohexyl)methoxy)acetic acid;

2-(((1r,4r)-4-(((4-chlorophenyl)(phenyl)carbamoyloxy)methyl)cyclohexyl)methoxy)acetic acid;
2-(((1r,4r)-4-(((3-fluorophenyl)(phenyl)carbamoyloxy)methyl)cyclohexyl)methoxy)acetic acid;
2-(((1s,4s)-4-(((4-methoxyphenyl)(phenyl)carbamoyloxy)methyl)cyclohexyl)methoxy)acetic acid;
2-(((1s,4s)-4-(((4-chlorophenyl)(phenyl)carbamoyloxy)methyl)cyclohexyl)methoxy)acetic acid;
2-(((1r,4r)-4-((phenyl(m-tolyl)carbamoyloxy)methyl)cyclohexyl)methoxy)acetic acid;
2-(((1r,4r)-4-(((3-chlorophenyl)(phenyl)carbamoyloxy)methyl)cyclohexyl)methoxy)acetic acid;
2-(((1r,4r)-4-((phenylcarbamoyloxy)methyl)cyclohexyl)methoxy)acetic acid;
2-(((1s,4s)-4-(((3-chlorophenyl)(phenyl)carbamoyloxy)methyl)cyclohexyl)methoxy)acetic acid;
2-(((1s,4s)-4-((phenyl(m-tolyl)carbamoyloxy)methyl)cyclohexyl)methoxy)acetic acid;
2-(((1s,4s)-4-(((2-methoxyphenyl)(phenyl)carbamoyloxy)methyl)cyclohexyl)methoxy)acetic acid;
2-(((1s,4s)-4-(((3-methoxyphenyl)(phenyl)carbamoyloxy)methyl)cyclohexyl)methoxy)acetic acid;
2-(((1s,4s)-4-((phenyl(p-tolyl)carbamoyloxy)methyl)cyclohexyl)methoxy)acetic acid;
2-(((1s,4s)-4-(((4-fluorophenyl)(phenyl)carbamoyloxy)methyl)cyclohexyl)methoxy)acetic acid;
2-(((1r,4r)-4-(((4-chloro-3-fluorophenyl)(phenyl)carbamoyloxy)methyl)cyclohexyl)methoxy)acetic acid;
2-(((1r,4r)-4-(((3-chloro-4-fluorophenyl)(phenyl)carbamoyloxy)methyl)cyclohexyl)methoxy)acetic acid;
2-(((1r,4r)-4-(((3-fluoro-4-methylphenyl)(phenyl)carbamoyloxy)methyl)cyclohexyl)methoxy)acetic acid;
2-(((1r,4r)-4-(((3,5-difluorophenyl)(phenyl)carbamoyloxy)methyl)cyclohexyl)methoxy)acetic acid;
2-(((1r,4r)-4-(((3,4-difluorophenyl)(phenyl)carbamoyloxy)methyl)cyclohexyl)methoxy)acetic acid;
2-(((1r,4r)-4-(((4-fluorophenyl)(phenyl)carbamoyloxy)methyl)cyclohexyl)methoxy)acetic acid;
2-(((1r,4r)-4-((phenyl(p-tolyl)carbamoyloxy)methyl)cyclohexyl)methoxy)acetic acid;
2-(((1r,4r)-4-((3-(2,3-difluorophenyl)-3-phenylureido)methyl)cyclohexyl)methoxy)acetic acid;
2-(((1r,4r)-4-((3-(3,5-difluorophenyl)-3-phenylureido)methyl)cyclohexyl)methoxy)acetic acid;
2-(((1r,4r)-4-((3-(3-chloro-2-fluorophenyl)-3-phenylureido)methyl)cyclohexyl)methoxy)acetic acid;
2-(((1r,4r)-4-(((3-chloro-5-fluorophenyl)(phenyl)carbamoyloxy)methyl)cyclohexyl)methoxy)acetic acid;
2-(((1r,4r)-4-((3-(3-chloro-5-fluorophenyl)-3-phenylureido)methyl)cyclohexyl)methoxy)acetic acid;
2-(((1r,4r)-4-((3-benzhydryl-3-methylureido)methyl)cyclohexyl)methoxy)acetic acid;
2-(((1r,4r)-4-((phenyl(pyridin-3-yl)carbamoyloxy)methyl)cyclohexyl)methoxy)acetic acid;
2-(((1r,4r)-4-(((5-methylthiophen-2-yl)(phenyl)carbamoyloxy)methyl)cyclohexyl)methoxy)acetic acid;
2-(((1r,4r)-4-(((2,3-difluorophenyl)(phenyl)carbamoyloxy)methyl)cyclohexyl)methoxy)acetic acid;
2-(((1r,4r)-4-((3-(4-chloro-3-fluorophenyl)-3-phenylureido)methyl)cyclohexyl)methoxy)acetic acid;
2-(((1r,4r)-4-(((3-(2-fluoro-3-methoxyphenyl)-3-phenylureido)methyl)cyclohexyl)methoxy)acetic acid;
2-(((1r,4r)-4-((3-(3,4-difluorophenyl)-3-phenylureido)methyl)cyclohexyl)methoxy)acetic acid;
2-(((1r,4r)-4-(((3-fluorophenyl)(4-methoxyphenyl)carbamoyloxy)methyl)cyclohexyl)methoxy)acetic acid;
2-(((1r,4r)-4-(((4-chlorophenyl)(3-fluorophenyl)carbamoyloxy)methyl)cyclohexyl)methoxy)acetic acid;
2-(((1r,4r)-4-(((3-fluorophenyl)(4-fluorophenyl)carbamoyloxy)methyl)cyclohexyl)methoxy)acetic acid;
2-(((1r,4r)-4-(((3-chlorophenyl)(3-fluorophenyl)carbamoyloxy)methyl)cyclohexyl)methoxy)acetic acid;
2-(((1r,4r)-4-(((3-fluorophenyl)(m-tolyl)carbamoyloxy)methyl)cyclohexyl)methoxy)acetic acid;
2-(((1r,4r)-4-(((4-chloro-3-fluorophenyl)(3-fluorophenyl)carbamoyloxy)methyl)cyclohexyl)methoxy)acetic acid;
2-(((1r,4r)-4-(((3-chloro-4-fluorophenyl)(3-fluorophenyl)carbamoyloxy)methyl)cyclohexyl)methoxy)acetic acid;
2-(((1r,4r)-4-(((3-fluoro-4-methylphenyl)(3-fluorophenyl)carbamoyloxy)methyl)cyclohexyl)methoxy)acetic acid;
2-(((1r,4r)-4-((phenyl(pyridin-2-yl)carbamoyloxy)methyl)cyclohexyl)methoxy)acetic acid;
2-(((1r,4r)-4-(((3,5-difluorophenyl)(3-fluorophenyl)carbamoyloxy)methyl)cyclohexyl)methoxy)acetic acid;
2-(((1r,4r)-4-(((3,4-difluorophenyl)(3-fluorophenyl)carbamoyloxy)methyl)cyclohexyl)methoxy)acetic acid;
2-(((1r,4r)-4-((bis(3-fluorophenyl)carbamoyloxy)methyl)cyclohexyl)methoxy)acetic acid;
2-(((1r,4r)-4-(((3-fluorophenyl)(3-methoxyphenyl)carbamoyloxy)methyl)cyclohexyl)methoxy)acetic acid;
2-(((1r,4r)-4-(((3,5-dimethylphenyl)(3-fluorophenyl)carbamoyloxy)methyl)cyclohexyl)methoxy)acetic acid;
2-(((1r,4r)-4-(((3-fluorophenyl)(p-tolyl)carbamoyloxy)methyl)cyclohexyl)methoxy)acetic acid;
2-(((1r,4r)-4-(((3-fluorophenyl)(6-fluoropyridin-3-yl)carbamoyloxy)methyl)cyclohexyl)methoxy)acetic acid;
2-(((1r,4r)-4-(((3-fluorophenyl)(5-methylthiophen-2-yl)carbamoyloxy)methyl)cyclohexyl)methoxy)acetic acid;
2-(((1r,4r)-4-(((4-ethoxyphenyl)(3-fluorophenyl)carbamoyloxy)methyl)cyclohexyl)methoxy)acetic acid;
2-(((1r,4r)-4-(((3-fluorophenyl)(3-(trifluoromethoxy)phenyl)carbamoyloxy)methyl)cyclohexyl)methoxy)acetic acid;
2-(((1r,4r)-4-(((3-fluorophenyl)(pyridin-3-yl)carbamoyloxy)methyl)cyclohexyl)methoxy)acetic acid;
2-(((1r,4r)-4-(((3-fluorophenyl)(pyrazin-2-yl)carbamoyloxy)methyl)cyclohexyl)methoxy)acetic acid;
2-(((1r,4r)-4-(((4-chlorophenyl)(4-fluorophenyl)carbamoyloxy)methyl)cyclohexyl)methoxy)acetic acid;
2-(((1r,4r)-4-(((4-fluorophenyl)(5-methylthiophenyl-2-yl)carbamoyloxy)methyl)cyclohexyl)methoxy)acetic acid;
2-(((1r,4r)-4-(((3-chlorophenyl)(4-fluorophenyl)carbamoyloxy)methyl)cyclohexyl)methoxy)acetic acid;
2-(((1r,4r)-4-(((4-fluorophenyl)(pyridin-3-yl)carbamoyloxy)methyl)cyclohexyl)methoxy)acetic acid;
2-(((1r,4r)-4-(((4-ethoxyphenyl)(4-fluorophenyl)carbamoyloxy)methyl)cyclohexyl)methoxy)acetic acid;
2-(((1r,4r)-4-(((4-fluorophenyl)(4-trifluoromethoxy)phenyl)carbamoyloxy)methyl)cyclohexyl)methoxy)acetic acid;
2-(((1r,4r)-4-(((4-fluorophenyl)(m-tolyl)carbamoyloxy)methyl)cyclohexyl)methoxy)acetic acid;
2-(((1r,4r)-4-((bis(4-fluorophenyl)carbamoyloxy)methyl)cyclohexyl)methoxy)acetic acid;
2-(((1r,4r)-4-(((6-fluoropyridin-3-yl)(phenyl)carbamoyloxy)methyl)cyclohexyl)methoxy)acetic acid;
2-(((1r,4r)-4-((phenyl(pyrazin-2-yl)carbamoyloxy)methyl)cyclohexyl)methoxy)acetic acid;

2-(((1r,4r)-4-((benzhydryl(methyl)carbamoyloxy)methyl)cyclohexyl)methoxy)acetic acid;

2-(((1r,4r)-4-((3-benzhydryl-1,3-dimethylureido)methyl)cyclohexyl)methoxy)acetic acid;

2-(((1r,4r)-4-(((4-ethoxyphenyl)(phenyl)carbamoyloxy)methyl)cyclohexyl)methoxy)acetic acid;

2-(((1r,4r)-4-(((2-fluoropyridin-4-yl)(phenyl)carbamoyloxy)methyl)cyclohexyl)methoxy)acetic acid;

2-(((1r,4r)-4-(((5-methoxypyridin-3-yl)(phenyl)carbamoyloxy)methyl)cyclohexyl)methoxy)acetic acid;

2-(((1r,4r)-4-(((5-fluoropyridin-2-yl)(phenyl)carbamoyloxy)methyl)cyclohexyl)methoxy)acetic acid;

2-(((1r,4r)-4-((phenyl(5-(trifluoromethyl)pyrazin-2-yl)carbamoyloxy)methyl)cyclohexyl)methoxy)acetic acid;

2-(((1r,4r)-4-(((5-methylpyridin-3-yl)(phenyl)carbamoyloxy)methyl)cyclohexyl)methoxy)acetic acid;

2-(((1r,4r)-4-(((5-chloropyridin-2-yl)(phenyl)carbamoyloxy)methyl)cyclohexyl)methoxy)acetic acid;

2-(((1r,4r)-4-(((5-fluoropyridin-3-yl)(phenyl)carbamoyloxy)methyl)cyclohexyl)methoxy)acetic acid;

2-(((1r,4r)-4-((benzhydryl(propyl)carbamoyloxy)methyl)cyclohexyl)methoxy)acetic acid; and 2-(((1r,4r)-4-(((5-methylthiazol-2-yl)(phenyl)carbamoyloxy)methyl)cyclohexyl)methoxy)acetic acid.]

[13. The method according to claim 1, wherein the compound is selected from the following pharmaceutically acceptable salts of compounds of Formula XIIIa and solvates and hydrates thereof:

sodium 2-(((1r,4r)-4-((diphenylcarbamoyloxy)methyl)cyclohexyl)methoxy)acetate;

sodium 2-(((1r,4r)-4-(((4-chlorophenyl)(phenyl)carbamoyloxy)methyl)cyclohexyl)methoxy)acetate;

sodium 2-(((1r,4r)-4-(((4-fluorophenyl)(phenyl)carbamoyloxy)methyl)cyclohexyl)methoxy)acetate;

sodium 2-(((1r,4r)-4-(((3-fluorophenyl)(phenyl)carbamoyloxy)methyl)cyclohexyl)methoxy)acetate;

magnesium 2-(((1r,4r)-4-(((3-fluorophenyl)(phenyl)carbamoyloxy)methyl)cyclohexyl)methoxy)acetate;

potassium 2-(((1r,4r)-4-(((3-fluorophenyl)(phenyl)carbamoyloxy)methyl)cyclohexyl)methoxy)acetate; and calcium 2-(((1r,4r)-4-(((3-fluorophenyl)(phenyl)carbamoyloxy)methyl)cyclohexyl)methoxy)acetate.]

[14. The method according to claim 1, wherein the compound is selected from the following solvates and hydrates:

sodium 2-(((1r,4r)-4-(((4-chlorophenyl)(phenyl)carbamoyloxy)methyl)cyclohexyl)methoxy)acetate hydrate;

sodium 2-(((1r,4r)-4-(((3-fluorophenyl)(phenyl)carbamoyloxy)methyl)cyclohexyl)methoxy)acetate hydrate;

magnesium 2-(((1r,4r)-4-(((3-fluorophenyl)(phenyl)carbamoyloxy)methyl)cyclohexyl)methoxy)acetate isopropanol solvate;

potassium 2-(((1r,4r)-4-(((3-fluorophenyl)(phenyl)carbamoyloxy)methyl)cyclohexyl)methoxy)acetate isopropanol solvate; and calcium 2-(((1r,4r)-4-(((3-fluorophenyl)(phenyl)carbamoyloxy)methyl)cyclohexyl)methoxy)acetate isopropanol solvate.]

[15. The method according to claim 1 wherein the compound is selected from the following compound and pharmaceutically acceptable salts, solvates and hydrates thereof:

2-(((1r,4r)-4-(((4-chlorophenyl)(phenyl)carbamoyloxy)methyl)cyclohexyl)methoxy)acetic acid.]

[16. The method according to claim 1 wherein the compound is selected from the following pharmaceutically acceptable salt and solvates and hydrates thereof:

sodium 2-(((1r,4r)-4-(((4-chlorophenyl)(phenyl)carbamoyloxy)methyl)cyclohexyl)methoxy)acetate.]

[17. The method according to claim 1 wherein the compound is:

sodium 2-(((1r,4r)-4-(((4-chlorophenyl)(phenyl)carbamoyloxy)methyl)cyclohexyl)methoxy)acetate hydrate.]

[18. The method according to claim 1, wherein the individual has a disorder comprising platelet aggregation, coronary artery disease, myocardial infarction, transient ischemic attack, angina, stroke, atrial fibrillation, blood clot formation, atherosclerosis, atherothrombosis, asthma, diabetic neuropathy, diabetic peripheral neuropathy, diabetic retinopathy, vasoconstriction, platelet aggregation in a diabetic patient, glaucoma, hypertension, inflammation, psoriasis, psoriatic arthritis, rheumatoid arthritis, Crohn's disease, transplant rejection, multiple sclerosis, systemic lupus erythematosus, ulcerative colitis, ischemia-reperfusion injury, restenosis, acne, type 1 diabetes, type 2 diabetes, sepsis, or chronic obstructive pulmonary disease.]

[19. The method according to claim 1, wherein the individual has pulmonary arterial hypertension (PAH).]

[20. The method according to claim 19, wherein the PAH is selected from:

idiopathic PAH;

familial PAH;

PAH associated with a collagen vascular disease selected from: scleroderma, CREST syndrome, systemic lupus erythematosus (SLE), rheumatoid arthritis, Takayasu's arteritis, polymyositis, and dermatomyositis;

PAH associated with a congenital heart disease selected from: atrial septic defect (ASD), ventricular septic defect (VSD) and patent ductus arteriosus in an individual;

PAH associated with portal hypertension;

PAH associated with HIV infection;

PAH associated with ingestion of a drug or toxin;

PAH associated with hereditary hemorrhagic telangiectasia;

PAH associated with splenectomy;

PAH associated with significant venous or capillary involvement;

PAH associated with pulmonary venoocclusive disease (PVOD); and

PAH associated with pulmonary capillary hemangiomatosis (PCH).]

[21. A method for modulating a prostacyclin (PGI2) receptor in an individual comprising administering to the individual in need thereof, a therapeutically effective amount of 2-(((1r,4r)-4-(((4-chlorophenyl)(phenyl)carbamoyloxy)methyl)cyclohexyl)methoxy)acetic acid, or hydrate thereof.]

[22. The method according to claim 21, wherein the individual has a disorder comprising platelet aggregation, coronary artery disease, myocardial infarction, transient ischemic attack, angina, stroke, atrial fibrillation, blood clot formation, atherosclerosis, atherothrombosis, asthma, diabetic neuropathy, diabetic peripheral neuropathy, diabetic retinopathy, vasoconstriction, platelet aggregation in a diabetic patient, glaucoma, hypertension, inflammation, psoriasis, psoriatic arthritis, rheumatoid arthritis, Crohn's disease, transplant rejection, multiple sclerosis, systemic lupus erythematosus, ulcerative colitis, ischemia-reperfusion injury, restenosis, acne, type 1 diabetes, type 2 diabetes, sepsis, or chronic obstructive pulmonary disease.]

[23. The method of claim 21, wherein the individual has pulmonary arterial hypertension (PAH).]

[24. The method according to claim 23, wherein the PAH is selected from:

idiopathic PAH;

familial PAH;

PAH associated with a collagen vascular disease selected from: scleroderma, CREST syndrome, systemic lupus erythematosus (SLE), rheumatoid arthritis, Takayasu's arteritis, polymyositis, and dermatomyositis;

PAH associated with a congenital heart disease selected from: atrial septic defect (ASD), ventricular septic defect (VSD) and patent ductus arteriosus in an individual;

PAH associated with portal hypertension;

PAH associated with HIV infection;

PAH associated with ingestion of a drug or toxin;

PAH associated with hereditary hemorrhagic telangiectasia;

PAH associated with splenectomy;

PAH associated with significant venous or capillary involvement;

PAH associated with pulmonary venooclusive disease (PVOD); and

PAH associated with pulmonary capillary hemangiomatosis (PCH).]

[25. A method for inhibiting platelet aggregation in an individual, comprising administering to the individual in need thereof, a therapeutically effective amount of a compound of Formula (XIIIa), or a pharmaceutically acceptable salt, solvate, or hydrate thereof:

(XIIIa)

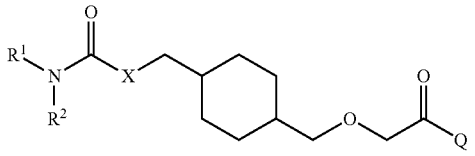

wherein:

$R^1$ and $R^2$ are each independently selected from: H, $C_1$-$C_6$ alkyl, aryl and heteroaryl;

wherein $C_1$-$C_6$ alkyl, aryl and heteroaryl are each optionally substituted with one or two substituents selected from: $C_1$-$C_6$alkoxy, $C_1$-$C_6$ alkyl, aryl, $C_1$-$C_6$haloalkoxy, $C_1$-$C_6$haloalkyl and halogen;

X is O or $NR^3$;

$R^3$ is selected from H and $C_1$-$C_6$ alkyl; and

Q is selected from: OH, —$NHCH_2CH_2SO_3H$, 1-carboxyethylamino, 1-carboxy-4-guanidinobutylamino, 3-amino-1-carboxy-3-oxopropylamino, 1,2-dicarboxyethylamino, 1-carboxy-2-mercaptoethylamino, 4-amino-1-carboxy-4-oxobutylamino, 3-carboxy-1-carboxylatopropylamino, carboxymethylamino, 1-carboxy-2-(1H-imidazol-4-yl)ethylamino, 1-carboxy-2-methylbutylamino, 1-carboxy-3-methylbutylamino, 5-amino-1-carboxypentylamino, 1-carboxy-3-(methylthio)propylamino, 1-carboxy-2-phenylethylamino, 2-carboxypyrrolidin-1-yl, 1-carboxy-2-hydroxyethylamino, 1-carboxy-2-hydroxypropylamino, 1-carboxy-2-(1H-indol-3-yl)ethylamino, 1-carboxy-2-(4-hydroxyphenyl)ethylamino and 1-carboxy-2-methylpropylamino.]

[26. The method according to claim 25, wherein the compound has the structure of Formula (Ik), or a pharmaceutically acceptable salt, solvate, or hydrate thereof:

(Ik)

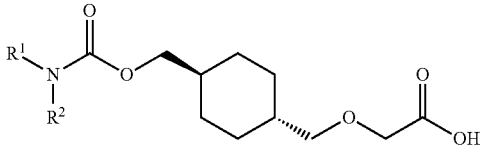

wherein:

$R^1$ is selected from: diphenylmethyl, 2,3-difluorophenyl, 2-fluoro-3-methoxyphenyl, 2-fluorophenyl, 2-fluoropyridin-4-yl, 2-methoxyphenyl, 3-(trifluoromethoxy)phenyl, 3,4-difluorophenyl, 3,5-difluorophenyl, 3,5-dimethylphenyl, 3-chloro-2-fluorophenyl, 3-chloro-4-fluorophenyl, 3-chloro-5-fluorophenyl, 3-chlorophenyl, 3-fluoro-4-methylphenyl, 3-fluorophenyl, 3-methoxyphenyl, 3-tolyl, 3-(trifluoromethyl)phenyl, 4-trifluoromethoxy)phenyl, 4-chloro-3-fluorophenyl, 4-chlorophenyl, 4-ethoxyphenyl, 4-fluorophenyl, 4-methoxy-2-methylphenyl, 4-methoxyphenyl, 4-tolyl, 5-(trifluoromethyl)pyridin-2-yl, 5-chloropyridin-2-yl, 5-fluoropyridin-2-yl, 5-fluoropyridin-3-yl, 5-methoxypyridin-3-yl, 5-methylpyridin-3-yl, 5-methylthiazol-2-yl, 5-methylthiophen-2-yl, 6-fluoropyridin-3-yl, phenyl, pyrazin-2-yl, pyridin-2-yl and pyridin-3-yl; and $R^2$ is selected from: H, methyl, n-propyl, phenyl, 3-tolyl, 4-tolyl, 3-fluorophenyl and 4-fluorophenyl.]

[27. The method according to claim 26, wherein the compound is:

2-(((1r,4r)-4-((3-benzhydrylureido)methyl)cyclohexyl)methoxy)acetic acid;

2-(((1r,4r)-4-((3,3-diphenylureido)methyl)cyclohexyl)methoxy)acetic acid;

2-(((1r,4r)-4-((3-(3-fluorophenyl)-3-phenylureido)methyl)cyclohexyl)methoxy)acetic acid;

2-(((1r,4r)-4-(1-methyl-3,3-diphenylureido)methyl)cyclohexyl)methoxy)acetic acid;

2-(((1r,4r)-4-((diphenylcarbamoyloxy)methyl)cyclohexyl)methoxy)acetic acid;

2-(((1r,4r)-4-((3-(3-chlorophenyl)-3-phenylureido)methyl)cyclohexyl)methoxy)acetic acid;

2-(((1s,4s)-4-((diphenylcarbamoyloxy)methyl)cyclohexyl)methoxy)acetic acid;

2-(((1r,4r)-4-((3-(4-fluorophenyl)-3-phenylureido)methyl)cyclohexyl)methoxy)acetic acid;

2-(((1s,4s)-4-((3,3-diphenylureido)methyl)cyclohexyl)methoxy)acetic acid;

2-(((1r,4r)-4-((3-(2-fluorophenyl)-3-phenylureido)methyl)cyclohexyl)methoxy)acetic acid;

2-(((1r,4r)-4-((3-(4-chlorophenyl)-3-phenylureido)methyl)cyclohexyl)methoxy)acetic acid;

2-(((1r,4r)-4-((3-phenyl-3-m-tolylureido)methyl)cyclohexyl)methoxy)acetic acid;

2-(((1r,4r)-4-((3-phenyl-3-p-tolylureido)methyl)cyclohexyl)methoxy)acetic acid;

2-(((1r,4r)-4-(((3-methoxyphenyl)(phenyl)carbamoyloxy)methyl)cyclohexyl)methoxy)acetic acid;

2-(((1r,4r)-4-((3,3-di p-tolylureido)methyl)cyclohexyl)methoxy)acetic acid;

2-(((1r,4r)-4-((3,3-di m-tolylureido)methyl)cyclohexyl)methoxy)acetic acid;

2-(((1r,4r)-4-((3-(3-methoxyphenyl)-3-phenylureido)methyl)cyclohexyl)methoxy)acetic acid;

2-(((1r,4r)-4-((3-(4-methoxyphenyl)-3-phenylureido)methyl)cyclohexyl)methoxy)acetic acid;
2-(((1r,4r)-4-((3-(4-methoxy-2-methylphenyl)-3-phenylureido)methyl)cyclohexyl)methoxy)acetic acid;
2-(((1r,4r)-4-((3-phenyl-3-(3-trifluoromethyl)phenyl)ureido)methyl)cyclohexyl)methoxy)acetic acid;
2-(((1r,4r)-4-(((4-methoxyphenyl)(phenyl)carbamoyloxy)methyl)cyclohexyl)methoxy)acetic acid;
2-(((1r,4r)-4-(((4-chlorophenyl)(phenyl)carbamoyloxy)methyl)cyclohexyl)methoxy)acetic acid;
2-(((1r,4r)-4-(((3-fluorophenyl)(phenyl)carbamoyloxy)methyl)cyclohexyl)methoxy)acetic acid;
2-(((1s,4s)-4-(((4-methoxyphenyl)(phenyl)carbamoyloxy)methyl)cyclohexyl)methoxy)acetic acid;
2-(((1s,4s)-4-(((4-chlorophenyl)(phenyl)carbamoyloxy)methyl)cyclohexyl)methoxy)acetic acid;
2-(((1r,4r)-4-((phenyl(m-tolyl)carbamoyloxy)methyl)cyclohexyl)methoxy)acetic acid;
2-(((1r,4r)-4-(((3-chlorophenyl)(phenyl)carbamoyloxy)methyl)cyclohexyl)methoxy)acetic acid;
2-(((1r,4r)-4-((phenylcarbamoyloxy)methyl)cyclohexyl)methoxy)acetic acid;
2-(((1s,4s)-4-(((3-chlorophenyl)(phenyl)carbamoyloxy)methyl)cyclohexyl)methoxy)acetic acid;
2-(((1s,4s)-4-((phenyl(m-tolyl)carbamoyloxy)methyl)cyclohexyl)methoxy)acetic acid;
2-(((1s,4s)-4-(((2-methoxyphenyl)(phenyl)carbamoyloxy)methyl)cyclohexyl)methoxy)acetic acid;
2-(((1s,4s)-4-(((3-methoxyphenyl)(phenyl)carbamoyloxy)methyl)cyclohexyl)methoxy)acetic acid;
2-(((1s,4s)-4-((phenyl(p-tolyl)carbamoyloxy)methyl)cyclohexyl)methoxy)acetic acid;
2-(((1s,4s)-4-(((4-fluorophenyl)(phenyl)carbamoyloxy)methyl)cyclohexyl)methoxy)acetic acid;
2-(((1r,4r)-4-(((4-chloro-3-fluorophenyl)(phenyl)carbamoyloxy)methyl)cyclohexyl)methoxy)acetic acid;
2-(((1r,4r)-4-(((3-chloro-4-fluorophenyl)(phenyl)carbamoyloxy)methyl)cyclohexyl)methoxy)acetic acid;
2-(((1r,4r)-4-(((3-fluoro-4-methylphenyl)(phenyl)carbamoyloxy)methyl)cyclohexyl)methoxy)acetic acid;
2-(((1r,4r)-4-(((3,5-difluorophenyl)(phenyl)carbamoyloxy)methyl)cyclohexyl)methoxy)acetic acid;
2-(((1r,4r)-4-(((3,4-difluorophenyl)(phenyl)carbamoyloxy)methyl)cyclohexyl)methoxy)acetic acid;
2-(((1r,4r)-4-(((4-fluorophenyl)(phenyl)carbamoyloxy)methyl)cyclohexyl)methoxy)acetic acid;
2-(((1r,4r)-4-((phenyl(p-tolyl)carbamoyloxy)methyl)cyclohexyl)methoxy)acetic acid;
2-(((1r,4r)-4-((3-(2,3-difluorophenyl)-3-phenylureido)methyl)cyclohexyl)methoxy)acetic acid;
2-(((1r,4r)-4-((3-(3,5-difluorophenyl)-3-phenylureido)methyl)cyclohexyl)methoxy)acetic acid;
2-(((1r,4r)-4-((3-(3-chloro-2-fluorophenyl)-3-phenylureido)methyl)cyclohexyl)methoxy)acetic acid;
2-(((1r,4r)-4-(((3-chloro-5-fluorophenyl)(phenyl)carbamoyloxy)methyl)cyclohexyl)methoxy)acetic acid;
2-(((1r,4r)-4-((3-(3-chloro-5-fluorophenyl)-3-phenylureido)methyl)cyclohexyl)methoxy)acetic acid;
2-(((1r,4r)-4-((3-benzhydryl-3-methylureido)methyl)cyclohexyl)methoxy)acetic acid;
2-(((1r,4r)-4-((phenyl(pyridin-3-yl)carbamoyloxy)methyl)cyclohexyl)methoxy)acetic acid;
2-(((1r,4r)-4-(((5-methylthiophen-2-yl)(phenyl)carbamoyloxy)methyl)cyclohexyl)methoxy)acetic acid;
2-(((1r,4r)-4-(((2,3-difluorophenyl)(phenyl)carbamoyloxy)methyl)cyclohexyl)methoxy)acetic acid;
2-(((1r,4r)-4-(((3-(4-chloro-3-fluorophenyl)-3-phenylureido)methyl)cyclohexyl)methoxy)acetic acid;
2-(((1r,4r)-4-(((3-(2-fluoro-3-methoxyphenyl)-3-phenylureido)methyl)cyclohexyl)methoxy)acetic acid;
2-(((1r,4r)-4-((3-(3,4-difluorophenyl)-3-phenylureido)methyl)cyclohexyl)methoxy)acetic acid;
2-(((1r,4r)-4-(((3-fluorophenyl)(4-methoxyphenyl)carbamoyloxy)methyl)cyclohexyl)methoxy)acetic acid;
2-(((1r,4r)-4-(((4-chlorophenyl)(3-fluorophenyl)carbamoyloxy)methyl)cyclohexyl)methoxy)acetic acid;
2-(((1r,4r)-4-(((3-fluorophenyl)(4-fluorophenyl)carbamoyloxy)methyl)cyclohexyl)methoxy)acetic acid;
2-(((1r,4r)-4-(((3-chlorophenyl)(3-fluorophenyl)carbamoyloxy)methyl)cyclohexyl)methoxy)acetic acid;
2-(((1r,4r)-4-(((3-fluorophenyl)(m-tolyl)carbamoyloxy)methyl)cyclohexyl)methoxy)acetic acid;
2-(((1r,4r)-4-(((4-chloro-3-fluorophenyl)(3-fluorophenyl)carbamoyloxy)methyl)cyclohexyl)methoxy)acetic acid;
2-(((1r,4r)-4-(((3-chloro-4-fluorophenyl)(3-fluorophenyl)carbamoyloxy)methyl)cyclohexyl)methoxy)acetic acid;
2-(((1r,4r)-4-(((3-fluoro-4-methylphenyl)(3-fluorophenyl)carbamoyloxy)methyl)cyclohexyl)methoxy)acetic acid;
2-(((1r,4r)-4-((phenyl(pyridin-2-yl)carbamoyloxy)methyl)cyclohexyl)methoxy)acetic acid;
2-(((1r,4r)-4-(((3,5-difluorophenyl)(3-fluorophenyl)carbamoyloxy)methyl)cyclohexyl)methoxy)acetic acid;
2-(((1r,4r)-4-(((3,4-difluorophenyl)(3-fluorophenyl)carbamoyloxy)methyl)cyclohexyl)methoxy)acetic acid;
2-(((1r,4r)-4-((bis(3-fluorophenyl)carbamoyloxy)methyl)cyclohexyl)methoxy)acetic acid;
2-(((1r,4r)-4-(((3-fluorophenyl)(3-methoxyphenyl)carbamoyloxy)methyl)cyclohexyl)methoxy)acetic acid;
2-(((1r,4r)-4-(((3,5-dimethylphenyl)(3-fluorophenyl)carbamoyloxy)methyl)cyclohexyl)methoxy)acetic acid;
2-(((1r,4r)-4-(((3-fluorophenyl)(p-tolyl)carbamoyloxy)methyl)cyclohexyl)methoxy)acetic acid;
2-(((1r,4r)-4-(((3-fluorophenyl)(6-fluoropyridin-3-yl)carbamoyloxy)methyl)cyclohexyl)methoxy)acetic acid;
2-(((1r,4r)-4-(((3-fluorophenyl)(5-methylthiophen-2-yl)carbamoyloxy)methyl)cyclohexyl)methoxy)acetic acid;
2-(((1r,4r)-4-(((4-ethoxyphenyl)(3-fluorophenyl)carbamoyloxy)methyl)cyclohexyl)methoxy)acetic acid;
2-(((1r,4r)-4-(((3-fluorophenyl)(3-(trifluoromethoxy)phenyl)carbamoyloxy)methyl)cyclohexyl)methoxy)acetic acid;
2-(((1r,4r)-4-(((3-fluorophenyl)(pyridin-3-yl)carbamoyloxy)methyl)cyclohexyl)methoxy)acetic acid;
2-(((1r,4r)-4-(((3-fluorophenyl)(pyrazin-2-yl)carbamoyloxy)methyl)cyclohexyl)methoxy)acetic acid;
2-(((1r,4r)-4-(((4-chlorophenyl)(4-fluorophenyl)carbamoyloxy)methyl)cyclohexyl)methoxy)acetic acid;
2-(((1r,4r)-4-(((4-fluorophenyl)(5-methylthiophenyl-2-yl)carbamoyloxy)methyl)cyclohexyl)methoxy)acetic acid;
2-(((1r,4r)-4-(((3-chlorophenyl)(4-fluorophenyl)carbamoyloxy)methyl)cyclohexyl)methoxy)acetic acid;
2-(((1r,4r)-4-(((4-fluorophenyl)(pyridin-3-yl)carbamoyloxy)methyl)cyclohexyl)methoxy)acetic acid;
2-(((1r,4r)-4-(((4-ethoxyphenyl)(4-fluorophenyl)carbamoyloxy)methyl)cyclohexyl)methoxy)acetic acid;
2-(((1r,4r)-4-(((4-fluorophenyl)(4-(trifluoromethoxy)phenyl)carbamoyloxy)methyl)cyclohexyl)methoxy)acetic acid;

2-(((1r,4r)-4-(((4-fluorophenyl)(m-tolyl)carbamoyloxy)methyl)cyclohexyl)methoxy)acetic acid;
2-(((1r,4r)-4-((bis(4-fluorophenyl)carbamoyloxy)methyl)cyclohexyl)methoxy)acetic acid;
2-(((1r,4r)-4-(((6-fluoropyridin-3-yl)(phenyl)carbamoyloxy)methyl)cyclohexyl)methoxy)acetic acid;
2-(((1r,4r)-4-((phenyl(pyrazin-2-yl)carbamoyloxy)methyl)cyclohexyl)methoxy)acetic acid;
2-(((1r,4r)-4-((benzhydryl(methyl)carbamoyloxy)methyl)cyclohexyl)methoxy)acetic acid;
2-(((1r,4r)-4-((3-benzhydryl-1,3-dimethylureido)methyl)cyclohexyl)methoxy)acetic acid;
2-(((1r,4r)-4-(((4-ethoxyphenyl)(phenyl)carbamoyloxy)methyl)cyclohexyl)methoxy)acetic acid;
2-(((1r,4r)-4-(((2-fluoropyridin-4-yl)(phenyl)carbamoyloxy)methyl)cyclohexyl)methoxy)acetic acid;
2-(((1r,4r)-4-(((5-methoxypyridin-3-yl)(phenyl)carbamoyloxy)methyl)cyclohexyl)methoxy)acetic acid;
2-(((1r,4r)-4-(((5-fluoropyridin-2-yl)(phenyl)carbamoyloxy)methyl)cyclohexyl)methoxy)acetic acid;
2-(((1r,4r)-4-((phenyl(5-(trifluoromethyl)pyrazin-2-yl)carbamoyloxy)methyl)cyclohexyl)methoxy)acetic acid;
2-(((1r,4r)-4-(((5-methylpyridin-3-yl)(phenyl)carbamoyloxy)methyl)cyclohexyl)methoxy)acetic acid;
2-(((1r,4r)-4-(((5-chloropyridin-2-yl)(phenyl)carbamoyloxy)methyl)cyclohexyl)methoxy)acetic acid;
2-(((1r,4r)-4-(((5-fluoropyridin-3-yl)(phenyl)carbamoyloxy)methyl)cyclohexyl)methoxy)acetic acid;
2-(((1r,4r)-4-((benzhydryl(propyl)carbamoyloxy)methyl)cyclohexyl)methoxy)acetic acid; or
2-(((1r,4r)-4-(((5-methylthiazol-2-yl)(phenyl)carbamoyloxy)methyl)cyclohexyl)methoxy)acetic acid;
or a pharmaceutically acceptable salt, solvate, or hydrate thereof, of any one of the preceding compounds.]

[28. The method of claim 25, wherein the individual has pulmonary arterial hypertension (PAH).]

[29. The method according to claim 28, wherein the PAH is selected from:
idiopathic PAH;
familial PAH;
PAH associated with a collagen vascular disease selected from: scleroderma, CREST syndrome, systemic lupus erythematosus (SLE), rheumatoid arthritis, Takayasu's arteritis, polymyositis, and dermatomyositis;
PAH associated with a congenital heart disease selected from: atrial septic defect (ASD), ventricular septic defect (VSD) and patent ductus arteriosus in an individual;
PAH associated with portal hypertension;
PAH associated with HIV infection;
PAH associated with ingestion of a drug or toxin;
PAH associated with hereditary hemorrhage telangiectasia;
PAH associated with splenectomy;
PAH associated with significant venous or capillary involvement;
PAH associated with pulmonary venooclusive disease (PVOD); and
PAH associated with pulmonary capillary hemangiomatosis (PCH).]

[30. A method for inhibiting platelet aggregation in an individual comprising administering to the individual in need thereof, a therapeutically effective amount of 2-(((1r,4r)-4-(((4-chlorophenyl)(phenyl)carbamoyloxy)methyl)cyclohexyl)methoxy)acetic acid, or a pharmaceutically acceptable salt, solvate or hydrate thereof.]

[31. The method of claim 30, wherein the individual has pulmonary arterial hypertension (PAH).]

[32. The method according to claim 31, wherein the PAH is selected from:
idiopathic PAH;
familial PAH;
PAH associated with a collagen vascular disease selected from: scleroderma, CREST syndrome, systemic lupus erythematous (SLE), rheumatoid arthritis, Takayasu's arteritis, polymyositis, and dermatomyositis;
PAH associated with a congenital heart disease selected from: atrial septic defect (ASD), ventricular septic defect (VSD) and patent ductus arteriosus in an individual;
PAH associated with portal hypertension;
PAH associated with HIV infection;
PAH associated with ingestion of a drug or toxin;
PAH associated with hereditary hemorrhagic telangiectasia;
PAH associated with splenectomy;
PAH associated with significant venous or capillary involvement;
PAH associated with pulmonary venooclusive disease (PVOD); and
PAH associated with pulmonary capillary hemangiomatosis (PCH).]

*33. The method of claim 1, wherein the individual has type 1 diabetes or type 2 diabetes.*

*34. The method of claim 1, wherein $R^{11}$ is H.*

*35. A process for the preparation of a compound of Formula (III):*

(III)

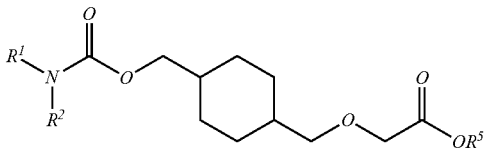

*or a salt form thereof,*
*wherein:*
*$R^1$ is selected from $C_1$-$C_6$ alkyl, aryl and heteroaryl;*
*$R^2$ is selected from: H, $C_1$-$C_6$ alkyl and aryl; and*
*$R^5$ is $C_1$-$C_6$ alkyl;*
*comprising reacting a compound of Formula (IV):*

(IV)

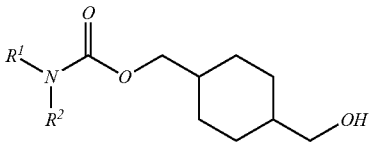

*or a salt from thereof; with a compound of Formula (V):*

(V)

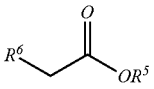

*wherein* $R^6$ *is selected from:* $C_1$-$C_6$ *alkylarylsulfonate,* $C_1$-$C_6$ *alkylsulfonate, arylsulfonate,* $C_1$-$C_6$ *haloalkylsulfonate and halogen;*

*in the presence of a base to form a compound of Formula (III) or a salt form thereof.*

* * * * *